(12) United States Patent
Kobayashi et al.

(10) Patent No.: US 11,013,803 B2
(45) Date of Patent: May 25, 2021

(54) NEAR INFRARED PHOTOIMMUNOTHERAPY (NIR-PIT) OF SUPPRESSOR CELLS TO TREAT CANCER

(71) Applicant: THE UNITED STATES OF AMERICA, as represented by the Secretary, Department of Health and Human, Bethesda, MD (US)

(72) Inventors: Hisataka Kobayashi, Laurel, MD (US); Peter Choyke, Rockville, MD (US); Kazuhide Sato, North Bethesda, MD (US); Noriko Sato, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/749,028

(22) PCT Filed: Aug. 2, 2016

(86) PCT No.: PCT/US2016/045090
§ 371 (c)(1),
(2) Date: Jan. 30, 2018

(87) PCT Pub. No.: WO2017/027247
PCT Pub. Date: Feb. 16, 2017

(65) Prior Publication Data
US 2018/0236076 A1 Aug. 23, 2018

Related U.S. Application Data

(60) Provisional application No. 62/202,252, filed on Aug. 7, 2015.

(51) Int. Cl.
*A61K 41/00* (2020.01)
*C07K 16/28* (2006.01)
*A61K 47/68* (2017.01)
*A61P 35/04* (2006.01)
*A61K 39/00* (2006.01)

(52) U.S. Cl.
CPC ...... *A61K 41/0038* (2013.01); *A61K 47/6803* (2017.08); *A61K 47/6849* (2017.08); *A61P 35/04* (2018.01); *C07K 16/2812* (2013.01); *C07K 16/2815* (2013.01); *C07K 16/2866* (2013.01); *A61K 2039/505* (2013.01); *C07K 2317/54* (2013.01); *C07K 2317/73* (2013.01)

(58) Field of Classification Search
CPC ............ A61K 41/0057; A61K 47/6803; A61K 47/6849
See application file for complete search history.

(56) References Cited

U.S. PATENT DOCUMENTS

| | | |
|---|---|---|
| 5,196,005 A | 3/1993 | Doiron et al. |
| 5,494,793 A | 2/1996 | Schindele et al. |
| 6,344,050 B1 | 2/2002 | Chen |
| 6,534,041 B1 | 3/2003 | Licha et al. |
| 7,005,518 B2 | 2/2006 | Peng et al. |
| 7,498,029 B2 | 3/2009 | Hasan et al. |
| 8,524,239 B2 | 9/2013 | Kobayashi et al. |
| 8,623,354 B2 | 1/2014 | Brown et al. |
| 9,358,306 B2 | 6/2016 | Kobayashi et al. |
| 10,537,641 B2 | 1/2020 | Kobayashi et al. |
| 10,538,590 B2 | 1/2020 | Kobayashi et al. |
| 2001/0044124 A1 | 11/2001 | Bacus |
| 2004/0120949 A1 | 6/2004 | Adolf et al. |
| 2005/0157292 A1 | 7/2005 | Saitoh et al. |

(Continued)

FOREIGN PATENT DOCUMENTS

| | | |
|---|---|---|
| CN | 102585003 | 7/2012 |
| CN | 103781495 A | 5/2014 |

(Continued)

OTHER PUBLICATIONS

Steele et al., Suppressor deletion therapy: selective elimination of T suppressor cells in vivo using a hematoporphyrin conjugated monoclonal antibody permits animals to reject syngeneic tumor cells. Cancer Immunol. Immunother. 26, 125-131, 1988. (Year: 1988).*
McHugh et al.—The role of suppressor T cells in regulation of immune responses. J. Allerg. Clin. Immunol., 110, 693-702, 2002. (Year: 2002).*
Gajewski et al., Current Protocols in Immunology (2001) 20.4.1-20.4.18 by John Wiley & Sons, Inc., 2001. (Year: 2001).*
Anonymous, "Anodyne: Tratamento com tecnologia MIRE," Forumenfermagem-Projecto Feridas, Jan. 24, 2011, XP002686605, retrieved from the internet: URL:http://forumenfermagem.org/feridas/?s=anodyne, retrieved on Nov. 7, 2012. Re-submitted w/European Patent Office, International Search Report and Written Opinion dated Nov. 26, 2012 for International Application No. PCT/US2012/044421, which dislcoses/discusses relevance.

(Continued)

*Primary Examiner* — Elly-Gerald Stoica
(74) *Attorney, Agent, or Firm* — Klarquist Sparkman, LLP

(57) ABSTRACT

It is shown that CD25-targeted near-infrared photo-immunotherapy causes a unique, rapid and spatially selective depletion of Tregs leading to regression of the treated tumor and inducing systemic immunologic responses in untreated tumors. Based on these observations, provided are compositions and methods of killing immune suppressor cells, for example to treat cancer. Reducing the number of suppressor cells in a subject can remove suppression of effector T cells, for example, to treat cancer using the subject's own immune system. In particular examples, the method includes contacting suppressor cells having a suppressor cell surface protein with an antibody-IR700 molecule, wherein the antibody specifically binds to the suppressor cell surface protein, and in some examples the antibody does not have a functional Fc region. The cell is subsequently irradiated, such as at a wavelength of 660 to 740 nm, for example at a dose of at least 4 J cm$^{-2}$.

15 Claims, 60 Drawing Sheets

(56) References Cited

U.S. PATENT DOCUMENTS

| | | |
|---|---|---|
| 2006/0231107 A1 | 10/2006 | Glickman et al. |
| 2007/0020272 A1 | 1/2007 | Hasan |
| 2007/0133086 A1 | 6/2007 | Wilhelm et al. |
| 2008/0073566 A1 | 3/2008 | Frangioni |
| 2008/0095699 A1 | 4/2008 | Zheng et al. |
| 2008/0253960 A1 | 10/2008 | Zheng et al. |
| 2010/0255057 A1 | 10/2010 | Hyde et al. |
| 2011/0082412 A1 | 4/2011 | Hyde et al. |
| 2012/0010558 A1 | 1/2012 | Kobayashi et al. |
| 2012/0070377 A1 | 3/2012 | Yahioglu et al. |
| 2013/0287688 A1 | 10/2013 | Jain et al. |
| 2013/0336995 A1 | 12/2013 | Kobayashi et al. |
| 2014/0120119 A1 | 5/2014 | Kobayashi et al. |
| 2014/0309578 A1 | 10/2014 | Anvari |
| 2015/0140022 A1 | 5/2015 | Barth et al. |
| 2015/0343060 A1 | 12/2015 | Kovar et al. |
| 2015/0343084 A1 | 12/2015 | Dilley |
| 2015/0374819 A1 | 12/2015 | Kovar |
| 2016/0256564 A2 | 9/2016 | Kobayashi et al. |
| 2017/0122853 A1 | 5/2017 | Kobayashi et al. |
| 2018/0113246 A1 | 4/2018 | Rose et al. |
| 2018/0113247 A1 | 4/2018 | Rose et al. |
| 2018/0149658 A1 | 5/2018 | Wu et al. |
| 2018/0236076 A1 | 8/2018 | Kobayashi et al. |
| 2018/0239074 A1 | 8/2018 | Rose et al. |
| 2018/0250405 A1 | 9/2018 | Biel et al. |
| 2018/0371095 A1 | 12/2018 | Aggeler et al. |
| 2019/0015510 A1 | 1/2019 | Makings et al. |
| 2019/0194322 A1 | 6/2019 | Kalabokis et al. |

FOREIGN PATENT DOCUMENTS

| | | |
|---|---|---|
| CN | 104203286 A | 12/2014 |
| DE | 197 17 904 A1 | 10/1998 |
| EP | 1512963 A1 | 3/2005 |
| EP | 2731626 B1 | 12/2018 |
| JP | 2003-284757 A | 10/2003 |
| JP | 2003-344284 A | 12/2003 |
| JP | 2006-515892 A | 6/2006 |
| JP | 2006-517230 A | 7/2006 |
| JP | 2007-155722 A | 6/2007 |
| JP | 2014-523907 A | 9/2014 |
| WO | WO 2001057495 | 8/2001 |
| WO | WO 2003/011106 A2 | 2/2003 |
| WO | WO 2003/083811 A1 | 10/2003 |
| WO | WO 2004/067038 A1 | 8/2004 |
| WO | WO 2004/071571 A1 | 8/2004 |
| WO | WO 2005099689 | 10/2005 |
| WO | WO 2006/092598 A2 | 9/2006 |
| WO | WO 2008/120134 A1 | 10/2008 |
| WO | WO 2008152424 | 12/2008 |
| WO | WO 2009038776 | 3/2009 |
| WO | WO 2009092062 | 7/2009 |
| WO | WO 2010/047611 A1 | 4/2010 |
| WO | WO 2010/085651 A1 | 7/2010 |
| WO | WO 2010121163 | 10/2010 |
| WO | WO 2011025950 | 3/2011 |
| WO | WO 2011038006 | 3/2011 |
| WO | WO 2012076631 | 6/2012 |
| WO | WO 2012082118 | 6/2012 |
| WO | WO 2013/009475 A1 | 1/2013 |
| WO | WO 2013044156 | 3/2013 |
| WO | WO 2014/084394 A1 | 6/2014 |
| WO | WO 2014089247 | 6/2014 |
| WO | WO 2014127365 | 8/2014 |
| WO | WO 2014168950 | 10/2014 |
| WO | WO 2015057692 | 4/2015 |
| WO | WO 2015187651 | 12/2015 |
| WO | WO 2015187677 | 12/2015 |
| WO | WO 2016/022896 A1 | 2/2016 |
| WO | WO 2017027247 | 2/2017 |
| WO | WO 2017031363 | 2/2017 |
| WO | WO 2017031367 | 2/2017 |
| WO | WO 2018080952 | 5/2018 |
| WO | WO 2018156815 | 8/2018 |
| WO | WO 2018/175403 A1 | 9/2018 |
| WO | WO 2019009941 | 1/2019 |

OTHER PUBLICATIONS

Anonymous, "Near Infrared Light for the Treatment of Painful Peripheral Neuropathy," U.S. National Institutes of Health, Aug. 2, 2012, XP002686617, retrieved from the internet: URL:http://www.clinicaltrials.gov/ct2/show/NCT00125268, retrieved on Nov. 7, 2011.

Anonymous, "Near IR Signature Management for Combat Clothing and Equipment," Australian Government Department of Defence, DSTO, Apr. 7, 2005, XP002686606, retrieved from the internet: URL:http://www.dsto.defence.gov.au/reserach/3214/?print=true, retrieved on Nov. 6, 2012.

Ballou et al., "Tumor Labeling in Vivo Using Cyanine-Conjugated Monoclonal Antibodies," *Cancer Immunol. Immunother.* 41:257-263, 1995.

Baolin et al., Practical Pathophysiology, Qing Dao Ocean University Press, Dec. 1995. (see English translation of CN201280043973.2 Notification of Reexamination (pp. 5-6) for relevance).

Barrett et al., "In vivo Diagnosis of Epidermal Growth Factor Receptor Expression using Molecular Imaging with a Cocktail of Optically Labeled Monoclonal Antibodies," *Clin Cancer Res.* 13:6639-6648, 2007.

Carter et al., "Identification and Validation of Cell Surface Antigens for Antibody Targeting in Oncology," *Endocr Relat Cancer* 11:659-687, 2004.

Davis et al., "Nanoparticle Therapeutics: An Emerging Treatment Modality for Cancer," *Nat Rev Drug Dis.* 7:771-782, 2008.

Del Governatore et al., "Experimental Photoimmunotherapy of Hepatic Metastases of Colorectal Cancer with a 17.1A chlorin$_{e6}$ Immunoconjugate," *Cancer Res.* 60:4200-4205, 2000.

Duska et al., Combination Photoimmunotherapy and Cisplatin: Effects on Human Ovarian Cancer Ex Vivo, *J Nat Cancer Inst.* 91:1557-1563, 1999.

Gao et al., "In vivo Cancer Targeting and Imaging With Semiconductor Quantum Dots," *Nat Biotechnol.* 22:969-976 and 5 pages of supplemental notes, 2004.

Gleysteen et al., "Fluorescently labeled cetuximab to evaluate head and neck cancer response to treatment," *Cancer Biol Ther.* 6:e1-e5, 2007.

Kines et al., "HPV Based Photodynamic Therapy: A New Approach for Anti-Cancer Therapy," *J. Immunol.* 192(1): Supplement 206.8, 2014.

Kirveliene et al., "Schedule-Dependent Interaction Between Doxorubicin and mTHPC-Mediated Photodynamic Therapy in Murine Hepatoma In Vitro and In Vivo," Cancer Chemother. Pharmacol. 57:65-72, 2005.

Kobayashi, "Activatable Fluorescent Imaging Probes for Cancer Detection and Diagnosis," Abstract presented at the American Chemical Society meeting in San Francisco, 2014.

Kovar et al., "A Systematic Approach to the Development of Fluorescent Contrast Agents for Optical Imagining of Mouse Cancer Models," *Anal. Biochem.* 367:1-12, 2007.

Li-Cor, "IRDye® Infrared Dyes: Advancing Discovery with Infrared Imaging," 2010.

Maya et al., "Synthesis, Aggregation Behavior and Nonlinear Absorption Properties of Lead Phthalocyanines Substituted with Siloxane Chains," *J Materials Chem.* 13:1603-1613, 2003.

Mitchell et al., "Comparison of Two Infrared Devices in Their Effectiveness in Reducing Symptoms Associated with RLS," Physiother. Theory Prac., 2011, XP002686651, retrieved from the internet: URL:http://www.ncbi.nlm.nih.gov.pubmed/20950168, retrieved on Nov. 8, 2012.

Mitchell et al., "Comparison of Two Infrared Devices in Their Effectiveness in Reducing Symptoms Associated with RLS," *Physiother. Theory Pract.* 27:352-359, 2011.

Mitsunaga et al., "Abstract 3618: Target-Specific Photo-Activatable Immunotherapy (PIT) for Cancer Based on a Monoclonal Antibody-Photosensitizer Conjugate," in *Proceedings of the 102nd Annual*

(56) References Cited

OTHER PUBLICATIONS

*Meeting of the American Association for Cancer Research*; Apr. 2-6, 2011; Orlando, FL. Philadelphia (PA): AACR; *Cancer Res.* 71:3618, 2011.

Mitsunaga et al., "Cancer Cell-Selective in Vivo Near Infrared Photomimmunotherapy Targeting Specific Membrane Molecules," *Nat. Med.* 17:1685-1691, 2011.

Mitsunaga et al., "Near-Infrared Theranostic Photoimmunotherapy (PIT): Repeated Exposure of Light Enhances the Effect of Immunoconjugate," *Bioconjug. Chem.* 23:604-609, 2012.

Nakajima et al., "Improving the Efficacy of Photoimmunotherapy (PIT) Using a Cocktail of Antibody Conjugates in a Multiple Antigen Tumor Model," *Theranostics* 3:357-365, 2013.

Nowis et al., "The influence of photodynamic therapy on the immune response," *Photodiagnosis Photodyn Ther.* 2:283-298, 2005.

Ogawa et al., "In vivo Molecular Imaging of Cancer with a Quenching Near-Infrared Fluorescent Probe Using Conjugates of Monoclonal Antibodies and Indocyanine Green," *Cancer Res.* 69:1268-1272, 2009.

Peng et al., "Phthalocyanine Dye as an Extremely Photostable and Highly Fluorescent Near-Infrared Labeling Reagent," *Proceedings of SPIE* 6097:60970E-1-60970E-12, 2006.

Rosenthal et al., "In Vivo Detection of Head and Neck Cancer Orthotopic Xenografts by Immunofluorescence," *Laryngoscope* 116:1636-1641, 2006.

Sano et al., "Markedly Enhanced Permeability and Retention Effects Induced by Photo-Immunotherapy of Tumors," *ACS Nano.* 7:717-724, 2013, including 19 pages of supporting information).

Sato et al., "Spatially selective depletion of tumor-associated regulatory T cells with near-infrared photoimmunotherapy," *Sci Transl Med.* 8:352ra110, 2016.

Savellano et al., "Multiepitope HER2 Targeting Enhances Photoimmunotherapy of HER2-Overexpressing Cancer Cells with Pyropheophorbide-a Immunoconjugates," *Cancer Res.* 65:6371-6379, 2005.

Scully et al., "Application of Fluorescence Lifetime Imaging Microscopy to the Investigation of Intracellular PDT Mechanisms," *Bioimaging* 5:9-18, 1997.

Serebrovskaya et al., "Targeting Cancer Cells by Using an Antireceptor Antibody-Photosensitizer Fusion Protein," *Proc Nat Acad Sci.* 106:9221-9225, 2009.

Soukos et al., "Epidermal Growth Factor Receptor-Targeted Immunophotodiagnosis and Photoimmunotherapy of Oral Precancer in Vivo," *Cancer Res.* 61:4490-4496, 2001.

Sugiyama et al, "Anti-CCR4 mAb selectively depletes effector-type FoxP3+CD4+ regulatory T cells, evoking antitumor immune responses in humans," *Proc Natl Acad Sci. USA* 110:17945-17950, 2013.

Van Dongen et al., "Photosensitizer-Antibody Conjugates for Detection and Therapy of Cancer," *Adv Drug Deliv Rev.* 56:31-52, 2004.

Vrouenraets et al., "Targeting of Aluminum (III) Phthalocyanine Tetrasulfonate by Use of Internalizing Monoclonal Antibodies: Improved Efficacy in Photodynamic Therapy," *Cancer Res.* 61:1970-1975, 2001.

Watanabe et al., "Photoimmunotherapy Targeting Prostate-Specific Membrane Antigen: Are Antibody Fragments as Effective as Antibodies?," *J Nucl Med.* 56:140-144, 2015.

Xu et al., "Antibody Conjugated Magnetic Iron Oxide Nanoparticles for Cancer Cell Separation in Fresh Whole Blood," *Biomaterials* 32:9758-9765, 2011.

Zhu et al., "Visualization of $P53_{264-272}$/HLA-A*0201 Complexes Naturally Presented on Tumor Cell Surface by a Multimeric Soluble Single-Chain T Cell Receptor," *J. Immunol.* 176:3223-3232, 2006.

Zuluaga et al., "Combination of Photodynamic Therapy With Anti-Cancer Agents," *Curr. Med. Chem.* 15:1655-1673, 2008.

CN 201280043973.2 First Office Action dated Nov. 24, 2014, with English translation (19 pages).

CN 201280043973.2 Office Action dated Feb. 22, 2016 for Application No. 201280043973.2 (with English translation).

CN 201280043973.2 Reexamination Notification dated Nov. 17, 2016, with English translation.

CN 201280043973.2 Second Office Action dated Aug. 12, 2015, with English translation (15 pages).

EP12738664.7 Examination Report dated Jul. 6, 2016.

JP 2014520202 Final Official Action dated Sep. 28, 2016, with English translation.

JP 2014-520202 Office Action dated Feb. 3, 2016, with English translation.

PCT/US2012/044421 International Search Report and Written Opinion dated Nov. 26, 2012 (18 pages).

PCT/US2015/044168 International Search Report and Written Opinion dated Oct. 19, 2016 (11 pages).

PCT/US2016/045090 International Search Report and Written Opinion dated Oct. 11, 2016 (12 pages).

SG 2013091822 Search Report and Written Opinion dated Mar. 23, 2015 (9 pages).

SG 2013091822 Written Opinion dated Nov. 11, 2015 (10 pages).

Ali et al., "Dynamic fluorescent imaging with indocyanine green for monitoring the therapeutic effects of photoimmunotherapy," *Contrast Media Mol Imaging* 9(4):276-282, 2014.

Amoury et al., "Photoimmunotheranostic agents for triple-negative breast cancer diagnosis and therapy that can be activated on demand," *Oncotarget* 7(34):54925-54936, 2016.

Carcenac et al., "Internalisation enhances photo-induced cytotoxicity of monoclonal antibody-phthalocyanine conjugates." *Br J. Cancer* 85:1787-1793, 2001.

Chiarello, K., "In between the light and the dark: developments in Photosensitive Pharmaceuticals," *Pharmaceutical Tecnology*, pp. 48-54, Dec. 2004.

Chopra, "IRDye 700DX-Labeled annexin V," Molecular Imaging and Contrast Agent Database (MICAD) [Internet]. Bethesda (MD): National Center for Biotechnology Information (US); 2004-2013. Oct. 27, 2009 [updated Dec. 17, 2009].

De Boer et al., "A standardized light-emitting diode device for photoimmunotherapy," *J Nucl Med.* 55(11):1893-1898, 2014.

De Boer et al., "Biodistribution Study of Intravenously Injected Cetuximab-IRDye700DX in Cynomolgus Macaques," *Mol Imaging Biol.* 18(2):232-242, 2016.

Denis et al., "Synthesis, bioanalysis and biodistribution of photosensitizer conjugates for photodynamic therapy," *Bioanalysis* 5:1099-1114, 2013.

Dixit et al., "Transferrin Receptor-Targeted Theranostic Gold Nanoparticles for Photosensitizer Delivery in Brain Tumors," *Nanoscale*, 7(5):1782-1790, 2015.

Hanaoka et al., "Glypican-3 targeted human heavy chain antibody as a drug carrier for hepatocellular carcinoma therapy," *Mol Pharm.* 12(6):2151-2157, 2015.

Hanaoka et al., "Photoimmunotherapy of hepatocellular carcinoma-targeting Glypican-3 combined with nanosized albumin-bound paclitaxel," *Nanomedicine (Lond).* 10(7):1139-1147, 2015.

Heukers et al., "Nanobody-photosensitizer conjugates for targeted photodynamic therapy," *Nanomedicine* 10:1441-1451, 2014.

Hiroshima et al., "Photoimmunotherapy Inhibits Tumor Recurrence After Surgical Resection on a Pancreatic Cancer Patient-Derived Orthotopic Xenograft (PDOX) Nude Mouse Model," *Ann Surg Oncol.* 22 Suppl 3:S1469-S1474, 2015.

Iqbal et al., "Phthalocyanine-Biomolecule Conjugated Photosensitizers for Targeted Photodynamic Therapy and Imaging," *Curr Drug Metab.* 16(9):816-832, 2015.

Ishida et al., "Trastuzumab-Based Photoimmunotherapy Integrated with Viral HER2 Transduction Inhibits Peritoneally Disseminated HER2-Negative Cancer," *Mol Cancer Ther.* 15(3):402-411, 2016.

Ito et al., "Molecular targeted photoimmunotherapy for HER2-positive human gastric cancer in combination with chemotherapy results in improved treatment outcomes through different cytotoxic mechanisms," *BMC Cancer* 16:37, 2016.

Jia et al., "Cannabinoid CB2 receptor as a new phototherapy target for the inhibition of tumor growth," *Mol Pharm.* 11(6):1919-1929, 2014.

Jing et al., "Imaging and Selective Elimination of Glioblastoma Stem Cells with Theranostic Near-Infrared-Labeled CD133-Specific Antibodies," *Theranostics* 6(6):862-874, 2016.

(56) References Cited

OTHER PUBLICATIONS

Kijanka et al., "Optical imaging of pre-invasive breast cancer with a combination of VHHs targeting CAIX and HER2 increases contrast and facilitates tumour characterization," *EJNMMI Res.* 6(1):14, 2016.

Kishimoto et al., "Evaluation of oxygen dependence on in vitro and in vivo cytotoxicity of photoimmunotherapy using IR-700-antibody conjugates," *Free Radic Biol Med.* 85:24-32, 2015.

Kobayashi, "Near infrared photoimmunotherapy: A new cancer therapy kills cancer cells with exposure of harmless near infrared light," Poster Presentation, at NEST Conference, Tokyo, Japan, Apr. 2018.

Licor, "High Photostability of IRDye® 700DX," Retrieved on Aug. 23, 2018. Retrieve on https://www.licor.com/bio/products/reagents/irdye/700dx/photostability.html.

Maawy et al., "Near infra-red photoimmunotherapy with anti-CEA-IR700 results in extensive tumor lysis and a significant decrease in tumor burden in orthotopic mouse models of pancreatic cancer," *PLoS One* 10(3):e0121989, 2015.

Mitsunaga et al., "Immediate in vivo target-specific cancer cell death after near infrared photoimmunotherapy," *BMC Cancer.* 12:345, 2012.

Moore et al., "Photoimmunotherapy of residual disease after incomplete surgical resection in head and neck cancer models," *Cancer Med.* 5(7):1526-1534, 2016.

Nagaya et al., "Near Infrared Photoimmunotherapy Targeting EGFR Positive Triple Negative Breast Cancer: Optimizing the Conjugate-Light Regimen," *PLoS One* 10(8):e0136829, 2015.

Nagaya et al., "Near infrared photoimmunotherapy with an anti-mesothelin antibody," *Oncotarget* 7(17):23361-23369, 2016.

Nagaya et al., "Improved micro-distribution of antibody-photon absorber conjugates after initial near infrared photoimmunotherapy (NIR-PIT)," *J Control Release* 232:1-8, 2016.

Nagaya et al., "Syngeneic Mouse Models of Oral Cancer Are Effectively Targeted by Anti-CD44-Based NIR-PIT," *Mol Cancer Res.* 15:1667-1677, 2017.

Nagaya et al., "Near infrared photoimmunotherapy with avelumab, an anti-programmed death-ligand 1 (PD-L1) antibody," *Oncotarget* 8:8807-8817, 2017.

Nagaya et al., "Near infrared photoimmunotherapy targeting bladder cancer with a canine anti-epidermal growth factor receptor (EGFR) antibody," *Oncotarget* 9:19026-19038, 2018.

Nagaya et al., "Host Immunity Following Near-Infrared Photoimmunotherapy is Enhanced with PD-1 Checkpoint Blockade to Eradicate Established Antigenic Tumors," *Cancer Immunol Res.* 7:401-413, 2019.

Nakajima et al., "Real-time monitoring of in vivo acute necrotic cancer cell death induced by near infrared photoimmunotherapy using fluorescence lifetime imaging," *Cancer Res.* 72(18):4622-4628, 2012.

Nakajima et al., "The effects of conjugate and light dose on photo-immunotherapy induced cytotoxicity," *BMC Cancer* 30;14:389, 2014.

Nakamura et al., "MR imaging biomarkers for evaluating therapeutic effects shortly after near infrared photoimmunotherapy," *Oncotarget* 7(13):17254-17264, 2016.

Sano et al., "Acute cytotoxic effects of photoimmunotherapy assessed by 18F-FDG PET," *J Nucl Med.* 54(5):770-775, 2013.

Sano et al., "The effect of photoimmunotherapy (PIT) followed by liposomal daunorubicin in a mixed tumor model: A demonstration of the super-enhanced permeability and retention (SUPR) effect after PIT," *Mol Cancer Ther.* 13(2):426-432, 2014.

Sato et al., "Photoimmunotherapy: comparative effectiveness of two monoclonal antibodies targeting the epidermal growth factor receptor," *Mol Oncol.* 8(3):620-632, 2014.

Sato et al., "Photoimmunotherapy of gastric cancer peritoneal carcinomatosis in a mouse model," *PLoS One* 9(11):e113276, 2014.

Sato et al., "Near infrared photoimmunotherapy for lung metastases," *Cancer Lett.* 365(1):112-121, 2015.

Sato et al., "Near infrared photoimmunotherapy in the treatment of disseminated peritoneal ovarian cancer," *Mol Cancer Ther.* 14(1):141-150, 2015.

Sato et al., "Near infrared photoimmunotherapy in the treatment of pleural disseminated NSCLC: preclinical experience," *Theranostics* 5(7):698-709, 2015.

Sato et al., "Selective cell elimination in vitro and in vivo from tissues and tumors using antibodies conjugated with a near infrared phthalocyanine," *RSC Adv.* 5(32):25105-25114, 2015.

Sato et al., "Comparative effectiveness of light emitting diodes (LEDs) and Lasers in near infrared photoimmunotherapy," *Oncotarget* 7(12):14324-14335, 2016.

Sato et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy," *ACS Cent Sci.* 4:1559-1569, 2018.

Shimoyama et al., "Viral transduction of the HER2-extracellular domain expands trastuzumab-based photoimmunotherapy for HER2-negative breast cancer cells," *Breast Cancer Res Treat.* 149(3):597-605, 2015.

Shirasu et al., "Potent and specific antitumor effect of CEA-targeted photoimmunotherapy," *Int J Cancer.* 135(11):2697-710, 2014.

Van Driel et al., "EGFR targeted nanobody-photosensitizer conjugates for photodynamic therapy in a pre-clinical model of head and neck cancer," *J Control Release* 229:93-105, 2016.

Von Felbert et al., "A specific photoimmunotheranostics agent to detect and eliminate skin cancer cells expressing EGFR," *J Cancer Res Clin Oncol.* 142(5):1003-1011, 2016.

Wang et al., "Theranostic Agents for Photodynamic Therapy of Prostate Cancer by Targeting Prostate-Specific Membrane Antigen," *Mol. Cancer Ther.* 15(8):1834-1844, 2016.

PCT/US2019/026488 International Search Report and Written Opinion dated Jun. 26, 2019 (15 pages).

Chen et al., "Tumor vascular permeabilization by vascular-targeting photosensitization: effects, mechanism, and therapeutic implications," *Clin Cancer Res.* 12:917-923, 2006.

Greish, Khaled, "Enhanced permeability and retention of macromolecular drugs in solid tumors: a royal gate for targeted anticancer nanomedicines," *J Drug Target.* 15:457-464, 2007.

Snyder et al., "Photodynamic therapy: a means to enhanced drug delivery to tumors," *Cancer Res.* 63:8126-8131, 2003.

Supplementary materials from Mitsunaga et al., "Cancer Cell-Selective in Vivo Near Infrared Photoimmunotherapy Targeting Specific Membrane Molecules," *Nat. Med.* 17:1685-1691, 2011. (15 pages).

Supplementary materials from Sugiyama et al., "Anti-CCR4 mAb selectively depletes effector-type FoxP3+CD4+ regulatory T cells, evoking antitumor immune responses in humans," *Proc Natl Acad Sci. USA* 110:17945-17950, 2013. (5 pages).

Waite and Roth, "Nanoscale drug delivery systems for enhanced drug penetration into solid tumors: current progress and opportunities," *Crit Rev Biomed Eng.* 40:21-41, 2012.

Wessels et al., "Advances in cellular, subcellular, and nanoscale imaging in vitro and in vivo," *Cytometry A:* 77:667-676, 2010.

Clinical Trial Identifier NCT02422979, first posted on Apr. 22, 2015, last updated on Sep. 20, 2019 (9 pages).

Maawy et al., "Photoimmunotherapy lowers recurrence after pancreatic cancer surgery in orthotopic nude mouse models," *J Surg Res.* 197:5-11, 2015.

Nagaya et al., "Near infrared photoimmunotherapy of B-cell lymphoma," *Mol Oncol.* 10:1404-1414, 2016.

Sanchez-Barcelo et al., "Recent Patents on Light Based Therapies: Photodynamic Therapy, Photothermal Therapy and Photoimmunotherapy," *Recent Patents on Endocrine, Metabolic & Immune Drug Discovery* 8:1-8, 2014.

Serebrovskaia et al., "Genetically Encoded Photoimmunosensitizer," *Bioorg. Khim.* 37:137-144, 2011 (English Abstract Only).

Yoon et al., "Advance in Photosensitizers and Light Delivery for Photodynamic Therapy," *Clin Endosc.* 46:7-23, 2013.

Zhang et al., "Target-selective phototherapy using a ligand-based photosensitizer for type 2 cannabinoid receptor," *Chem Biol.* 21:338-344, 2014 (with 7 pages of Supplementary Materials).

(56) References Cited

OTHER PUBLICATIONS

Zhang et al., "Tumor mitochondria-targeted photodynamic therapy with a translocator protein (TSPO)-specific photosensitizer," *Acta Biomater*. 28:160-170, 2015 (with 6 pages of Supplementary Materials).

Zinn et al., "IND-Directed Safety and Biodistribution Study of Intravenously Injected Cetuximab-IRDye800 in Cynomolgus Macaques." *Mol Imaging Biol*. 17:49-57, 2015.

Doane et al., "Observation and Photophysical Characterization of Silicon Phthalocyanine J-Aggregate Dimers in Aqueous Solutions," *Chem Eur J*. 20:8030-8039, 2014.

Dougherty et al., "Photodynamic Therapy," *J Natl Cancer Inst*. 90:889-905, 1998.

Ishii et al., "Defucosylated Humanized Anti-CCR4 Monoclonal Antibody KW-0761 as a Novel Immunotherapeutic Agent for Adult T-cell Leukemia/Lymphoma," *Clin Cancer Res*. 16:1520-1531, 2010.

Ito et al., "Combination photoimmunotherapy with monoclonal antibodies recognizing different epitopes of human epidermal growth factor receptor 2: an assessment of phototherapeutic effect based on fluorescence molecular imaging," *Oncotarget* 7:14143-14152, 2016.

Rosas-Arellano et al., "A simple solution for antibody signal enhancement in immunofluorescence and triple immunogold assays," *Histochem Cell Biol*. 146:421-430, 2016.

Onizuka et al., "Tumor Rejection by in Vivo Administration of Anti-CD25 (Interleukin-2 Receptor α) Monoclonal Antibody," *Cancer Res*. 59:3128-3133, 1999.

Marabelle et al., "Depleting tumor-specific Tregs at a single site eradicates disseminated tumors," *J Clin Invest*. 123:2447-2463, 2013.

Maruoka et al., "Combined CD44- and CD25-targeted Near-Infrared Photoimmunotherapy to Selectively Kill Cancer and Regulatory T cells in Syngeneic Mouse Cancer Models," *Cancer Immunol Res*. 8:345-355, 2020.

Wooldridge et al.., "Immunostimulatory Oligodeoxynucleotides Containing CpG Motifs Enhance the Efficacy of Monoclonal Antibody Therapy of Lymphoma," *Blood* 89:2994-2998, 1997.

\* cited by examiner

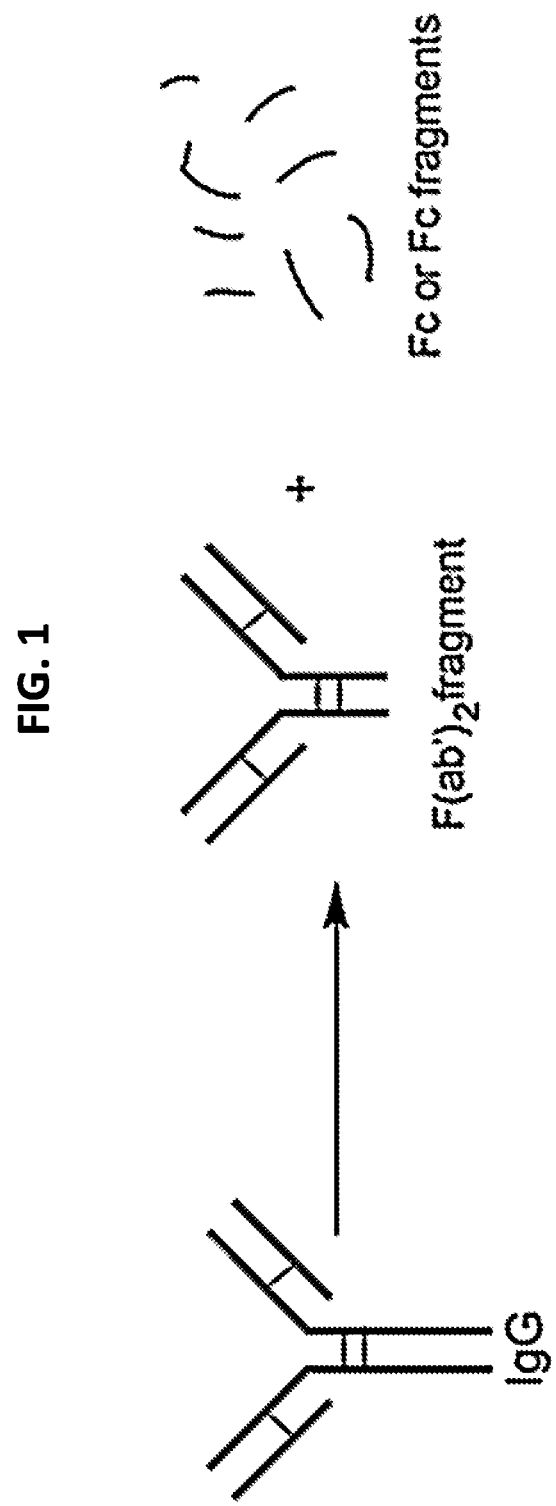

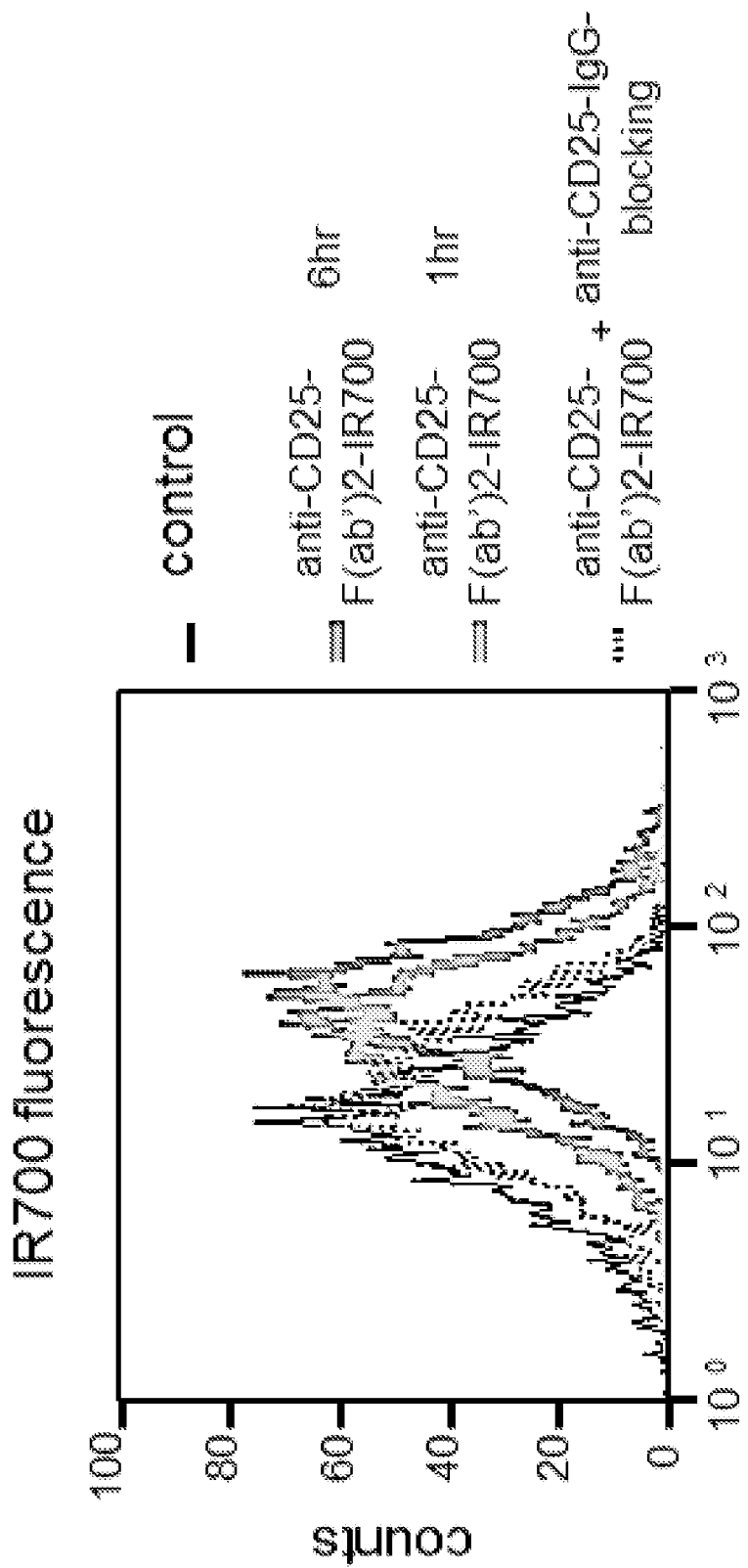

(a) before PIT
(b) day 1
(c) day 2
(d) day 3

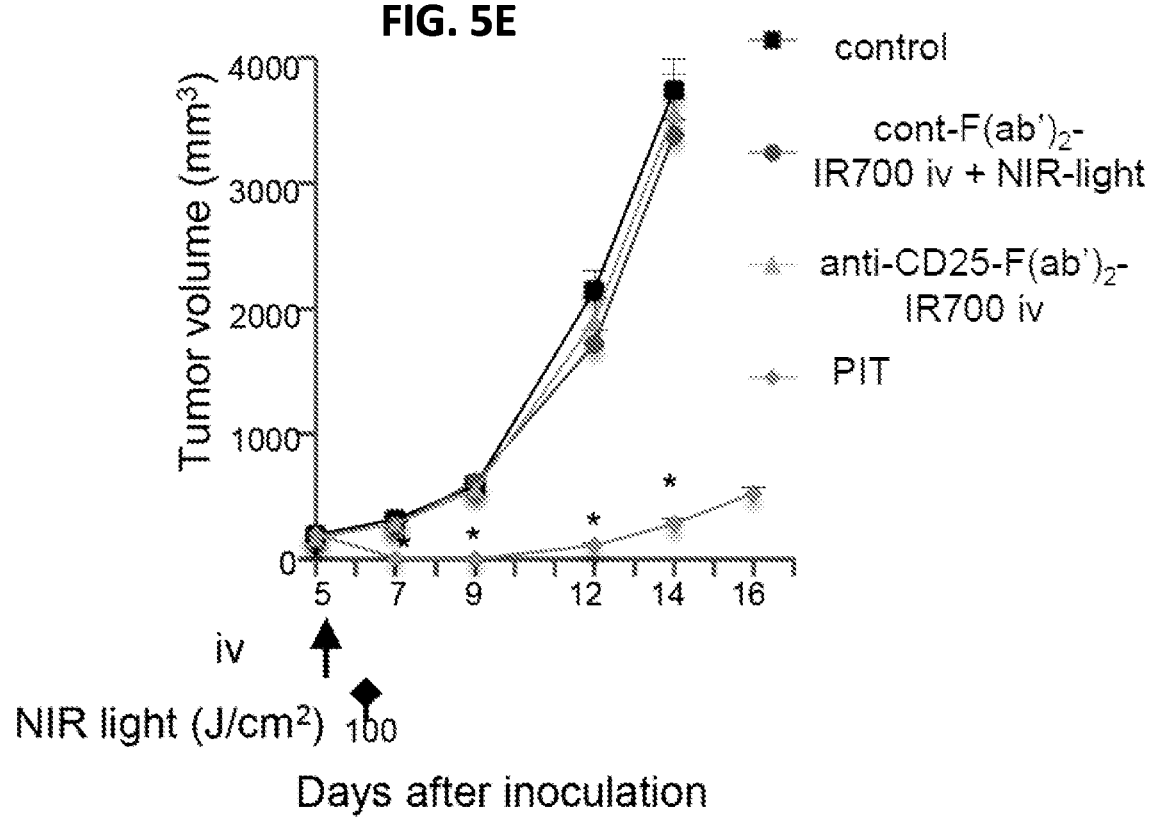
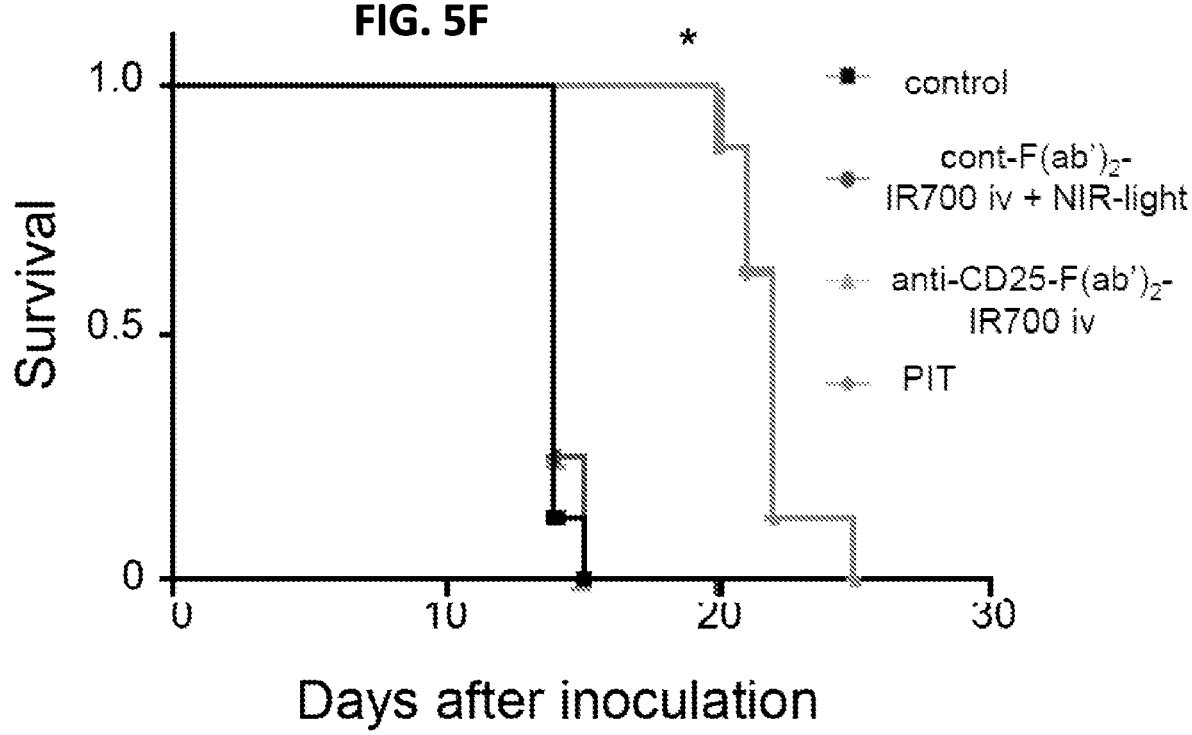

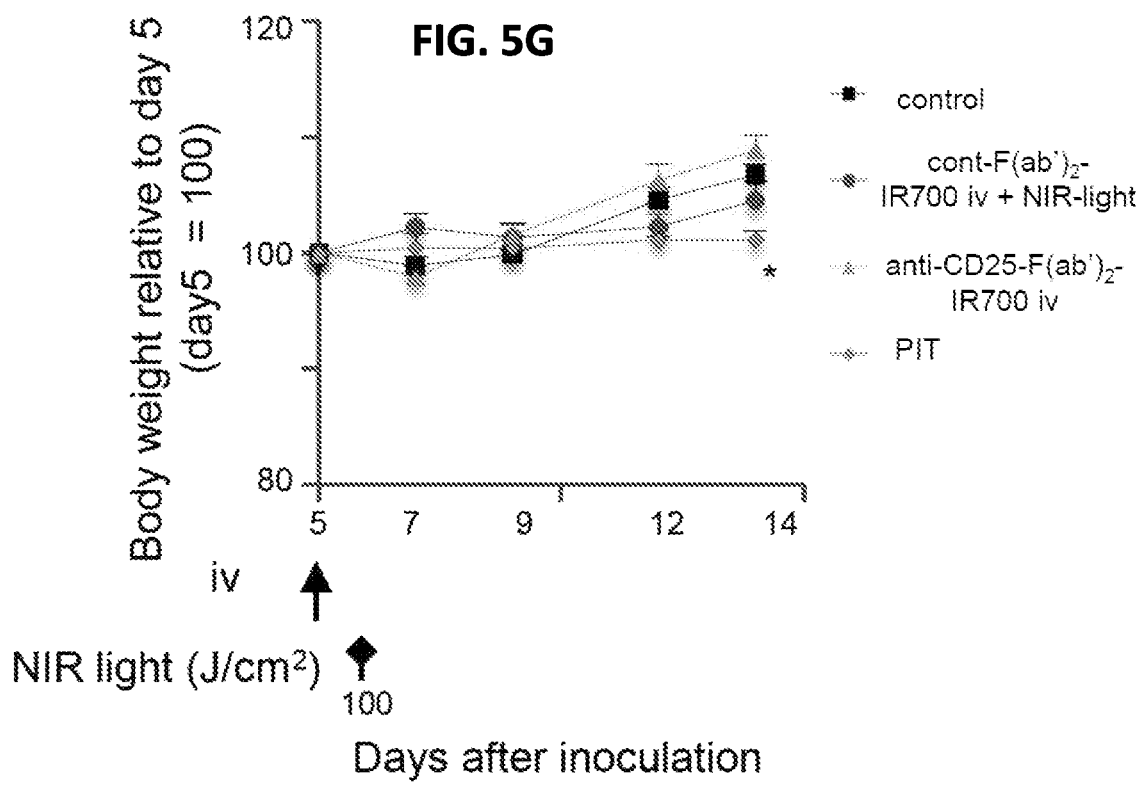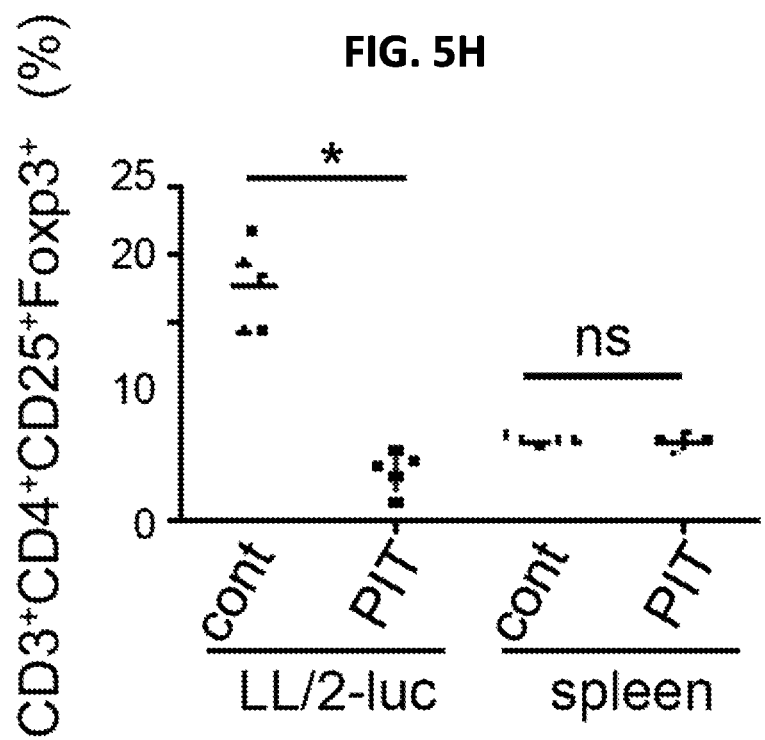

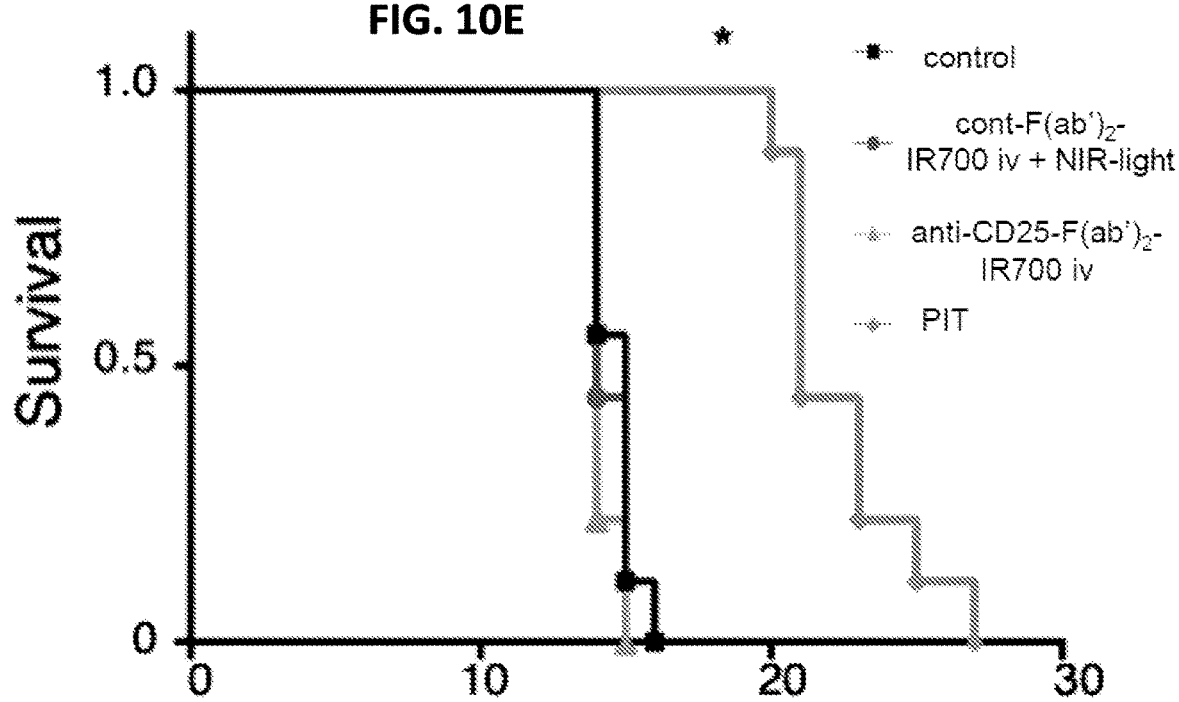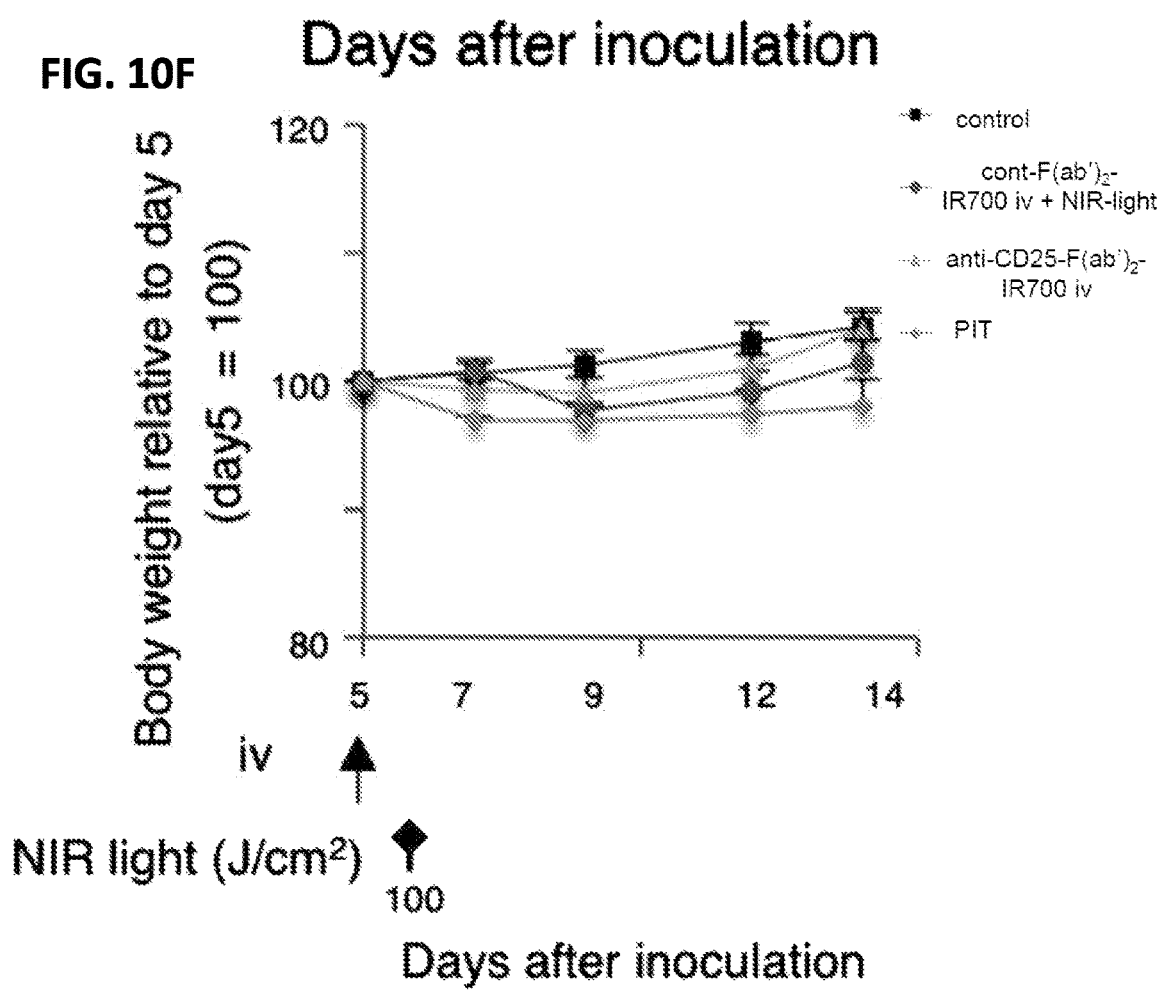

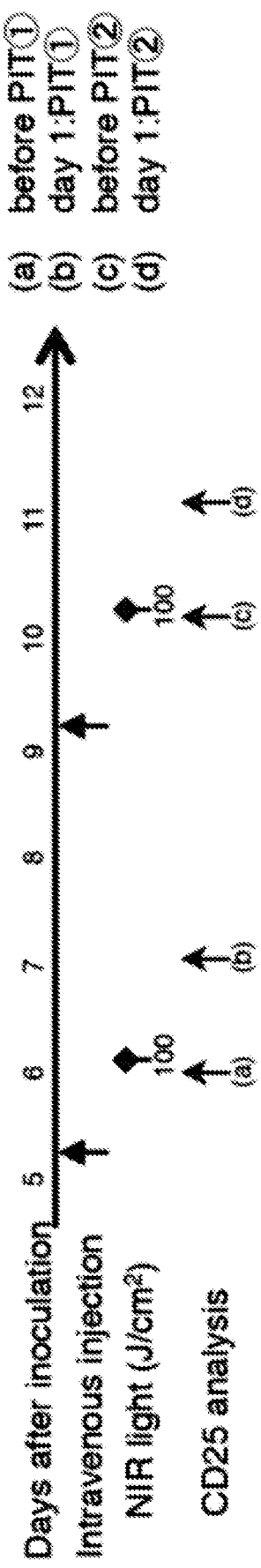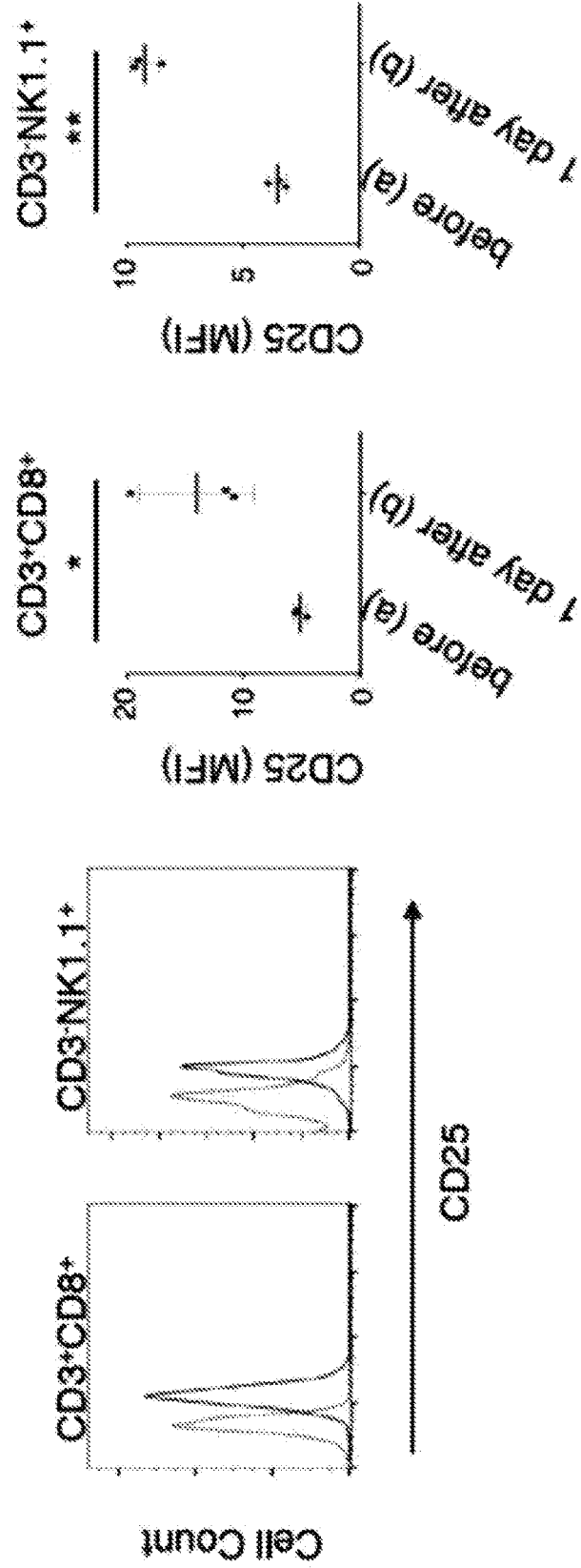
FIG. 14A
FIG. 14B

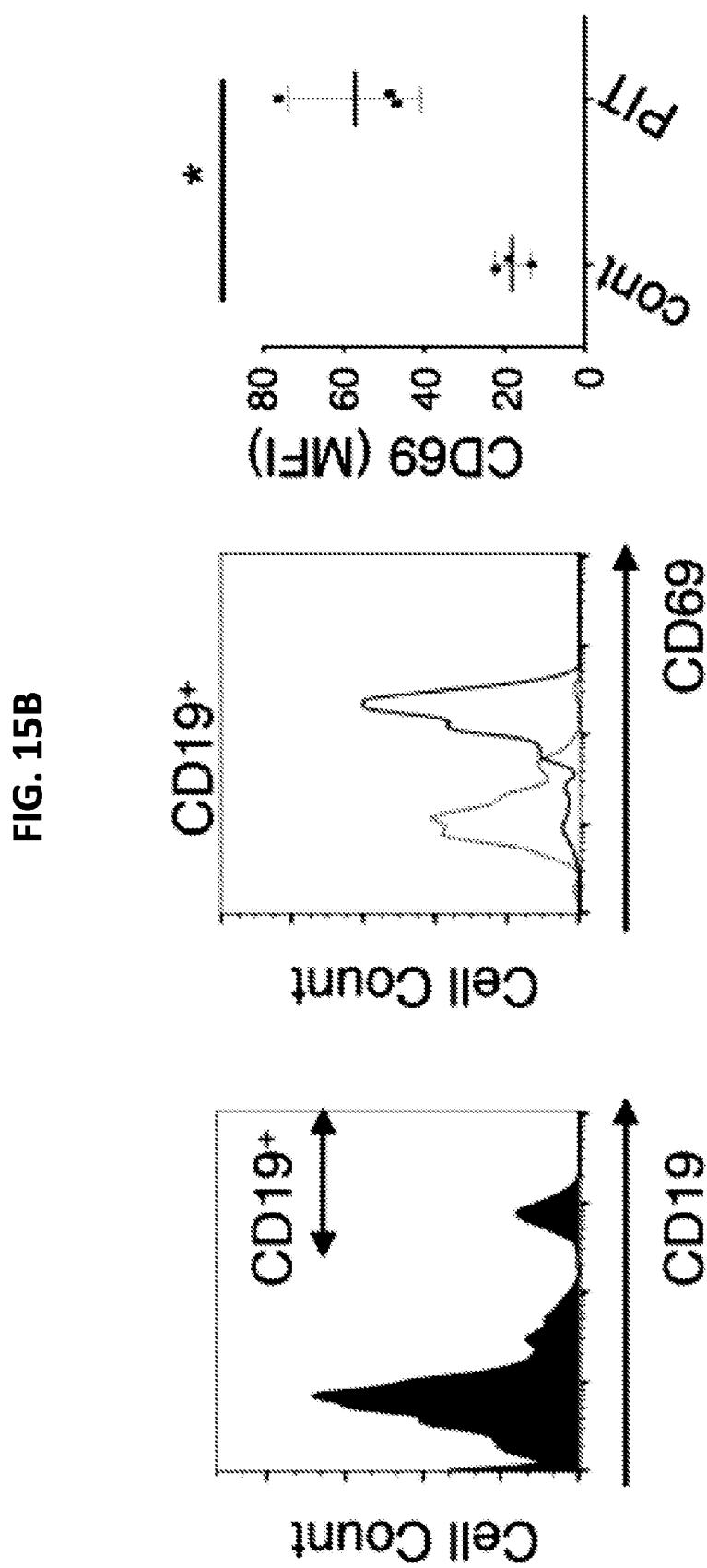

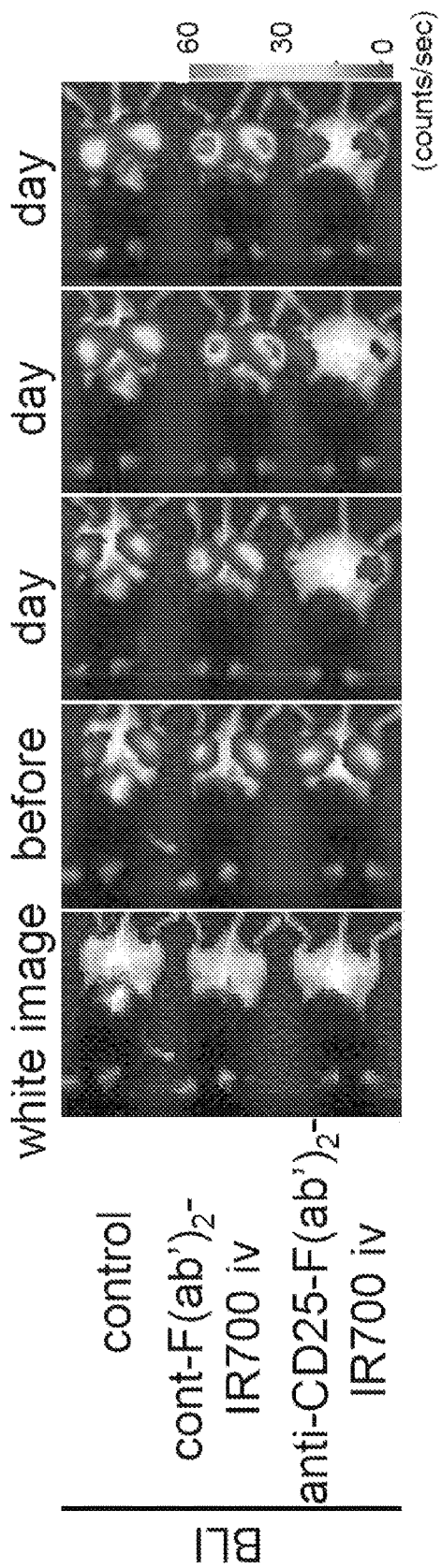
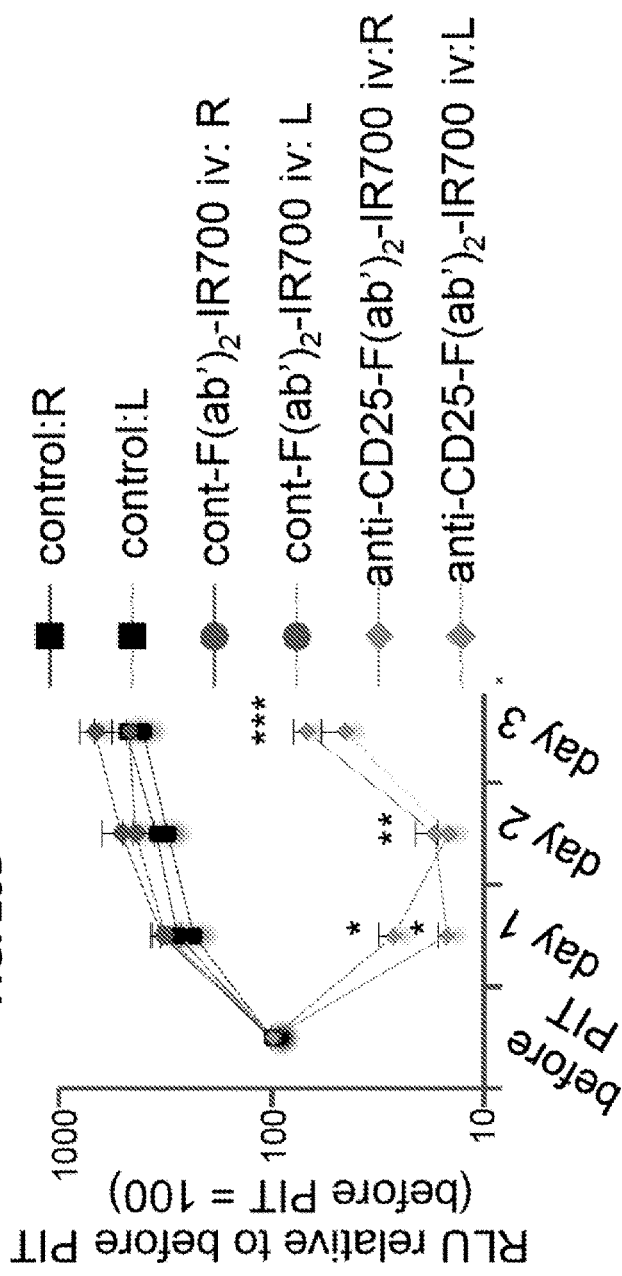
FIG. 20C
FIG. 20D

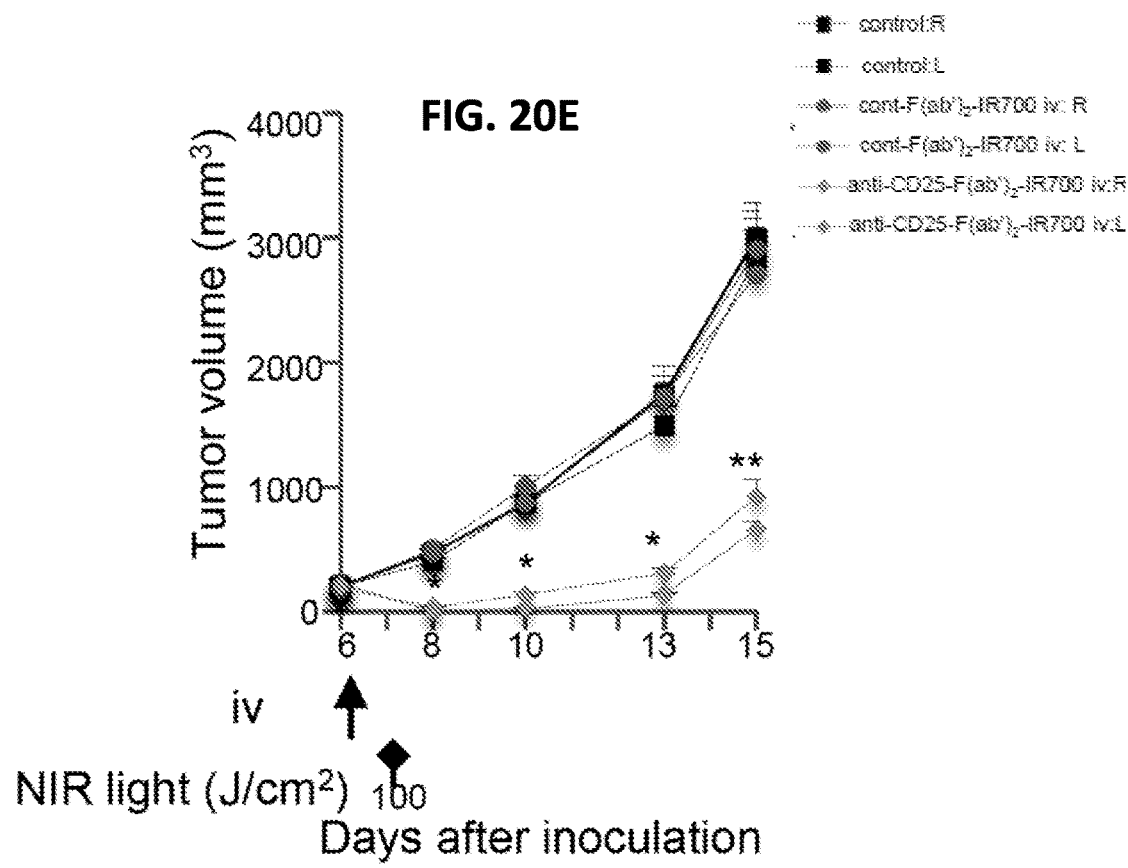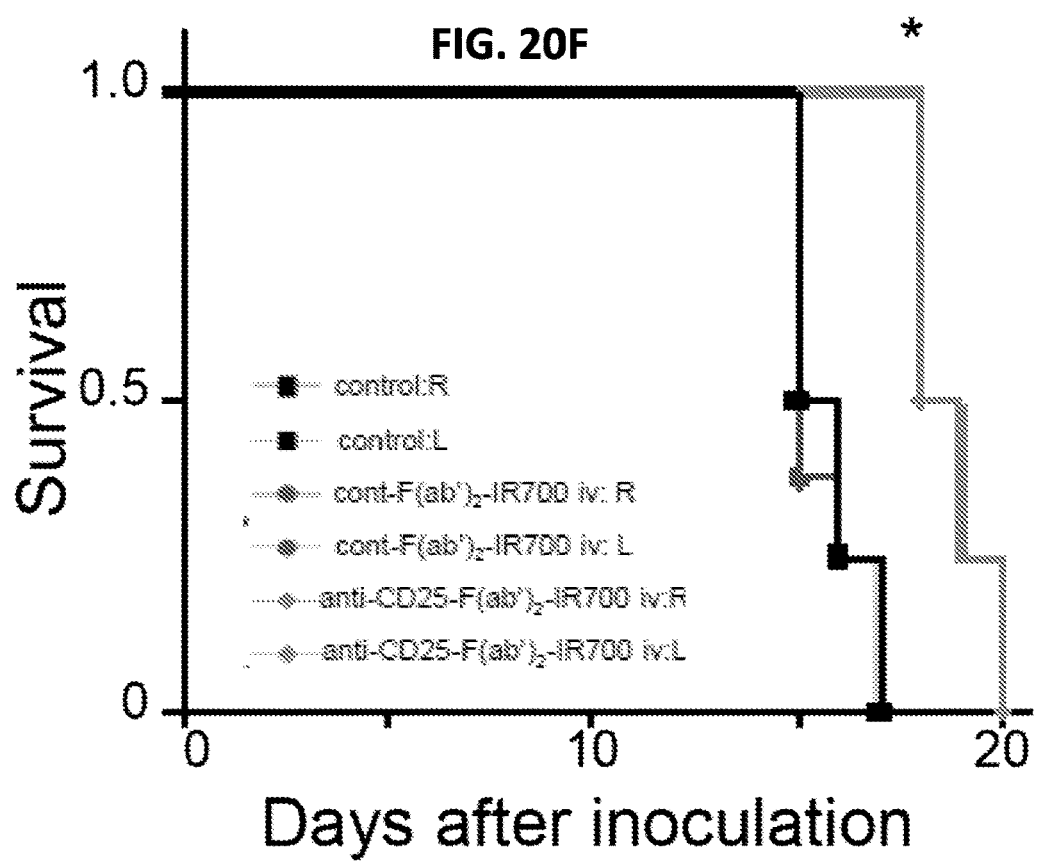

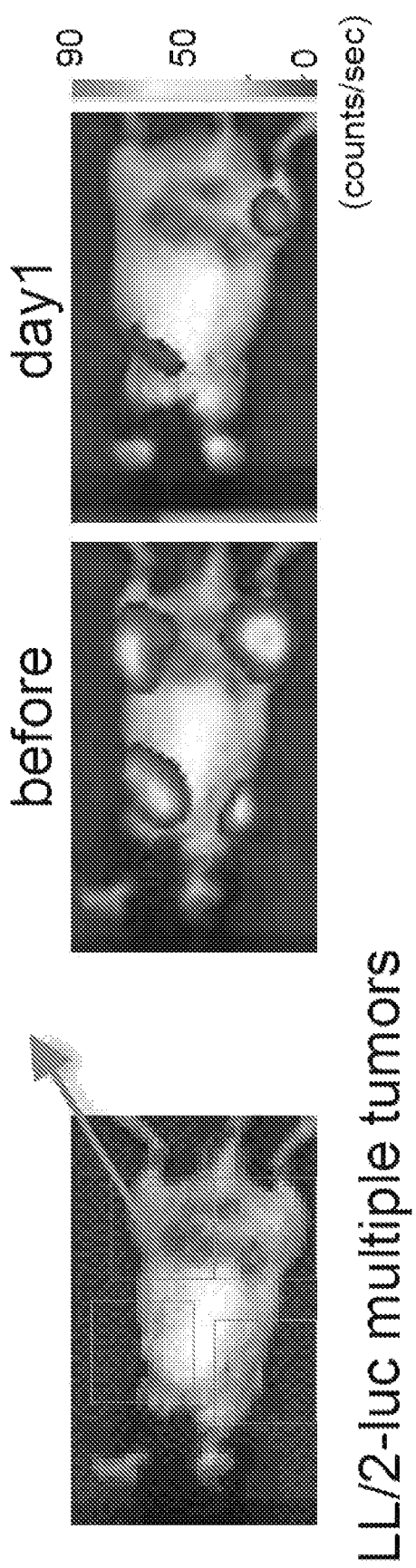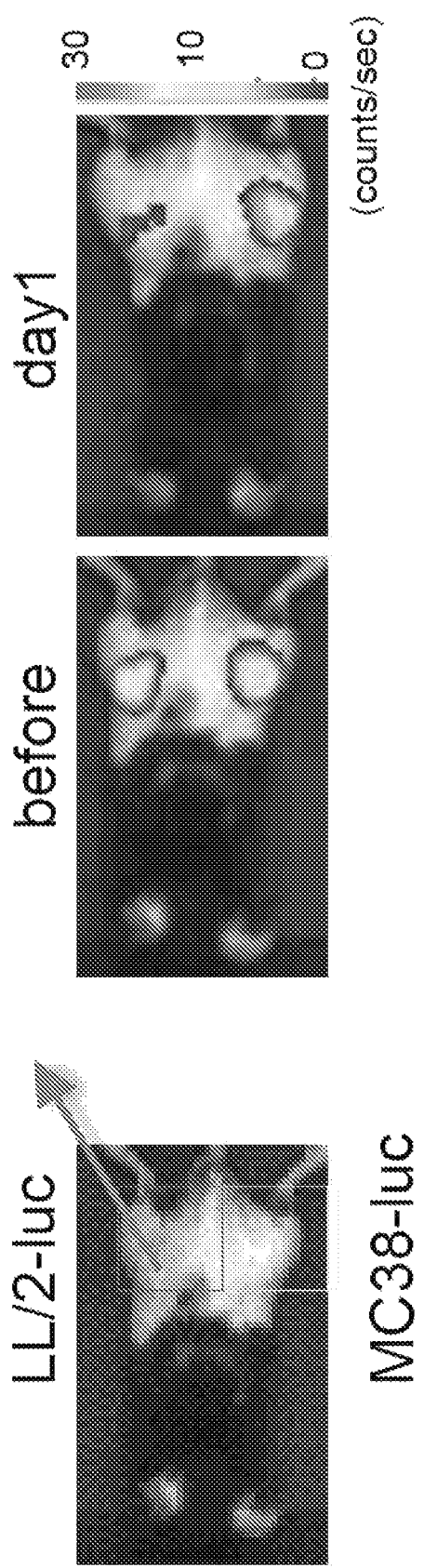

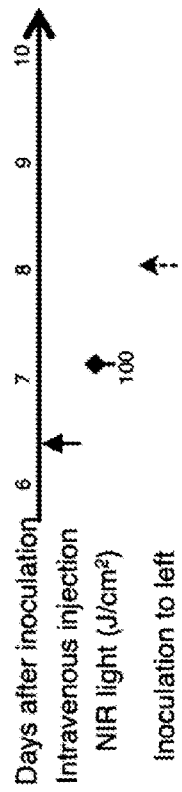
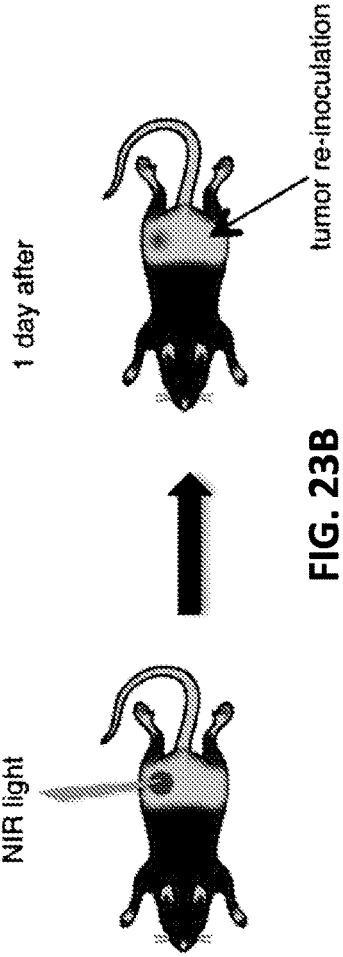
FIG. 23A
FIG. 23B
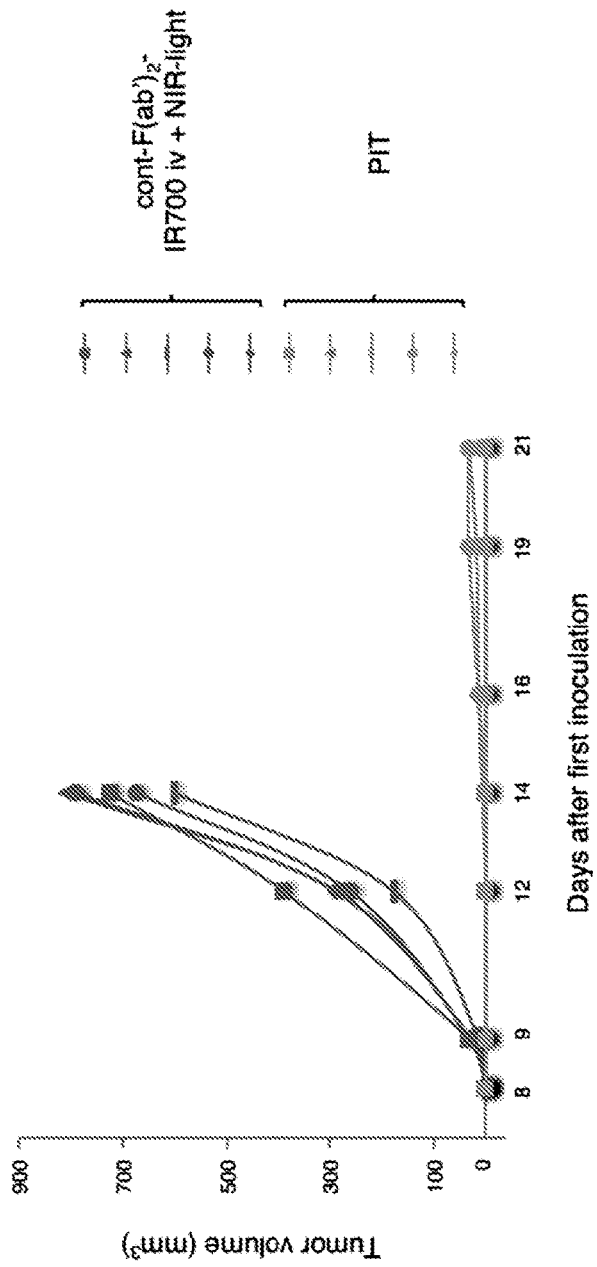

NEAR INFRARED PHOTOIMMUNOTHERAPY (NIR-PIT) OF SUPPRESSOR CELLS TO TREAT CANCER

CROSS-REFERENCE TO RELATED APPLICATION

This is the U.S. National Stage of International Application No. PCT/US2016/045090, filed Aug. 2, 2016, which was published in English under PCT Article 21(2), which in turn claims the benefit of U.S. Provisional Application No. 62/202,252 filed Aug. 7, 2015, both herein incorporated by reference.

ACKNOWLEDGEMENT OF GOVERNMENT SUPPORT

This invention was made with Government support under project number NIH Z01 #: ZIA-BC011513-02 by the National Institutes of Health, National Cancer Institute. The Government has certain rights in the invention.

FIELD

This application relates to antibody-IR700 conjugates, and methods of their use to kill suppressor cells that specifically bind to the antibody following irradiation with near infrared (NIR) light. Also provided are methods of treating cancer by killing suppressor cells using these methods.

BACKGROUND

Cancer immunotherapy, which includes the use of immune modulatory antibodies, cancer vaccines, and cell-based therapies, has become an important strategy in the control of cancer (1-4). These therapies, while minimally invasive, still have room for improvement (5, 6). Recently, improved understanding of the interactions between immune cells and cancer cells have led to the development of immune checkpoint inhibitors which have shown remarkable therapeutic efficacy (7-9). A variety of strategies have been developed to inhibit immunosuppressive regulatory mechanisms, thus enhancing anti-cancer immune responses, however, systemic blockade of these same functions in normal organs have led to life-threatening and, therefore, dose-limiting autoimmune side effects (10-13). A method that selectively and locally suppresses regulatory T cells within tumors, but not systemically, could avoid systemic adverse effects.

Near-infrared photoimmunotherapy (NIR-PIT) is a method of treating cancers that uses activation of an antibody-photoabsorber conjugate activated by near-infrared light to kill cells (14). The antibody binds to the appropriate cell surface antigen and the photo-activatable silica-phthalocyanine dye (IRDye700DX) induces lethal damage to cell membrane after NIR-light exposure. NIR-light exposure (690 nm) induces highly selective, necrotic cancer cell death within minutes without damage to adjoining cells. A phase I human study of NIR-PIT using cetuximab-IR700, targeting tumor EGFR, is currently underway for the treatment of inoperable head and neck cancers. NIR-PIT appears to specifically kill target cells while leaving adjacent normal cells unharmed (15-17).

Within the cancer tissue, T cells and NK cells that recognize cancer cells are often present in large numbers, but their cytotoxic function is suppressed by nearby immune suppressor cells, such as regulatory T cells (Tregs) (21, 22). Thus, controlling tumor infiltrating $CD4^+CD25^+Foxp3^+$ Tregs has been considered an essential step for enhancing anti-cancer immune reactions (23-25). A variety of approaches have been employed to deplete or ablate Tregs but they have met with limited success (22, 26-28). For instance, depletion of Tregs using systemic anti-CD25 antibodies also depletes CD25-expressing anti-tumor effector cells, reducing the therapeutic effectiveness of Tregs depletion (29). In research settings, elimination of Tregs has been achieved with intratumoral injection of anti-CD4 antibodies (30). Alternatively, genetically engineered animal models have been designed to permit transient conditional ablation of Tregs (31-33). However, this method is impossible to translate clinically. Therefore, a practical technique that enables local, selective depletion of tumor-infiltrating Tregs, without depleting other cell types and/or systemic Tregs, is highly desirable.

SUMMARY OF THE DISCLOSURE

The inventors employed CD25-targeted NIR-PIT to selectively deplete $CD4^+CD25^+Foxp3^+$Tregs within the tumor microenvironment to induce activation of anti-tumor effector cells in a syngeneic tumor model. It is shown herein that agents targeting suppressor cells (e.g., $CD4^+CD25^+foxp3^+$ regulatory T cells (Tregs)), such as anti-CD25 antibodies for CD4+CD25+ foxp3+ Tregs without an Fc region (e.g., $F(ab')_2$ fragments), conjugated to a photon absorber, can selectively kill these suppressor cells only after exposure to near infrared light (NIR) both in vitro and in vivo. It is also shown that such treatment can result in rapid and effective tumor killing. Based on these observations, methods of killing suppressor cells, for example to treat a tumor, are provided. Also provided are antibody-IR700 molecules, wherein the antibody specifically binds to a suppressor cells surface protein and in some examples does not include a functional Fc region. Such molecules can be used in the disclosed methods.

Provided herein are methods of killing suppressor cells. In particular examples, the methods are specific in that non-target cells, such as non suppressor cells, are not killed in significant numbers (such as less than 1% or less than 0.1% of non suppressor cells are killed), but the target suppressor cells are. However, in some examples, not all of the suppressor cells are killed in vivo, as such could lead to development of autoimmunity. Thus, in some examples, the method reduces the number of suppressor cells targeted by the antibody-IR700 molecule in an area of subject, such as in the area of a tumor or an area that used to have a tumor, by at least 50%, at least 60%, at least 75%, at least 80%, at least 90%, or at least 95%. In some examples, the method reduces the total number of suppressor cells targeted by the antibody-IR700 molecule in a subject by at least 50%, at least 60%, at least 75%, at least 80%, at least 90%, or at least 95%.

In some examples, the methods include contacting a suppressor cell that expresses a suppressor cell surface protein with a therapeutically effective amount of one or more antibody-IR700 molecules, wherein the antibody specifically binds to the suppressor cells surface protein (such as CD25, CD4, C-X-C chemokine receptor type 4 (CXCR4), C-C chemokine receptor type 4 (CCR4), cytotoxic T-lymphocyte-associated protein 4 (CTLA4), glucocorticoid induced TNF receptor (GITR), OX40, folate receptor 4 (FR4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), interleukin-1 decoy receptor, CD103, fibroblast activation protein (FAP), CXCR2, CD33, and CD66b) and in some examples does not include a functional Fc region (e.g., consists of one or more F(ab')$_2$ fragments). The presence of a functional Fc portion can result in autoimmune toxicity (such as antibody-dependent cell-mediated cytotoxicity (ADCC)). The result of ADCC is that too many suppressor cells may be killed, instead of only those suppressor cells exposed to the NIR light. Thus, the Fc portion of the antibody can be mutated or removed to substantially decrease its function (such as a reduction of at least 50%, at least 75% at least 80%, at least 90%, at least 95%, at least 99%, or 100% of the Fc function as compared to a non-mutated Fc region, such as an ability to bind to the Fcγ receptor).

The suppressor cell surface protein is one that is at least partially or entirely on the cell surface of the suppressor cell, such that it can be bound by an appropriate specific antibody (or fragment thereof). For example, the suppressor cell surface protein can be a transmembrane protein, wherein the extracellular domain can be bound by the antibody (or fragment thereof) of the antibody-IR700 molecule. In some examples, the protein(s) on the suppressor cell surface is not significantly found on other cells (such as non-T cells) and thus the antibody will not significantly bind to the non-target cells. Examples of such suppressor cell surface proteins that can be targeted include but are not limited to, CD25, CD4, C-X-C chemokine receptor type 4 (CXCR4), C-C chemokine receptor type 4 (CCR4), GITR, OX40, folate receptor 4 (FR4), cytotoxic T-lymphocyte-associated protein 4 (CTLA4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), interleukin-1 decoy receptor, CD103, fibroblast activation protein (FAP), CXCR2, CD33, and CD66b. For example, the suppressor cells and the one or more antibody-IR700 molecules can be incubated under conditions that allow the one or more antibody-IR700 molecules to bind to the suppressor cell surface protein(s). The suppressor cells are then irradiated at a wavelength of 660 to 740 nm, such as 660 to 710 nm (for example, 680 nm or 690 nm) at a dose of at least 1 J cm$^{-2}$ (such as at least 2, at least 3, at least 4, at least 5, at least 6, at least 7, at least 8, at least 9, at least 10, at least 20, at least 30, at least 40, at least 50, at least 75, or at least 100 J cm$^{-2}$) thereby killing the suppressor cells exposed to the NIR light. Examples of suppressor cells that can be targeted with this method include, but are not limited to: CD4$^+$CD25$^+$Foxp3$^+$ Tregs, type II natural killer T cells (type II NKT cells), CD8$^+$CD122$^+$ Tregs, M2 macrophages, tumor infiltrating fibroblasts, myeloid-derived suppressor cells, as well as combinations thereof (e.g., by using multiple antibody-IR700 molecules, each specific for a particular type of suppressor cell). In some examples, the method kills at least a portion of 1, 2, 3, 4, 5, or all 6 of these types of suppressor cells.

Such methods can be performed in vitro, for example by incubating a culture of suppressor cells with the one or more antibody-IR700 molecules and then irradiating the cells at a wavelength of 660 to 740 nm at a dose of at least 1 J cm$^{-2}$, thereby killing the suppressor cells. In another example, the suppressor cells are present in a subject, and contacting the suppressor cells with the one or more antibody-IR700 molecules includes administering a therapeutically effective amount of the one or more antibody-IR700 molecules to the subject (e.g., by injection). The subject (e.g., a tumor in the subject or another part of the subject) is then irradiated at a wavelength of 660 to 740 nm at a dose of at least 4 J cm$^{-2}$, thereby killing the suppressor cells in the subject that were exposed to the NIR light. For example, the method can include irradiating suppressor cells by using a device worn by the subject, wherein the device includes a NIR light emitting diode (LED), thereby killing suppressor cells having bound thereto the antibody-IR700 molecules and which are exposed to the NIR light.

The disclosed methods in some examples can be used to treat a tumor, such as a cancer, in vitro or in vivo. Subjects treated with the disclosed therapies can receive other treatment, such as additional anti-neoplastic therapy. For example, the method can reduce the volume of a tumor, the size of a tumor, the weight of a tumor, the number of metastases, or combinations thereof by at least 20%, at least 25%, at least 30%, at least 40%, at least 50%, at least 75%, at least 90%, or at least 95%, relative to the absence of treatment. In some examples, the methods increases survival time of the subject relative to an absence of administration of the antibody-IR700 molecule and irradiation. In some examples the method can reduce the volume of a metastasis, the size of a metastasis, the weight of a metastasis, the number of metastases, or combinations thereof by at least 20%, at least 25%, at least 30%, at least 40%, at least 50%, at least 75%, at least 90%, or at least 95%, even when the metastasis itself is not irradiated with the NIR light (but instead only the primary tumor is irradiated with NIR light), for example as compared to the volume of a metastasis, the size of a metastasis, the weight of a metastasis, or the number of metastases, prior to treatment with the disclosed methods.

Also provided are antibody-IR700 molecules, wherein the antibody specifically binds to a suppressor cell surface protein, and in some examples does not include a functional Fc region. For example, the suppressor cell surface protein can be CD25, CD4, C-X-C chemokine receptor type 4 (CXCR4), C-C chemokine receptor type 4 (CCR4), cytotoxic T-lymphocyte-associated protein 4 (CTLA4), GITR, OX40, folate receptor 4 (FR4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), CD103, interleukin-1 decoy receptor, fibroblast activation protein (FAP), CXCR2, CD33, and CD66b. In some examples, the antibody is one or more Fab or F(ab')$_2$ fragments. In one example, the antibody is specific for CD103. In some examples, the ratio of antibody to IR700 is about 1:3.

The foregoing and other features of the disclosure will become more apparent from the following detailed description of a several embodiments which proceeds with reference to the accompanying figures.

BRIEF DESCRIPTION OF THE FIGURES

FIG. 1 is an image schematically showing how anti-CD25-F(ab')$_2$ antibody fragments were generated.

FIGS. 2A-2C are images showing in vitro targeting of CD25 using anti-CD25-F(ab')$_2$-IR700. (A) SDS-PAGE analysis of anti-CD25-F(ab')$_2$ and control-F(ab')$_2$ digested from control IgG and their IR700 conjugates. Both anti-CD25-F(ab')$_2$-IR700 and control-F(ab')$_2$-IR700 bands showed similar IR700-fluorescence, which was confirmed by (B) quantitation of fluorescence intensity (n=3)(*ns, Mann-Whitney test). (C) Flow cytometry analysis of binding of anti-CD25-F(ab')2-IR700 to HT-2 A5E cells expressing CD25.

FIGS. 5A-5I show in vivo local CD25-targeted-NIR-PIT induces regression of treated LL/2-luc tumors. (A) An increased CD4$^+$CD25$^+$Foxp3$^+$Tregs population in CD4 T cells was observed in the tumors (LL/2-luc or MC38-luc) compared to that in the spleen (n=3) (*p<0.001, **p<0.001, vs control, one way ANOVA with Dunnet test). (B) The regimen of a local NIR-PIT is shown. (C) In vivo BLI are shown for the tumor bearing mice that were untreated, received a control-F(ab')$_2$-IR700 administration followed by a NIR-PIT, administered with CD25-F(ab')$_2$-IR700 alone, or treated with local CD25-targeted-NIR-PIT. Prior to NIR-PIT, tumors sizes were equivalent, exhibiting similar bioluminescence, but only the CD25-targeted-NIR-PIT showed decrease in BLI. (D) Quantitative RLU showed a significant RLU decrease in the experimental tumors (n=6 mice in each group)(*p=0.0217 (day 1), 0.0243 (day 2)<0.05, PIT vs. control, Tukey's test with ANOVA). (E) Local CD25-targeted-NIR-PIT led to reductions in tumor volume (n=8 mice in each group, *p<0.0001, PIT vs. others, Tukey's test with ANOVA). Treatment schedule indicated below the graph corresponds to that in (B). (F) Local CD25-targeted-NIR-PIT led to prolonged survival of the mice (n=8 mice in each group)(*p<0.0001, PIT vs control, Log-rank test and Wilcoxon test). (G) The body weight of mice not receiving CD25-targeted-NIR-PIT gradually increased due to the tumor growth, contrasting to the PIT group showing significantly lower body weight at day 14 (n=8 mice in each group) (*p=0.0128<0.05, PIT vs control at day 14). (H) A Local CD25-targeted-NIR-PIT resulted in a depletion of intratumoral CD4$^+$CD25$^+$Foxp3$^+$Tregs, but not in the spleen (n=5) (*p<0.01, ns: not significant, Mann-Whitney test). (I) A Local CD25-targeted-NIR-PIT did not significantly affect the number of CD8 T cells (CD3+CD8+) or NK cells (CD3$^-$NK1.1$^+$) (n=5)(ns: not significant, Mann-Whitney test).

FIGS. 10A-10H show local CD25-targeted-NIR-PIT at a MC38-luc tumor induces regression of the tumor. (A) The regimen of local NIR-PIT is shown. (B) In vivo BLI are shown for the tumor bearing mice that were untreated, received a control-F(ab')2-IR700 administration followed by NIR-PIT, administered with CD25-F(ab')2-IR700 alone, or treated with local CD25-targeted-NIR-PIT. Only the CD25-targeted-NIR-PIT resulted in a decrease of the signals. (C) Quantitative RLU showed a significant decrease in signal in the NIR-PIT-treated tumors (n=7 mice in each group) (*p<0.0005, p<0.005, *p=0.0268 (vs. control), 0.0236 (vs. control-F(ab')2-IR700+NIR-light), 0.0056 (vs. anti-CD25-F(ab')2-IR700 iv)<0.05, Tukey's test with ANOVA). (D) Local CD25-targeted-NIR-PIT led to reductions in tumor volume (n=9 mice in each group)(*p<0.0001, PIT vs. others, Tukey's test with ANOVA) and (E) led to prolonged survival of the mice (n=9 mice in each group)(*p<0.0001, PIT vs. control, Long-rank test and Wilcoxon test). (F) The groups of mice did not show significant difference in the body weight changes during the course of the treatments (n=9 mice in each group). (G) Local CD25-targeted-NIR-PIT of the tumor resulted in the depletion of CD4+CD25+ Foxp3+Tregs in CD4 population (n=5)(*p<0.01, ns: not significant, Mann-Whitney test) without affecting the Tregs in the spleen. (H) The CD25-targeted-NIR-PIT did not significantly affect the number of CD8 T cells (CD3+CD8+) nor NK cells (CD3-NK1.1+) in the tumor (n=5)(ns: not significant, Mann-Whitney test).

FIGS. 14A-14C show that repeated local CD25-targeted-NIR-PIT induces up-regulation of CD25 expression on CD8 T and NK cells at each treatment. (A) The regimen of analysis of CD25 expression in repeated local NIR-PIT is shown. (B) MFI (geometric mean fluorescence intensity) of CD25 expression was increased after the first local CD25-targeted-NIR-PIT (n=3)(*p=0.0376<0.05, p<0.0005, unpaired t-test). (C) Four days after the first NIR-PIT, the levels of CD25 expression returned to the pre-treatment level. The second local NIR-PIT induced activation and up-regulation of CD25 expression on CD8 T and NK cells again (n=3)(*p<0.001, ****p<0.005, unpaired t test).

FIGS. 15A-15D show that local CD25-targeted-NIR-PIT induces activation of tumor-infiltrating dendritic cells and other antigen presenting cells. Flow cytometry of tumor infiltrating immune cells indicated that CD25-targeted-NIR-PIT induced activation of tumor-infiltrating (A) dendritic cells (CD11c+), (B) B cells (CD19+), (C) monocyte (CD11b+Ly6Chigh), and (D) macrophages (CD11b+Ly6Clow-int) at 1 day after the treatment (n=3) (*p=0.0104<0.05, unpaired t test). The population of the analysis was indicated in the left side panel.

FIGS. 20A-20K show that the therapeutic effects of local CD25-targeted-NIR-PIT extend to distant non-irradiated tumors. (A) The regimen of NIR-PIT is shown. (B) Mice with bilateral flank tumors were either not injected (control) or injected with control-F(ab')$_2$-IR700 or anti-CD25 F(ab')$_2$-IR700 followed by NIR-light irradiation of only the right tumor. (C) In vivo BLI showed changes in bioluminescence signals in the tumor in response to local CD25-targeted-NIR-PIT only. Prior to NIR-PIT, tumors were approximately the same size and exhibited similar bioluminescence. (D) Quantitative RLU showed a significant decrease in signal in NIR-PIT-treated right side tumors and even in non-irradiated left side tumors (n=6 mice in each group) (*p<0.001, p<0.01, *p=0.0197 (PIT:R), =0.0142 (PIT:L)<0.05, PIT vs. cont-F(ab')$_2$-IR700 iv:R, Tukey's test with ANOVA). (E) Local CD25-targeted-NIR-PIT led to size reductions of NIR-PIT-treated right tumors as well as non-irradiated left tumors (n=8 mice in each group)(*p<0.0001, **p<0.0005, PIT vs. others, Tukey's test with ANOVA). Time of treatments is indicated below the graph. (F) Local CD25-targeted-NIR-PIT led to prolonged survival of the mice (n=8 mice in each group)(*p<0.0001, PIT vs. control, Long-rank test and Wilcoxon test). (G) Body weight changes of tumor bearing mice were followed. After NIR-PIT, both right and left dorsa became edematous and mice gained weight (n=8 mice in each group) (*p<0.001, PIT vs. others, Tukey's test with ANOVA), which started to disappear by day 10. (H) Local CD25-targeted-NIR-PIT on the right dorsal tumor caused edema bilaterally (arrow). (I) The NIR-PIT depleted CD4$^+$CD25$^+$Foxp3$^+$Tregs within the irradiated tumor on the right dorsum, but not Tregs in the left non-irradiated tumors. Mice not injected (control) or injected with control-F(ab')$_2$-IR700 showed no significant difference in Tregs population between the right and left tumors (n=5 in each group) (*p<0.0001, Tukey's test with ANOVA). (J) Local CD25-targeted-NIR-PIT on the right dorsal LL/2-luc tumor caused regression of other multiple LL/2-luc tumors at 1 day after the treatment. (K) Local CD25-targeted NIR-PIT on right dorsal LL/2-luc tumor had negligible anti-tumor effects on the left dorsal MC38-luc tumor at 1 day after PIT.

FIGS. 23A-23B show that local CD25-targeted-NIR-PIT inhibits the growth of tumor challenged on the contralateral side. (A) The regimen of tumor challenge at 1 day after CD25-targeted-NIR-PIT is shown. The schematic representation is also indicated. (B) LL/2-luc tumor inoculated on the contralateral side 1 day after local CD25-targeted-NIR-PIT of the same kind tumor was inhibited compared to the tumor inoculated to the control mice receiving control-F(ab')2-IR700 administration with NIR-light irradiation (n=5).

DETAILED DESCRIPTION OF SEVERAL EMBODIMENTS

Figure 2A:
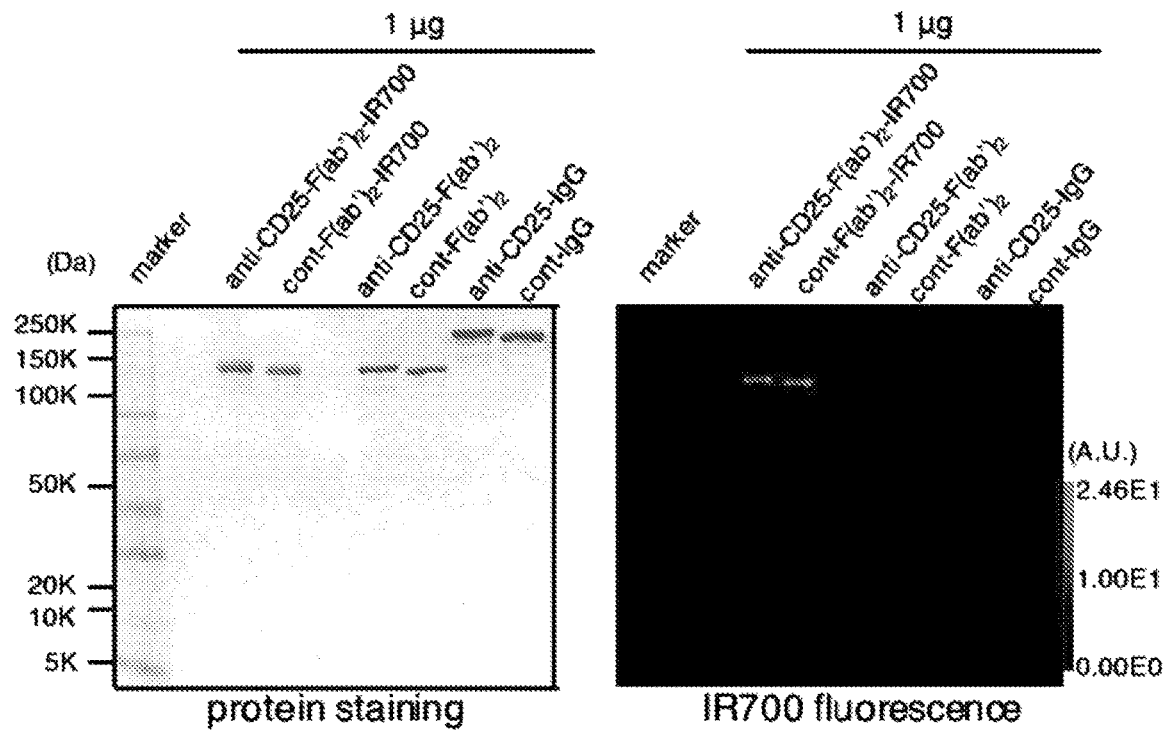

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used, such as those in for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual,* Cold Spring Harbor Laboratory Press, 1990; and Harlow and Lane, *Using Antibodies: A Laboratory Manual,* Cold Spring Harbor Laboratory Press, 1999.

All references, including patents and patent applications, are herein incorporated by reference. In addition, the sequences associated with all GenBank® Accession numbers referenced herein are incorporated by reference for the sequence available on Aug. 7, 2015.

In order to facilitate review of the various embodiments of the disclosure, the following explanations of specific terms are provided:

Administration: To provide or give a subject an agent, such as an antibody-IR700 molecule, by any effective route. Exemplary routes of administration include, but are not limited to, topical, injection (such as subcutaneous, intramuscular, intradermal, intraperitoneal, intratumoral, and intravenous), oral, ocular, sublingual, rectal, transdermal, intranasal, vaginal and inhalation routes.

Antibody: A polypeptide ligand comprising at least a light chain or heavy chain immunoglobulin variable region which specifically recognizes and binds an epitope of an antigen, such as a tumor-specific protein. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include portions of antibodies, such as those not having an Fc region, such as Fab fragments, Fab' fragments, F(ab')$_2$ fragments, CH2 deleted Ab, single domain V-region Ab, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

In some examples, antibodies include immunoglobulins that have an Fc region that is mutated or even deleted to substantially decrease the function of the Fc region. In some examples, the mutation decreases the function of the Fc region, such as an ability to bind to Fcγ receptor, by at least 50%, at least 75%, at least 80%, at least 90%, at least 95%, at least 99%, or 100% as compared to the function of the Fc region without the mutation.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

"Specifically binds" refers to the ability of individual antibodies to specifically immunoreact with an antigen, such as a suppressor cell surface antigen, relative to binding to unrelated proteins, such as non-suppressor cell proteins, for example albumin. For example, a CD25-specific binding agent binds substantially only the CD25 protein in vitro or in vivo. As used herein, the term "suppressor cell surface-specific binding agent" includes suppressor cell surface-specific antibodies and other agents that bind substantially only to a suppressor cell surface protein in that preparation.

The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody".

In some examples, an antibody or fragment thereof (such as an antibody-IR700 molecule) specifically binds to a target (such as a suppressor cell surface protein) with a binding constant that is at least $10^3$ $M^{-1}$ greater, $10^4$ $M^{-1}$ greater or $10^5$ $M^{-1}$ greater than a binding constant for other molecules in a sample or subject. In some examples, an antibody (e.g., monoclonal antibody) or fragments thereof, has an equilibrium constant (Kd) of 1 nM or less. For example, an antibody or fragment thereof binds to a target, such as suppressor cell surface protein with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Antibody-dependent cell-mediated cytotoxicity (ADCC): A mechanism of cell-mediated immune defense whereby an effector cell of the immune system actively lyses a target cell, whose membrane-surface antigens have been bound by specific antibodies. ADCC can be mediated by natural killer (NK) cells, monocytes/macrophages, neutrophils and eosinophils. The ability of an antibody to recruit the killing machinery of the cellular immune system is dependent on the interaction between the antibody Fc domain and Fc receptors found on cells such as macrophages and natural killer cells.

Antibody-IR700 molecule or antibody-IR700 conjugate: A molecule that includes both an antibody, such as a suppressor cell surface antibody, conjugated to IR700. In some examples the antibody does not have a functional Fc region (e.g., only has Fab region(s) or a mutated Fc region). In some examples the antibody is a humanized antibody (such as a humanized monoclonal antibody) that specifically binds to a surface protein on a suppressor cell and in some examples does not have a functional Fc region (e.g., only has Fab region(s) or a mutated Fc region).

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Contacting: Placement in direct physical association, including both a solid and liquid form. Contacting can occur in vitro, for example, by adding a reagent to isolated cells, such as suppressor cell, or in vivo by administering to a subject (such as a subject with a tumor).

Decrease: To reduce the quality, amount, or strength of something. In one example, a therapeutic composition that includes one or more antibody-IR700 molecules decreases the viability of cells to which the antibody-IR700 molecule specifically binds, following irradiation of the cells with NIR light (for example at a wavelength of 690 nm+/−20 nm, such as about 680 nm) at a dose of at least 1 or at least 4 J/cm², for example as compared to the response in the absence of the antibody-IR700 molecule. In some examples such a decrease is evidenced by the killing of the cells. In some examples, the decrease in the viability of cells is at least 20%, at least 50%, at least 75%, at least 80%, at least 85%, at least 90%, at least 95%, or even at least 99%, relative to the viability observed with a composition that does not include an antibody-IR700 molecule or includes the antibody-IR700 molecule but is not exposed to NIR light. In other examples, decreases are expressed as a fold change, such as a decrease in the cell viability by at least 2-fold, at least 3-fold, at least 4-fold, at least 5-fold, at least 8-fold, at least 10-fold, or even at least 15 or 20-fold, relative to the viability observed with a composition that does not include an antibody-IR700 molecule or includes the antibody-IR700 molecule but is not exposed to NIR light. Such decreases can be measured using the methods disclosed herein.

Fragment, antigen-binding (Fab) region (of an antibody): The "top" of the "Y" of an antibody, which binds to antigen. It is composed of one constant and one variable domain of each of the heavy and the light chain. The enzyme papain can be used to cleave an immunoglobulin monomer into two Fab fragments and an Fc fragment. The enzyme pepsin or ficin cleaves below hinge region, generating an F(ab')2 fragment and a pFc' fragment. In another example, the enzyme IdeS (immunoglobulin degrading enzyme from *Streptococcus pyogenes*, trade name FabRICATOR) cleaves IgG in a sequence specific manner at neutral pH, resulting in an F(ab')2 fragment, which can be split into two Fab' fragments by mild reduction. Other methods of generating F(ab')2 fragments from an intact antibody are disclosed in Example 1.

Fragment, crystallizable (Fc) region (of an antibody): The base of the "Y" of an antibody, which plays a role in modulating immune cell activity. This region is composed of two heavy chains that contribute two or three constant domains depending on the class of the antibody. Since only the constant domains of the heavy chains make up the Fc region of an antibody, the classes of heavy chain in antibodies determine their class effects. Classes of heavy chains in antibodies include alpha, gamma, delta, epsilon, and mu, and they define the antibody's isotypes IgA, G, D, E, and M, respectively. The Fc region ensures that each antibody generates an appropriate immune response for a given antigen, by binding to a specific class of Fc receptors, and other immune molecules, such as complement proteins. By doing this, it mediates different physiological effects including recognition of opsonized particles (binding to FcγR), lysis of cells (binding to complement), and degranulation of mast cells, basophils, and eosinophils (binding to FcεR).

IR700 (IRDye® 700DX): A phthalocyanine dye having the following formula

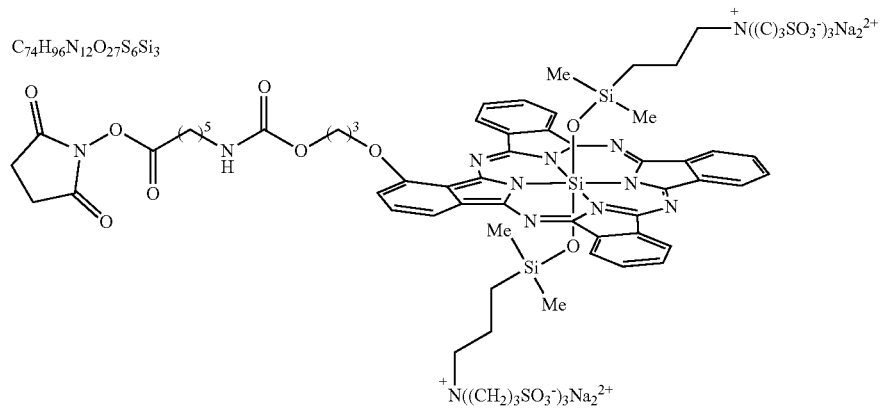

Also includes derivatives of such molecules, including the ester shown below

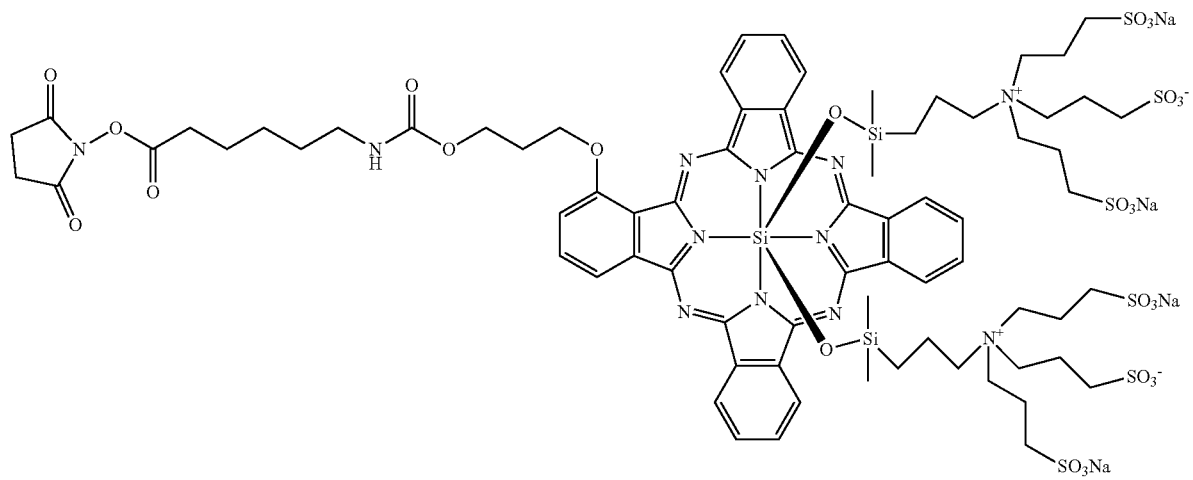

C$_{74}$H$_{96}$N$_{12}$Na$_4$O$_{27}$S$_6$Si$_3$
Exact Mass: 1952.37306
Mol. Wt: 1954.22
IRDye 700DX NHS Ester Commercially available from LI-COR (Lincoln, Nebr.) Amino-reactive IR700 is a relatively hydrophilic dye and can be covalently conjugated with an antibody or antibody fragment, for example using the NHS ester of IR700.

Pharmaceutical composition: A chemical compound or composition capable of inducing a desired therapeutic or prophylactic effect when properly administered to a subject. A pharmaceutical composition can include a therapeutic agent, such as one or more antibody-IR700 molecules. A therapeutic or pharmaceutical agent is one that alone or together with an additional compound induces the desired response (such as inducing a therapeutic or prophylactic effect when administered to a subject). In a particular example, a pharmaceutical composition includes a therapeutically effective amount of at least one antibody-IR700 molecule.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 19th Edition (1995), describes compositions and formulations suitable for pharmaceutical delivery of one or more therapeutic compounds, such as one or more antibody-IR700 molecules.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Photoimmunotherapy (PIT): A molecular targeted therapeutic that utilizes a target-specific photosensitizer based on a near infrared (NIR) phthalocyanine dye, IR700, conjugated to one or more antibodies (or other specific binding agent) specific for a target protein (e.g., a suppressor cell surface protein) and in some examples having a substantially non-functional Fc region (or no Fc region). Exemplary suppressor cell surface proteins are provided herein, and thus PIT can be used to kill such cells. Thus, cell death of the cells occurs when the antibody-IR700 molecule binds to the suppressor cells and the suppressor cells are irradiated with NIR, while cells that do not express the suppressor cell surface protein recognized the antibody-IR700 molecule are not killed in significant numbers.

Subject or patient: A term that includes human and non-human mammals. In one example, the subject is a human or veterinary subject, such as a mouse, cat, dog, rat or non-human primate. In some examples, the subject is a mammal (such as a human) who has cancer, or is being treated for cancer.

Suppressor cells: A subpopulation of immune cells which modulate the immune system, maintain tolerance to self-antigens, and abrogate autoimmune disease. These cells generally suppress or downregulate induction, proliferation, and function of other immune cells such as effector T cells, NK cells and dendritic cells. Suppressor cells come in many forms, including those that express CD4, CD25, and Foxp3 (CD4+CD25+Foxp3 regulatory T cells). Other examples of suppressor cells that can be targeted by the disclosed therapies include type II natural killer T (NK-T) cells, $CD8^+$ $CD122^+$ Treg, M2 macrophages, tumor infiltrating fibroblasts, and myeloid-derived suppressor cells A suppressor cell surface protein is a protein expressed at least in part on the surface of a suppressor cell, which that the protein can specially bind to an antibody or antibody fragment. Thus, the suppressor cell surface protein can be one that only found on the surface, or has a portion on the surface (such as a transmembrane protein having one or more extracellular domains that can specifically bind to an appropriate antibody). Examples of suppressor cell surface proteins include but are not limited to: CD25, CD4, C-X-C chemokine receptor type 4 (CXCR4), C-C chemokine receptor type 4 (CCR4), cytotoxic T-lymphocyte-associated protein 4 (CTLA4), glucocorticoid induced TNF receptor (GITR), OX40, folate receptor 4 (FR4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), CD103, interleukin-1 decoy receptor, fibroblast activation protein (FAP), CXCR2, CD33, and CD66b).

Therapeutically effective amount: An amount of a composition that alone, or together with an additional therapeutic agent(s) (such as a chemotherapeutic or biologic agent) sufficient to achieve a desired effect in a subject, or in a cell, being treated with the agent. The effective amount of the agent (such as an antibody-IR700 molecule) can be dependent on several factors, including, but not limited to the subject or cells being treated, the particular therapeutic agent, and the manner of administration of the therapeutic composition. In one example, a therapeutically effective amount or concentration is one that is sufficient to kill a suppressor cell or population of suppressor cells. In some examples, a therapeutically effective amount or concentration is one that is sufficient to prevent advancement (such as metastasis), delay progression, or to cause regression of a disease, or which is capable of reducing symptoms caused by the disease, such as cancer. In one example, a therapeutically effective amount or concentration is one that is sufficient to increase the survival time of a patient with a tumor.

In one example, a desired response is to reduce the number of suppressor cells, for example by killing a suppressor cell or population of suppressor cells. The suppressor cells or a subpopulation of suppressor cells do not have to be completely eliminated for the composition to be effective. In one example, at least 10%, at least 20%, at least 30%, at least 40%, at least 50%, at least 60%, at least 70%, at least 80%, at least 85%, at least 90%, at least 95%, at least 98% or at least 99% of $CD25^+/CD4+/Foxp3^+$ regulatory T cells are killed using the antibody-IR700 molecule, as compound to an amount of such cells prior to the treatment. In one example, at least 10%, at least 20%, at least 30%, at least 40%, at least 50%, at least 60%, at least 70%, at least 80%, at least 85%, at least 90%, at least 95%, at least 98% or at least 99% of Type II NKT cells are killed using the antibody-IR700 molecule, as compound to an amount of such cells prior to the treatment. In one example, at least 10%, at least 20%, at least 30%, at least 40%, at least 50%, at least 60%, at least 70%, at least 80%, at least 85%, at least 90%, at least 95%, at least 98% or at least 99% of $CD8^+CD122^+$ regulatory T cells are killed using the antibody-IR700 molecule, as compound to an amount of such cells prior to the treatment. In one example, at least 10%, at least 20%, at least 30%, at least 40%, at least 50%, at least 60%, at least 70%, at least 80%, at least 90%, at least 95%, at least 98% or at least 99% of M2 macrophages cells are killed using the antibody-IR700 molecule, as compound to an amount of such cells prior to the treatment.

In one example, a desired response is to reduce or inhibit one or more symptoms associated with cancer. The one or more symptoms do not have to be completely eliminated for the composition to be effective. For example, administration of a composition containing an antibody-IR700 molecule followed by irradiation can decrease the size of a tumor (such as the volume or weight of a tumor, or metastasis of a tumor), for example by at least 20%, at least 50%, at least 80%, at least 90%, at least 95%, at least 98%, or even at least 100%, as compared to the tumor/metastasis size (or number of metastases) in the absence of the antibody-IR700 molecule and NIR irradiation. In one particular example, a desired response is to kill cancer cells by a desired amount, for example by killing at least 20%, at least 50%, at least 60%, at least 70%, at least 80%, at least 90%, at least 95%, at least 98%, or even at least 100% of the cells, as compared to the cell killing in the absence of the antibody-IR700 molecule and NIR irradiation. In one example, administration of a composition containing an antibody-IR700 molecule followed by NIR irradiation of a primary tumor can decrease the size and/or number of a distant non-irradiated metastasis (such as the volume of a metastasis, weight of a metastasis, number of metastases, or combinations thereof), for example by at least 20%, at least 50%, at least 80%, at least 90%, at least 95%, at least 98%, or even at least 100%, as compared to the volume/weight/number of metastases in the absence of the antibody-IR700 molecule and NIR irradiation of the primary tumor. In one particular example, a desired response is to increase the survival time of a patient with a tumor (or who has had a tumor recently removed) by a desired amount, for example increase survival by at least 20%, at least 50%, at least 60%, at least 70%, at least 80%, at least 90%, at least 95%, at least 98%, or even at least 100%, as compared to the survival time in the absence of the antibody-IR700 molecule and NIR irradiation.

The effective amount of an agent that includes one of the disclosed antibody-IR700 molecules, that is administered to a human or veterinary subject will vary depending upon a number of factors associated with that subject, for example the overall health of the subject. An effective amount of an agent can be determined by varying the dosage of the product and measuring the resulting therapeutic response, such as the regression of a tumor. Effective amounts also can be determined through various in vitro, in vivo or in situ immunoassays. The disclosed agents can be administered in a single dose, or in several doses, as needed to obtain the desired response. However, the effective amount of can be dependent on the source applied, the subject being treated, the severity and type of the condition being treated, and the manner of administration.

In particular examples, a therapeutically effective dose of an antibody-IR700 molecule is at least 0.5 milligram per 60 kilogram (mg/kg), at least 5 mg/60 kg, at least 10 mg/60 kg, at least 20 mg/60 kg, at least 30 mg/60 kg, at least 50 mg/60 kg, for example 0.5 to 50 mg/60 kg, such as a dose of 1 mg/60 kg, 2 mg/60 kg, 5 mg/60 kg, 20 mg/60 kg, or 50 mg/60 kg, for example when administered iv. In another example, a therapeutically effective dose of an antibody-IR700 molecule is at least 10 µg/kg, such as at least 100 µg/kg, at least 500 µg/kg, or at least 500 µg/kg, for example 10 µg/kg to 1000 µg/kg, such as a dose of 100 µg/kg, 250 µg/kg, about 500 µg/kg, 750 µg/kg, or 1000 µg/kg, for example when administered intratumorally or ip. In one example, a therapeutically effective dose is at least 1 µg/ml, such as at least 500 µg/ml, such as between 20 µg/ml to 100 µg/ml, such as 10 µg/ml, 20 µg/ml, 30 µg/ml, 40 µg/ml, 50 µg/ml, 60 µg/ml, 70 µg/ml, 80 µg/ml, 90 µg/ml or 100 µg/ml administered in topical solution. However, one skilled in the art will recognize that higher or lower dosages also could be used, for example depending on the particular antibody-IR700 molecule. In particular examples, a daily dosage is administered in one or more divided doses (such as 2, 3, or 4 doses) or in a single formulation. In particular examples, the subject receives multiple administrations of the antibody-IR700 molecule (such as at least 2, at least 3, at least 4, at least 5, at least 10, at least 15, or at least 20 separate administrations, such as 2, 3, 4, 5, 6, 7, 8, 9, 10, 11, 12, 13, 14, 15, 16, 17, 18, 19, 20, 25, 30, 40, or 50 separate administrations over time, such as over a week, month(s), or year(s)), followed by NIR irradiation. The disclosed antibody-IR700 molecules can be administered alone, in the presence of a pharmaceutically acceptable carrier, in the presence of other therapeutic agents (such as other antineoplastic agents).

Generally a suitable dose of irradiation following administration of the antibody-IR700 is at least 1 J cm$^{-2}$ at a wavelength of 660-740 nm, for example, at least 4 J cm$^{-2}$ at a wavelength of 660-740 nm, at least 5 J cm$^{-2}$ at a wavelength of 660-740 nm, at least 10 J cm$^{-2}$ at a wavelength of 660-740 nm, at least 50 J cm$^{-2}$ at a wavelength of 660-740 nm, or at least 100 J cm$^{-2}$ at a wavelength of 660-740 nm, for example 1 to 500 J cm$^{-2}$ at a wavelength of 660-740 nm, 4 to 50 J cm$^{-2}$ at a wavelength of 660-740 nm, or 4 to 8 J cm$^{-2}$ at a wavelength of 660-740 nm, such as 4, 5, 6, 7, 8, 9, or 10 J cm$^{-2}$ at a wavelength of 670 to 710 nm. In some examples the wavelength is 660 to 710 nm. In specific examples, a suitable dose of irradiation following administration of the antibody-IR700 molecule is at least 1.0 J cm$^{-2}$ at a wavelength of 690 nm+/−20 nm (e.g., 680 nm) for example, at least 10 J cm$^{-2}$ at a wavelength of 690 nm+/−20 nm (e.g., 680 nm), at least 50 J cm$^{-2}$ at a wavelength of 690 nm+/−20 nm (e.g., 680 nm), or at least 100 J cm$^{-2}$ at a wavelength of 690 nm+/−20 nm (e.g., 680 nm), for example 1 to 500 1.0 J cm$^{-2}$ at a wavelength of 690 nm+/−20 nm (e.g., 680 nm). In particular examples, multiple irradiations are performed (such as at least 2, at least 3, or at least 4 irradiations, such as 2, 3, 4, 5, 6, 7, 8, 9 or 10 separate administrations), following administration of the antibody-IR700 molecule.

Treating: A term when used to refer to the treatment of a cell or tissue with a therapeutic agent, includes contacting or incubating an agent (such as an antibody-IR700 molecule) with the cell or tissue. A treated cell is a cell that has been contacted with a desired composition in an amount and under conditions sufficient for the desired response. In one example, a treated cell is a cell that has been exposed to an antibody-IR700 molecule under conditions sufficient for the antibody to bind to a surface protein on the cell, followed by NIR irradiation, until sufficient cell killing is achieved.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be treated with the disclosed methods include solid tumors, such as breast carcinomas (e.g. lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, and lymphatic tumors (including B-cell and T-cell malignant lymphoma). In one example, the tumor is an adenocarcinoma.

The methods can also be used to treat liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), lymphomas (such as Hodgkin's lymphoma and non-Hodgkin's lymphoma), and myelomas).

Under conditions sufficient for: A phrase that is used to describe any environment that permits the desired activity. In one example, "under conditions sufficient for" includes administering an antibody-IR700 molecule to a subject sufficient to allow the antibody-IR700 molecule to bind to cell surface protein(s) on a suppressor cell. In particular examples, the desired activity is killing the cells to which the antibody-IR700 molecule is bound, following therapeutic NIR irradiation of the cells.

Untreated cell/subject: A cell/subject that has not been contacted with a desired agent, such as an antibody-IR700 molecule. In an example, an untreated cell/subject is a cell/subject that receives the vehicle in which the desired agent was delivered.

Disclosure of certain specific examples is not meant to exclude other embodiments. In addition, any treatments described herein are not necessarily exclusive of other treatment, but can be combined with other bioactive agents or treatment modalities.

Overview

Cancer immunotherapy by inhibiting immune suppressors, such as by immune checkpoint inhibitors, can be used to treat cancer. However, a problem with these agents is the potential for systemic autoimmune reactions, as activation of the immune system can be seen both in the target cancer and also in normal tissues. Thus, methods are needed that allow for manipulation of the balance between suppressor and effector cells within the tumor without disturbing homeostasis elsewhere in the body. $CD4^+CD25^+Foxp3^+$ regulatory T cells (Tregs) are immune-suppressor cells that play a key role in tumor immuno-evasion and have been the target of systemic immunotherapies.

In cancer therapies, systemic administration of drugs inhibiting immune suppressive cells and immune checkpoint inhibitors, while providing therapeutic benefit in some patients, often introduce severe side effects, such as autoimmune-like disease and acute interstitial pneumonia-acute respiratory distress syndrome (AIP-ARDS) (36, 37). An alternative approach is to inhibit or kill immune suppressive cells only within the tumor but not systemically. However, methods that can selectively remove such cells from the tumor microenvironment without damaging effector cells are limited.

In contrast to currently available cancer immunotherapy methods, the disclosed methods use near infrared photoimmunotherapy (NIR-PIT) to selectively kill suppressor cells, for example those specifically in the tumor microenvironment. This is accomplished by using antibodies or antibody fragments (e.g., an antibody or antibody fragment that does not have a functional Fc region) targeting, for instance, antigens on the surface of suppressor cells, that are also conjugated to a NIR photon absorber (referred to herein as antibody-IR700 molecules). After application of NIR light, suppressor cells bound to the antibody-IR700 molecules and exposed to the NIR light are selectively eliminated from the microenvironment of the tumor. Thus, NIR-PIT targeting of suppressor cells can induce highly effective anti-cancer host immune activation leading to cancer cell death and with minimal systemic autoimmune side effects.

The data herein show that antibody-photosensitizer conjugates specific for CD25 and NIR light effectively killed $CD4^+CD25^+foxp3^+$ Tregs in vitro and eliminated $CD4^+CD25^+foxp3^+$ Tregs from NIR-PIT treated tumors in vivo. Furthermore, the methods successfully induced reduction of non-PIT treated distant tumors (e.g., metastases) in vivo. Thus the disclosed methods can also treat secondary tumors or metastases by eliciting host immunity. The disclosed methods activate CD8 T and NK cells and restore local anti-tumor immunity, which leads to regression of the treated tumor but also induces responses in separate untreated tumors of the same cell-line derivation. Therefore, CD25-targeted-NIR-PIT causes spatially selective depletion of Tregs, thereby enabling an alternative approach to cancer immunotherapy.

This minimally invasive method employed an antibody-photoabsorber conjugate that targeted CD25. The conjugate was administered systemically, but it was only activated at sites where the antibody-photoabsorber conjugate was bound to the cells and exposed to NIR-light; both conditions had to be met for effective killing of $CD4^+CD25^+Foxp3^+$ Tregs. Meanwhile, because this method only depleted Tregs locally, Tregs were maintained normally in other organs. The killing of Tregs in the tumor led to activation of CD8 T and NK cells already present in the tumor but suppressed by the Tregs. At the time of NIR-PIT, the existing intratumoral CD8 T and NK cells did not express CD25. Thus, CD25-targeted-NIR-PIT selectively killed Tregs while leaving tumor infiltrating non-activated CD8 T and NK cells unharmed. After local CD25-targeted-NIR-PIT, intratumoral CD8 T and NK cells quickly became activated and exhibited cytotoxicity against the tumor. Only at this point, well after NIR-PIT had been applied, did these cells up-regulate CD25. Moreover, in case of repeated NIR-PIT, CD25 on intratumoral effector cells were already down-regulated before the repeated PIT after the 4 day-interval. Thus, local CD25-targeted-NIR-PIT of Tregs enables activation of effector cells without systemically eliminating suppressor cells. These findings are in contrast to previously reported methods of whole-body Treg depletion with systemic administration of anti-CD25 antibodies or IL-2-toxin conjugates, which deplete both Tregs and activated effector cells because of the long half-life of such antibodies (29, 38). Consequently, methods using anti-CD25 antibodies to systemically deplete Tregs only prevented engraftment of tumors but did not interfere with the growth of established tumors even while causing autoimmune-like side effects (22). Consistent with prior studies (27, 39), the anti-tumor effect of the disclosed local CD25-targeted-NIR-PIT was partially abrogated when CD8 T cells or NK cells were depleted or IFNγ was neutralized.

An attempt to deplete the subpopulation of mature Tregs, rather than eliminating all Tregs populations, to maintain self-tolerance has been made in patients with adult T cell leukemia (28). Systemic administration of an antibody targeted against a C-C chemokine receptor, CCR4, which is highly expressed on terminally differentiated Tregs as well as on the leukemic cells was used as a treatment. Although Th2 cells and some central memory CD8 T cells also express CCR4, this strategy spared naïve and precursor Tregs, resulting in a reduction in the number of leukemic cells. By locally targeting CD25-positive cells including mature and naïve Tregs within the tumor microenvironment, CD25-targeted-NIR-PIT can produce more potent and prolonged elimination of immune-suppressor function in the tumor microenvironment than the CCR4-targeting strategy, without inducing systemic autoimmune-like side effects. Thus, local CD25-targeted-NIR-PIT can be used in combination with other immune-modulatory therapies such as immune checkpoint inhibitors or cancer type specific therapies, or can be modified to include two different anti-CD25 clones (40) (such as antibodies that recognize different CD25 epitopes), or CD103-targeted NIR-PIT for effector Treg depletion (41, 42), to augment the therapeutic efficacy of the method (CD103 is expressed on effector (mature) Treg-cells). For example, an anti-CD103-IR100 conjugate can be used, such as one where the anti-CD103 antibody of the IR700 conjugate does not have a functional Fc region such. In one example, the local CD25-targeted-NIR-PIT includes use of daclizumab-IR700 and basiliximab-IR700, wherein the antibody of the IR700 conjugate does not have a functional Fc region.

Unlike conventional NIR-PIT, which requires tumor-specific antibody-photoabsorber conjugate for each tumor, CD25-targeted-NIR-PIT is effective against a broad range of tumors as Tregs expressing high levels of CD25 are often abundant in tumors regardless of their type (22). Thus, rather than developing a whole host of target conjugates, anti-CD25-IR700 conjugates are useful in many different types of tumors (22, 26). For instance, it is shown herein that local CD25-targeted-NIR-PIT using the same conjugates was effective in three different cancer models (lung, colon, prostate).

CD25-targeted-NIR-PIT led to rapid tumor killing by activated CD8 T and NK cells and likely induced activation of multiple cell types in the tumor. A "cytokine storm" (34, 35) not only within tumors, but also in the serum within a few hours after the treatment was observed, indicating additional activation of immune responses outside of the treated tumor. Cytokines and chemokines highly increased included those with pro-inflammatory and anti-inflammatory characteristics, some of which may have been of macrophage origin. Release of cytokines, such as IFNγ and IL-2, leading to full activation of effector cells, partly explains anti-tumor effects in distant tumors that were not directly treated with NIR-PIT. Although the presence of a cytokine storm following treatment may cause severe, if temporary, side effects, the elevated cytokines/chemokines, including IL-6, began to decrease within 1 day of therapy and thus, were self-limited. Thus, it is likely that the clinical side effects would be modest and short-lived based on the temporary elevation of cytokines/chemokines observed. Were symptoms to develop after NIR-PIT treatment in patients, anti-cytokine treatments such as tocilizumab for IL-6 could be used (43).

Figure 28:
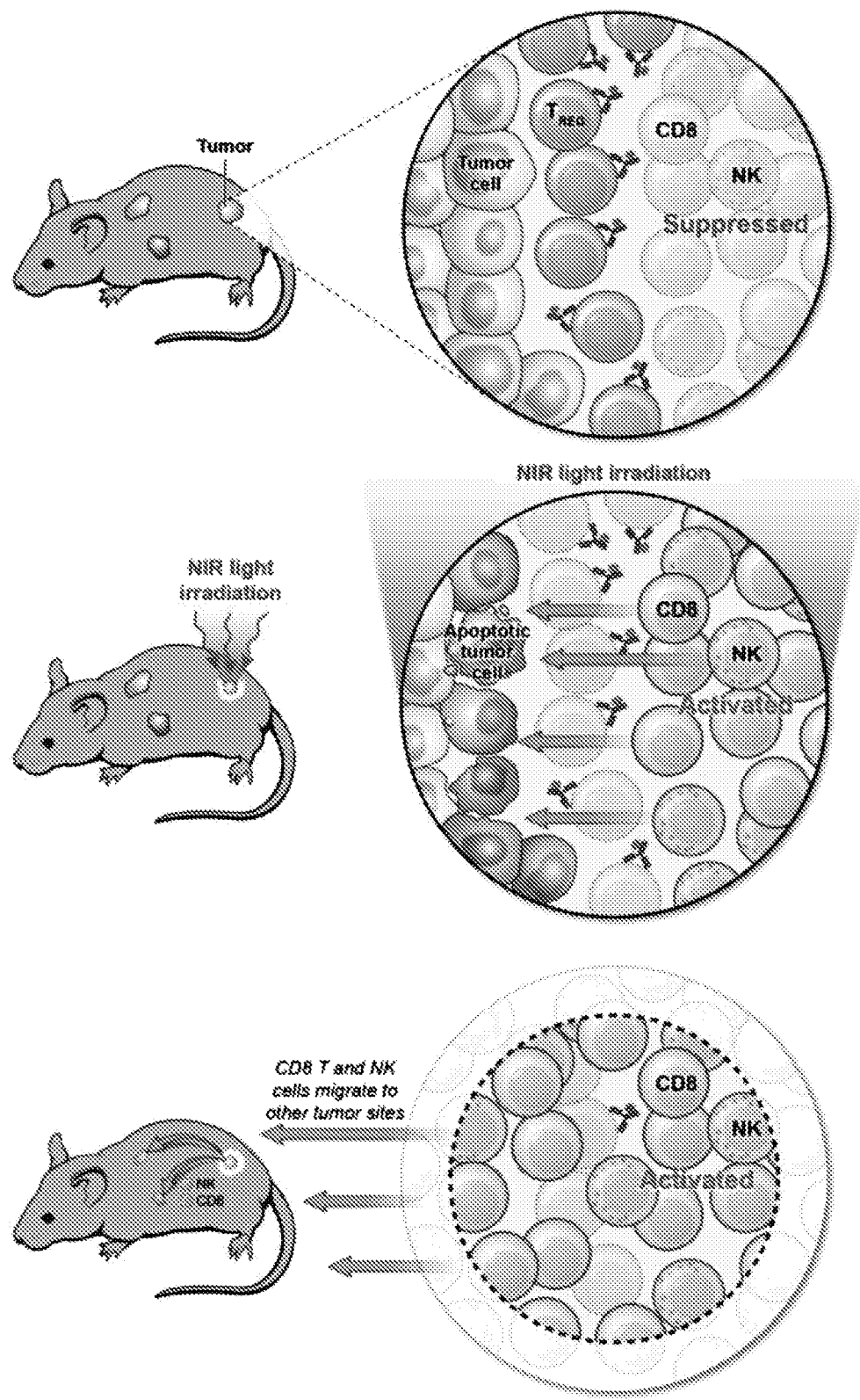
FIG. 28 is a schematic drawing showing a proposed mechanism of local CD25-targeted-NIR-PIT-induced immunotherapy. Tregs suppress CD8 T cell and NK cell activation, proving a permissive environment for tumor growth (upper panel). Once Tregs are selectively depleted following NIR-PIT, CD8 T cells and NK cells are activated against the tumor (middle panel). Activated CD8 T cells and NK cells can leave the treated tumor to attack distant tumors in collaboration with released cytokines and chemokines (lower panel).

It is shown herein that local CD25-targeted-NIR-PIT can selectively deplete tumor-infiltrating Tregs without eliminating local effector cells or Tregs in other organs. This results in rapid activation of CD8 T and NK cells leading to cell-mediated cancer killing. Local CD25-targeted-NIR-PIT also leads to tumor type-specific, systemic anti-tumor effects, which alters the growth of distant tumors of the same type (FIG. 28). Thus, local CD25-targeted-NIR-PIT can be used for reducing immune suppression caused by Tregs thus, augmenting effector cell mediated tumor killing. Because CD25-expressing Tregs are present in many tumors, this approach is effective across a broad range of cancer types, even while self-tolerance by Tregs is maintained in other tissues.

Based on these observations, provided herein are methods of killing suppressor cells using NIR-PIT, which can locally kill any selective target suppressor cells, including $CD4^+$ $CD25^+Foxp3^+$ Tregs, with minimal damage to surrounding cells or other cells not targeted by the antibody-IR700 molecule. Since $CD4^+CD25^+Foxp3^+$ Tregs protect cancer cells from host immunity, local killing of these and/or other suppressor cells in a tumor (or in a subject with a tumor) induces a rapid and highly effective anti-tumor host immune activation employing NK and CD8+ T-cells resulting in highly effective treatment of various cancers using the subject's own immune system, both locally and even in distant metastases away from the treated site with minimal side effects. If suppressor cells are systemically eliminated, steps can be taken to prevent occurrence of undesired auto-immunity. For example, methods can be performed to ensure that not all suppressor cells bound to antibody-IR700 molecule are killed, for example the by reducing the amount or area of exposure to NIR, by reducing the amount of antibody-IR700 molecule administered, repeated exposure to NIR light, and/or by adoptive transfer of ex vivo expanded $CD4^+CD25^+Foxp3^+$ Tregs after the tumor elimination. These methods can be used in a broad spectrum of patients with a variety of cancers including those with multiple distant metastasis as suppressor cells are involved in immunotolerance found in cancers. In some examples, treatment of a single local site with the disclosed methods permits systemic host immunity against cancers, leading to rapid tumor regression at the treated site as well as untreated distant metastatic lesions while inducing minimal side effects.

Methods for Killing Suppressor Cells and Treating Tumors

The present disclosure provides methods for killing suppressor cells. Suppressor cells express protein(s) on its surface, which can specifically bind to an antibody that is conjugated to a photosensitizer, such as IR700 (referred to herein as an antibody-IR700 molecule). The suppressor cell is contacted with a therapeutically effective amount of one or more antibody-IR700 molecules (for example in the presence of a pharmaceutically acceptable carrier, such as a pharmaceutically and physiologically acceptable fluid), under conditions that permit the antibody to specifically bind to the suppressor cell surface protein. For example, the antibody-IR700 molecule can be present in a pharmaceutically effective carrier, such as water, physiological saline, balanced salt solutions (such as PBS/EDTA), aqueous dextrose, sesame oil, glycerol, ethanol, combinations thereof, or the like, as a vehicle. The carrier and composition can be sterile, and the formulation suits the mode of administration. The suppressor cells are exposed to light in the NIR range, leading to killing of the suppressor cells that were exposed to NIR and had bound to the suppressor cell membrane antibody-IR700 molecule(s). Although the antibody-IR700 molecule(s) can distribute throughout the body, it is only active where the NIR is applied, reducing the likelihood of off-target effects.

Provided herein are methods of killing suppressor cells. In particular examples the methods are specific in that non-target cells, such as non suppressor cells, are not killed in significant numbers. In some examples, cells not both bound to an antibody-IR700 molecule and exposed to an appropriate dose of NIR light, are not killed in any significant amount, such as less than 1% of such cells, less than 0.5%, or less than 0.1% of such cells, but suppressor cells both bound to an antibody-IR700 molecule and exposed to an appropriate dose of NIR light, are killed in significant numbers. However, in some examples not all of the targeted suppressor cells are killed, as such could lead to undesired auto-immunity. Thus, in some examples, the method reduces the number of suppressor cells targeted by the antibody-IR700 molecule in an area of subject, such as in the area of a tumor or an area that used to have a tumor, by at least 50%, at least 60%, at least 75%, at least 80%, at least 85%, at least 90%, at least 95%, or at least 99%. The area of a tumor or an area that previously had a tumor can include the tumor itself or the area that used to have a tumor, and in some examples an additional area that includes at least 1 cm, at least 2 cm, at least 3 cm, at least 4 cm or at least 5 cm surrounding the tumor or prior area of the tumor. In some examples, the method reduces the total number of suppressor cells targeted by the antibody-IR700 molecule in a subject by at least 50%, at least 60%, at least 75%, at least 80%, at least 85%, at least 90%, at least 95%, or at least 99%.

In some examples, the methods include contacting a suppressor cell that expresses a suppressor cell surface protein(s) with a therapeutically effective amount of one or more antibody-IR700 molecules, wherein the antibody specifically binds to the suppressor cells surface protein and in some examples does not include a functional Fc region (e.g., consists of one or more Fab or F(ab')$_2$ fragments). The presence of a functional Fc portion can result in autoimmune toxicity (such as antibody-dependent cell-mediated cytotoxicity (ADCC)). Thus, the Fc portion of the antibody can be mutated or removed to substantially decrease its function (such as the ability to bind to FcγR). In some examples, the function of the Fc region is reduced by at least 50%, at least 75% at least 80%, at least 90%, at least 95%, at least 99%, or 100%, as compared to the Fc function without the mutation. In some examples, mutating or removing the Fc region of the antibody decreases the half-life of the antibody. For example, a full IgG may have a half-life of about 2 weeks, while an IgG without a function an Fc region may have a shorter half-life of about one day. Thus, in some examples, the antibody of the antibody-IR700 molecule has a half-life of less than 14 days, such as less than 10 days, less than 7 days, less than 5 days, less than 4 days, less than 3 days, or less than 2 days, such as 1 to 7 days, such as 0.5 to 7 days, such as 1 to 3 days, or as 0.5 to 2 days. Exemplary methods of mutating an antibody include deletion, insertion and/or substitution of one more amino acids in the Fc region, such as deletion, insertion and/or substitution of at least 10, at least 25, at least 50, at least 100, or at least 200 amino acids of an Fc region.

The suppressor cell surface protein is one that is at least partially or entirely on the cell surface of the suppressor cell, such that it can bind to an appropriate specific antibody (or fragment thereof). For example, the suppressor cell surface protein can be a transmembrane protein, wherein the extracellular domain can bind to the antibody (or fragment thereof) of the antibody-IR700 molecule. In some examples, the wherein the protein(s) on the suppressor cell surface is not significantly found on other cells (such as epithelial cells) and thus the antibody will not significantly bind to the non-target cells. Examples of such suppressor cell surface proteins that can be targeted include but are not limited to, CD25, CD4, C-X-C chemokine receptor type 4 (CXCR4), C-C chemokine receptor type 4 (CCR4), cytotoxic T-lymphocyte-associated protein 4 (CTLA4), glucocorticoid induced TNF receptor (GITR), OX40, folate receptor 4 (FR4), CD16, CD56, CD8, CD122, CD23, CD163, CD11b, Gr-1, CD14, interleukin 4 receptor alpha chain (IL-4Ra), interleukin-1 receptor alpha (IL-1Ra), interleukin-1 decoy receptor, CD103, fibroblast activation protein (FAP), CXCR2, CD33, and CD66b. In some examples, the suppressor cell surface protein is not CD25.

For example, the suppressor cells and the one or more antibody-IR700 molecules can be incubated under conditions that allow the one or more antibody-IR700 molecules to bind to the suppressor cell surface protein(s). The suppressor cells are then irradiated at a wavelength of 660 to 740 nm, such as 660 to 710 nm (for example, 690 nm+/−20 nm, e.g., 680 nm) at a dose of at least 1 or at least 4 J cm$^{-2}$ (such as 4 to 8 J cm$^{-2}$) thereby killing the suppressor cells. Examples of suppressor cells that can be targeted with this method include, but are not limited to: CD4+CD25±Foxp3$^+$ Tregs, type II NKT cells, CD8$^+$CD122$^+$ Tregs, M2 macrophages, tumor infiltrating fibroblasts, myeloid-derived suppressor cells, as well as combinations thereof (e.g., by using multiple antibody-IR700 molecules, each specific for a particular type of suppressor cell). Thus, the disclosed methods in some examples kill at least 10%, for example at least 20%, at least 40%, at least 50%, at least 80%, at least 85%, at least 90%, at least 95%, or at least 98%, of the treated CD4$^+$CD25$^+$Foxp3$^+$ Tregs (for example as a % of the total number of CD4$^+$CD25$^+$Foxp3$^+$ Tregs in a subject prior to treatment or a % of the total number of CD4$^+$CD25$^+$Foxp3$^+$ Tregs in the area of a tumor (such as an area that includes the tumor and at least 1 mm (such as at last 2 mm, at least 3 mm, at least 4 mm, or at least 5 mm) surrounding the tumor prior to treatment) relative to the absence of treatment with of one or more antibody-IR700 molecules and NIR. In some examples, the disclosed methods in some examples kill at least 10%, for example at least 20%, at least 40%, at least 50%, at least 80%, at least 85%, at least 90%, at least 95%, or at least 98%, of the treated type II NKT cells (for example as a % of the total number of type II NKT cells in a subject prior to treatment or a % of the total number of type II NKT cells in the area of a tumor (such as an area that includes the tumor and at least 1 mm (such as at last 2 mm, at least 3 mm, at least 4 mm, or at least 5 mm) relative to the absence of treatment with of one or more antibody-IR700 molecules and NIR. In some examples, the disclosed methods in some examples kill at least 10%, for example at least 20%, at least 40%, at least 50%, at least 80%, at least 85%, at least 90%, at least 95%, or at least 98%, of the treated CD8$^+$CD122$^+$ Tregs (for example as a % of the total number of CD8$^+$CD122$^+$ Tregs cells in a subject prior to treatment or a % of the total number of CD8$^+$CD122$^+$ Tregs in the area of a tumor (such as an area that includes the tumor and at least 1 mm (such as at last 2 mm, at least 3 mm, at least 4 mm, or at least 5 mm) relative to the absence of treatment with of one or more antibody-IR700 molecules and NIR. In some examples, the disclosed methods in some examples kill at least 10%, for example at least 20%, at least 40%, at least 50%, at least 80%, at least 85%, at least 90%, at least 95%, or at least 98%, of the treated M2 macrophages (for example as a % of the total number of M2 macrophages in a subject prior to treatment or a % of the total number of M2 macrophages in the area of a tumor (such as an area that includes the tumor and at least 1 mm (such as at last 2 mm, at least 3 mm, at least 4 mm, or at least 5 mm) relative to the absence of treatment with of one or more antibody-IR700 molecules and NIR. In some examples, the disclosed methods in some examples kill at least 10%, for example at least 20%, at least 40%, at least 50%, at least 80%, at least 85%, at least 90%, at least 95%, or at least 98%, of the treated tumor infiltrating fibroblasts (for example as a % of the total number of tumor infiltrating fibroblasts in a subject prior to treatment or a % of the total number of tumor infiltrating fibroblasts in the area of a tumor (such as an area that includes the tumor and at least 1 mm (such as at last 2 mm, at least 3 mm, at least 4 mm, or at least 5 mm) relative to the absence of treatment with of one or more antibody-IR700 molecules and NIR. In some examples, the disclosed methods in some examples kill at least 10%, for example at least 20%, at least 40%, at least 50%, at least 80%, at least 85%, at least 90%, at least 95%, or at least 98%, of the treated myeloid-derived suppressor cells (for example as a % of the total number of M2 macrophages in a subject prior to treatment or a % of the total number of myeloid-derived suppressor cells in the area of a tumor (such as an area that includes the tumor and at least 1 mm (such as at last 2 mm, at least 3 mm, at least 4 mm, or at least 5 mm) relative to the absence of treatment with of one or more antibody-IR700 molecules and NIR. Combinations of these suppressor cells are achieved, such as 1, 2, 3, 4, 5 or all 6 suppressor cell types.

In one example, a patient is treated with at least two different antibody-IR700 molecules. In one example, the two different antibody-IR700 molecules are specific for the same protein (such as CD25), but are specific for different epitopes of the protein (such as epitope 1 and epitope 2 of CD25). In another example, the two different antibody-IR700 molecules are specific for two different proteins or antigens, such as one antibody specific for CD4, and another antibody specific for CD25. For example, anti CD4-IR700 and anti CD25-IR700 could be injected together as a cocktail to facilitate killing of cells bearing either CD4 or CD25. In another example, the two different antibody-IR700 molecules are specific for two different proteins or antigens, such as one antibody specific for CD103, and another antibody specific for CD25. For example, anti CD103-IR700 and anti CD25-IR700 could be injected together as a cocktail to facilitate killing of cells bearing either CD103 or CD25. Specific combinations based on the information in Table 1 can be generated.

Such methods can be performed in vitro, for example by incubating a culture of suppressor cells with the one or more antibody-IR700 molecules and then irradiating the cells at a wavelength of 660 to 740 nm at a dose of at least 1 or at least 4 J cm', thereby killing the suppressor cells having bound thereto the antibody-IR700 molecule and exposed to NIR light. In another example, the suppressor cells are present in a subject, and contacting the suppressor cells with the one or more antibody-IR700 molecules includes administering a therapeutically effective amount of the one or more antibody-IR700 molecules to the subject (e.g., by injection). The subject or part of the subject (e.g., a tumor in the subject) is then irradiated at a wavelength of 660 to 740 nm at a dose of at least 1 or at least 4 J cm$^{-2}$, thereby killing the suppressor cells in the subject having bound thereto the antibody-IR700 molecule and exposed to NIR light. In one example, the method can include irradiating the suppressor cells by irradiating the blood using a device worn by the subject, wherein the device includes a near infrared (NIR) light emitting diode (LED).

After contacting or administering the one or more antibody-IR700 molecules under conditions that allow the one or more antibody-IR700 molecules to bind to their target on the surface of suppressor cells, suppressor cells are then irradiated under conditions that permit killing of the suppressor cells, for example irradiation at a wavelength of 660 to 740 nm at a dose of at least 1 or at least 4 J cm$^{-2}$. Suppressor cells that both have bound to their surface antibody-IR700 molecules and have been exposed to the NIR light, will be killed. In one example, there is at least 10 minutes, at least 30 minutes, at least 1 hour, at least 4 hours, at least 8 hours, at least 12 hours, or at least 24 hours (such as 1 to 4 hours, 30 minutes to 1 hour, 10 minutes to 60 minutes, or 30 minutes to 8 hours) in between contacting the cell with the antibody-IR700 molecules and the irradiation. The NIR excitation light wavelength allows penetration of at least several centimeters into tissues. For example, by using fiber-coupled laser diodes with diffuser tips, NIR light can be delivered within several centimeters of otherwise inaccessible tumors located deep to the body surface. In addition to treating solid cancers, circulating tumor cells can be targeted since they can be excited when they traverse superficial vessels (for example using a NIR LED wearable device).

The disclosed methods in some examples can be used to treat a tumor, such as a cancer, in vitro or in vivo. Exemplary cancers include those of the breast, liver, colon, ovary, prostate, pancreas, brain, cervix, bone, skin, head and neck, lung, and blood. Specific exemplary cancers are provided herein. In some examples, the cancer treated is a metastatic cancer.

For example, administration of one or more antibody-IR700 molecules to a subject having a tumor, in combination with NIR light kills suppressor cells that express a suppressor cell surface protein that can specifically bind to the antibody and that were exposed to the NIR, thereby allowing Teff cells to kill the cancer cells. For example, the use of antibody-IR700 molecules in combination with NIR light can reduce the volume of a tumor, the size of a tumor, the weight of a tumor, the number of metastases, volume of a metastases, the size of a metastases, the weight of a metastases, or combinations thereof by at least 20%, at least 25%, at least 30%, at least 40%, at least 50%, at least 75%, at least 80%, at least 85%, at least 90%, or at least 95%, relative to the absence of treatment. In some examples a metastasis is treated without directly exposing it to NIR light, as treatment of the primary tumor with antibody-IR700 molecules (e.g., locally or systemically) and NIR light can result in a general immune response that can treat the metastasis (e.g., by reducing or removing the inhibition of Teff cells by suppressor cells). The use of antibody-IR700 molecules in combination with NIR light can in some examples slow the growth of a tumor, decrease or slow metastasis of the tumor (for example by reducing the number of metastases or decreasing the weight, volume or size of a metastasis), or combinations thereof.

The disclosed methods can result in a decrease in the symptoms associated with a tumor and/or a metastatic tumor. For example, the disclosed methods can reduce tumor size, weight, volume, and/or a metastatic tumor cell volume, weight, or size (or number of metastatic tumors), or combinations thereof, such as by at least 10%, for example by at least 20%, at least 40%, at least 50%, at least 80%, at least 85%, at least 90%, or more, relative to the absence of administration of one or more antibody-IR700 molecules followed by NIR light. In one example, administration of the disclosed compositions slows the growth of a tumor and/or metastasis, such as by at least 10%, for example by at least 20%, at least 40%, at least 50%, at least 80%, at least 85%, at least 90%, or more, relative to the absence of administration of the antibody-IR700 molecules followed by NIR light. In one example, the volume of a tumor and/or metastasis treated with the antibody-IR700 molecules in combination with NIR light is at least 2-fold, at least 3-fold, at least 4-fold, or even at least 5-fold smaller than the volume of a tumor not treated with the antibody-IR700 molecules/NIR light (for example after at least 7 days, at least 10 days, at least 14 days, at least 30 days, at least 60 days, at least 90 days, or at least 120 days after the treatment). In one example, the size of a tumor and/or metastasis treated with the antibody-IR700 molecules in combination with NIR light is at least 2-fold, at least 3-fold, at least 4-fold, or even at least 5-fold smaller than the size of a tumor not treated with the antibody-IR700 molecules/NIR light (for example after at least 7 days, at least 10 days, at least 14 days, at least 30 days, at least 60 days, at least 90 days, or at least 120 days after the treatment).

The disclosed methods can increase cytokine and chemokine production. For example, the disclosed methods can increase detectable cytokine and chemokine production (such as one or more of G-CSF, IL10, IL6, KC, MIP1β, TNF-α, and others in FIGS. 18A and 18B) in the tumor and/or serum by at least 10%, for example by at least 20%, at least 40%, at least 50%, at least 80%, at least 85%, at least 90%, at least 100%, at least 200, at least 300%, at least 400%, or at least 500%, relative to the absence of administration of one or more antibody-IR700 molecules followed by NIR light.

The disclosed methods can activate NK and CD8 T cells, for example as indicated by increased expression of one or more of INFγ, IL2, CD69, CD25, G-CSF, MCP1, MIP2, and MIP1α. For example, the disclosed methods can increase expression of one or more of INFγ, IL2, CD69, CD25, G-CSF, MCP1, MIP2, and MIP1 α, in the tumor by at least 10%, for example by at least 20%, at least 40%, at least 50%, at least 80%, at least 85%, at least 90%, at least 100%, at least 200, at least 300%, at least 400%, or at least 500%, relative to the absence of administration of one or more antibody-IR700 molecules followed by NIR light.

The disclosed methods can increase expression of cytokines by dendritic cells (DCs) and APCs. For example, the disclosed methods can increase expression of one or more of MHCI, CD86, and CD40 by DC, or CD69 by APCs, by at least 10%, for example by at least 20%, at least 40%, at least 50%, at least 80%, at least 85%, at least 90%, at least 100%, at least 200, at least 300%, at least 400%, or at least 500%, relative to the absence of administration of one or more antibody-IR700 molecules followed by NIR light.

The disclosed methods can increase granulocyte production by the tumor, for example by at least 10%, for example by at least 20%, at least 40%, at least 50%, at least 80%, at least 85%, at least 90%, at least 100%, at least 200, at least 300%, at least 400%, or at least 500%, relative to the absence of administration of one or more antibody-IR700 molecules followed by NIR light.

In some examples, the methods increases survival time of the subject relative to an absence of administration of the antibody-IR700 molecule and irradiation. In one example, the survival time of a subject having a tumor treated with the antibody-IR700 molecules in combination with NIR light is at least 10%, for example by at least 20%, at least 40%, at least 50%, at least 80%, at least 85%, at least 90%, at least 100%, at least 2-fold, at least 3-fold, at least 4-fold, at least 5-fold, at least 6-fold, at least 7-fold, or at least 10-fold longer than survival time of a subject having a tumor not treated with the antibody-IR700 molecules (for example after a specified period of time, such as at least 14 days, at least 30 days, at least 60 days, at least 90 days, at least 120 days, at least 6 months, at least 12 months, at least 24 months, or at least 5 years after the treatment, more subjects treated with the antibody-IR700 molecules/NIR therapy will be alive than if not treated with the antibody-IR700 molecules/NIR light). In some examples, the disclosed methods can increase a subject's survival time by at least 3 months, at least 6 months, at least 12 months, at least 18 months, at least 24 months, at least 36 months or more, relative to average survival time in the absence of administration of the antibody-IR700 molecule and NIR light.

In some examples, the method further includes contacting the suppressor cells with (or administering to a subject) one or more additional therapeutic agents. The one or more additional therapeutic agents can be contacted with the (or administered to a subject) contemporaneously or sequentially with the PIT. In one example, the additional therapeutic agent(s) are administered after the irradiation, for example, at least 10 minutes, at least 30 minutes, at least 60 minutes, at least 2 hours, at least 3 hours, at least 4, hours, at least 5 hours, at least 6 hours, at least 7 hours, at least 8 hours, at least 10 hours, at least 12 hours, at least 24 hours, at least 48 hours, at least 72 hours, at least 1 week, at least 1 month, or at least 1 year after the irradiation, such as 1 hour to 10 hours, 1 hour to 9 hours 1 hour to 8 hours, 2 hours to 8 hours, 4 hours to 8 hours, 1 hour to 24 hours, or 1 hour to 48 hours after irradiation. In another example, the additional therapeutic agent(s) are administered just before the irradiation (such as about 10 minutes to 120 minutes before irradiation, such as 10 minutes to 60 minutes or 10 minutes to 30 minutes before irradiation).

In some examples, combining the antibody-IR700 molecules/NIR light with the additional therapy (such as antineoplastic agents), enhances the effectiveness of the treatment of the tumor. For example, combining the antibody-IR700 molecules/NIR light with the additional therapy (such as other anti-neoplastic agents) can result in a tumor volume that is less than the tumor volume would be if it were treated with either the antibody-IR700 molecules/NIR light alone or the additional therapy alone, that is, there is a synergistic effect. In one example, the volume of a tumor and/or metastasis treated with the combination therapy is at least 2-fold, at least 3-fold, at least 4-fold, or even at least 5-fold smaller than the volume of a tumor and/or metastasis treated with either the antibody-IR700 molecules/NIR light alone or the additional therapy alone (for example after at least 7 days, at least 10 days, at least 14 days, at least 30 days, at least 60 days, at least 90 days, or at least 120 days after the treatment). In one example, the size of a tumor and/or metastasis treated with the combination therapy is at least 5-fold, at least 6-fold, at least 7-fold, or even at least 10-fold smaller than the size of a control untreated tumor (for example after at least 7 days, at least 10 days, at least 14 days, at least 30 days, at least 60 days, at least 90 days, or at least 120 days after the treatment). In another or additional example, combining the antibody-IR700 molecules/NIR light with the additional therapy (such as anti-neoplastic agents) can increase the survival time of a subject having a tumor relative to the survival time of the subject if the tumor was treated with either the antibody-IR700 molecules/NIR light alone or the additional therapy alone, that is, there is a synergistic effect. In one example, the survival time of a subject having a tumor treated with the combination therapy is at least 2-fold, at least 3-fold, at least 4-fold, at least 5-fold, at least 6-fold, at least 7-fold, or at least 10-fold longer than survival time of a subject having a tumor treated with either the antibody-IR700 molecules/NIR light alone or the additional therapy alone (for example after a specified period of time, such as at least 14 days, at least 30 days, at least 60 days, at least 90 days, at least 120 days, at least 6 months, at least 12 months, at least 24 months, or at least 5 years after the treatment, more subjects treated with the combination therapy will be alive than if treated with either therapy alone).

Exemplary additional therapeutic agents that can be used include anti-neoplastic agents, such as chemotherapeutic and anti-angiogenic agents or therapies, such as radiation therapy. In one example the agent is a chemotherapy immunosuppressant (such as Rituximab, steroids) or a cytokine (such as GM-CSF). Chemotherapeutic agents are known (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993). Exemplary chemotherapeutic agents that can be used with the methods provided herein include but are not limited to, carboplatin, cisplatin, paclitaxel, docetaxel, doxorubicin, epirubicin, topotecan, irinotecan, gemcitabine, iazofurine, gemcitabine, etoposide, vinorelbine, tamoxifen, valspodar, cyclophosphamide, methotrexate, fluorouracil, mitoxantrone, Doxil (liposome encapculated doxiorubicine) and vinorelbine. In one example, the additional therapeutic agents that can be used include antibody-IR700 molecules, wherein the antibody specifically binds to a tumor-specific protein, such as a Panitumumab-IR700 molecule, Trastuzumab-IR700 molecule, Basilitumab-IR700 molecule, Zenapax-IR700 molecule, Simitect-IR700 molecule, Cetuximab-IR700 molecule or J591-IR700 molecule (e.g., see U.S. Pat. No. 8,524,239 and U.S. Publication No. 2014/0120119 A1, both herein incorporated by reference). Other exemplary additional treatments are provided herein.

The disclosed methods can be used to treat fixed tumors in the body as well as tumors in the circulation (e.g., leukemia cells, metastases, circulating tumor cells). In one example, circulating suppressor cells are irradiated using a device that can be worn, or that covers parts of the body. For example, such a device can be worn for short or extended time periods. Everyday wearable items (e.g., wristwatches, jewelry (such as a necklace or bracelet), blankets, clothing (e.g., underwear, socks, and shoe inserts) and other everyday wearable items) which incorporate NIR emitting light emitting diodes (LEDs) and a battery pack, can be used. Such devices produce light on the skin underlying the device over desired periods leading to exposure of light to superficial vessels over prolonged periods. Circulating suppressor cells are exposed to the light as they transit thru the area underlying the device.

After administration of the one or more antibody-IR700 molecules (e.g., intravenously), circulating suppressor cells are bound by antibody-IR700 conjugates and become susceptible to killing by PIT. As these suppressor cells flow within the vessels adjacent to the LED present in the everyday wearable item (e.g., bracelet or wristwatch), they are exposed to NIR light rendering them susceptible to cell killing. The dose of light may be adjustable according to diagnosis and suppressor cell type.

In some examples, the method further includes monitoring the therapy, such as killing of suppressor cells. In some examples, this is done in real time. In such examples, the antibody-IR700 conjugate is contacted with the cells (or administered to the subject) and the cells/subject/tumor irradiated as described above. Such methods are useful for example, to ensure sufficient amounts of antibody-IR700 molecules and/or one or more therapeutic agents, or sufficient amounts of irradiation, were administered to achieve cell killing. These methods can permit detection of cell killing before morphological changes become evident. In one example, the methods include contacting suppressor cells having a suppressor cell surface protein with a therapeutically effective amount of one or more antibody-IR700 molecules (such as at least 0.01 nM, at least 0.1 nM, at least 1 nM, or at least 10 nM, such as 0.1 to 2 nM, 0.5 to 1.5 nM, such as 1 nM of the of one or more antibody-IR700 molecules), wherein the antibody specifically binds to the suppressor cell surface protein; irradiating the cell at a wavelength of 660 to 740 nm and at a dose of at least 20 J $cm^{-2}$; and detecting the cell with fluorescence lifetime imaging (FLI) about 0 to 48 hours after irradiating the cell (such as at least 1 hour, at least 2 hours, at least 4 hours, at least 6 hours, at least 12 hours, at least 18 hours, at least 24 hours, at least 36 hours, at least 48 hours, or at least 72 hours after irradiating the cell, for example 1 minute to 30 minutes, 10 minutes to 30 minutes, 10 minutes to 1 hour, 1 hour to 8 hours, 6 hours to 24 hours, or 6 hours to 48 hours after irradiating the cell), thereby detecting the cell killing in real-time. Shortening FLT serves as an indicator of acute membrane damage induced by PIT. Thus, the cell is irradiated under conditions sufficient to shorten IR700 FLT by at least 25%, such as at least 40%, at least 50%, at least 60% or at least 75%. In one example, the cell is irradiated at a wavelength of 660 nm to 740 nm (such as 680 nm to 700 nm) and at a dose of at least 20 J $cm^{-2}$ or at least 30 J $cm^{-2}$, such as at least 40 J $cm^{-2}$ or at least $50^{-2}$ J $cm^{-2}$ or at least 60 J $cm^{-2}$, such as 30 to 50 J $cm^{-2}$.

Exemplary Suppressor Cells and Suppressor Cell Surface Proteins

The suppressor cell killed by the one or more antibody-IR700 molecules can be growing in culture, or present in a mammal to be treated, such as a patient with cancer. Any type of suppressor cells can be killed with the disclosed methods. Suppressor cells express a cell surface protein, to which an antibody can be selected or generated that specifically binds to such a suppressor cells surface protein, and an antibody-IR700 molecule generated for that suppressor cells surface protein. Table 1 provides exemplary suppressor cells and suppressor cell surface proteins that can be targeted with the disclosed therapies. The antibody or antibody fragment of the antibody-IR700 molecule can be one that specifically binds to a suppressor cell surface protein listed in Table 1, or a portion of the protein that is present on the cell surface (such as an cell surface epitope of a protein provided in a GenBank® Accession number provided below for these proteins).

TABLE 1

Exemplary suppressor cells and suppressor cell surface proteins

| | Suppressor Cell | | | | | |
|---|---|---|---|---|---|---|
| | CD4+CD25+Foxp3+ cell | Type II NKT cell | CD8 + CD122 + Treg | M2 macrophage | tumor infiltrating fibroblasts | myeloid-derived suppressor cells |
| Target on Suppressor Cell Surface | CD25<br>CD4<br>CXCR4<br>CCR4<br>GITR<br>OX40<br>FR4<br>CTLA4<br>CD103 | CD16<br>CD56 | CD8<br>CD122 | CD23<br>CD163<br>CD206<br>CD11b<br>GR-1<br>CD14<br>IL4-Ra<br>IL-1Ra<br>interleukin-1 decoy receptor | fibroblast activation protein (FAP) | CXCR2<br>CD11b<br>CD14<br>CD33<br>CD66b | fibroblast activation protein (FAP), CXCR2, CD33, and CD66b

Examples of suppressor cells that can be targeted by the disclosed therapies include one or more of a CD4+CD25+Foxp3+ Tregs, a type II natural killer T (NKT) cell, a CD8+CD122+Treg, a M2 macrophage, a tumor infiltrating fibroblast, and a myeloid-derived suppressor cell. CD4+CD25+Foxp3+ Tregs are a type of suppressor cell that express CD25 and CD4 protein on their cell surface and transcription factor forkhead box P3 (Foxp3) protein intracellularly. Regulatory T cells characterized by CD4, CD25, and transcription factor Foxp3, are a subpopulation of CD4+ T cells specialized for immune suppression. Type II NKT cells are a heterogeneous group of T cells that share properties of both T cells and natural killer cells, are CD1d-restricted T cells, and co-express an α§ T cell receptor as well as NK1.1. CD8+CD122+ Tregs are involved in maintaining immune homeostasis. Such cells express both CD8 and CD122 on their surface. A M2 macrophage is a type of macrophage that decreases inflammation and encourages tissue repair, for example by metabolizing ornithine.

Suppressor cell surface proteins are proteins expressed by a suppressor cell, wherein at least a portion of the protein is present and detectable on its cell surface. For example the protein may be entirely present on the surface, or can be a transmembrane protein having an extracellular portion(s) that has a unique epitope that can bind to a specific antibody or fragment thereof (e.g., Fab or F(ab')2 fragment). In some examples, the suppressor cell surface proteins are unique to the suppressor cell or are much more abundant on those cells, as compared to other cells, such as a cancer cell. Exemplary suppressor cell surface proteins (and to which an antibody specific for that protein can be used to formulate an antibody-IR700 molecule), include but are not limited to: CD25, CD4, C-X-C chemokine receptor type 4 (CXCR4), C-C chemokine receptor type 4 (CCR4), cytotoxic T-lymphocyte-associated protein 4 (CTLA4), glucocorticoid induced TNF receptor (GITR), OX40, folate receptor 4 (FR4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), interleukin-1 decoy receptor, CD103, fibroblast activation protein (FAP), CXCR2, CD33, and CD66b.

CD4+CD25+Foxp3+ Regulatory T Cells

If the suppressor cell to be killed/targeted is a CD4+CD25+Foxp3+ Treg, anti-CD4, anti-CD25, anti-CXCR4, anti-CCR4, anti-GITR, anti-OX40, anti-FR4, and/or anti-CTLA4 antibodies (e.g., without a functional Fc region) can be used as part of the antibody-IR700 molecule.

CD4 (cluster of differentiation 4) is a glycoprotein found on the surface of some immune cells, and acts as a co-receptor to assist the T cell receptor in communicating with an antigen-presenting cell. CD4 has for immunoglobulin domains ($D_1$ to $D_4$) expressed on the surface of the cell. CD4 sequences are known for several organisms (e.g., see GenBank® Accession Nos: NP_000607.1, NP_038516.1, P01730.1, XP_004052630.1, and XP_008761502.1). In addition, antibodies specific for CD4 are publicly available from commercial sources (e.g., catalog #sc-514571, sc-514746, and sc-07219 from Santa Cruz Biotechnology, Dallas, Tex.; clone 4B12 from Dako, Denmark, and catalog #ab133616, ab25475, and ab51037 from abcam, Cambridge, Mass.). CD4 antibodies can be modified to remove/inactivate the Fc region, for example using the methods described in Example 1 or pepsin.

CD25 is the alpha chain of the IL-2 receptor (also referred to as IL2RA). It is a transmembrane protein found on activated T cells, activated B cells, some thymocytes, myeloid precursors, and oligodendrocytes. CD25 sequences are known for several organisms (e.g., see GenBank® Accession Nos: NP_000408.1, NP_001295172.1, NP_001295171.1, AAI14438.1, NP_999000.1, and CAA44297.1). In addition, antibodies specific for CD25 are publicly available from commercial sources (e.g., catalog #sc-376665, sc-365912, and sc-1628, from Santa Cruz Biotechnology, Dallas, Tex.; and catalog #ab8235, ab9496, and ab61777 from abcam, Cambridge, Mass.). In one example, the CD25 antibody is daclizumab (e.g., one containing on FC portion). In one example, the CD25 antibody is basiliximab (e.g., one containing on FC portion), such as one that does not contain a functional Fc region. In one example, the CD25 antibody is daclizumab, such as one that does not contain a functional Fc region. CD25 antibodies can be modified to remove/inactivate the Fc portion, for example using the methods described in Example 1 or pepsin. In some examples, the methods provided herein use two different anti-CD25-F(ab')2-IR700 molecules, such as anti-CD25-IR700 molecules containing basiliximab and daclizumab with a non-functional Fc region.

C-X-C chemokine receptor type 4 (CXCR4), also known as fusion or CD184, is an alpha chemokine receptor specific for stromal-derived-factor 1. CXCR4 is one of several chemokine receptors that HIV can use to infect CD4+ T cells. CXCR4 sequences are known for several organisms (e.g., see GenBank® Accession Nos: CAA12166.1, NP_001008540.1, NP_034041.2, AAZ32767.1, and XP_004032646.1). In addition, antibodies specific for CXCR4 are publicly available from commercial sources (e.g., BMS-936564 (MDX-1338) from Bristol-Myers Squibb, catalog #sc-12764, sc-53534, and sc-6279, from Santa Cruz Biotechnology, Dallas, Tex.; and catalog #ab2074, ab124824, and ab7199 from abcam, Cambridge, Mass.). CXCR4 antibodies can be modified to remove/inactivate the Fc region, for example using the methods described in Example 1 or pepsin.

C-C chemokine receptor type 4 (CCR4), also known as CD194, is a G protein-coupled receptor for chemokines CCL2, CCL4, CCL5, CCL17 and CCL22. CCR4 sequences are known for several organisms (e.g., see GenBank® Accession Nos: NP_005499.1, NP_034046.2, P51680.2, NP_598216.2, and NP_001252949.1). In addition, antibodies specific for CCR4 are publicly available from commercial sources (e.g., catalog #sc-101375 and sc-32133, from Santa Cruz Biotechnology, Dallas, Tex.; and catalog #ab1669, ab1664, and ab59550 from abcam, Cambridge, Mass.). CCR4 antibodies can be modified to remove/inactivate the Fc region, for example using the methods described in Example 1 or pepsin.

Glucocorticoid induced tumor necrosis factor (TNF) receptor (GITR) is a surface receptor molecule involved in inhibiting the suppressive activity of T-regulatory cells and extending the survival of T-effector cells. GITR sequences are known for several organisms (e.g., see GenBank® Accession Nos: NP_004186.1, NP_033426.1, NP_001171879.1, NP_001019520.2, and NP_001026045.1). In addition, antibodies specific for GITR are publicly available from commercial sources (e.g., catalog #sc-5759, sc-53972, and sc-355391, from Santa Cruz Biotechnology, Dallas, Tex.; and catalog #ab129272, ab86574, and ab10030 from abcam, Cambridge, Mass.). GITR antibodies can be modified to remove/inactivate the Fc region, for example using the methods described in Example 1 or pepsin.

OX40, also known as tumor necrosis factor receptor superfamily, member 4 (TNFRSF4) or CD134, is a secondary co-stimulatory immune checkpoint molecule, expressed after 24 to 72 hours following activation. OX40 sequences are known for several organisms (e.g., see GenBank® Accession Nos: NP_003318.1, CAA59476.1, NP_035789.1, CAB96543.1, and NP_037181.1). In addition, antibodies specific for OX40 are publicly available from commercial sources (e.g., catalog #sc-20073, sc-10938, and sc-11404, from Santa Cruz Biotechnology, Dallas, Tex.; and catalog #ab203220, ab119904, and ab76000 from abcam, Cambridge, Mass.). OX40 antibodies can be modified to remove/inactivate the Fc region, for example using the methods described in Example 1 or pepsin.

Folate receptor 4 (FR4), also known as Juno and IZUMO1R, is located on the surface of the mammalian egg cell that recognizes its sperm-riding counterpart, IZUMO1, and facilitates fertilization. FR4 is also expressed at high levels in transforming growth factor-beta (TGF-β)-induced Tregs and natural Tregs. The FR4 transcript variant, FR4D3, in which exon 3 is deleted, is predominantly expressed in CD4+CD25+ Treg cells. FR4 sequences are known for several organisms (e.g., see GenBank® Accession Nos: A6ND01.3, XP_006510599.1, and XP_006510596.1). In addition, antibodies specific for FR4 are publicly available from commercial sources (e.g., catalog #sc-39969 from Santa Cruz Biotechnology, Dallas, Tex.; and catalog #ab53682 and ab170535 from abcam, Cambridge, Mass.). FR4 antibodies can be modified to remove/inactivate the Fc region, for example using the methods described in Example 1 or pepsin.

Cytotoxic T-lymphocyte-associated protein 4 (CTLA4), also known as CD152, is a protein receptor that, functioning as an immune checkpoint, downregulates the immune system. CTLA4 is found on the surface of T cells. CTLA4 sequences are known for several organisms (e.g., see GenBank® Accession Nos: P16410.3, NP_001268905.1, NP_113862.1, NP_001009236.1, and T09536). In addition, antibodies specific for CTLA4 are publicly available from commercial sources (e.g., catalog #sc-1630 and sc-909 from Santa Cruz Biotechnology, Dallas, Tex.; and catalog #ab134090, ab19792, and ab102730 from abcam, Cambridge, Mass.). In one example, the CTLA4 antibody is ipilimumab (e.g., one containing on FC portion). In one example, the CTLA4 antibody is tremelimumab (e.g., one containing on FC portion). CTLA4 antibodies can be modified to remove/inactivate the Fc region, for example using the methods described in Example 1 or pepsin.

CD103 (cluster of differentiation 103), also known as integrin alpha E (ITGAE), is an integrin found on the surface of mature Tregs. CD103 binds integrin beta 7 (β7-ITGB7) to form the complete heterodimeric integrin molecule αEβ7. CD103 sequences are known for several organisms (e.g., see GenBank® Accession Nos: NP_002199.3, NP_032425.2, AAM27173.1, AAI13437.1, and NP_113956.2). In addition, antibodies specific for CD103 are publicly available from commercial sources (e.g., monoclonal antibody Ber-ACT8 from Miltenyl Biotech and catalog #129202 and ab128756 from abcam, Cambridge, Mass.). CD103 antibodies can be modified to remove/inactivate the Fc region, for example using the methods described in Example 1 or pepsin.

Type II Natural Killer T Cells

If the suppressor cell to be killed/targeted is a Type II NKT cell, anti-CD16 and/or anti-CD56 antibodies (e.g., without a functional Fc region) can be used as part of the antibody-IR700 molecule.

CD16 has been identified as Fc receptors FcγRIIIa (CD16a) and FcγRIIIb (CD16b). These receptors bind to the Fc portion of IgG antibodies which then activates NK cells for antibody-dependent cell-mediated cytotoxicity. CD16 sequences are known for several organisms (e.g., see GenBank® Accession Nos: NP_001121064.1, NP_001231682.1, NP_034318.2, BAA92348.1, and AAH36723.1). In addition, antibodies specific for CD16 are publicly available from commercial sources (e.g., catalog #sc-19620, sc-58962, and sc-52376, from Santa Cruz Biotechnology, Dallas, Tex.; and catalog #ab183354, ab203883, and ab664 from abcam, Cambridge, Mass.). CD16 antibodies can be modified to remove/inactivate the Fc portion, for example using the methods described in Example 1 or pepsin.

CD56, also known as neural-cell adhesion molecule (NCAM), is a glycoprotein of the Ig-superfamily, which is expressed on resting and activated NK cells. The extracellular domain of CD56 consists of five immunoglobulin-like (Ig) domains followed by two fibronectin type III (FNIII) domains. CD56 sequences are known for several organisms (e.g., see GenBank® Accession Nos: NP_000606.3, NP_851996.2, NP_001074914.1, NP_851996.2, and NP_113709.1). In addition, antibodies specific for CD56 are publicly available from commercial sources (e.g., catalog #sc-71651 and sc-7326 from Santa Cruz Biotechnology, Dallas, Tex.; and catalog #ab191105 and ab9018 from abcam, Cambridge, Mass.). CD56 antibodies can be modified to remove/inactivate the Fc portion, for example using the methods described in Example 1 or pepsin.

CD8⁺CD122⁺ Treg

If the suppressor cell to be killed/targeted is a CD8⁺ CD122⁺ Treg, anti-CD8 and/or anti-CD122 antibodies (e.g., without a functional Fc region) can be used as part of the antibody-IR700 molecule.

Cluster of differentiation 8 (CD8) is a transmembrane glycoprotein that serves as a co-receptor for the T cell receptor, binds to the class I major histocompatibility complex (MHC). There are two isoforms, alpha and beta. CD8 sequences are known for several organisms (e.g., see GenBank® Accession Nos: NP_001139345.1, NP_001074579.1, XP_006505528.1, AAB21671.2, and EDK98935.1). In addition, antibodies specific for CD8 are publicly available from commercial sources (e.g., catalog #sc-1177, sc-7970, and sc-25277, from Santa Cruz Biotechnology, Dallas, Tex.; and catalog #ab93278, ab22378, and ab34364 from abcam, Cambridge, Mass.). CD8 antibodies can be modified to remove/inactivate the Fc portion, for example using the methods described in Example 1 or pepsin.

CD122, also known as interleukin-2 receptor subunit beta (IL2RB), is a type I membrane protein involved in T cell-mediated immune responses. CD122 sequences are known for several organisms (e.g., see GenBank® Accession Nos: NP_000869.1, NP_032394.1, NP_037327.1, NP_001274237.1, and P16297.1). In addition, antibodies specific for CD122 are publicly available from commercial sources (e.g., catalog #sc-19583 from Santa Cruz Biotechnology, Dallas, Tex.; and catalog #ab61195 and ab62699 from abcam, Cambridge, Mass.). CD122 antibodies can be modified to remove/inactivate the Fc portion, for example using the methods described in Example 1 or pepsin.

M2 Macrophage Cell

If the suppressor cell to be killed/targeted is a M2 macrophage cell, anti-CD23, anti-CD163, anti-CD206, anti-CD11b, anti-Gr-1, anti-CD14, anti-IL-4Ra, anti-IL-1Ra, and/or anti-IL-1 decoy receptor antibodies (e.g., without a functional Fc region) can be used as part of the antibody-IR700 molecule.

CD23, also known as Fc epsilon RII is the low-affinity receptor for IgE, and plays a role in antibody feedback regulation. Isoform CD23b is expressed on T-cells. CD23 sequences are known for several organisms (e.g., see GenBank® Accession Nos: NP_001193948.2, NP_001240666.1, and NP_598234.2). In addition, antibodies specific for CD23 are publicly available from commercial sources (e.g., catalog #sc-7023, sc-23923, and sc-18910, from Santa Cruz Biotechnology, Dallas, Tex.; and catalog #ab92495, ab16702, and ab135386 from abcam, Cambridge, Mass.). CD23 antibodies can be modified to remove/inactivate the Fc portion, for example using the methods described in Example 1 or pepsin.

Cluster of differentiation 163 (CD163) is a transmembrane scavenger receptor for the hemoglobin-haptoglobin complex. CD163 sequences are known for several organisms (e.g., see GenBank® Accession Nos: CAB45233.1, NP_004235.4, Q86VB7.2, NP_001163866.1, and Q2VLH6.2). In addition, antibodies specific for CD163 are publicly available from commercial sources (e.g., catalog #sc20066, sc33715, and sc-58965 from Santa Cruz Biotechnology, Dallas, Tex.; and catalog #ab17051 and ab87099 from abcam, Cambridge, Mass.). CD163 antibodies can be modified to remove/inactivate the Fc portion, for example using the methods described in Example 1 or pepsin.

Cluster of differentiation 206 (CD206), also known as mannose receptor C type 1 (MC1), is present on the surface of macrophages, immature dendritic cells, and surface of skin cells such as human dermal fibroblasts and keratinocytes. CD206 sequences are known for several organisms (e.g., see GenBank® Accession Nos: NP_002429.1, AAI41339.1, and NP_001086907.2). In addition, antibodies specific for CD206 are publicly available from commercial sources (e.g., catalog #sc-58986, sc-70585, and sc-70586, from Santa Cruz Biotechnology, Dallas, Tex.; and catalog #ab8918, ab64693, and ab117644 from abcam, Cambridge, Mass.). CD206 antibodies can be modified to remove/inactivate the Fc portion, for example using the methods described in Example 1 or pepsin.

Cluster of differentiation 11b (CD11b), also known as integrin alpha M (ITGAM), is one protein subunit that forms the heterodimeric integrin alpha-M beta-2 ($\alpha M\beta 2$) molecule. $\alpha M\beta 2$ is expressed on the surface of many leukocytes involved in the innate immune system, including monocytes, granulocytes, macrophages, and natural killer cells. CD11b sequences are known for several organisms (e.g., see GenBank® Accession Nos: NP_000623.2, NP_001076429.1, and EDM17198.1). In addition, antibodies specific for CD11b are publicly available from commercial sources (e.g., catalog #sc-20050, sc-1186, and sc28664, from Santa Cruz Biotechnology, Dallas, Tex.; and catalog #ab64347, ab52478, and ab8878 from abcam, Cambridge, Mass.). CD11b antibodies can be modified to remove/inactivate the Fc portion, for example using the methods described in Example 1 or pepsin.

Gr-1, also known as lymphocyte antigen 6 complex, locus C1 (Ly-6C) or lymphocyte antigen 6 complex, locus G (Ly-6G), is a glycosylphosphatidylinositol (GPI)-linked protein. It is a myeloid differentiation antigen expressed on granulocytes and macrophages. Gr-1 sequences are known for several organisms (e.g., see GenBank® Accession Nos: NP_001297367.1, AAA39469.1, and P35461.1). In addition, antibodies specific for Gr-1 are publicly available from commercial sources (e.g., catalog #sc-53515 and sc-103603 from Santa Cruz Biotechnology, Dallas, Tex.; and catalog #ab25377, ab171254, and ab134775 from abcam, Cambridge, Mass.). Gr-1 antibodies can be modified to remove/inactivate the Fc portion, for example using the methods described in Example 1 or pepsin.

Cluster of differentiation 14 (CD14) acts as a co-receptor (along with the Toll-like receptor TLR 4 and MD-2) for the detection of bacterial lipopolysaccharide. It is expressed by macrophgates and to a lesser extent by neutrophils and dendritic cells. CD14 sequences are known for several organisms (e.g., see GenBank® Accession Nos: NP_000582.1, P08571.2, NP_033971.1, CAA32166.1, and BAA21517.1). In addition, antibodies specific for CD14 are publicly available from commercial sources (e.g., catalog #sc-1182, sc-5749 and sc-6998 from Santa Cruz Biotechnology, Dallas, Tex.; and catalog #ab133335, ab183322, and ab182032 from abcam, Cambridge, Mass.). CD14 antibodies can be modified to remove/inactivate the Fc portion, for example using the methods described in Example 1 or pepsin.

IL-4Ra, also known as interleukin 4 receptor (IL4R), is the alpha chain of the IL4R and a type I transmembrane protein that can bind interleukin 4 to promote differentiation of Th2 cells. IL-4Ra sequences are known for several organisms (e.g., see GenBank® Accession Nos: NP_000409.1, NP_596871.2, NP_001008700.1, P24394.1, and NP_001075243.1). In addition, antibodies specific for IL-4Ra are publicly available from commercial sources (e.g., catalog #LS-C70896 from LifeSpan BioSciences, Inc., Seattle, Wash.; and catalog #ab131058 and ab50277 from abcam, Cambridge, Mass.). IL-4Ra antibodies can be modified to remove/inactivate the Fc portion, for example using the methods described in Example 1 or pepsin.

Interleukin-1 receptor alpha (IL-1Ra), also known as IL1 type I (IL-1R1) and CD121a) is a cytokine receptor that binds IL1 alpha, IL1 beta and IL1R antagonist. IL-1Ra sequences are known for several organisms (e.g., see GenBank® Accession Nos: NP_000868.1, NP_001116854.1, JAA43683.1, and NP_037255.3). In addition, antibodies specific for IL-1Ra are publicly available from commercial sources (e.g., catalog #sc-688 and sc-66054 from Santa Cruz Biotechnology, Dallas, Tex.; and catalog #ab106278 and ab115497 from abcam, Cambridge, Mass.). IL-1Ra antibodies can be modified to remove/inactivate the Fc portion, for example using the methods described in Example 1 or pepsin.

Interleukin-1 decoy receptor, also known as IL1 type II (IL-1R2) and CD121b) is a cytokine receptor that binds IL1 alpha, IL1 beta and IL-1Ra, and acts as a decoy receptor that inhibits the activity of its ligands. IL-1 decoy receptor sequences are known for several organisms (e.g., see GenBank® Accession Nos: AAH39031.1, NP_001248348.1, NP_034685.1, and AAH91564.1). In addition, antibodies specific for IL-1 decoy receptor are publicly available from commercial sources (e.g., catalog #sc-27854 and sc-52678 from Santa Cruz Biotechnology, Dallas, Tex.; and catalog #ab89159 and ab97388 from abcam, Cambridge, Mass.). IL-1 decoy receptor antibodies can be modified to remove/inactivate the Fc portion, for example using the methods described in Example 1 or pepsin.

Tumor Infiltrating Fibroblast

If the suppressor cell to be killed/targeted is a tumor infiltrating fibroblast, anti-fibroblast activation protein (FAP) antibodies (e.g., without a functional Fc region) can be used as part of the antibody-IR700 molecule.

FAP, also known as seprase, is a homodimeric integral membrane gelatinase belonging to the serine protease family. FAP is selectively expressed in reactive stromal fibroblasts of epithelial cancers, granulation tissue of healing wounds, and malignant cells of bone and soft tissue sarcomas. FAP sequences are known for several organisms (e.g., see GenBank® Accession Nos: AAB49652.1, CAA71116.1, BAI47344.1, JAA21430.1, and DAA32677.1). In addition, antibodies specific for FAP are publicly available from commercial sources (e.g., catalog #ab53066 and ab54651 from abcam, Cambridge, Mass.), and disclosed in US 2012/0258119. FAP antibodies can be modified to remove/inactivate the Fc portion, for example using the methods described in Example 1 or pepsin.

Myeloid-Derived Suppressor Cell

If the suppressor cell to be killed/targeted is a myeloid-derived suppressor cell, anti-CXCR2, -CD11b, -CD14, -CD33, and -CD66b antibodies (e.g., without a functional Fc region) can be used as part of the antibody-IR700 molecule.

C-X-C chemokine receptor type 2 (CXCR2), also known as IL8R8, is a receptor for interleukin 8. It transduces the signal through a G-protein-activated second messenger system. This receptor also binds to chemokine (C-X-C motif) ligand 1 (CXCL1/MGSA), a protein with melanoma growth stimulating activity. In addition, it binds ligands CXCL2, CXCL3, and CXC. CXCR2 sequences are known for several organisms (e.g., see GenBank® Accession Nos: NP_001548.1, NP_001161770.1, NP_034039.1, NP_058879.1, and ABC59060.1). In addition, antibodies specific for CXCR2 are publicly available from commercial sources (e.g., catalog #600-401-P54 from Rockland (Limerick, Pa.), and ab14935 and ab61100 from abcam, Cambridge, Mass.). CXCR2 antibodies can be modified to remove/inactivate the Fc portion, for example using the methods described in Example 1 or pepsin.

Cluster of differentiation 11b (CD11b), also known as integrin alpha M (ITGAM), is one protein subunit that forms the heterodimeric integrin alpha-M beta-2 ($\alpha M\beta 2$) molecule. $\alpha M\beta 2$ is expressed on the surface of many leukocytes involved in the innate immune system, including monocytes, granulocytes, macrophages, and natural killer cells. CD11b sequences are known for several organisms (e.g., see GenBank® Accession Nos: NP_000623.2, NP_001076429.1, and EDM17198.1). In addition, antibodies specific for CD11b are publicly available from commercial sources (e.g., catalog #sc-20050, sc-1186, and sc28664, from Santa Cruz Biotechnology, Dallas, Tex.; and catalog #ab64347, ab52478, and ab8878 from abcam, Cambridge, Mass.). CD11b antibodies can be modified to remove/inactivate the Fc portion, for example using the methods described in Example 1 or pepsin.

Cluster of differentiation 14 (CD14) acts as a co-receptor (along with the Toll-like receptor TLR 4 and MD-2) for the detection of bacterial lipopolysaccharide. It is expressed by macrophgates and to a lesser extent by neutrophils and dendritic cells. CD14 sequences are known for several organisms (e.g., see GenBank® Accession Nos: NP_000582.1, P08571.2, NP_033971.1, CAA32166.1, and BAA21517.1). In addition, antibodies specific for CD14 are publicly available from commercial sources (e.g., catalog #sc-1182, sc-5749 and sc-6998 from Santa Cruz Biotechnology, Dallas, Tex.; and catalog #ab133335, ab183322, and ab182032 from abcam, Cambridge, Mass.). CD14 antibodies can be modified to remove/inactivate the Fc portion, for example using the methods described in Example 1 or pepsin.

Cluster of differentiation 33 (CD33), also known as siglec-3, gp67 and p67, is a transmembrane receptor expressed on cells of myeloid lineage, and is also found on some lymphoid cells. CD33 sequences are known for several organisms (e.g., see GenBank® Accession Nos: NP_001076087.1, NP_001171079.1, NP_001763.3, NP_001104528.1, and NP_067268.1). In addition, antibodies specific for CD33 are publicly available from commercial sources (e.g., the recombinant, humanized anti-CD33 monoclonal antibody (IgG4 κ antibody hP67.6) which is part of gemiuzumab ozogamicin (from Pfizer/Wyeth-Ayerst Laboratories), the anti-CD33 antibody that is part of vadastuximab talirine (SGN-CD33A) Seattle Genetics), clone M195 (humanized IgG2a monoclonal, see Caron and Scheinberg, *Leuk. Lymphom.* 11:1-6, 2009), and catalog #ab199432 and ab19462 from abcam, Cambridge, Mass.). CD33 antibodies can be modified to remove/inactivate the Fc portion, for example using the methods described in Example 1 or pepsin.

CD66b, also known as carcinoembryonic antigen-related adhesion molecule 8 (CEACAM8), is a homodimeric integral membrane gelatinase belonging to the serine protease family CD66b is expressed on granulocytes and is involved in cell adhesion, cell migration, and pathogen binding. CD66b sequences are known for several organisms (e.g., see GenBank® Accession Nos: NP_001807.2, AAH26263.1, AAI20205.1, and XP_009433977.1). In addition, antibodies specific for CD66b are publicly available from commercial sources (e.g., catalog #ab197678 and ab170875 from abcam, Cambridge, Mass. and catalog #60086 from Stemcell Technologies, Vancouver, Canada). CD66b antibodies can be modified to remove/inactivate the Fc portion, for example using the methods described in Example 1 or pepsin.

Exemplary Tumors

The disclosed methods of killing suppressor cells using one or more antibody-IR700 molecules, can be used to treat (e.g., kill) tumor cells, such as a cancer cell, such as a cell in a patient with cancer. Suppressor cells can suppress effector T cells (Teff), NK cells, and/or dendritic cells to drive immunosuppression and prevent immune-mediated rejection of cancer. Thus, by reducing the number of viable suppressor cells using the disclosed methods, Teff (e.g., cytotoxic $CD8^+$ cells) are then available to kill the tumor/cancer cells.

Exemplary tumors that can be treated (e.g., killed) with the disclosed methods include but are not limited to: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrdm's macroglobulinemia, heavy chain disease). In another example the cell is a solid tumor cell, such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinomna, lung cancer, colorectal cancer, head and neck cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Exemplary Subjects

In some examples the disclosed methods are used to treat a subject who has a tumor, such as a tumor described herein. In some examples, the tumor has been previously treated, such as surgically or chemically removed, and the disclosed methods are used subsequently to kill any remaining undesired tumor cells that may remain in the patient.

The disclosed methods can be used to treat any mammalian subject, such as a human, who has a tumor, such as a cancer, or has had such previously removed or treated. Subjects in need of the disclosed therapies can include human subjects having cancer. For example, the disclosed methods can be used as initial treatment for cancer either alone, or in combination with radiation or other chemotherapy or biotherapy (such as a monoclonal antibody therapy). The disclosed methods can also be used in patients who have failed previous radiation or chemotherapy. Thus, in some examples, the subject is one who has received other therapies, but those other therapies have not provided a desired therapeutic response. The disclosed methods can also be used in patients with localized and/or metastatic cancer.

Administration of Antibody-IR700 Molecules and Additional Therapeutic Agents

Antibody-IR700 molecules and additional therapeutic agents (such as anti-neoplastic agents) can be contacted with a suppressor cell in vitro, for example by adding the antibody-IR700 molecules and additional therapeutic to growth media in which the cells or growing, or can be contacted with a suppressor cell in vivo, for example by administering the antibody-IR700 molecules to the subject to be treated.

The antibody-IR700 molecules, as well as additional therapeutic agents, can be administered locally or systemically using any method known in the art, for example to subjects having a tumor, such as a cancer, or who has had a tumor previously removed (for example via surgery or other therapy). Although specific examples are provided, one skilled in the art will appreciate that alternative methods of administration of the disclosed antibody-IR700 molecules and additional therapeutic agents can be used. Such methods may include for example, the use of catheters or implantable pumps to provide continuous infusion over a period of several hours to several days into the subject in need of treatment.

In one example, the antibody-IR700 molecules and additional therapeutic agents are administered by parenteral means, including direct injection direct injection or infusion into a tumor (intratumorally). In some examples, the antibody-IR700 molecules and additional therapeutic agents are administered to the tumor by applying the antibody-IR700 molecules and additional therapeutic agents to the tumor, for example by bathing the tumor in a solution containing the antibody-IR700 molecules and additional therapeutic agents or by pouring the antibody-IR700 molecules and additional therapeutic agents onto the tumor.

In addition, or alternatively, the disclosed compositions (e.g., those containing one or more antibody-IR700 molecules) as well as additional therapeutic agents can be administered systemically, for example intravenously, intramuscularly, subcutaneously, intradermally, intraperitoneally, subcutaneously, or orally, to a subject having a tumor (such as cancer).

The dosages of the antibody-IR700 molecules (and additional therapeutic agents) to be administered to a subject are not subject to absolute limits, but will depend on the nature of the composition and its active ingredients and its unwanted side effects (e.g., immune response against the antibody), the subject being treated and the type of condition being treated and the manner of administration. Generally the dose will be a therapeutically effective amount, such as an amount sufficient to achieve a desired biological effect, for example an amount that is effective to decrease the size (e.g., volume and/or weight) of the tumor, or attenuate further growth of the tumor, or decrease undesired symptoms of the tumor. Dosages of additional therapeutic agents are known in the art.

For intravenous administration of the antibody-IR700 molecules, exemplary dosages for administration to a subject for a single treatment can range from 0.5 to 100 mg/60 kg of body weight, 1 to 100 mg/60 kg of body weight, 1 to 50 mg/60 kg of body weight, 1 to 20 mg/60 kg of body weight, for example about 1 or 2 mg/60 kg of body weight. In yet another example, a therapeutically effective amount of ip or intratumoral administered antibody-IR700 molecules can vary from 10 µg to 5000 µg of antibody-IR700 molecule to 1 kg of body weight, such as 10 µg/kg to 1000 µg/kg, 10 µg/kg to 500 µg/kg, or 100 µg/kg to 1000 µg/kg.

In one example, the dose of antibody-IR700 molecule administered to a human patient is at least 50 mg, such as at least 100 mg, at least 300 mg, at least 500 mg, at least 750 mg, or even 1 g, such as 50 to 100 mg.

Treatments with disclosed antibody-IR700 molecules (and additional therapeutic agents) can be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals. Thus, in some examples, the subject is treated at least 2 times, at least 3 times, at least 4 times, at least 5 times, at least 10 times, or at least 20 times (such as 2-5 times, or 3-4 times) with the disclosed antibody-IR700 molecules.

Irradiation of Suppressor Cells

After the suppressor cells are contacted with one or more antibody-IR700 molecules, they are irradiated. Methods of irradiation are well known in the art. As only suppressor cells expressing the suppressor cell surface protein(s) will be recognized by the antibody, only those suppressor cells will have sufficient amounts of the antibody-IR700 molecules bound to it. This decreases the likelihood of undesired side effects, such as killing of other immune cells, as the irradiation will only kill the cells to which the antibody-IR700 molecules are bound, not the other cells.

In some examples, suppressor cells are irradiated in vitro, such as in a tissue culture dish. In other examples, suppressor cells are irradiated in vivo, for example irradiating a subject who has previously been administered antibody-IR700 molecules. In some examples, the subject is irradiated, for example a tumor in the subject can be irradiated.

The suppressor cells (for example in a subject) are irradiated with a therapeutic dose of radiation at a wavelength of 660-710 nm, such as 660-700 nm, 680-700 nm, 670-690 nm, 670-710 nm, for example, 680 nm or 690 nm. In particular examples, suppressor cells (for example in a subject are irradiated at a dose of at least 1 J cm$^{-2}$, at least 2 J cm$^{-2}$, at least 3 J cm$^{-2}$, at least 4 J cm$^{-2}$, at least 5 J cm$^{-2}$, at least 6 J cm$^{-2}$, at least 7 J cm$^{-2}$, at least 8 J cm$^{-2}$, at least 9 J cm$^{-2}$, at least 10 J cm$^2$, at least 30 J cm', at least 50 J cm', at least 60 J cm', at least 100 J cm', or at least 500 J cm$^{-2}$ for example, 1-1000 J cm$^{-2}$, 1-500 J cm$^{-2}$, 4-10 J cm$^{-2}$, 4-8 J cm$^{-2}$, 4-65 J cm$^{-2}$, 30 to 50 J cm$^{-2}$, 10-100 J cm$^{-2}$, or 10-50 J cm$^{-2}$.

Suppressor cells (or patients) can be irradiated one or more times following administration of the antibody-IR700 molecules provided herein. Thus, irradiation can be completed in a single day, or may be done repeatedly on multiple days with the same or a different dosage (such as irradiation at least 2 different times, 3 different times, 4 different times 5 different times or 10 different times). Repeated irradiations may be done on the same day, on successive days, or every 1-3 days, every 3-7 days, every 1-2 weeks, every 2-4 weeks, every 1-2 months, or at even longer intervals. Thus, in some examples, the subject is irradiated with NIR at least 2 times, at least 3 times, at least 4 times, at least 5 times, at least 10 times, or at least 20 times.

Additional Treatments

As discussed above, prior to, during, or following administration of one or more antibody-IR700 molecules, the subject can receive one or more other therapies. In one example, the subject receives one or more treatments to remove or reduce the tumor prior to administration of the antibody-IR700 molecules. In one example, the subject receives one or more treatments following administration of the antibody-IR700 molecules. In some examples, the subject is treated with one or more anti-cytokine agents (such as tocilizumab, for example as an iv infusion at 4 to 8 mg/kg if following administration of one or more antibody-IR700 molecules and NIR irradiation, the subject suffers from side effects, for example due to the elevated cytokines/chemokines.

Examples of such therapies that can be used in combination with the disclosed methods, include but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and antioxidants, kinase inhibitors, biologics (e.g., antibodies) and other agents.

In some examples, the additional therapeutic agent (such as a radiotherapeutic agent, anti-neoplastic chemotherapeutic agent, antibiotic, alkylating agent, antioxidant, kinase inhibitors biologic (e.g., antibody, such as a monoclonal antibody) or other agents) is conjugated to (or otherwise associated with) a nanoparticle, such as one at least 1 nm in diameter (for example at least 10 nm in diameter, at least 30 nm in diameter, at least 100 nm in diameter, at least 200 nm in diameter, at least 300 nm in diameter, at least 500 nm in diameter, or at least 750 nm in diameter, such as 1 nm to 500 nm, 1 nm to 300 nm, 1 nm to 100 nm, 10 nm to 500 nm, or 10 nm to 300 nm in diameter).

Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, and gene regulators. These agents (which are administered at a therapeutically effective amount) and treatments can be used alone or in combination. Methods and therapeutic dosages of such agents are known to those skilled in the art, and can be determined by a skilled clinician.

"Microtubule binding agent" refers to an agent that interacts with tubulin to stabilize or destabilize microtubule formation thereby inhibiting cell division. Examples of microtubule binding agents that can be used in conjunction with the disclosed antibody-IR700 molecule therapies include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds can be used with the disclosed methods disclosed herein: suitable DNA and/or RNA transcription regulators, including, without limitation, anthracycline family members (for example, daunorubicin, doxorubicin, epirubicin, idarubicin, mitoxantrone, and valrubicin) and actinomycin D, as well as derivatives and analogs thereof also are suitable for use in combination with the disclosed therapies. DNA intercalators and cross-linking agents that can be administered to a subject include, without limitation, platinum compounds (for example, carboplatin, cisplatin, oxaliplatin, and BBR3464), mitomycins, such as mitomycin C, bleomycin, chlorambucil, cyclophosphamide, as well as busulfan, dacarbazine, mechlorethamine, procarbazine, temozolomide, thiotepa, and uramustine and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof. Kinase inhibitors include imatinib, gefitinib, and erolitinib that prevent phosphorylation and activation of growth factors.

In one example, the additional therapeutic agent is folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, gemcitabine, and derivatives and analogs thereof. In one example, the additional therapeutic agent is a plant alkaloid, such as *podophyllum* (for example, etoposide, and teniposide) and derivatives and analogs thereof. In one example, the additional therapeutic agent is an antimetabolite, such as cytotoxic/antitumor antibiotics, bleomycin, rifampicin, hydroxyurea, mitomyci, and derivatives and analogs thereof. In one example, the additional therapeutic agent is a topoisomerase inhibitor, such as topotecan, irinotecan, and derivatives and analogs thereof. In one example, the additional therapeutic agent is a photosensitizer, such as aminolevulinic acid, methyl aminolevulinate, porfimer sodium, verteporfin, and derivatives and analogs thereof. In one example, the additional therapeutic agent is a nitrogen mustard (for example, chlorambucil, chlormethine, cyclophosphamide, ifosfamide, and melphalan) or nitrosourea (for example, carmustine, fotemustine, lomustine, and streptozocin), and derivatives and analogs thereof.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, alitretinoin, altretamine, amsacrine, anagrelide, arsenic trioxide, asparaginase, axitinib, bexarotene, bevacizumab, bortezomib, celecoxib, denileukin diftitox, estramustine, hydroxycarbamide, lapatinib, pazopanib, pentostatin, masoprocol, mitotane, pegaspargase, tamoxifen, sorafenib, sunitinib, vemurafinib, vandetanib, tretinoin, and derivatives and analogs thereof.

Other therapeutic agents can include biologics, such as one or more therapeutic antibodies. Examples of such biologics include but are not limited to monoclonal antibodies, such as alemtuzumab, bevacizumab, cetuximab, gemtuzumab, rituximab, panitumumab, pertuzumab, trastuzumab, as well as those shown in Table 2. Other specific biologics and the corresponding tumors they can be used with are shown in Table 2.

TABLE 2

Exemplary Additional Treatments

| Exemplary Tumors | Exemplary Antibody/Small Molecules |
|---|---|
| Adenocarcinoma (e.g., colorectal cancer, head and neck cancer) | Cetuximab, panitumamab, zalutumumab, nimotuzumab, matuzumab. Small molecule inhibitors gefitinib, erlotinib, and lapatinib can also be used. |
| breast cancer, ovarian cancer, stomach cancer, uterine cancer | Trastuzumab (Herceptin ®), pertuzumab |
| Non-Hodgkin lymphoma | Tositumomab (Bexxar ®); Rituximab (Rituxan, Mabthera); or Ibritumomab tiuxetan (Zevalin, for example in combination with yttrium-90 or indium-111 therapy) |
| T-cell lymphoma | Daclizumab (Zenapax) |
| Acute myelogenous leukemia | Gemtuzumab (Mylotarg, for example in combination with calicheamicin therapy) |
| chronic lymphocytic leukemia | Alemtuzumab (Campath) |
| colorectal cancer, some gastric cancers, biliary cancer | CEA-scan (Fab fragment, approved by FDA), colo101 |
| ovarian cancer, mesothelioma, breast cancer | OC125 monoclonal antibody |
| hepatocellular carcinoma | ab75705 (available from Abcam) and other commercially available AFP antibodies |
| colorectal cancer, biliary cancer | B3 (Humanized) |
| adenocarcinomas including colorectal, pancreatic, gastric, ovarian, endometrial, mammary, and non-small cell lung cancer | B72.3 (FDA-approved monoclonal antibody) |
| Colorectal cancer | Bevacizumab (Avastin ®) |

In one example, the additional therapeutic agents that can be used include other antibody-IR700 molecules, wherein the antibody specifically binds to a tumor-specific protein, such as a Panitumumab-IR700 molecule, Trastuzumab-IR700 molecule, Basilitumab-IR700 molecule, Zenapax-IR700 molecule, Simitect-IR700 molecule, Cetuximab-IR700 molecule or J591-IR700 molecule. Other antibody-IR700 molecules that specifically bind to a tumor-specific protein include IR700 conjugated to one or more of the molecules listed in Table 2.

In one example, the additional therapeutic agent includes an anti-CD103-F(ab')2-IR700 molecule.

Specific examples of chemotherapies and bio-therapies that can be used with the disclosed methods include but are not limited to one or more of the following: 5-fluorouracil (e.g., Adrucil®, Efudex®, Fluoroplex®), Avastin® (bevacizumab), Camptosar® (Irinotecan Hydrochloride), capecitabine (e.g., Xeloda®), oxaliplatin (e.g., Eloxatin®), Erbitux® (cetuximab), leucovorin calcium, regorafenib, Stivarga® (Regorafenib), Vectibix® (Panitumumab), Wellcovorin® (Leucovorin Calcium), and Zaltrap® (Ziv-Aflibercept).

Examples of drug combinations that can be used in combination with the disclosed methods include but are not limited to: GSK2256098 and trametinib; VS-6063 and paclitaxel; Dasatinib and Erlotinib; Dasatinib and Bevacizumab; as well as Dasatinib and Dacarbazine.

In some examples, the subject receiving the therapeutic antibody-IR700 molecule composition is also administered interleukin-2 (IL-2), for example via intravenous administration. In particular examples, IL-2 (Chiron Corp., Emeryville, Calif.) is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the disclosed antibody-IR700 molecules are co-administered (or administered shortly before or after the NIR) with a fully human antibody to cytotoxic T-lymphocyte antigen-4 (anti-CTLA-4). In some example subjects receive at least 1 mg/kg anti-CTLA-4 (such as 3 mg/kg every 3 weeks or 3 mg/kg as the initial dose with subsequent doses reduced to 1 mg/kg every 3 weeks).

In one example, at least a portion of the tumor (such as a metastatic tumor) is surgically removed (for example via cryotherapy), irradiated, chemically treated (for example via chemoembolization), or combinations thereof, prior to administration of the disclosed therapies (such as administration of antibody-IR700 molecules). For example, a subject having a metastatic tumor can have all or part of the tumor surgically excised prior to administration of the disclosed therapies. In an example, one or more chemotherapeutic agents are administered following treatment with antibody-IR700 molecules and irradiation. In another particular example, the subject has a metastatic tumor and is administered radiation therapy, chemoembolization therapy, or both concurrently with the administration of the disclosed therapies.

Exemplary Devices Containing NIR LEDs

Any type of item that can be worn or placed on the body, and is amenable to the incorporation of NIR LEDs, can be used. In one example, the device is a chamber into which the patient is inserted. Such devices can be used to kill suppressor cells and/or tumor cells circulating in the blood or lymph, such as leukemias, lymphomas, as well as metastatic cells present in the blood or lymph.

In one example, suppressor cells circulating in the body are killed over an extended period of time, and in such cases the devices can be worn for an extended period of time, such as several weeks or months. Thus, these devices can be incorporated into every day clothing, jewelry and nightwear such as blankets. These devices make it possible to expose the patient to NIR light using portable everyday articles of clothing and jewelry so that treatment remains private and does not interfere with everyday activities. For instance, a necklace incorporating NIR LEDs can be customizable to the patient's tastes, and worn discreetly during the day for PIT therapy (for example by killing suppressor cells that pass through the carotid artery and other vasculature in the neck). Multiple devices of a similar "everyday" nature (blankets, bracelets, necklaces, underwear, socks, shoe inserts and the like) could be worn by the same patient during the treatment period. For example while sleeping, a patient could use the NIR blanket. The devices can also include a power supply, such as a battery, and a cooling element to prevent overheating for such devices as blankets.

In one example, the device is jewelry, such as a ring, watch, bracelet, or necklace. In another example, the item is an article of clothing or accessory, such as a shirt, belt, pants, underwear, socks, coat, shoe insert, scarf, hat, wrist guard, gloves, and the like. In another example, the device is an article that can cover the body, such as a blanket or towel. In another example, the device is a whole body light chamber that exposes the skin directly (such a device could also include a power supply and/or cooling supply).

By wearing the device that incorporates one or more NIR LEDs (such as at least 2, at least 3, at least 4, at least 5, at least 10, at least 20, or at least 50 NIR LEDs), suppressor cells to be killed that are present in the blood or lymph become exposed to the light generated by the NIR LEDs (such as an NIR LED that emits at 660 to 740 nm, such as 670 to 700 nm or 680 to 720 nm). The light emitted from the NIR LED can penetrate the skin and blood vessels (such as the carotid artery or microvasculature in the skin), thus allowing the light to activate the antibody-IR700 molecule bound to the target cells, thus killing the cells to which the antibody-IR700 molecule is bound. The NIR LEDs can be arranged in the device to ensure that the skin or the blood vessels or lymphatic system are targeted.

NIR LED devices that can be used in the methods provided herein are commercially available. The applicable products from one manufacturer, Marubeni America, are listed below. The first product, a molded LED, has low power but it could be used over a longer exposure time. The other options have higher power and thus may benefit from provisions for additional cooling. Except for the last one, which is packaged in a 25 mm×18 mm metal case, the others are applicable to wearable devices such as bracelets, necklace, underwear, socks, gloves, hats and other wearable items. All are usable in blankets, handheld devices or chambers.

For example, Marubeni America Corporation (tech-led.com/index.shtml) provides the following NIR LEDs with lens options to set the irradiation pattern: Molded LED (www.tech-led.com/data/L680-AU.pdf) which is 5 mm in diameter, has a total radiated power of 4 mW, calculated power density of 5 mW cm$^{-2}$ and a power requirement of 1.8V 20 mA; Surface Mount LED which is 3.5 mm×2.7 mm, has a total radiated power of 3 mW, calculated power density of 32 mW cm$^{-2}$, and a power requirement of 1.9V 50 mA; Super Beam (tech-led.com/Superbeam_LEDs.shtml) which is 7.6 mm×7.6 mm, has a total radiated power of 20-52 mW, calculated power density of 34-90 mW cm$^2$, and a power requirement of 1.65V 100 mA; High Power Surface Mount (tech-led.com/SMB_BL_LEDs.shtml) which is 5 mm×5 mm or 7 mm diameter, has a total radiated power of 90 mW, calculated power density of 360 mW cm$^{-2}$ and a power requirement of 2.4V 500 mA; and High Power Illuminators (tech-led.com/High_Power_Illuminators.shtml) which is 25 mm×18 mm, has a total radiated power of 150 mW, a calculated power density of 33 mW cm$^{-2}$ and a power requirement of 10V 120 mA. Alternatively, such devices can be made that emit light at 690 nm with a similar power with short strong intermittent pulse.

During in vitro experimentation, NIR light with a power density of 2.2 mW cm' (or 2.2 mJ s$^{-1}$ cm$^2$) induced cell death. Assuming an attenuation coefficient for tissue of 4 cm$^{-1}$, the intensity of the light would be down to 10% at 5.8 mm and 1% at 12 mm. This indicates that for in vivo applications, the power density may need to be 10-100 times larger. That is, the dose of light emitted by the NIR LED device in some examples is at least 20 mW cm$^{-2}$, such as at least 50 mW cm$^2$, at least 100 mW cm$^{-2}$, at least 150 mW cm$^{-2}$, at least 200 mW cm$^{-2}$ or, at least 300 mW cm$^{-2}$. Multiple NIR LEDs can be arranged in a two-dimensional array to cover larger areas. In one example, a laser is used as the NIR light source as an alternative to an LED.

The NIR LEDs can be powered by using a power supply (which may be directly or indirectly part of the device). The power supply requirement would depend on the number of LEDs in the device. For example, one or more batteries can be used to power the NIR LED. For some LEDs, 4 AA batteries can power 3 LEDs in series. An alkaline AA battery is rated at a maximum of 3000 mAh so this configuration provide powers for up to 150, 60, and 30 hr at 20, 50 and 100 mA.

In some examples, the device further includes a cooling device (which may be directly or indirectly part of the device). For example, heat sinks can be used for passive or active cooling. Another alternative is a thermoelectric effect (Peltier). This would draw additional power but it can be used in applications where the power requirements would need a plug-in AC adapter.

Another type of device that can be used with the disclosed methods is a flashlight-like device with NIR LEDs. Such a device can be used for focal therapy of lesions during surgery, or incorporated into endoscopes to apply NIR light to body surfaces after the administration of PIT agent. Such devices can be used by physicians or qualified health personnel to direct treatment to particular targets on the body.

Treatment Using Wearable NIR LEDs

As described herein, the disclosed methods are highly specific for suppressor cells. In some examples, suppressor cells circulating in the body can be killed in a patient wearing a device that incorporates an NIR LED. In some example the patient uses at least two devices, for example an article of clothing or jewelry during the day, and a blanket at night. In some example the patient uses at least two devices at the same time, for example two articles of clothing. These devices make it possible to expose the patient to NIR light using portable everyday articles of clothing and jewelry so that treatment remains private and does not interfere with everyday activities. In some examples, the device can be worn discreetly during the day for PIT therapy.

In one example, the patient is administered one or more antibody-IR700 molecules, using the methods described herein. The patient then wears a device that incorporates an NIR LED, permitting treatment (e.g., killing) of suppressor cells that are present in the blood or lymph. In some examples, the dose of irradiation is at least at least 1 J cm$^{-2}$, at least 10 J cm$^{-2}$, at least 20 J cm$^{-2}$, or at least 30 J cm$^2$, such as 20 J cm$^{-2}$ or 30 J/cm$^2$. In some examples, administration of the antibody-IR700 molecule is repeated over a period of time (such as bi-weekly or monthly, to ensure therapeutic levels are present in the body.

In some examples, the patient wears or uses the device, or combination of devices, for at least 1 week, such as at least 2 weeks, at least 4 weeks, at least 8 weeks, at least 12 weeks, at least 4 months, at least 6 months, or even at least 1 year. In some examples, the patient wears or uses the device, or combination of devices, for at least 1 hour a day, at least 2 hours 4 hours a day, such as at least 12 hours a day, at least 16 hours a day, at least 18 hours a day, or 24 hours a day, such as 1-2 hours per day, 1 to 4 hours per day, or 30 minutes to 6 hours per day. Multiple devices of a similar "everyday" nature (blankets, bracelets, necklaces, underwear, socks, shoe inserts) could be worn by the same patient during the treatment period. At night the patient can use the NIR LED blanket or other covering.

Antibody-IR700 Molecules

Also provided are antibody-IR700 molecules that can be used with the disclosed methods, wherein the antibody specifically binds to a suppressor cell surface protein, and in some examples does not include a functional Fc region. In some examples, the antibody is or consists of one or more F(ab')$_2$ fragments. In some examples, the antibody is or consists of one or more Fab fragments. In some examples, the ratio of antibody to IR700 is about 1:3. In some examples, the antibody is a monoclonal antibody or portion thereof (e.g., F(ab')$_2$ fragment or Fab fragment), such as a humanized monoclonal antibody or portion thereof (e.g., one or more F(ab')$_2$ fragments or Fab fragments).

In one example, the antibody that specifically binds to a suppressor cell surface protein is specific for: CD4, C-X-C chemokine receptor type 4 (CXCR4), C-C chemokine receptor type 4 (CCR4), cytotoxic T-lymphocyte-associated protein 4 (CTLA4), glucocorticoid induced TNF receptor (GITR), OX40, folate receptor 4 (FR4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), interleukin-1 decoy receptor, CD103, fibroblast activation protein (FAP), CXCR2, CD33, or CD66b. In one example, the antibody that specifically binds to a suppressor cell surface protein is specific for CD25, and the antibody does not include a functional Fc region. Because suppressor cell surface protein sequences are publically available (as for example shown above), one skilled in the art can make or purchase antibodies (or other small molecules that can be conjugated to IR700) specific for such proteins. For example, if the suppressor cell surface protein CD25 is selected as a target, antibodies specific for CD25 (such as daclizumab or basiliximab) can be purchased or generated and attached to the IR700 dye (e.g., see Example 1 below). In some examples, such antibodies are further modified to remove or inactivate the Fc region of the immunoglobulin.

In one example, the antibody-IR700 molecule is an anti-CD25-F(ab')2-IR700 molecule, such as one that includes daclizumab or basiliximab, for example daclizumab or basiliximab without a functional Fc region.

Thus, the disclosure also provides antibody-IR700 molecules, compositions that include such molecules, and kits that include such molecules. In one example a kit includes one or more antibody-IR700 molecules specific for: CD25 (such as basiliximab-IR700 or daclizumab-IR700, such as one that does not have a functional Fc region), CD4, C-X-C chemokine receptor type 4 (CXCR4), C-C chemokine receptor type 4 (CCR4), cytotoxic T-lymphocyte-associated protein 4 (CTLA4), glucocorticoid induced TNF receptor (GITR), OX40, folate receptor 4 (FR4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), interleukin-1 decoy receptor, CD103, fibroblast activation protein (FAP), CXCR2, CD33, or CD66b, and one or more additional anti-cancer therapies, such as a chemotherapeutic agent or biologic, or combinations thereof. Exemplary anti-cancer therapies that can be part of such a kit are provided above.

Example 1

Materials and Methods

Reagents

Water soluble, silicon-phthalocyanine derivative IRDye 700DX NHS ester was from LI-COR Bioscience (Lincoln, Nebr.). Anti-mouse CD25 antibody (PC-61.5.3) and Rat-IgG1 (HRPN) were from BioXCell (West Lebanon, N.H.). All other chemicals were of reagent grade.

Cell Culture

Luciferase expressing MC38 (mouse colon cancer), LL/2 (Lewis lung carcinoma), and TRAMP-C2 (prostate cancer) mouse cell lines (ATCC, Manassas, Va. MC38-luc, LL/2-luc, and TRAMP-C2-luc respectively) were established by transducing RediFect Red-FLuc lentiviral particles (PerkinElmer, Waltham, Mass.). High luciferase expression was confirmed with 10 passages. IL-2 dependent CD25-expressing mouse T lymphocyte HT-2 clone A5E cells (HT-2-A5E) were from ATCC. Cells were cultured in RPMI 1640 medium (Thermo Fisher Scientific Inc., Rockford, Ill.) supplemented with 10% fetal bovine serum and 100 IU/mL penicillin/100 μg/mL streptomycin (Thermo Fisher Scientific Inc.). For HT-2-A5E cell culture, 0.05 mM 2-mercaptoethanol and 0.1 nM human IL-2 (Roche, Nutley, N.J.) were also added.

Preparation of Anti-CD25-F(Ab')$_2$ and Control-F(Ab')$_2$

F(ab')$_2$ fragments of the anti-mouse CD25 antibody (PC-61.5.3, anti-CD25-F(ab')$_2$) and Rat-IgG1 as a control (control-F(ab')$_2$) were generated by digesting the whole antibody using immobilized ficin (Thermo Fisher Scientific Inc.) in 10 mM citrate buffer with 4 mM cysteine and 5 mM ethylenediaminetetraacetic acid (pH6.0) at 37° C. for 26 hr. After the digestion, the F(ab')$_2$ was purified with a high performance liquid chromatography (HPLC) using a G2000SWxL column and phosphate buffered saline (PBS) as the eluent (flow rate: 0.5 ml/min).

Conjugation of IR700 to the Anti-CD25-F(Ab')$_2$ or Control-F(Ab')$_2$

Anti-CD25-F(ab')$_2$ or control-F(ab')$_2$ (9.1 nmol) was incubated with IR700 NHS ester (45.5 nmol, LI-COR Bioscience) in 0.3 ml of 0.1 mol/L Na$_2$HPO$_4$ (pH 8.6) at room temperature for 1 hr. The mixture was purified with a Sephadex G25 column (PD-10; GE Healthcare, Piscataway, N.J.). The protein concentration was determined using the Coomassie Plus protein assay kit (Thermo Fisher Scientific Inc.) by measuring the absorption at 595 nm using 8453 Value System (Agilent Technologies, Santa Clara, Calif.). The concentration of IR700 was determined by measuring the absorption at 689 nm and the number of fluorophore molecules conjugated to each F(ab')$_2$ molecule was calculated. The conjugation was performed such that an average of three IR700 molecules were bound to a single F(ab')2.

SDS-PAGE was used to confirm the integrity of IR700 conjugated F(ab')$_2$ and the bioactivity was confirmed by examining its binding to the HT-2-A5E cells. The cells (1×10$^5$) were incubated with anti-CD25-F(ab')$_2$-IR700 (10 μg/mL) in medium for 1 to 6 hr at 37° C. To validate the specificity of the binding, a competition assay was performed by adding an excess untreated anti-CD25 antibody (50 μg). Cells were analyzed by flow cytometry (FACS Calibur, BD BioSciences, San Jose, Calif.) using CellQuest software (BD BioSciences).

Fluorescence Microscopy

The anti-CD25-F(ab')$_2$-IR700 was incubated with 10,000 HT-2-A5E cells at 10 μg/mL for 6 hr, washed with PBS, and added with propidium iodide (PI) (Life Technologies) at 2 μg/mL for 30 min. The cells were then exposed to near-infrared (NIR)-light (4 J/cm$^2$) and serial images were obtained using a fluorescence microscope (IX61; Olympus America, Melville, N.Y.) with a filter set for IR700 fluorescence (590-650 nm excitation filter; 665-740 nm band pass emission filter). The images were analyzed using the ImageJ software.

In Vitro NIR-PIT

One hundred thousand HT-2-A5E cells were seeded into 24-well plates and incubated with anti-CD25-F(ab')2-IR700 at 10 μg/mL for 6 hours at 37° C. After washing the cells with PBS, culture medium without phenol red was added. Then, the cells were irradiated with a NIR LED, which emits light at 670 to 710 nm wavelength (L690-66-60; Marubeni America Co., Santa Clara, Calif.). The actual power density (mW/cm$^2$) was measured with an optical power meter (PM 100, Thorlabs, Newton, N.J.). To determine the cytotoxic effects of PIT, PI was added to the cell suspension (final 2 μg/mL) 1 hour after irradiation, incubated at room temperature for 30 minutes, and then the PI stained (dead) cells were analyzed by flow cytometry.

Animal and Tumor Models

Eleven- to fifteen-week-old C57BL/6 mice or interferon gamma deficient (IFNγ-KO) mice (Jackson Laboratory, Bar Harbor, Me.) were inoculated with six million MC38-luc, LL/2-luc cells, or eight million TRAMP-C2-luc cells into right/left-dorsum. Mice with tumors approximately 150 mm$^3$ (6-7 mm in the diameter) were used for the experiments (around 5-7 days after inoculation). Mice were shaved at the tumor sites for irradiation and image analysis.

C57BL/6 albino mice were used for repeated local-NIR-PIT because C57BL/6 mice started to have skin pigmentation within 4 days after shaving and were not suitable for the experiments to detect luciferase activities. Mice were monitored daily, and tumor volumes were measured three times a week until the tumor (any tumor when mice have multiple tumors) diameter reached 2 cm, whereupon the mice were euthanized with carbon dioxide.

In Vivo IR700-Fluorescence Imaging

IR700-fluorescence images before and after the therapy were acquired serially with a fluorescence imager (Pearl Imager, LI-COR Bioscience).

In Vivo Local CD25-Targeted-NIR-PIT

Local CD25-targeted-NIR-PIT at the tumor was performed 6 days after the tumor inoculation for the mice bearing one tumor or at day 7 for the mice bearing multiple tumors. Mice were injected with 100 μg of anti-CD25-F(ab')$_2$-IR700 or control-F(ab')$_2$-IR700 and irradiated with NIR-light at 100 J/cm$^2$ unless otherwise specified to the right tumor on the following day.

Analysis of Tumor Infiltrating and Splenic Lung Lymphocytes

To determine the systemic effect of anti-CD25-F(ab')$_2$ administration on CD4$^+$CD25$^+$Foxp3$^+$Treg cells, 100 μg of anti-CD25-F(ab')$_2$ or anti-CD25-IgG were injected intravenously to mice and splenocytes were analyzed for the CD4$^+$CD25$^+$Foxp3$^+$Treg cells 1 day later. To determine the effects of anti-CD25-F(ab')$_2$-IR700 NIR-PIT on various lymphocytes, the tumors and spleen were harvested at indicated time after the NIR-PIT. To examine the potential side effects of local CD25-targeted-NIR-PIT, lungs were harvested at 1 day after the therapy. Single cell suspensions were prepared by passing the cut tissues through 70 μm filters, followed by ficoll centrifugation.

The cells were stained with antibodies against CD3e (145-2C11), CD8a (53-6.7), CD4 (RM4-5), CD25 (3C7), NK1.1 (PK136), CD19 (1D3), CD11c (N418), CD11b (M1/

70), Ly-6C (HK1.4), Ly-6G (1A8-Ly6g), CD86 (GL1), CD40 (3/23), and H-2Kb (AF6-88.5). Foxp3 and intracellular cytokine staining were performed using Foxp3/Transcription Factor Fixation/permeabilization concentrate and diluent (Affymetrics) and antibodies against Foxp3 (FJK-16s), IFNγ (XMG1.2) and IL-2 (JES6-5H4), following the manufactures instructions. All antibodies were from Affymetrics (San Diego, Calif.). The stained cells were applied to a flow cytometer and data were analyzed with FlowJo software (FlowJo LLC, Ashland, Oreg.).

Serum, Tissue, and Intratumoral Cytokine Analysis

Tumor Inoculation and treatment were performed as described. Serum was serially collected from the mice before and 1.5 hr and 1 day after the local CD25-targeted-NIR-PIT at the LL/2-luc tumor. Tumors were harvested and single cell suspensions were prepared by passing the cut tissues through 70 μm filters in PBS with Complete Protease Inhibitor Cocktail (Roche). Next, they were centrifuged at 5000 rpm for 15 min, and the supernatant was collected and filtered at 0.2 μm. The lungs or intestines were harvested and the samples were prepared in the same way. Protein concentrations of all samples were normalized using a BCA Assay (Thermo Fisher Scientific Inc.) and concentrations of various cytokines and chemokines were analyzed with Mouse Cytokine Array/Chemokine Array by EVE Technologies (Calgary, AB, Canada).

Immune Depletion of NK and CD8 T Cells and Neutralization of IFNγ In Vivo

Anti-NK1.1 (PK136) or anti-CD8a (2.43) depletion antibodies, or anti-IFNγ (XMG1.2) neutralization antibody were injected intraperitoneally every 2 days starting from 2 days before the PIT at a dose of 25 μg, 50 μg, 100 μg, respectively, until the mice were euthanized (See the regimen, FIG. 23A). All antibodies were from BioXCell.

Statistics

Data are expressed as means±s.e.m. from a minimum of four experiments, unless otherwise indicated. Statistical analyses were performed with a statistics program (GraphPad Prism; GraphPad Software, La Jolla, Calif.). For two group comparisons, Mann-Whitney test or unpaired t test was utilized. For multiple group comparisons, a one-way analysis of variance (ANOVA) with Tukey's test or Dunnett's test was used. The cumulative probability of survival, determined herein as the tumor diameter failing to reach 2 cm, was estimated in each group with the use of the Kaplan-Meier survival curve analysis, and the results were compared with the log-rank test and Wilcoxon test. $P<0.05$ was considered to indicate a statistically significant difference.

Example 2

Preparation of Anti-CD25-F(Ab')$_2$-IR700

A F(ab')$_2$ fragment of the anti-mouse CD25 antibody (anti-CD25-F(ab')$_2$) or Rat-IgG1 as a control, was generated as shown in FIG. 1. The resulting F(ab')$_2$ fragments do not have an Fc portion, and thus will not generate a significant ADCC response in vivo.

The resulting anti-CD25-F(ab')$_2$ antibody fragments were conjugated to IR700 as described in Example 1. The resulting conjugate (anti-CD25-F(ab')$_2$-IR700), having about three IR700 molecules per single F(ab')$_2$, was used in the experiments described below.

Example 3

In Vitro Characterization of Anti-CD25-F(Ab')$_2$-IR700

Figure 2B:
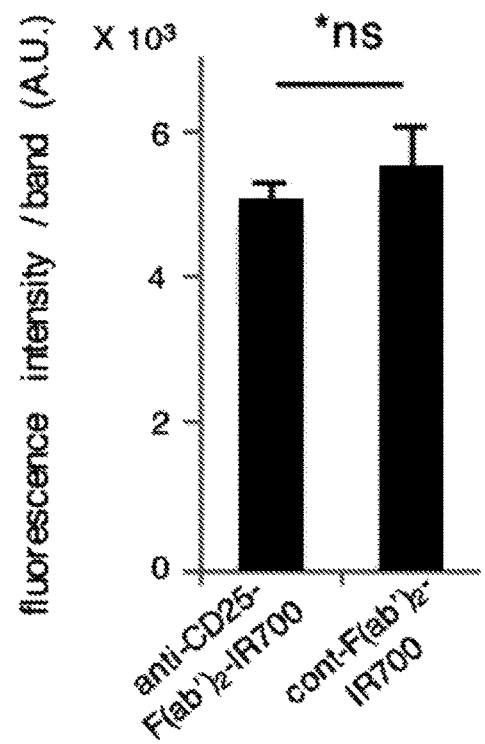

To avoid Fc-mediated antibody-dependent-cellular-cytotoxicity (ADCC) and complement-dependent-cytotoxicity (CDC) in vivo, F(ab')$_2$ were generated from an anti-CD25 antibody (anti-CD25-F(ab')$_2$) and a control IgG antibody (control-F(ab')$_2$). Both F(ab')$_2$ were purified using a high performance liquid chromatography (HPLC) with over 90% purity (about 97%) and conjugated with the IR700 dye (anti-CD25-F(ab')$_2$-IR700 and control-F(ab')$_2$-IR700, respectively) (FIGS. 2A and 2B). The anti-CD25-F(ab')2-IR700 demonstrated specific binding to CD25 expressed on a mouse T lymphocyte HT-2 clone A5E (HT-2-A5E) cells (FIG. 2C). These results indicated that the bioactivity and specificity of anti-CD25-F(ab')$_2$ was maintained during digestion, purification and conjugation.

Figure 3A:
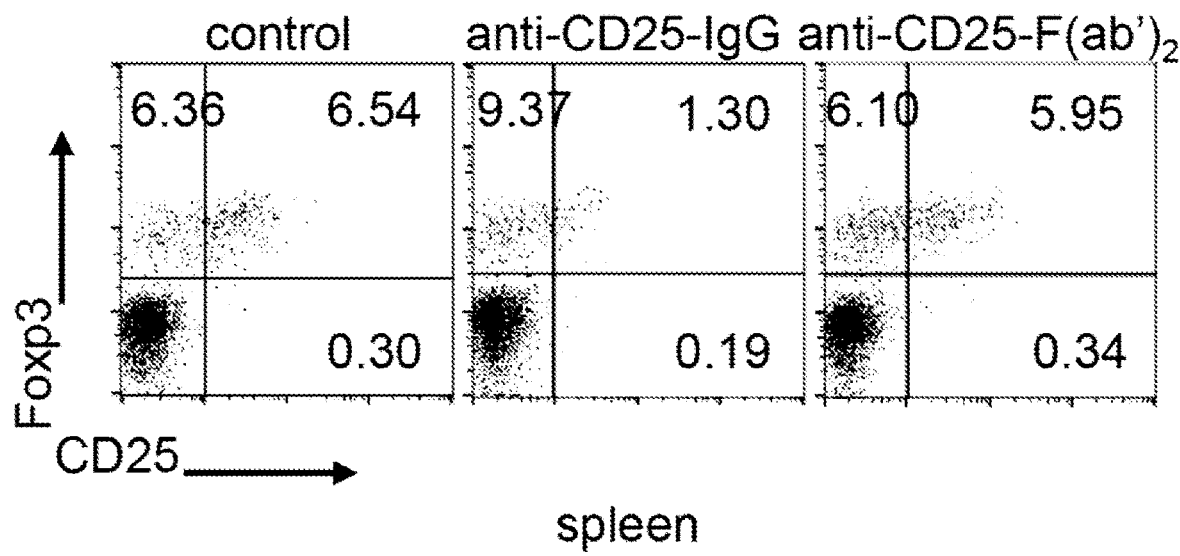
FIGS. 3A-3C show that anti-CD25-F(ab')2 administration lacks CD4+CD25+Foxp3+Treg depletion effect, but NIR- PIT with anti-CD25-F(ab')2-IR700 kills target cells. (A) Intravenously injected anti-CD25-IgG (100 μg) systemically depleted CD4+CD25+Foxp3+Tregs, but anti-CD25-F(ab')2 (100 μg) did not significantly deplete these cells within CD4 T cell population 1 day after the injection (n=3) (*p<0.0001, **ns, not significant, one way ANOVA with Dunnet test). (B) HT-2 A5E cells (mouse T lymphocyte) incubated with anti-CD25-F(ab')2-IR700 for 6 hr were examined under a microscope before and 0.5 hr after NIR-light irradiation (4 J/cm2). NIR-light irradiation induced cellular swelling, bleb formation, and necrosis of the cells as indicated with the propidium iodide (PI) staining (Bar=10 μm). (C) Necrotic cells death induced by NIR-PIT increased in a NIR-light dose-dependent manner when determined by flow cytometry analysis with PI staining (left graph. n=3, *:p<0.0001 vs. 0 J/cm2, unpaired t test). No significant cell killing was detected when a control-F(ab')2-IR700 was used (right graph, n=3, **ns, not significant vs. 0 J/cm2, unpaired t test).
Figure 3B:
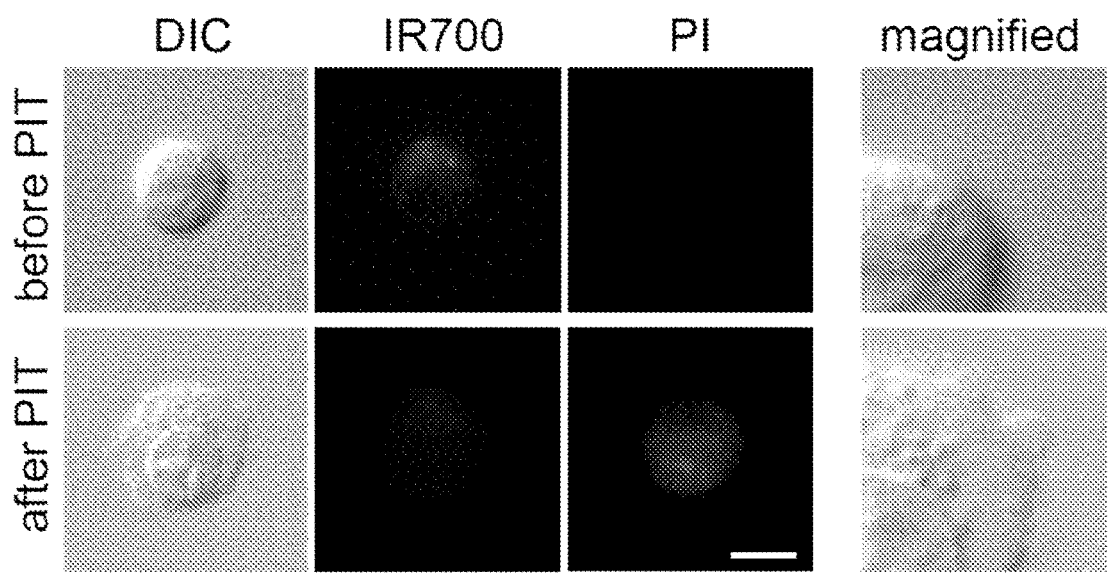
Figure 3C:
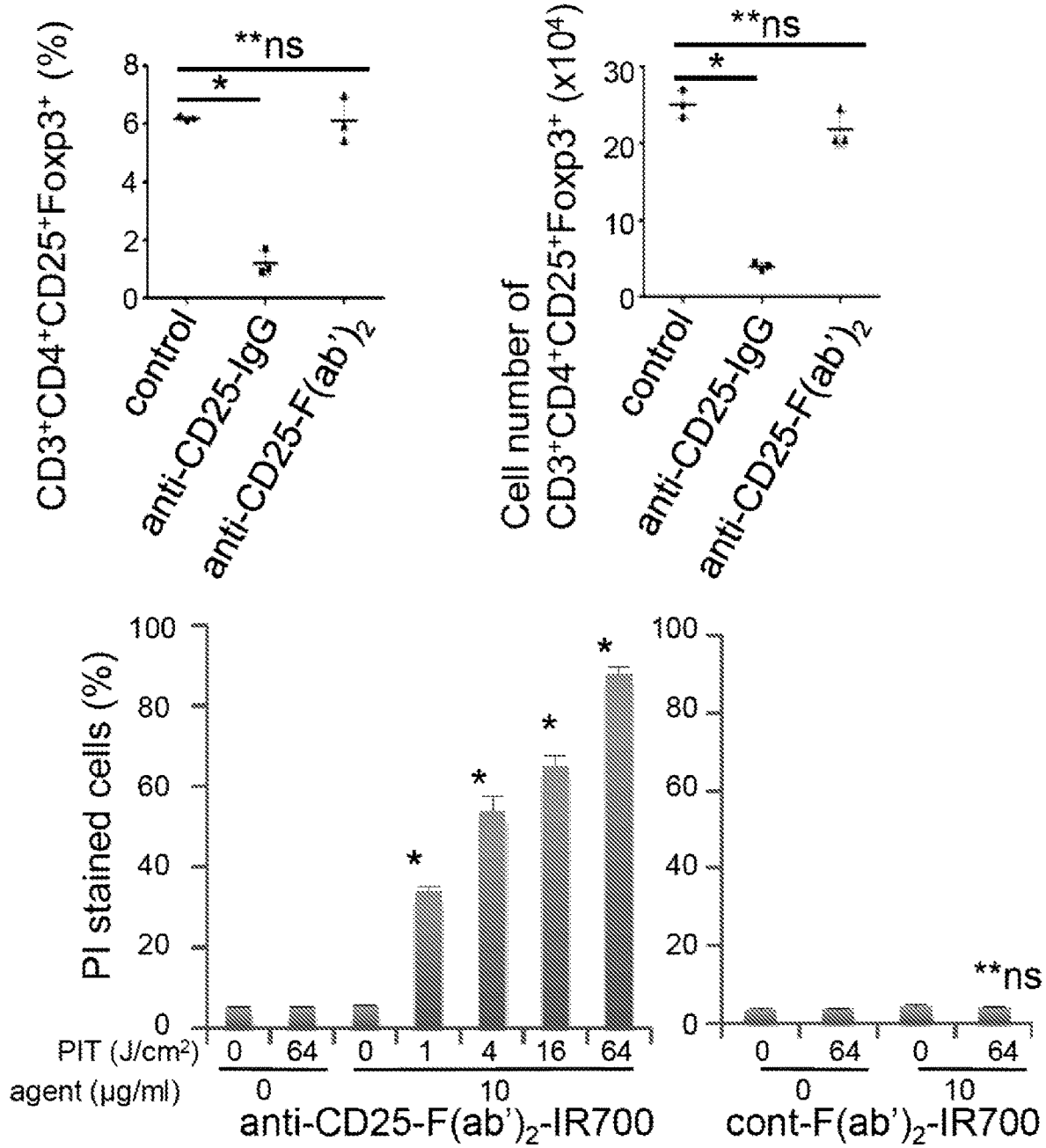
Figure 4A:
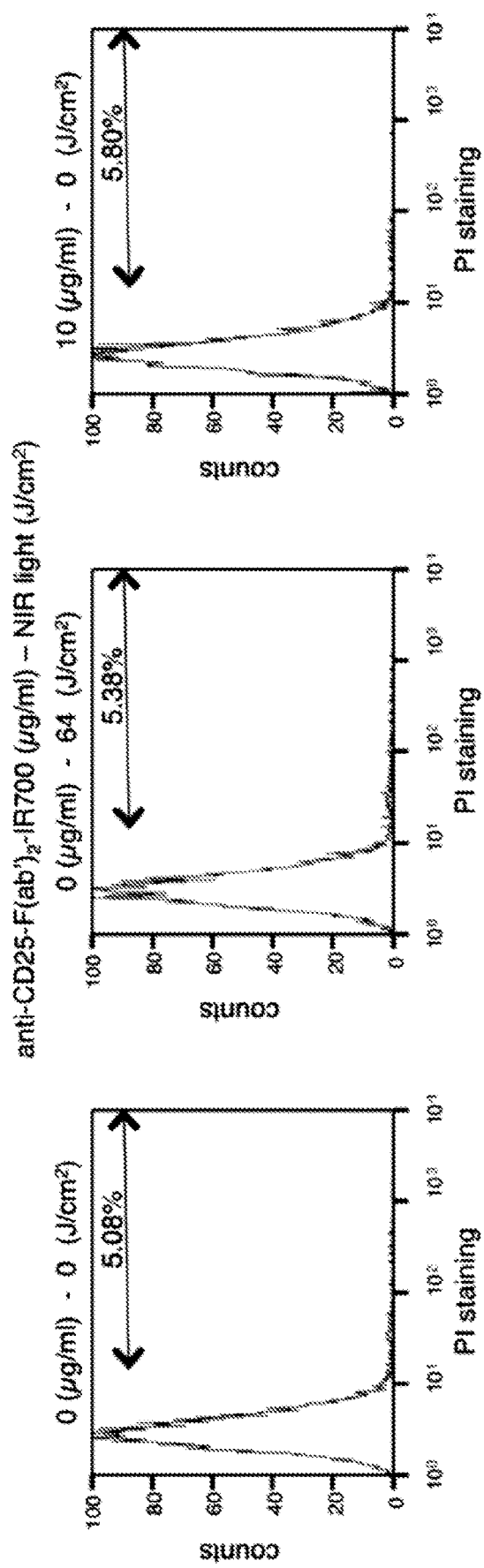
FIGS. 4A-4B are a series of graphs showing NIR-PIT using anti-CD25-F(ab')2-IR700 induces necrosis of CD25 expressing cells in a NIR-light dose-dependent manner. An in vitro anti-CD25-F(ab')2-IR700 NIR-PIT against CD25-expressing HT-2 A5E cells induced necrotic death of these cells in a NIR-light dose-dependent manner as indicated by the PI staining analyzed by flow cytometry.
Figure 4B:
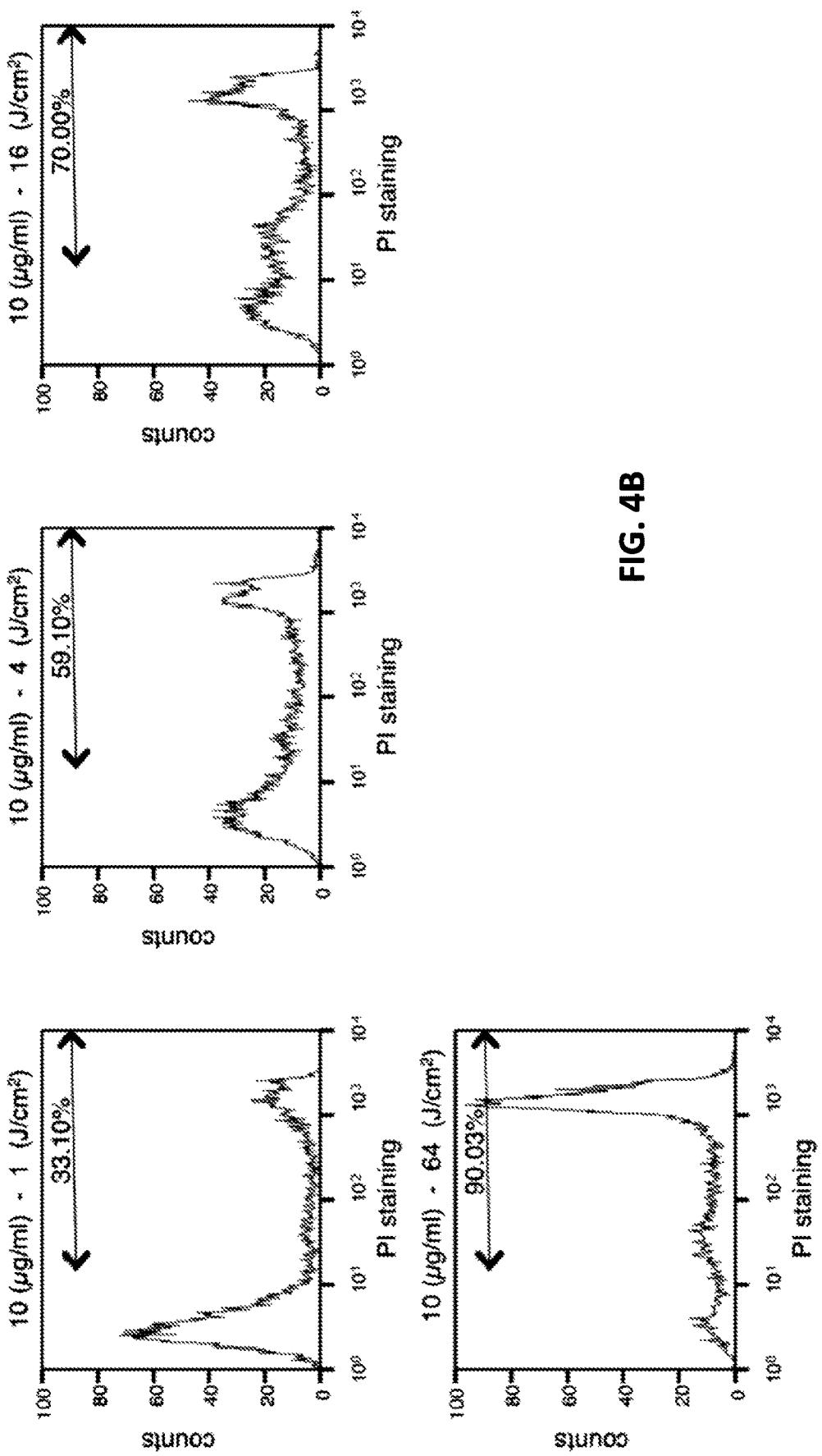

The absence of a systemic ADCC or CDC effect was confirmed by administering anti-CD25-F(ab')$_2$ (100 μg) to mice and analyzing the splenic CD4$^+$CD25$^+$Foxp3$^+$Tregs 1 day later. While administration of the intact anti-CD25-IgG caused a decrease in the frequency of Tregs among CD4 T cells, administration of Fc deficient anti-CD25-F(ab')$_2$ did not significantly deplete Tregs (FIG. 3A). In vitro NIR-PIT with anti-CD25-F(ab')$_2$-IR700 against HT-2-A5E cells induced cellular swelling and bleb formation (FIG. 3B), leading to necrotic cell death in a light-dose dependent manner (FIGS. 3C and 4A-4B). No significant cytotoxicity associated with NIR-light alone, anti-CD25-F(ab')$_2$-IR700 incubation alone or NIR light with control-F(ab')$_2$-IR700 incubation (FIG. 3C) was observed.

Thus, the anti-CD25-F(ab')$_2$-IR700 compound effectively induced necrotic cell death of CD25-expressing cells in vitro.

Example 4

CD4$^+$CD25+Foxp3$^+$ Tregs are Abundant in Tumors

Figure 5A:
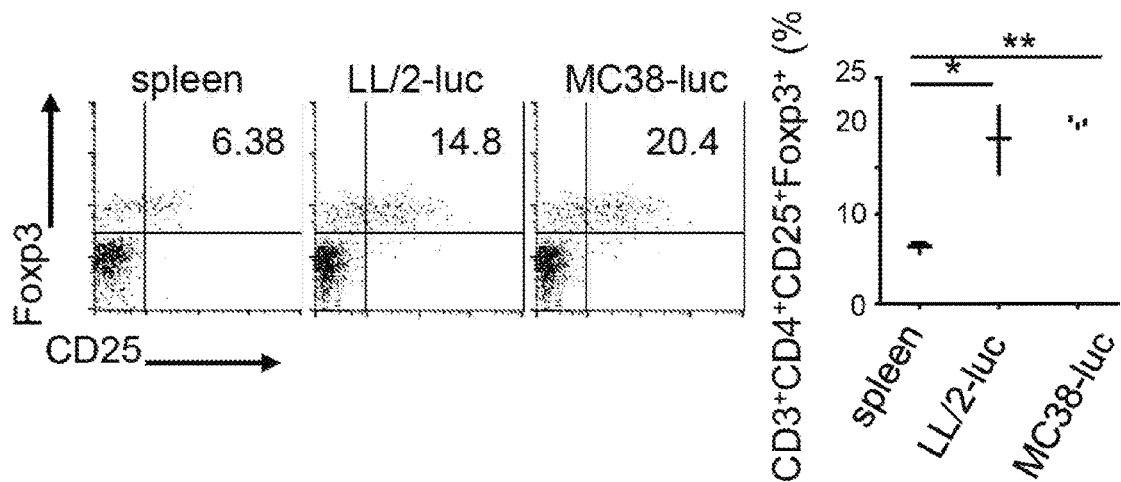
Figure 6:
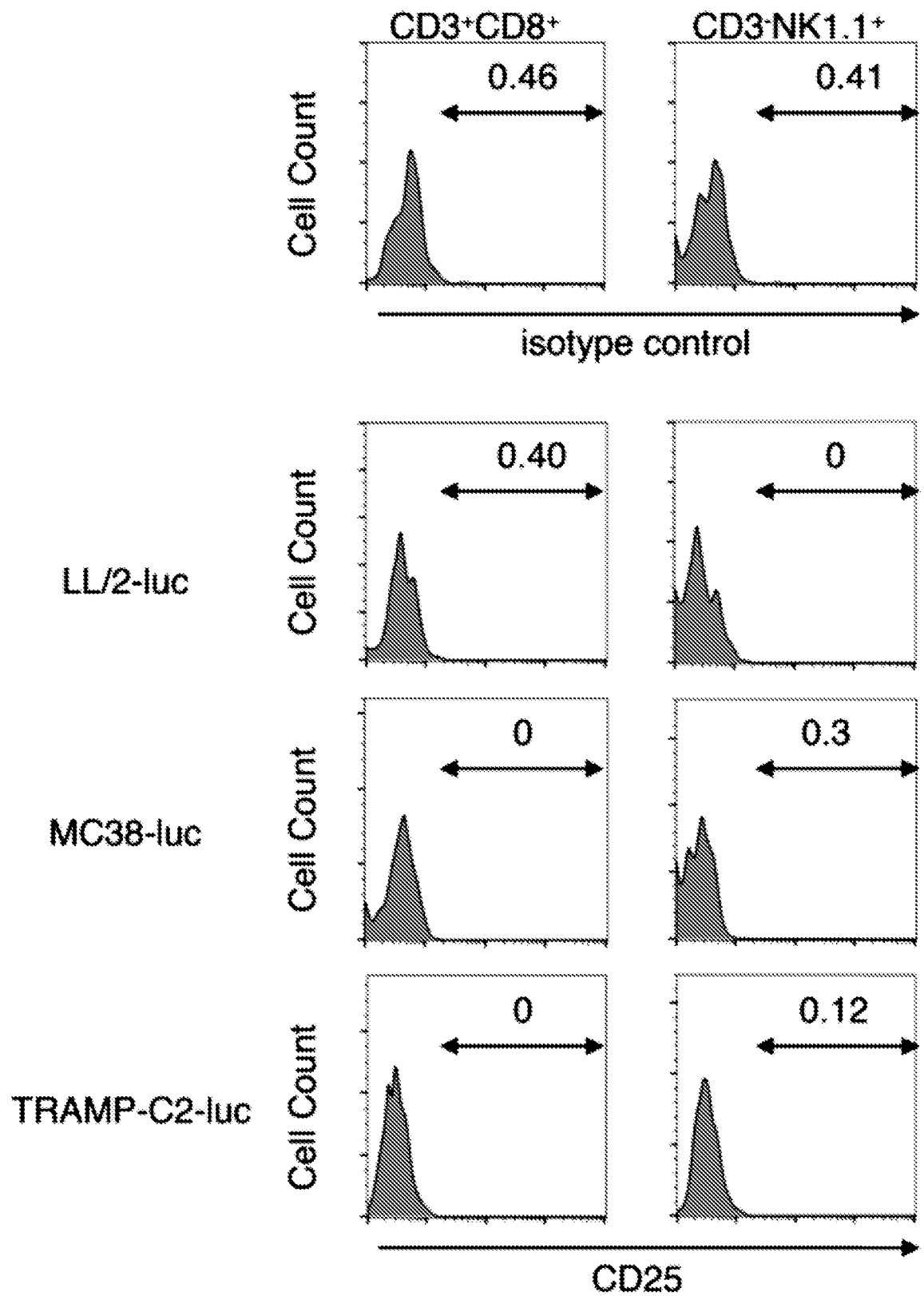
FIG. 6 shows a series of flow cytometry plots showing CD8 T and NK cells infiltrating tumors are not expressing CD25. Flow cytometry analysis of CD8 T cells and NK cells collected from LL/2-luc, MC38-luc, or TRAMP-C2 tumors indicated that these cells were not expressing CD25.
Figure 7:
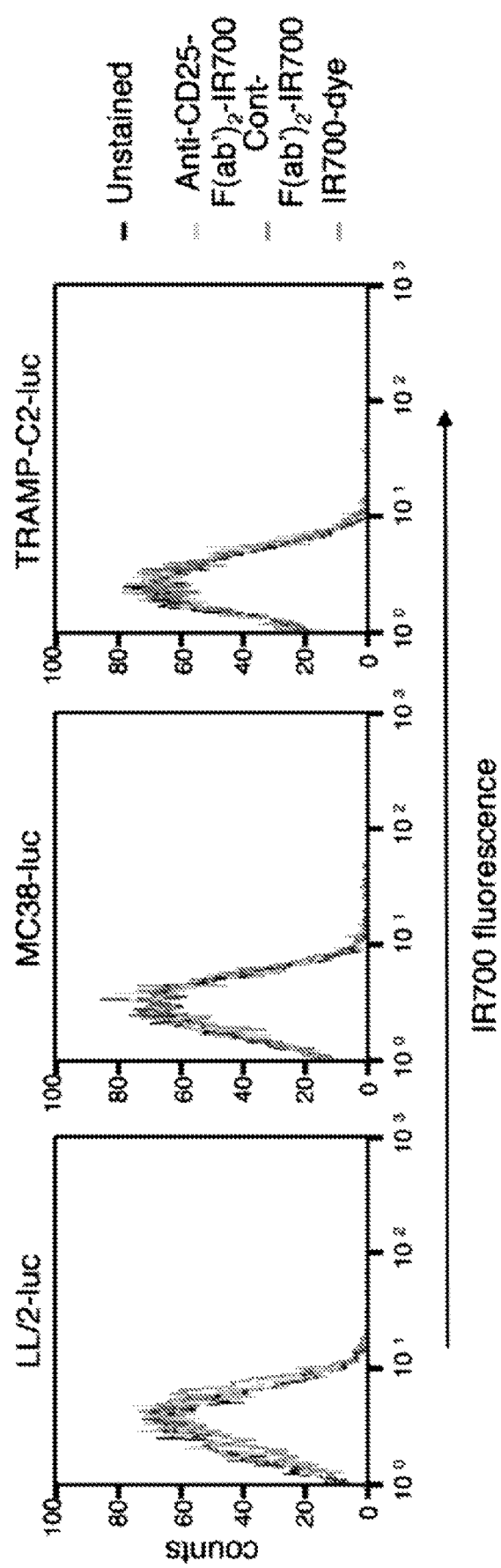
FIG. 7 shows a series of flow cytometry plots showing that anti-CD25-F(ab')2-IR700 does not bind to the tumor cells. Anti-CD25-F(ab')2-IR700, cont-IgG-F(ab')2-IR700, or IR700 dye incubated with LL/2-luc, MC38-luc, or TRAMP-C2 tumor cells showed no binding by flow cytometry analysis.

Tregs are abundant in various cancers (Colombo and Piconese, *Nat. Rev. Cancer* 7:880-887, 2007). Flow cytometry analysis of the CD25±Foxp3±Treg fraction in CD4 T cells indicated the increase of this cell population within LL/2-luc (Lewis lung cancer) and MC38-luc (colon cancer) tumors compared to the normal spleen (FIG. 5A). CD8 T cells and NK cells were also prevalent within tumors, which were CD25 negative before activation (FIG. 6). The anti-CD25-F(ab')$_2$-IR700 did not bind to the tumor cells (FIG. 7). These data indicate that CD4+CD25±Foxp3±Tregs are common within tumors and thus, are a target of anti-CD25-IR700 NIR-PIT.

Example 5

Figure 5B:
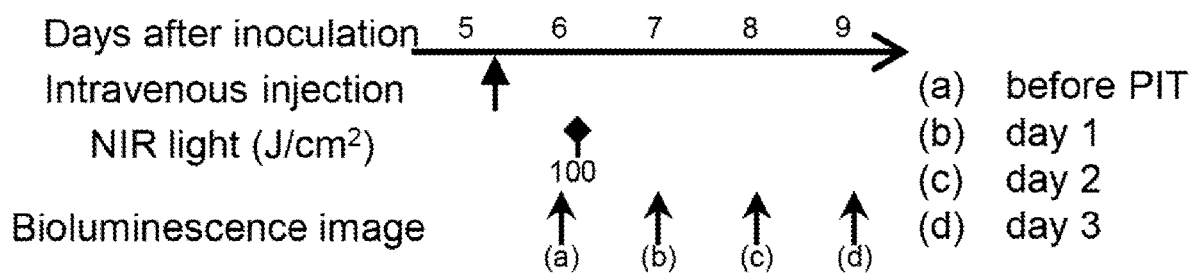
Figure 8:
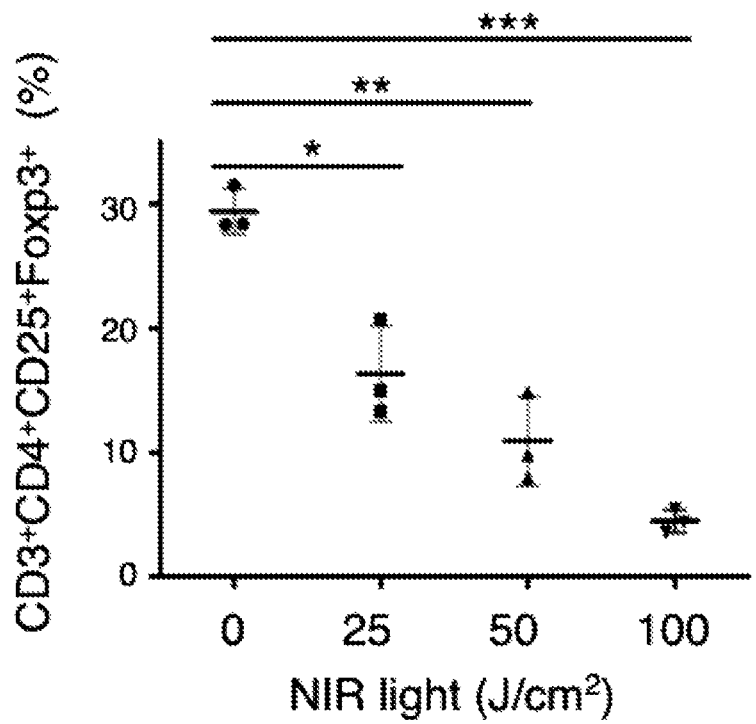
FIG. 8 is a plot showing that depletion of tumor-infiltrating CD4+CD25+Foxp3+Tregs with local CD25-targeted-NIR-PIT is NIR-light dose dependent. Lymphocytes were collected from LL/2-luc tumors before and 30 min after local CD25-targeted NIR-PIT using increasing doses of NIR-light. Flow cytometry analysis of CD4+CD25+Foxp3+ Tregs population within CD4 T cells indicated that Tregs decreased in a NIR-light dose-dependent manner (n=3) (*p<0.005, p<0.0005, *p<0.0001, vs. 0 J/cm2, Tukey's test with ANOVA).
Figure 9:
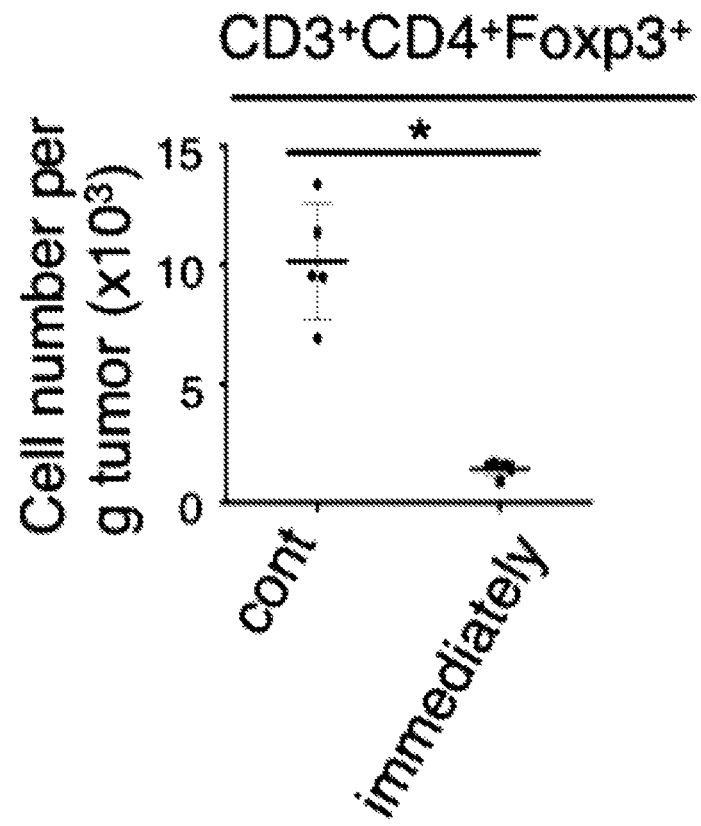
FIG. 9 is a plot showing that Tumor-infiltrating CD4+ Foxp3+ cells are depleted by local CD25-targeted NIR-PIT. Lymphocytes were collected from LL/2-luc tumors before and immediately (30 min) after local CD25-targeted NIR-PIT. Flow cytometry analysis of CD4+Foxp3+ cell number per gram indicated that CD4+Foxp3+ cell decreased after local CD25-targeted NIR-PIT (n=5) (*p<0.01, Mann-Whitney test).
Figure 10A:
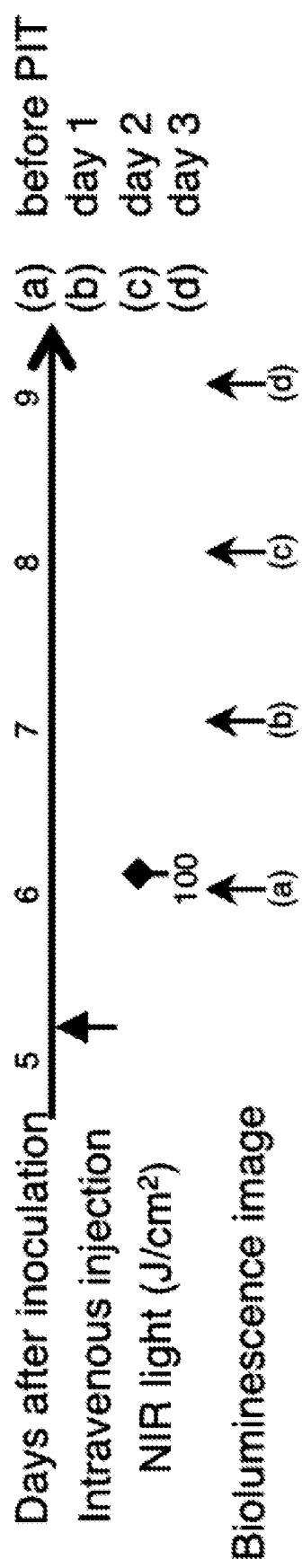
Figure 10B:
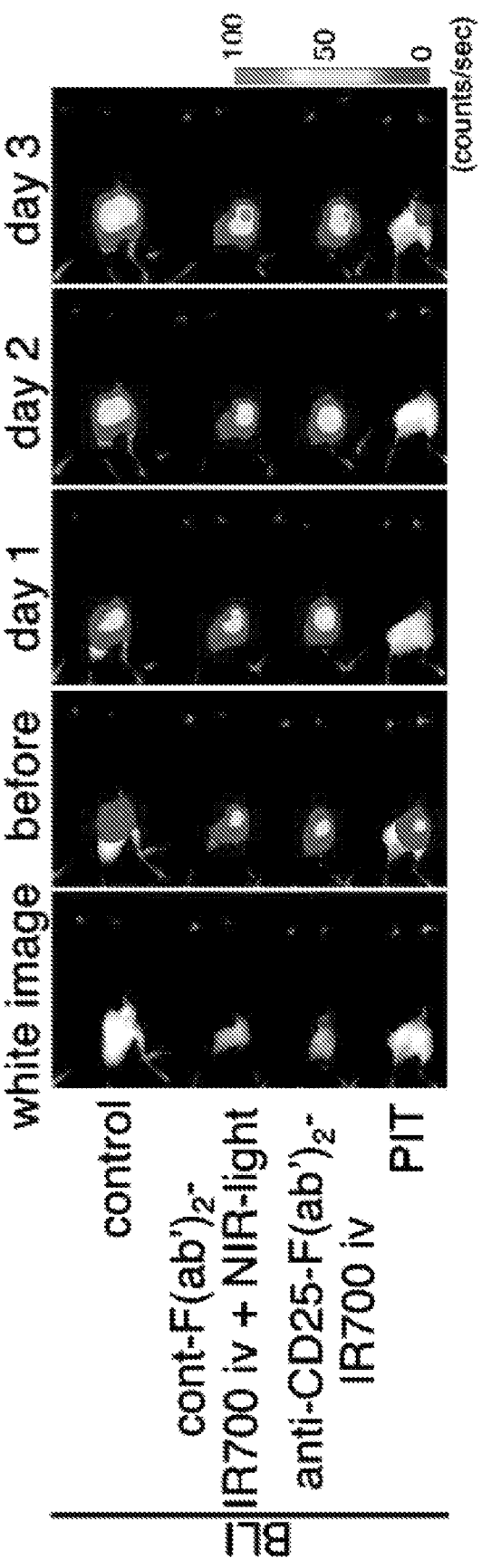
Figure 10C:
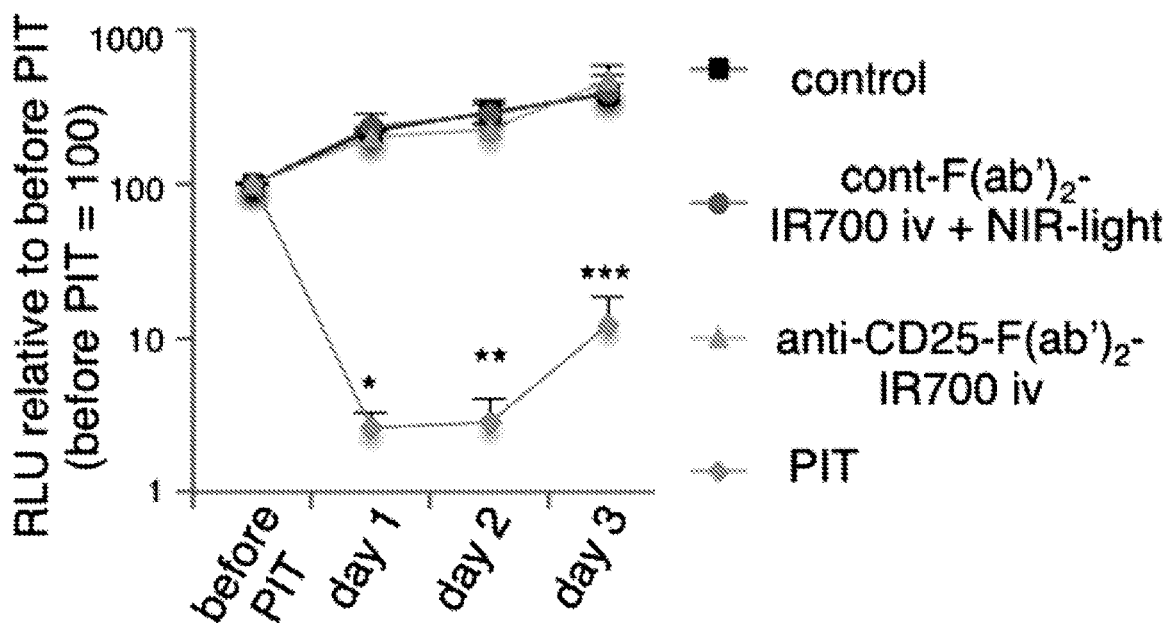
Figure 10D:
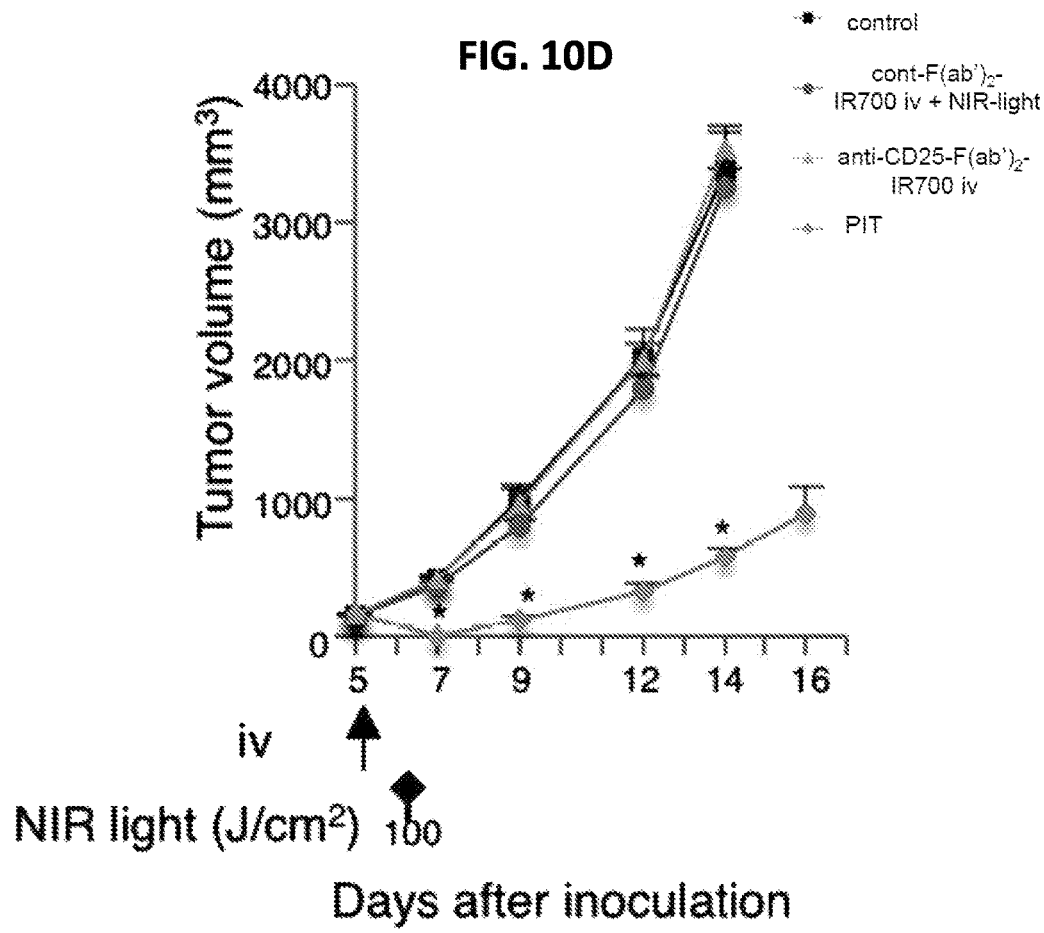
Figure 10G:
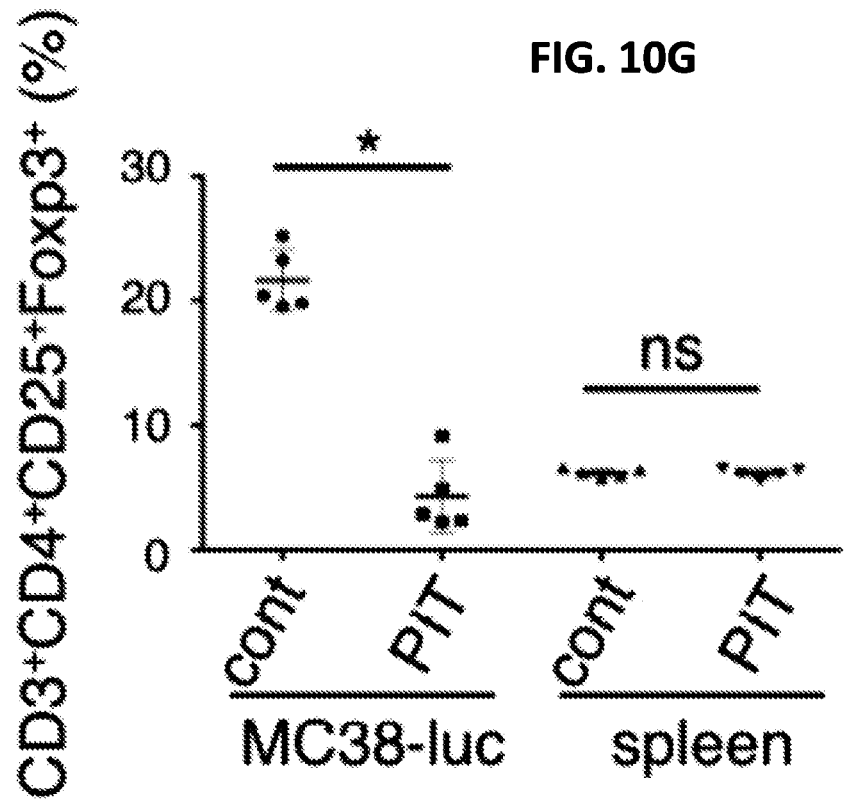
Figure 10H:
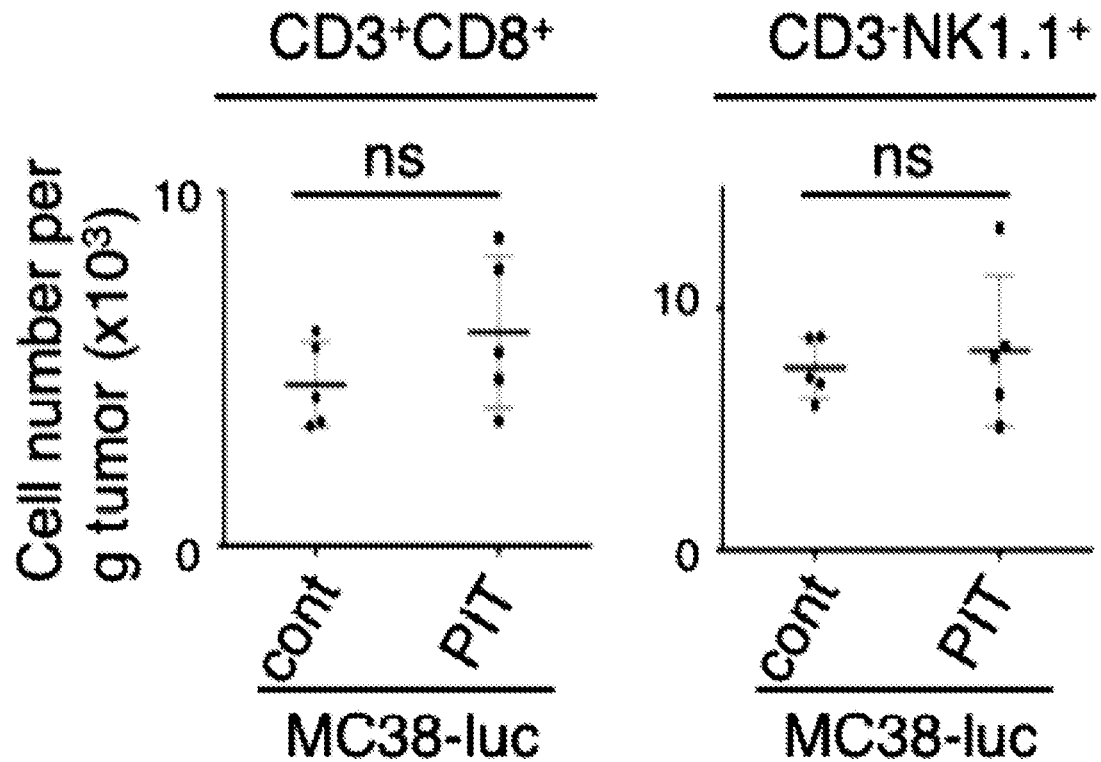
Figure 11A:
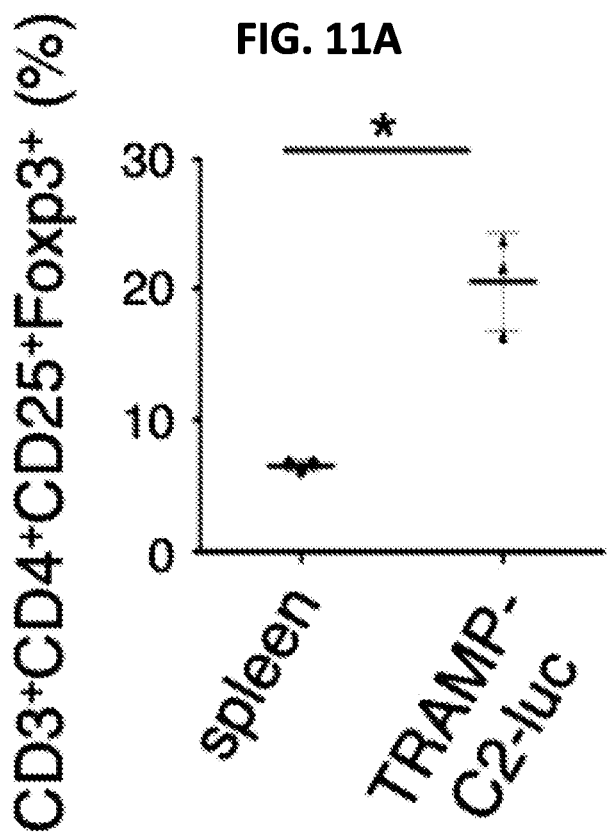
FIGS. 11A-11D show that local CD25-targeted-NIR-PIT induces regression of TRAMP-C2-luc flank tumors. (A) The fraction of CD4+CD25+Foxp3+Tregs population within CD4 T cells was increased in the TRAMP-C2-luc tumors compared to the spleen (n=3) (*p<0.01, Mann-Whitney test). (B) The regimen of local NIR-PIT is shown. (C) In vivo BLI of tumor bearing mice indicated a decrease of the bioluminescent signal in the tumor by CD25-targeted-NIR-PIT. (D) Quantitative RLU showed a significant decrease of the signal in NIR-PIT-treated tumors (n=5 mice in each group)(*p<0.01, PIT vs. control, Mann-Whitney test).
Figure 11D:
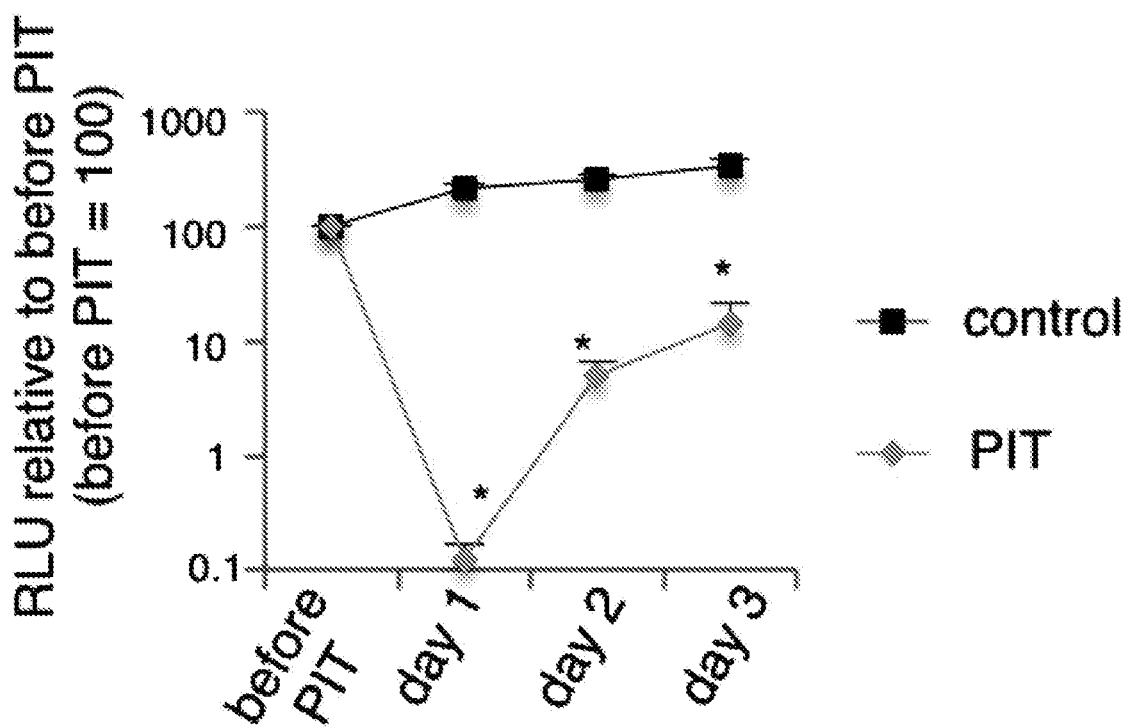
Figure 11B:
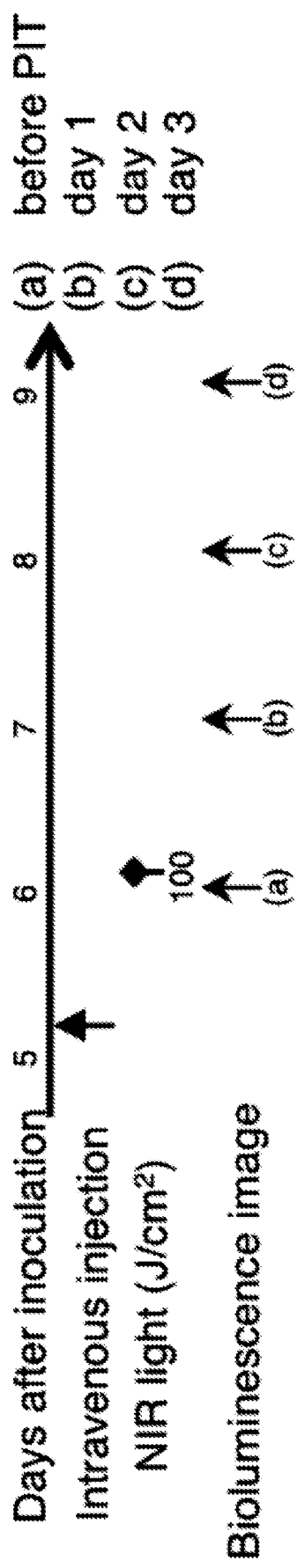
Figure 11C:
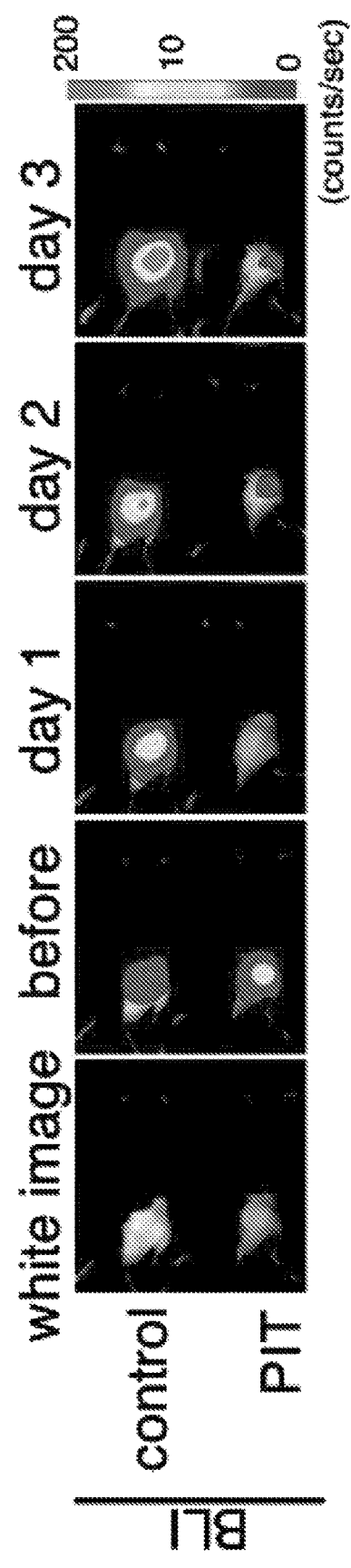

In Vivo NIR-PIT Targeting CD4$^+$CD25$^+$Foxp3$^+$ Tregs Induces Regression of Treated Tumors The effect of in vivo local NIR-PIT was determined with anti-CD25-IR700 (CD25-targeted-NIR-PIT) against intratumoral Tregs in LL/2-luc flank tumors (FIG. 5B). A NIR-light dose escalation study indicated that more than 85% depletion of CD25$^+$Foxp3$^+$Tregs in CD4 T cells occurred with 100 J/cm$^2$ of light power within 30 min (FIG. 8). With this light dose, the decrease of CD4$^+$Foxp3$^+$ cell number in the tumor was observed (FIG. 9), indicating that this observation was not a mere down-regulation of CD25 expression on Tregs, but actual depletion of the cells. Therefore, this light dose was chosen for in vivo treatment. This light dose is considered non-thermal and does not cause excessive heating locally upon exposure to the skin or tumor.

Figure 5C:
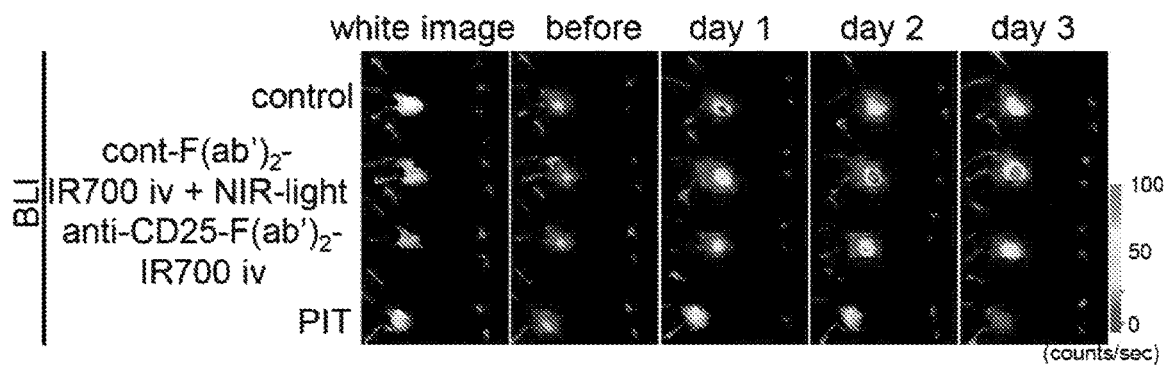
Figure 5D:
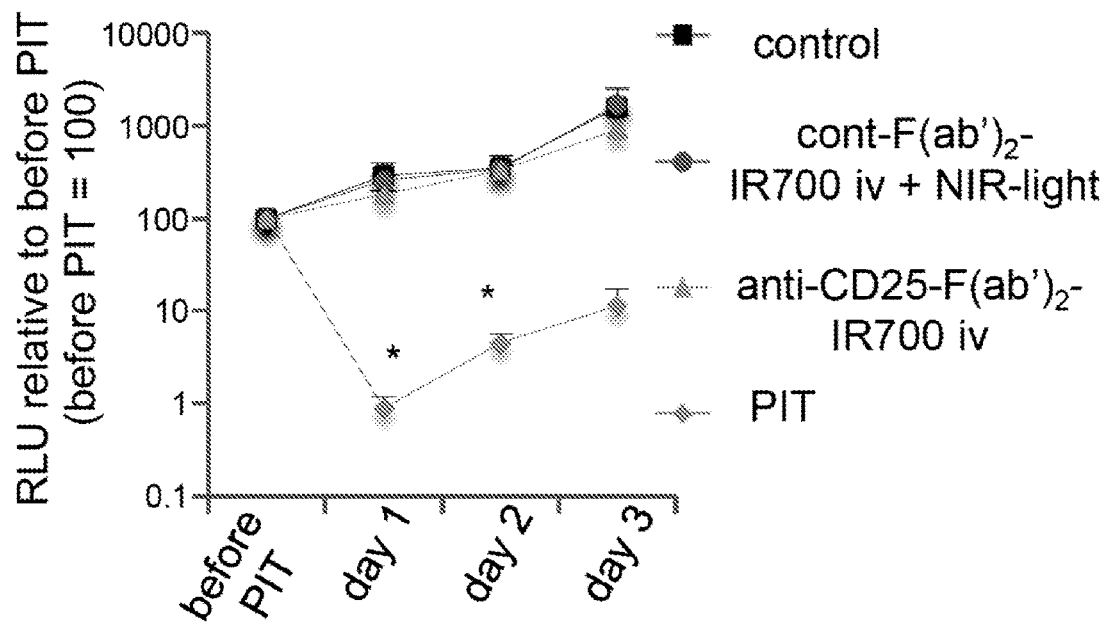
Figure 5I:
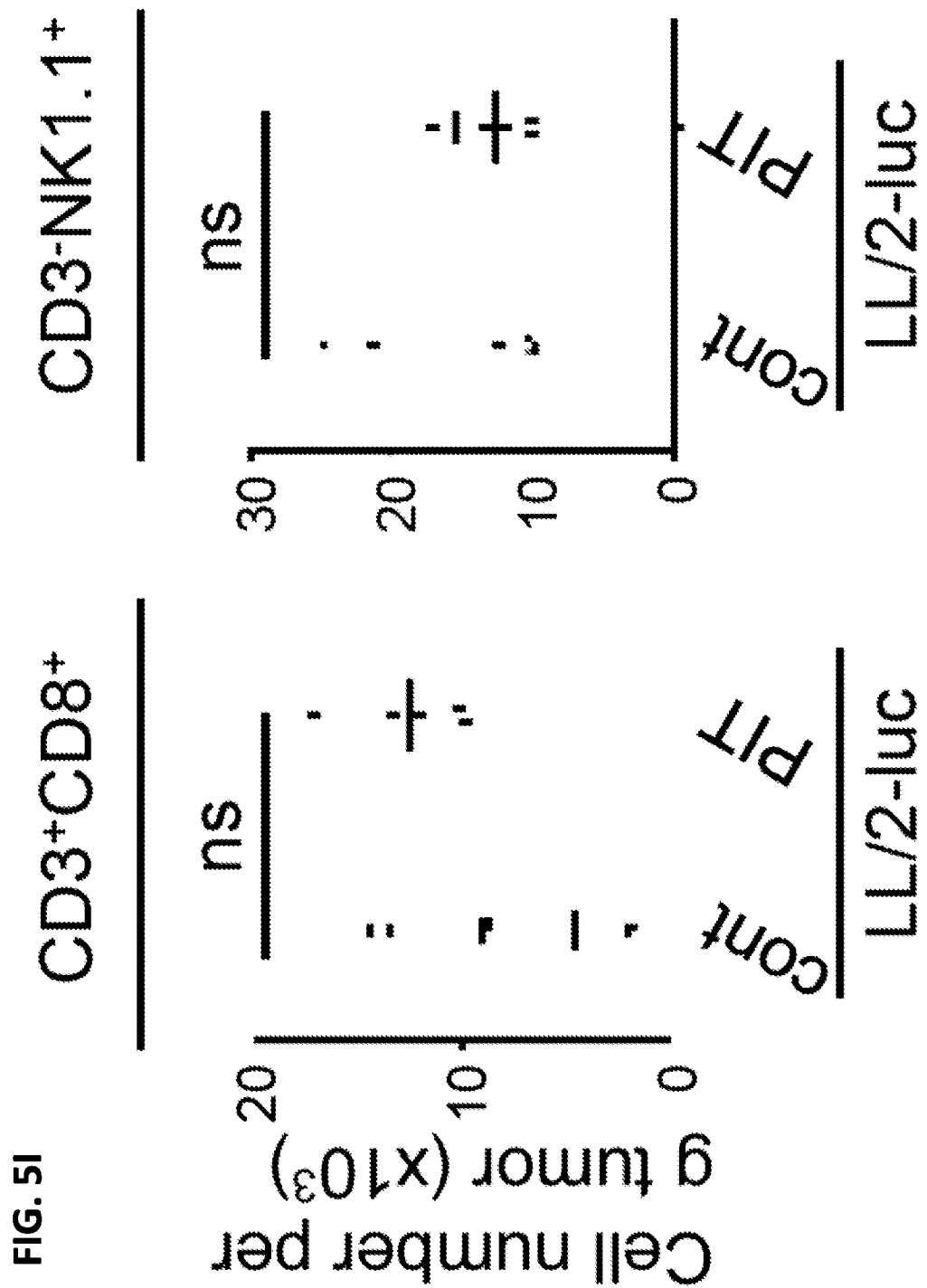

The experimental group of mice with LL/2-luc tumors received anti-CD25-F(ab')$_2$-IR700 injection followed by NIR-light exposure ("PIT" group). This group showed reduction of luciferase activity of tumor as indicated by bioluminescence imaging (BLI) at day 1, compared to the three control groups: non-treated mice, mice that received control-F(ab')$_2$-IR700 with NIR-light, and mice that received only the anti-CD25-F(ab')$_2$-IR700 but no light (FIGS. 5C and 5D). Quantitative analysis of luciferase activity showed significant decreases in RLU (relative light unit) in the PIT group for 2 days after the treatment (*p<0.05), while that of other groups gradually increased as the tumors grew (FIG. 5D). Consistent with the BLI data, the growth of tumors was also suppressed in the PIT group (FIG. 5E), leading to significantly prolonged survival of mice compared to the control groups (*p<0.0001) (FIG. 5F). The body weight of the mice (BW change) showed no significant difference among the groups for up to 14 days after tumor inoculation (FIG. 5G). Analysis of tumor infiltrating lymphocytes and splenic lymphocytes at 0.5 hr after the treatment confirmed that the depletion of CD4$^+$CD25$^+$Foxp3$^+$ Tregs was limited to the tumor and that it did not significantly affect CD8 T and NK cells (FIGS. 5H and 5I). Similar findings were observed when MC38-luc flank tumors were treated with local CD25-targeted-NIR-PIT (FIGS. 10A-10H). Furthermore, increased tumor-infiltrating Tregs were observed in the TRAMP-C2-luc prostate cancer model, and CD25-targeted-NIR-PIT successfully induced anti-tumor effects in this model (FIGS. 11A-11D). These data demonstrate that NIR-PIT targeting CD4$^+$CD25$^+$ Foxp3$^+$Tregs locally and specifically depletes these cells, followed by tumor reduction and prolonged survival, irrespective of the cancer type.

Figure 12A:
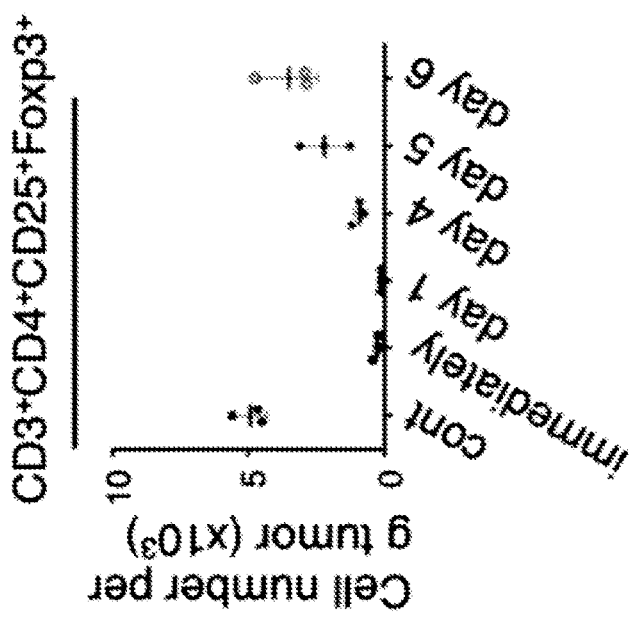
FIGS. 12A-12F show that repeated local CD25-targeted-NIR-PIT synchronizing with the re-population of Tregs in the tumor microenvironment enables prolonged suppression of tumor growth. (A) Flow cytometry analysis of lymphocytes collected from LL/2-luc tumor after local CD25-targeted-NIR-PIT indicated that the depletion of intratumoral CD4+CD25+Foxp3+Tregs lasted for approximately 4 days, after which they gradually re-populated in the tumor bed (n=3). (B) The regimen of repeated local NIR-PIT is shown. (C) BLI indicated that a repeated local CD25-targeted-NIR-PIT of LL/2-luc tumor inoculated in albino mice was capable of inducing the tumor regression repeatedly. (D) Quantitative RLU shows a significant decrease in signal in the NIR-PIT-treated tumors (n=7 mice in each group)(*p<0.001, Mann-Whitney test). (E) Repeated local CD25-targeted-NIR-PIT leads to reductions in tumor volume (n=7 mice in each group)(*p<0.01, **p<0.001, Mann-Whitney test) and (F) lead to prolonged survival of the mice (*p<0.0001, Long-rank test and Wilcoxon test).
Figure 12B:
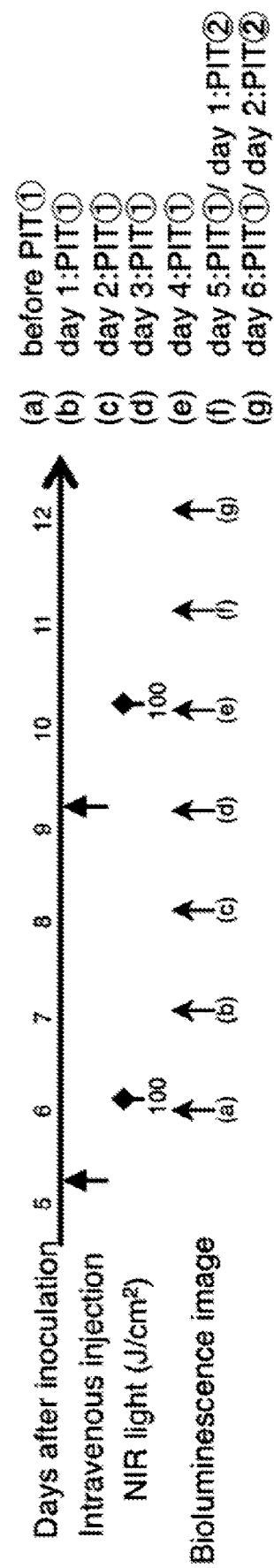
Figure 12C:
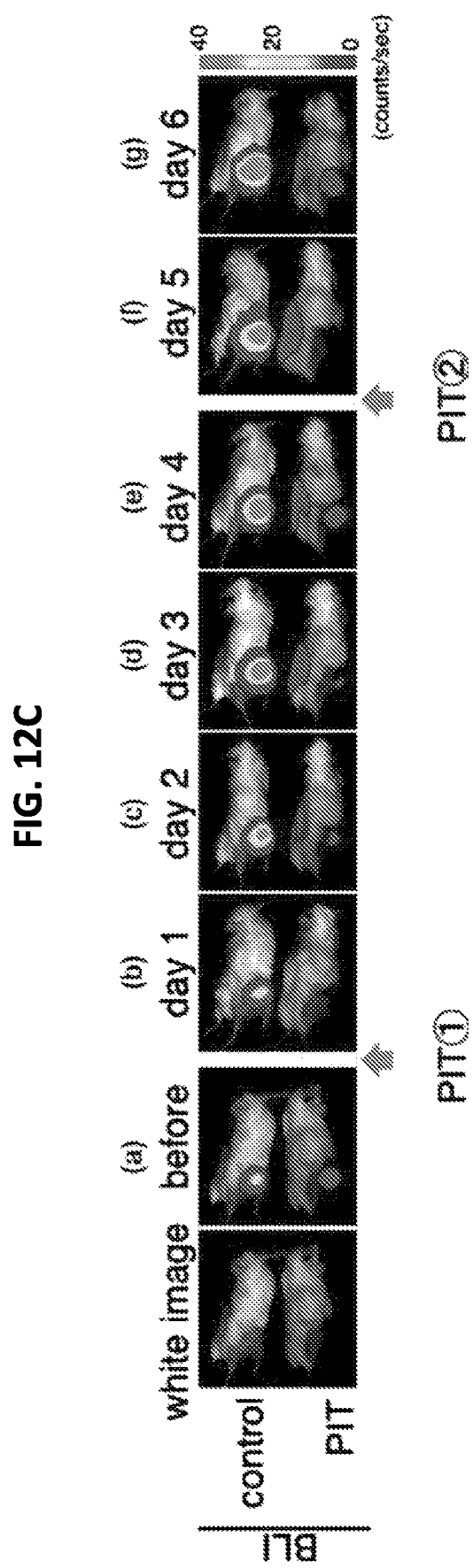
Figure 12D:
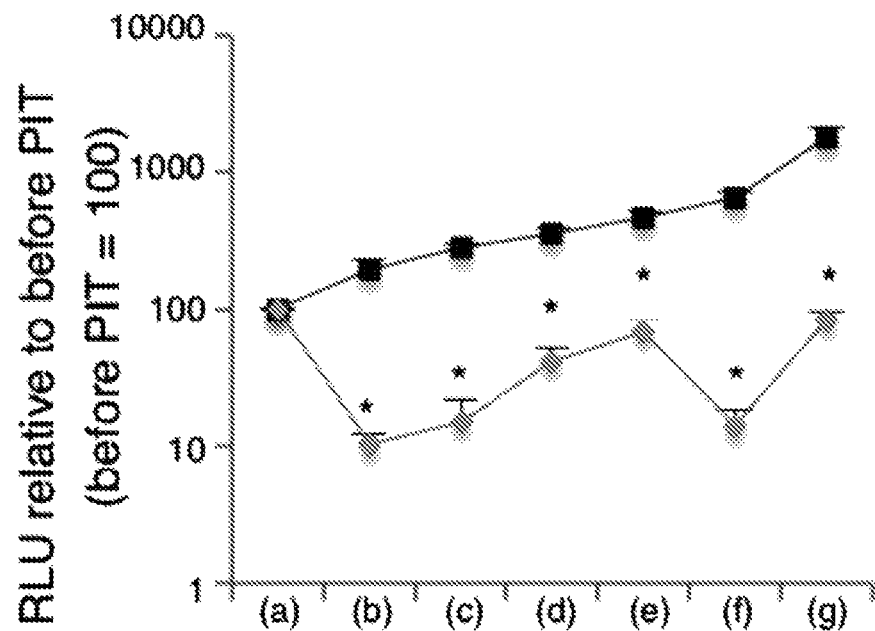
Figure 12E:
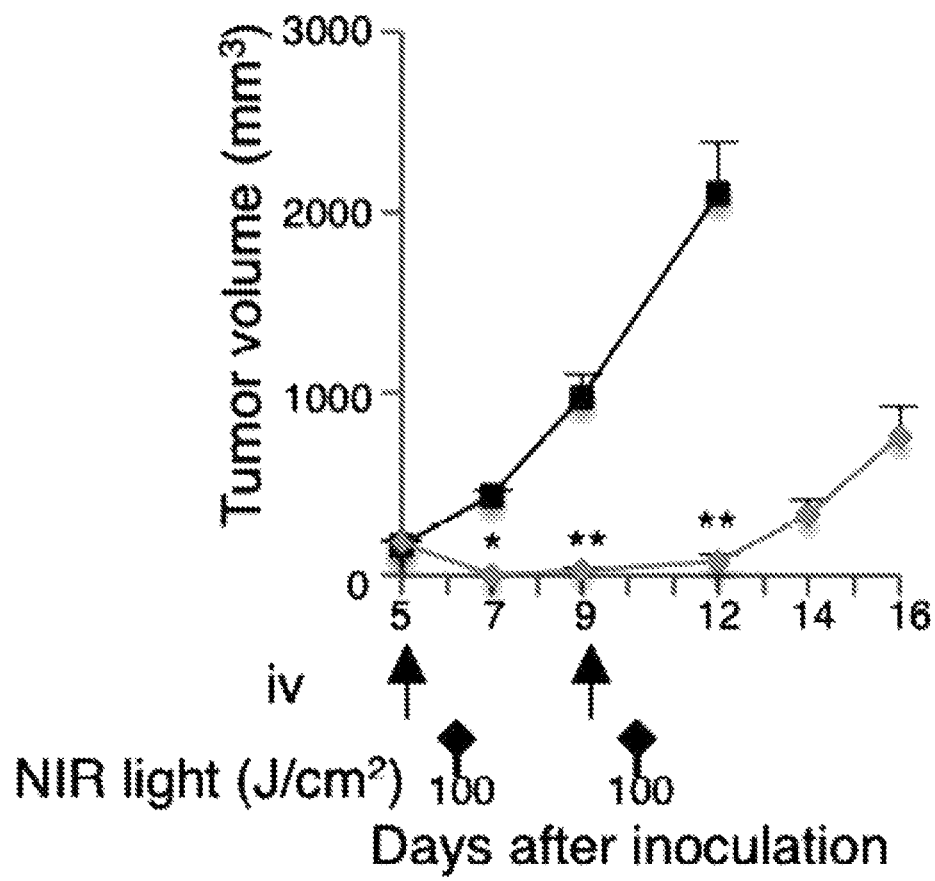
Figure 12F:
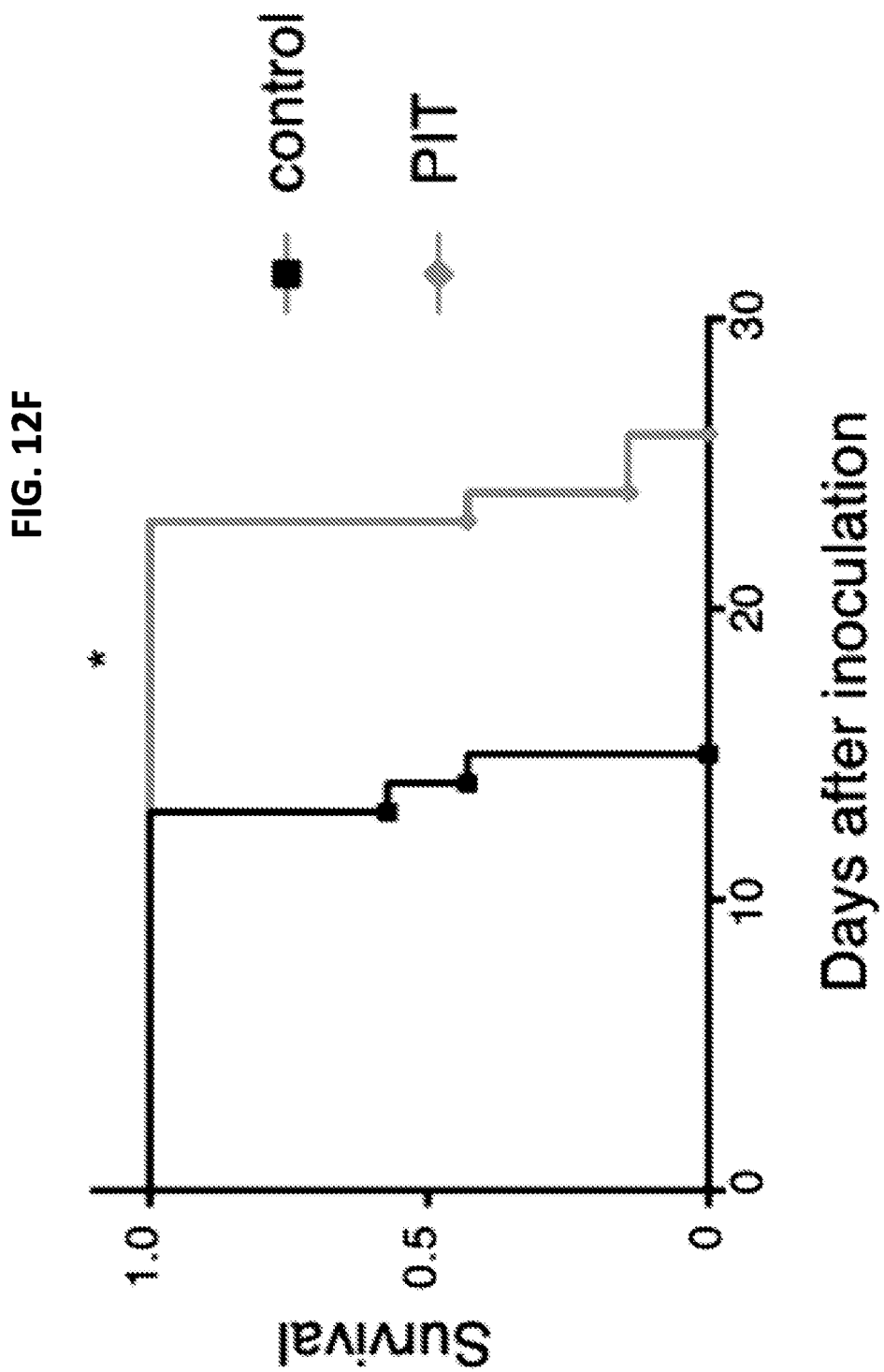

The depletion of intratumoral Tregs lasted for approximately 4 days, after which there was a gradual re-population of Tregs, reaching the pre-treatment level at approximately 6 days after the therapy (FIG. 12A). Gradual tumor re-growth was also observed (FIG. 5E). Repeat treatment with CD25-targeted-NIR-PIT induced prolonged tumor suppression and survival (FIGS. 12B-12F).

Example 6

In Vivo Local CD25-Targeted-NIR-PIT of the Tumor Induces Rapid Activation of Tumor Infiltrating CD8 T, and NK Cells and Activation of Antigen Presenting Cells To elucidate how the specific depletion of tumor-infiltrating Tregs with local CD25-targeted-NIR-PIT lead to tumor regression, it was determined whether intratumoral CD8 T cells and NK cells became activated after NIR-PIT.

Figure 13A:
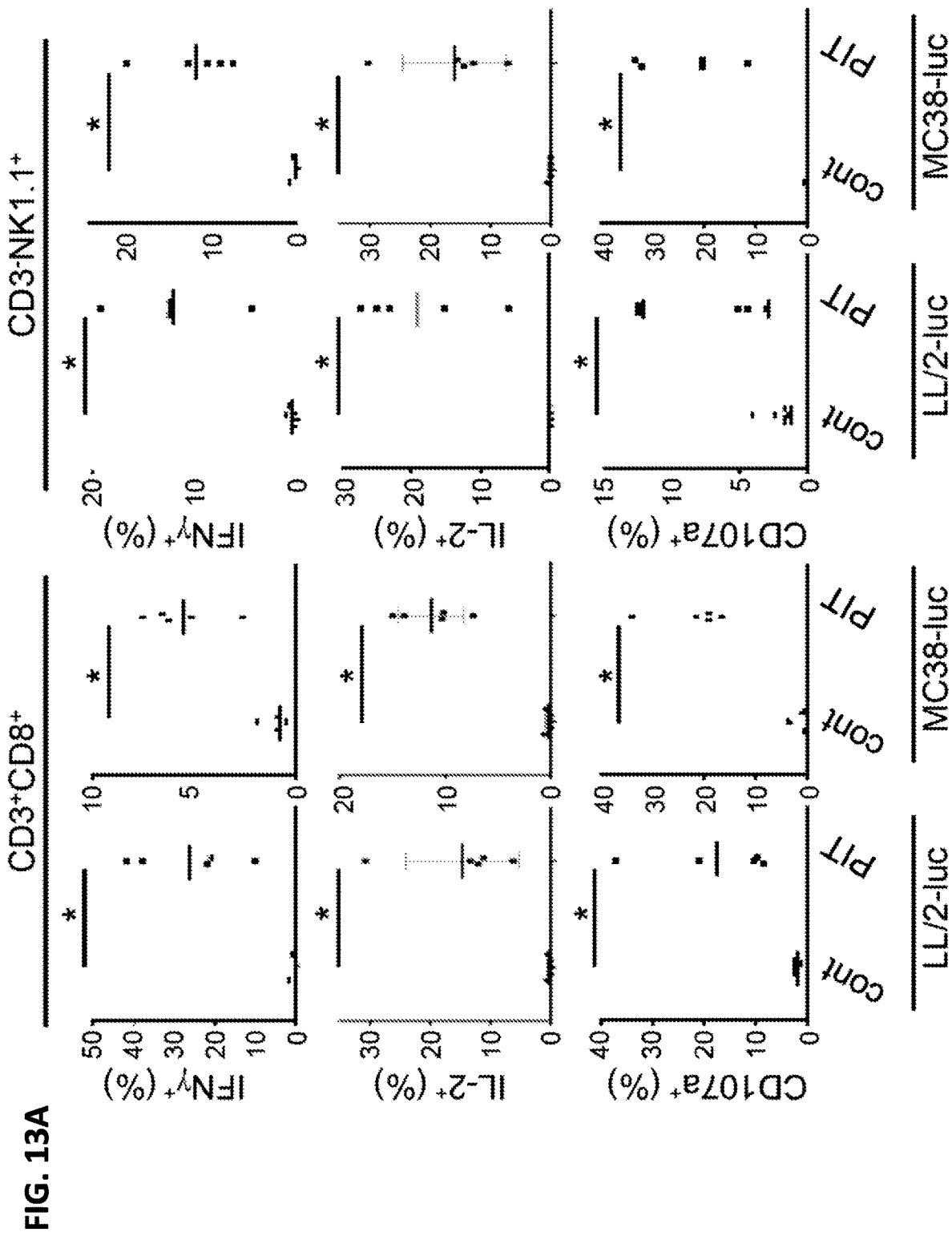
FIGS. 13A-13B show that in vivo local CD25-targeted-NIR-PIT induces rapid activation and cytotoxicity of intratumoral CD8 T cells and NK cells. (A) Cytotoxic action of CD8 T cells and NK cells infiltrating LL/2-luc or MC38-luc tumors was examined by flow cytometry analysis with or without a local CD25-targeted NIR-PIT. CD8 T and NK cells collected 1.5 hr after the PIT were producing IFNγ and IL-2, and had CD107a exposed on the cell surface, whereas the cells from non-treated tumors did not (n=5) (*p<0.01, Mann-Whitney test). (B) Expression of activation markers, CD69 and CD25, and production of IL-2 in both CD8 T cells and NK cells was up-regulated 1 day after the local CD25-targeted-NIR-PIT (n=5)(*p<0.01, Mann-Whitney test).
Figure 13B:
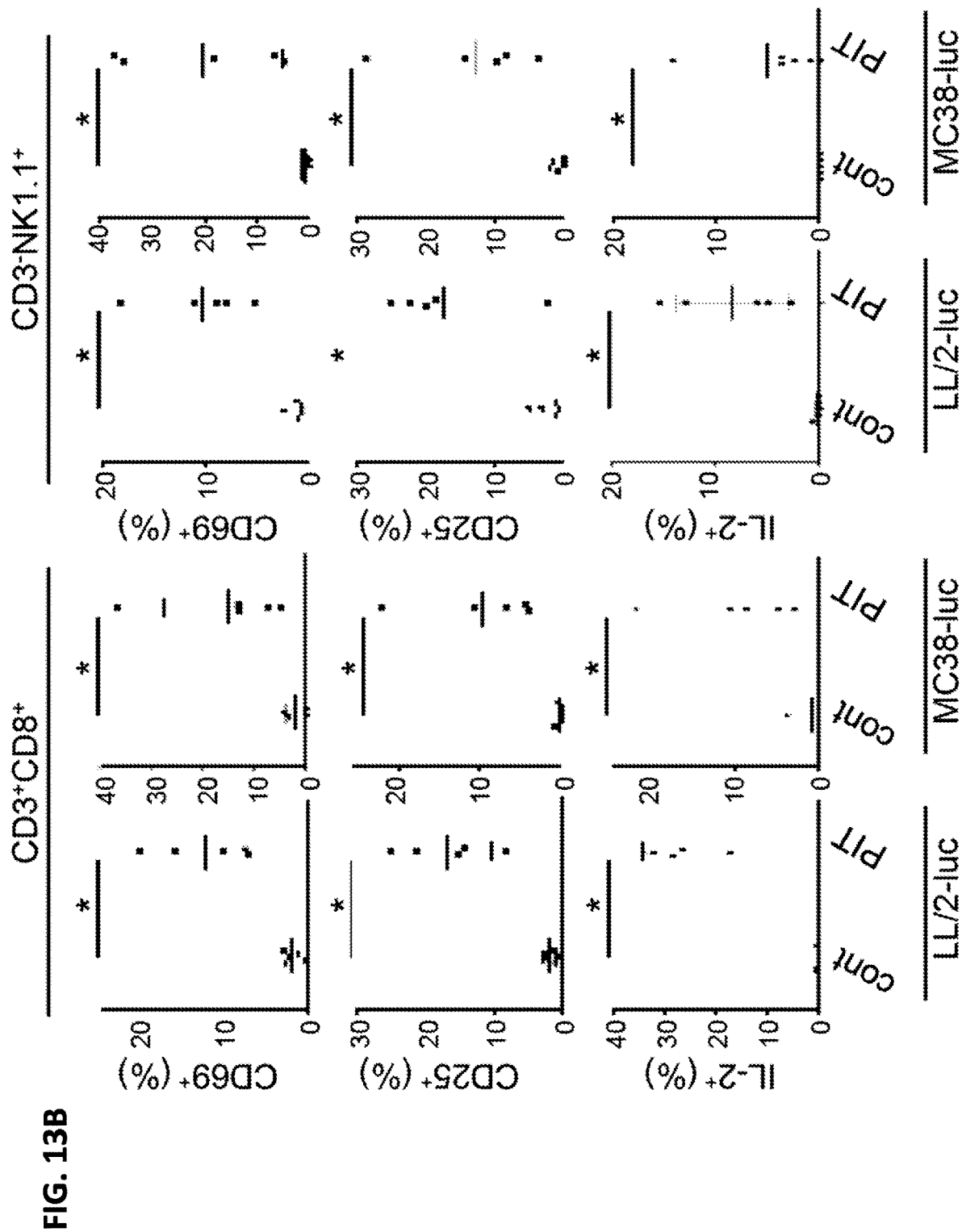
Figure 14C:
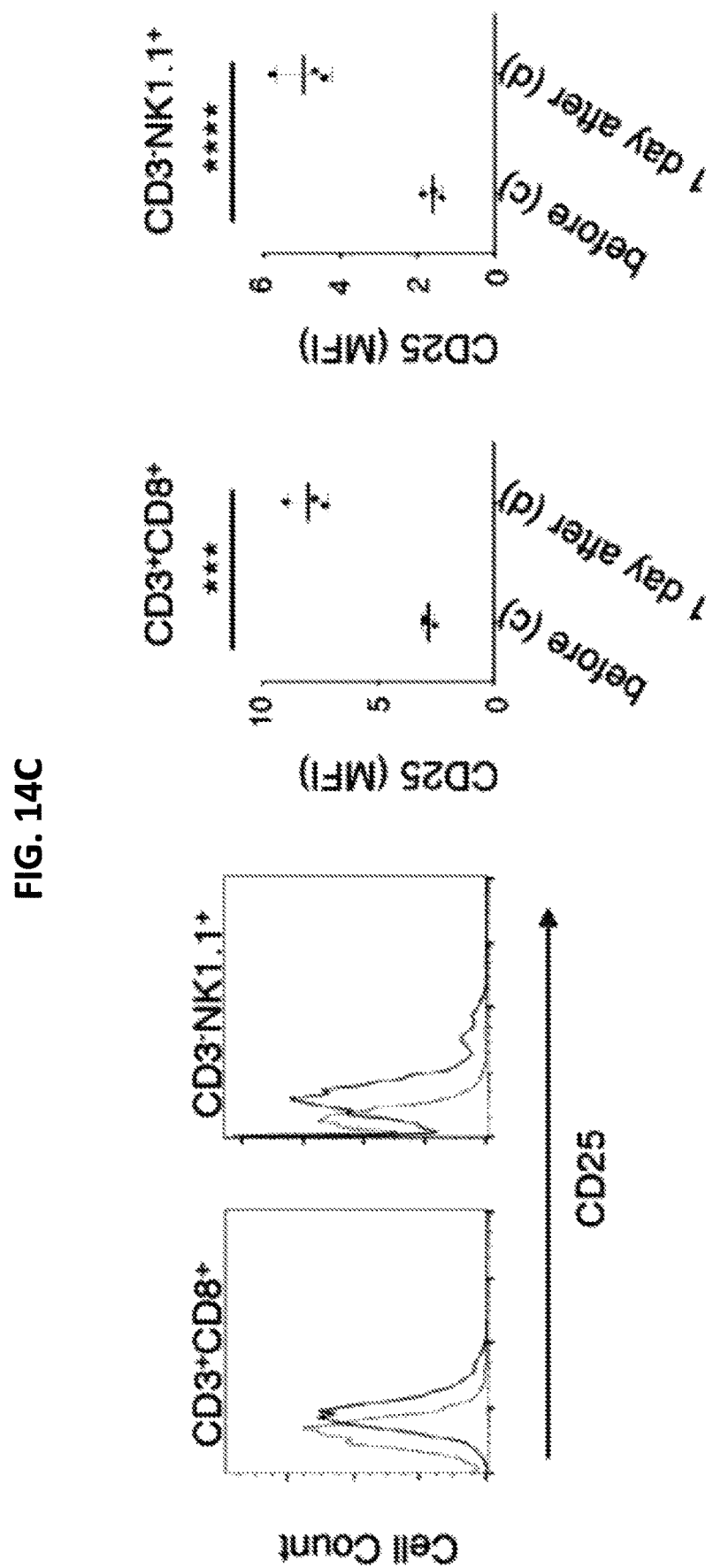

As early as 1.5 hr after the treatment, CD8 T and NK cells began to produce interferon gamma (IFNγ) and interleukin-2 (IL-2) and expose CD107a, indicating activation and killing of tumor cells (FIG. 13A). At 1 day after the treatment, an up-regulation of CD69 and CD25 and production of IL-2 was observed on these effector cells (FIG. 13B). However, the local CD25-targeted-NIR-PIT did not deplete effector cells, which were CD25 negative prior to NIR-PIT and only began to express CD25 after the NIR treatment (FIGS. 5I and 13B). Thus, Treg-depletion by NIR-PIT led to rapid activation of tumor-infiltrating CD8 T and NK cells resulting in tumor regression. Comparison of CD25 expression levels before and after local CD25-targeted-NIR-PIT in a repeated NIR-PIT regimen showed up-regulation of CD25 after the each PIT-treatment (FIGS. 14A-14C). CD25 was already down regulated to the pre-treatment levels by the time second PIT was performed after the 4-day interval from the first PIT.

Figure 15A:
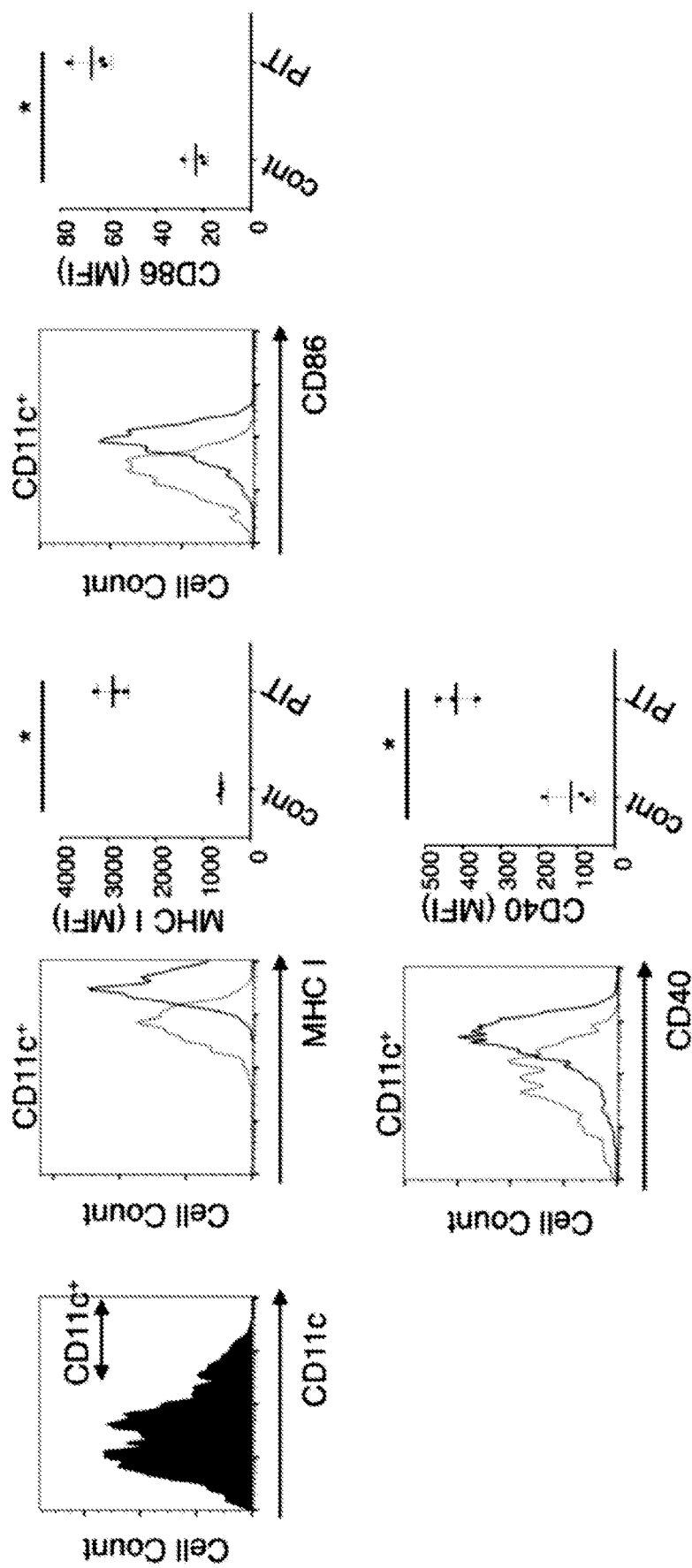
Figures 15C, 15D:
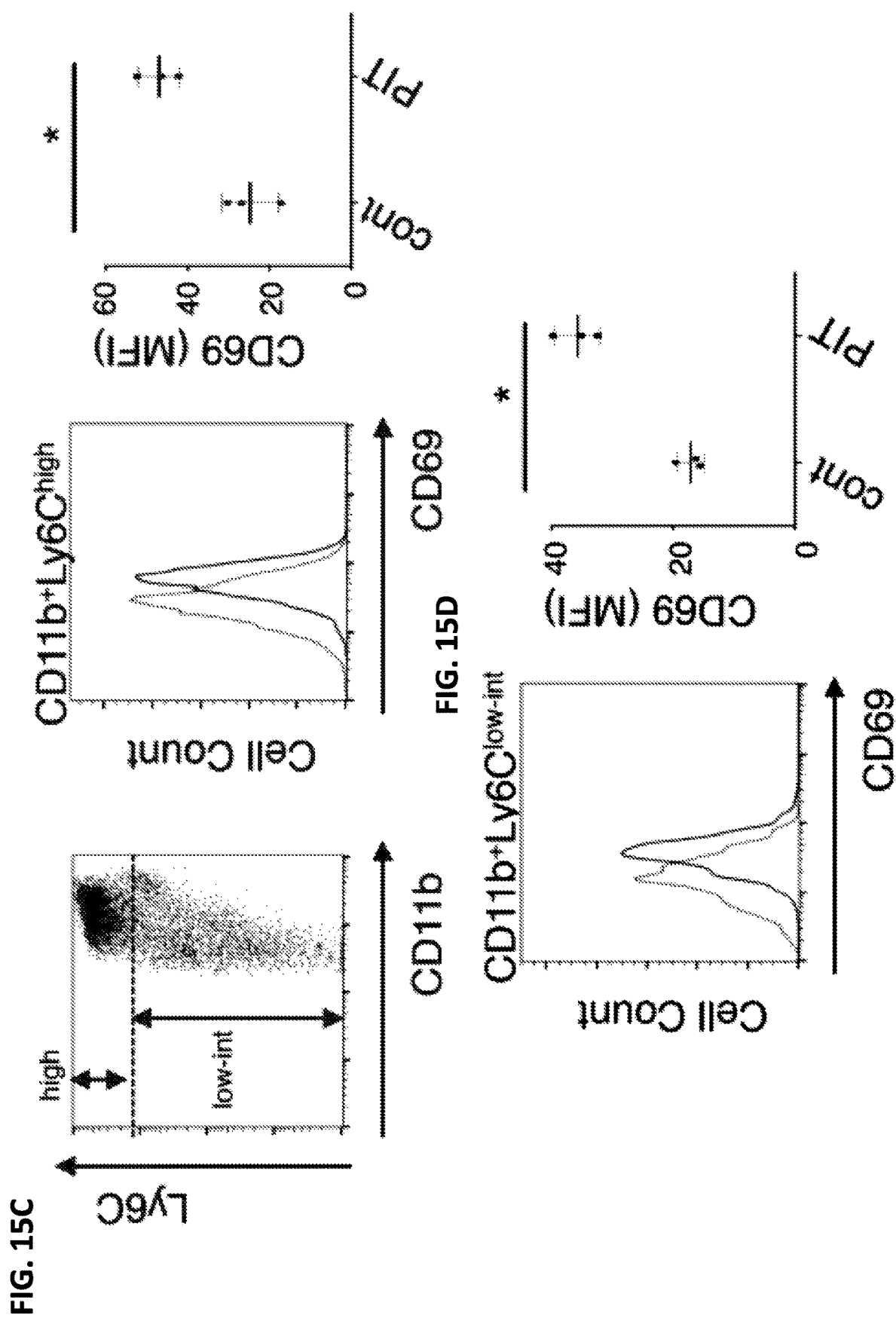
Figure 16:
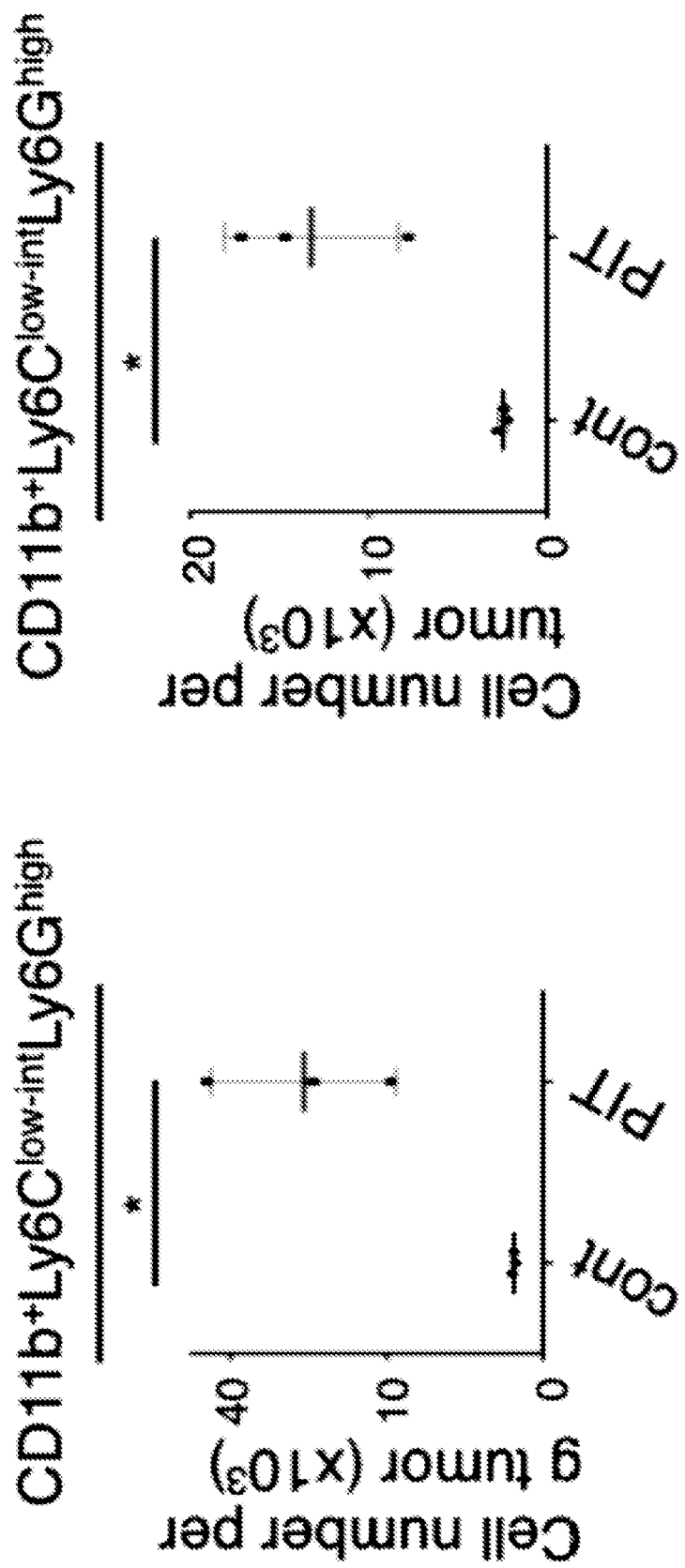
FIG. 16 are plots showing that local CD25-targeted-NIR-PIT induces increase of granulocytes inside treated tumors. Flow cytometry analysis of tumor-infiltrating granulocytes (CD11b$^+$Ly6C$^{low-int}$Ly6G$^{high}$) indicated that local CD25-targeted-NIR-PIT induced increase of these cells (n=3) (*p=0.0188 (per g tumor), 0.0168 (per tumor)<0.05, unpaired t test). Both cell number per g tumor and per tumor are shown.

It was determined whether antigen presenting cells (APCs) within the tumor were activated up on PIT of Tregs. Dendritic cells (DCs) found in the tumor expressed relatively high MHC I molecule, however, local CD25-targeted-NIR-PIT induced its further up-regulation (FIG. 15A). This up-regulation was accompanied by up-regulation of co-stimulatory molecules such as CD86 and CD40 (FIG. 15A). This activation may be caused by their exposure to the components of dead Tregs and also, to the components of tumor cells killed by CD8 T and NK cells. Other APCs such as B cells, monocytes and macrophages, also showed up-regulation of CD69, indicating their activation after local CD25-targeted-NIR-PIT (FIGS. 15B-15D). These findings indicate that after the Treg-targeting PIT, tumor cells were killed by the effector cells, which involved APCs-mediated "multi-antigen vaccine effects". Increase of granulocytes inside the treated tumor was also detected after the therapy (FIG. 16).

Example 7

Local CD25-Targeted-NIR-PIT Induces a Systemic and Intratumoral Cytokine Storm

Figure 17A:
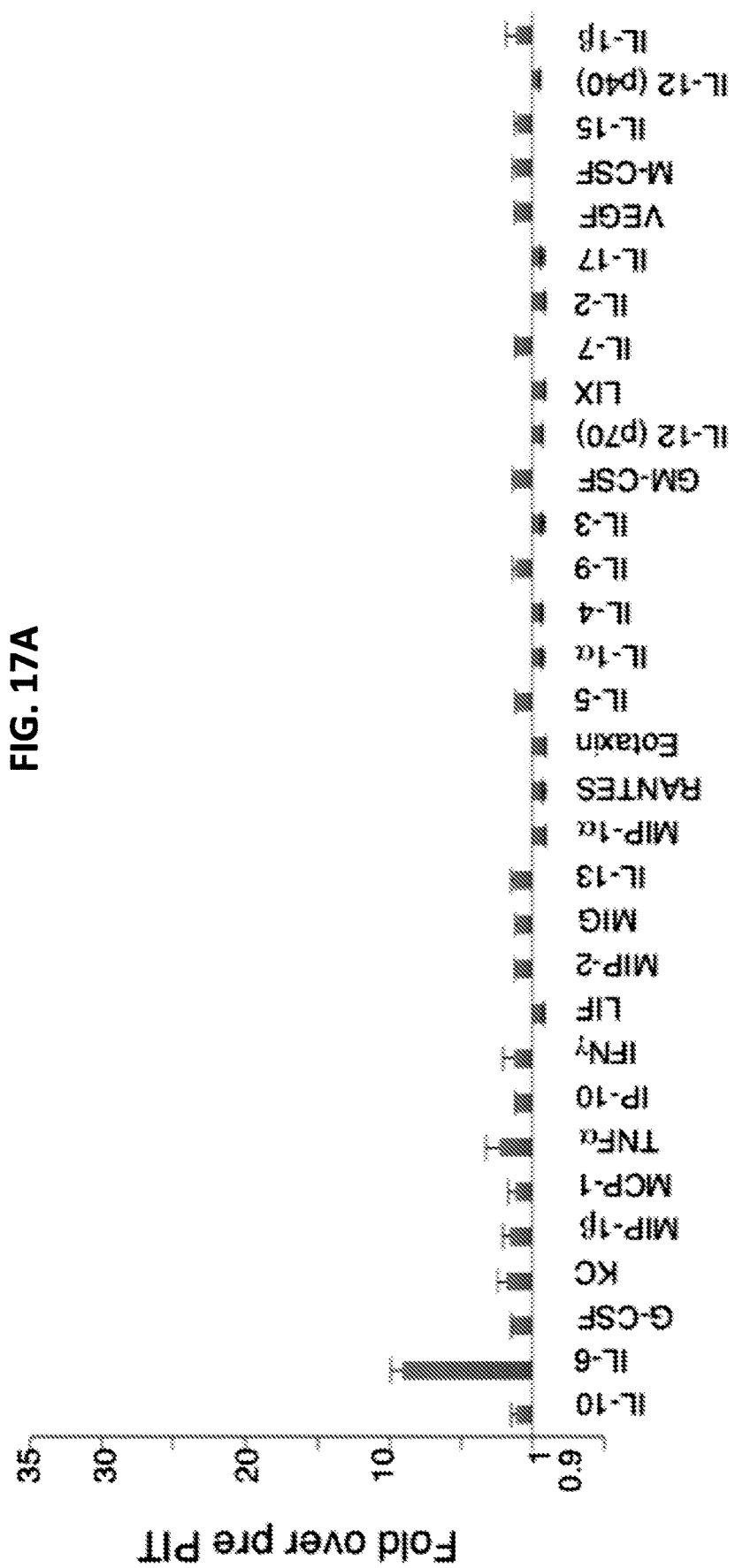
FIGS. 17A-17B are bar graphs showing that NIR-light irradiation on the tumor induces negligible levels of cytokine and chemokine production. (A) The serum cytokine and chemokine levels before and 1.5 hr after NIR-light irradiation at the tumor were measured in the same mouse. The results are indicated as fold increase (n=3). (B) Cytokine and chemokine levels within the tumor were compared between mice with NIR-light irradiated tumor and mice with non-NIR-light irradiated tumor. Tumors were harvested for collecting extra cellular fluid at 1.5 hr (n=3).
Figure 17B:
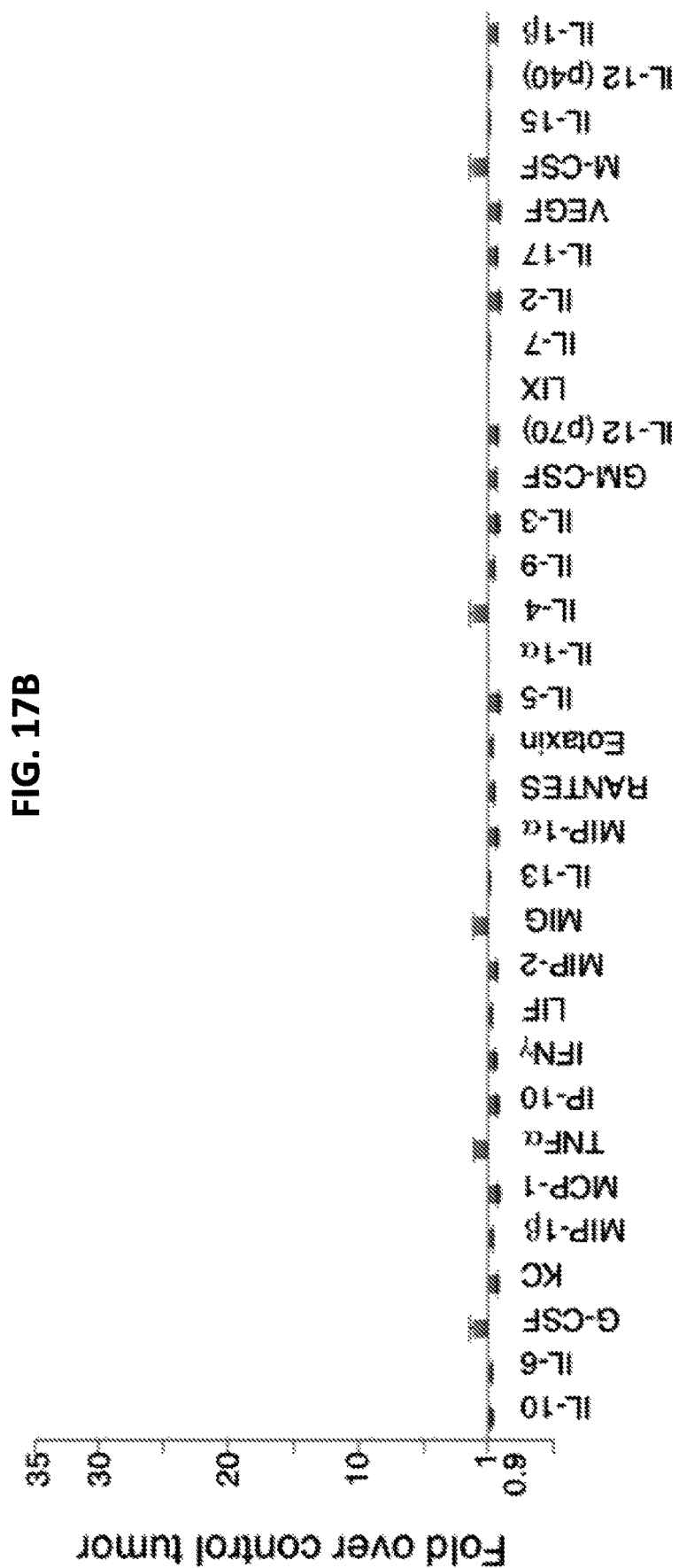
Figure 18A:
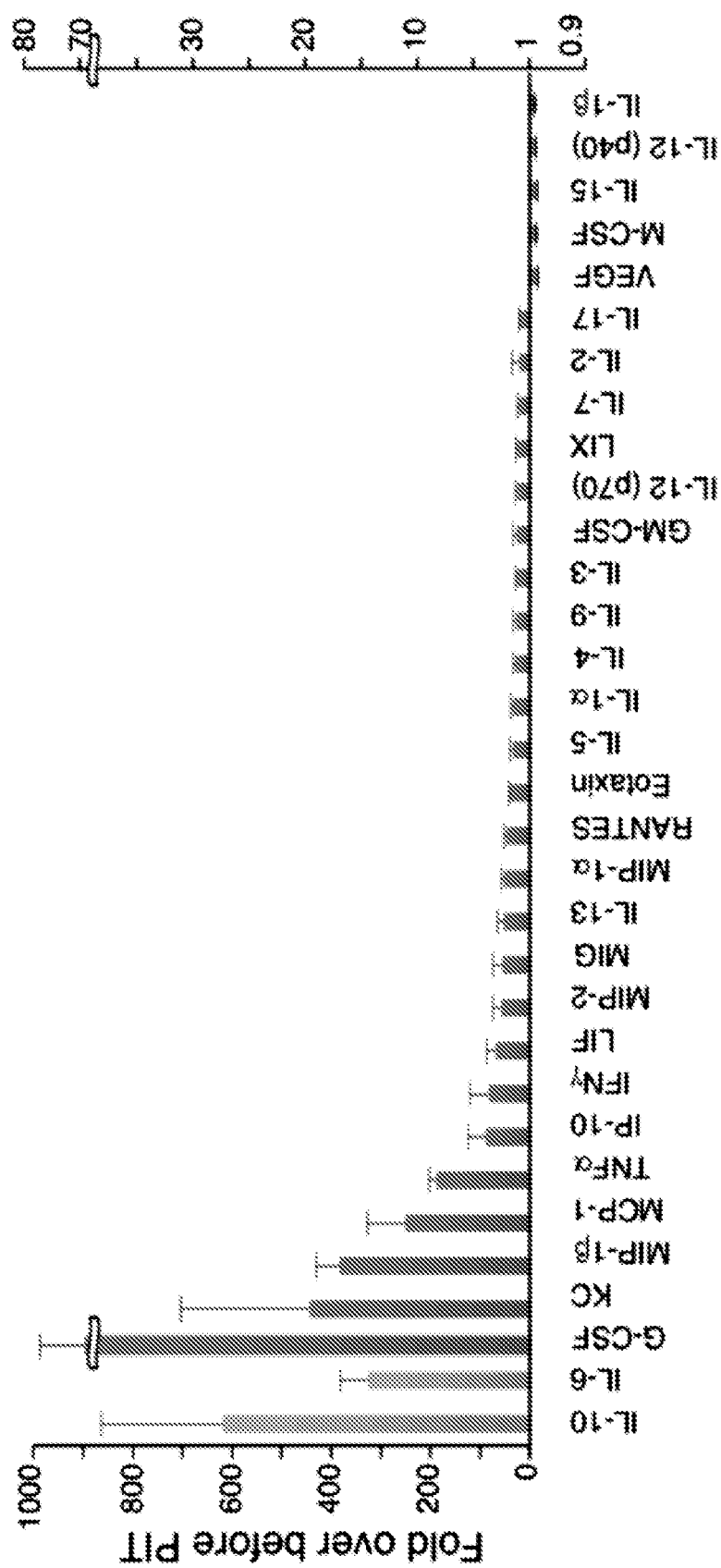
FIGS. 18A-18J are graphs showing that local CD25-targeted-NIR-PIT induces systemic and intratumoral cytokine storm. (A) The serum cytokine and chemokine levels before and 1.5 hr after a local CD25-targeted-NIR-PIT at the tumor were measured before and after treatment in the same mouse. The results are indicated as fold increase (IL-10 and IL-6 were measured using the left axis and others with right axis) (n=3). (B) Similarly, serum cytokine and chemokine levels were compared before and 1 day after the NIR-PIT (n=3). Cytokine and chemokine levels within the tumor were compared between mice with treated tumor and mice with non-treated tumor. Tumors were harvested for collecting extra cellular fluid at 1.5 hr (C) and 1 day (D) after the NIR-PIT (n=3). (E-G) Serum concentrations of (E) IFNγ (F) IL-6 and (G) G-CSF (n=3). (H-J) Intratumoral concentrations of (H) IFNγ (I) IL-6 and (J) G-CSF (n=3).
Figure 18B:
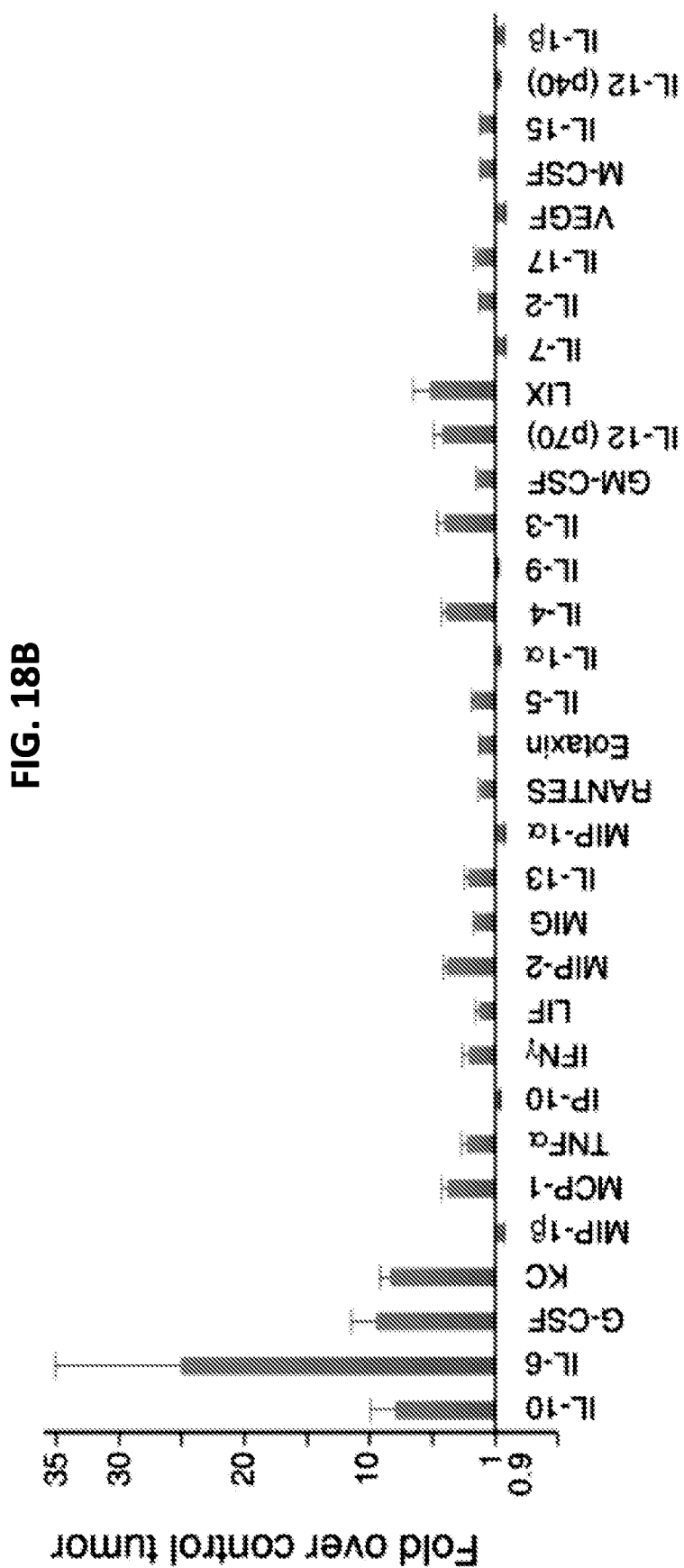
Figure 18C:
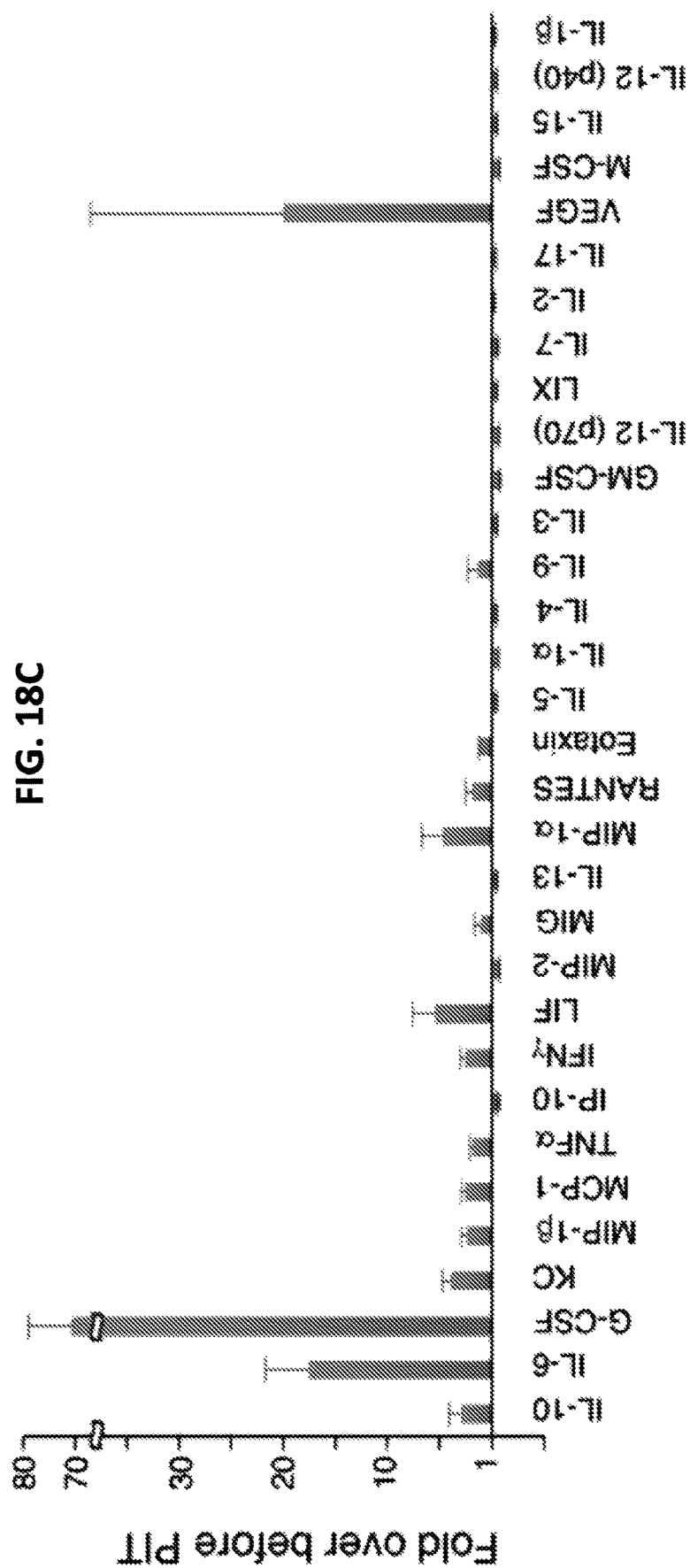
Figure 18D:
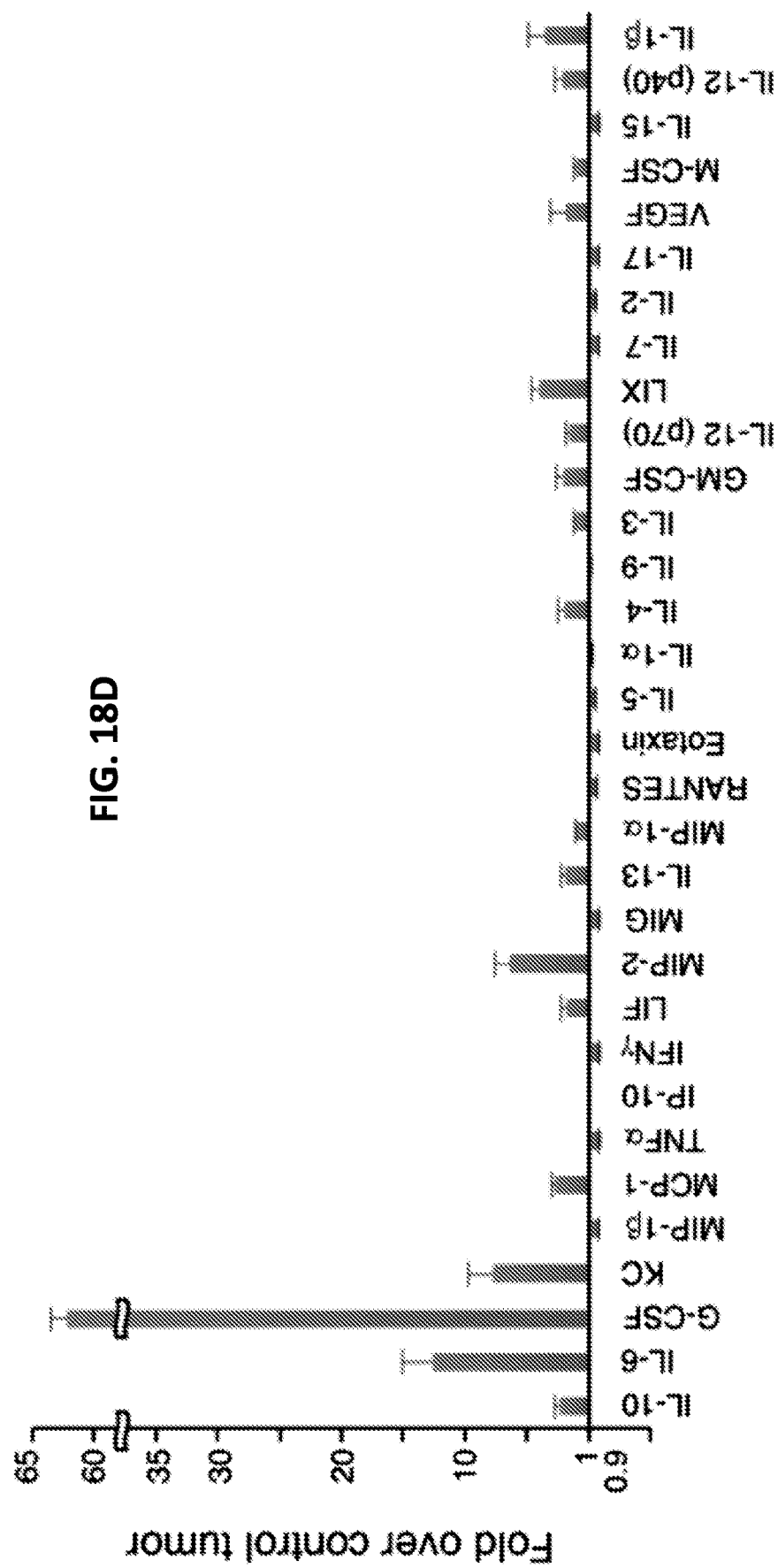
Figure 18E:
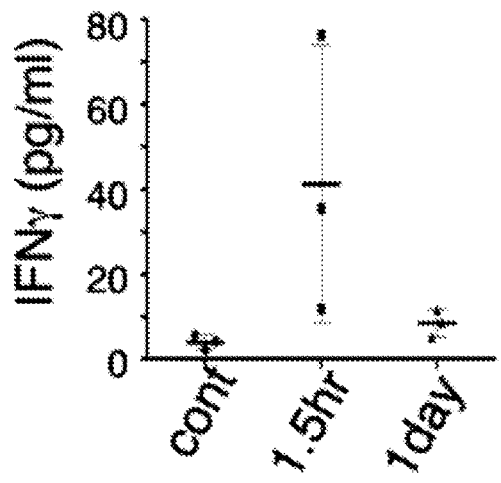
Figure 18F:
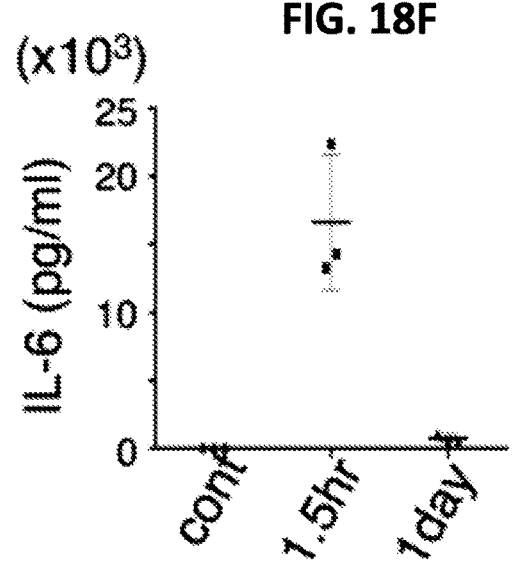
Figure 18G:
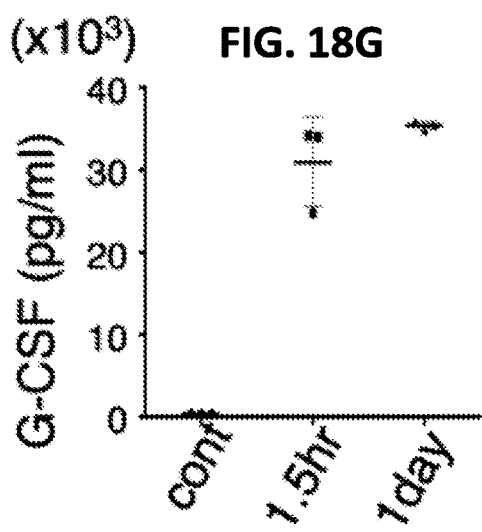
Figure 18H:
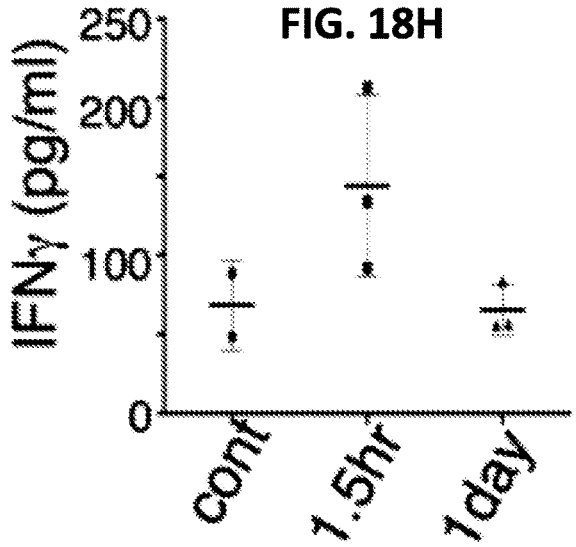
Figure 18I:
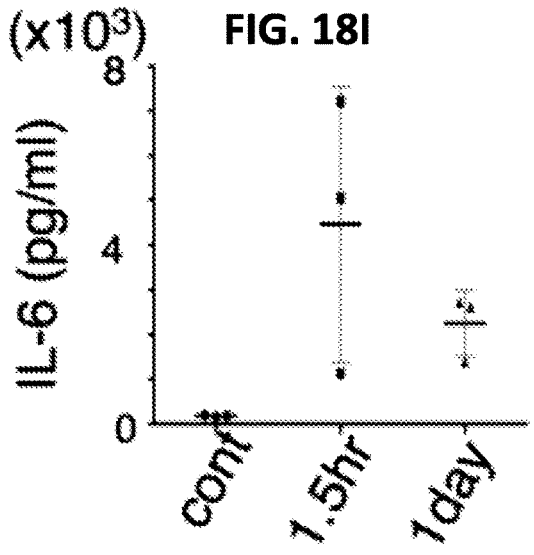
Figure 18J:
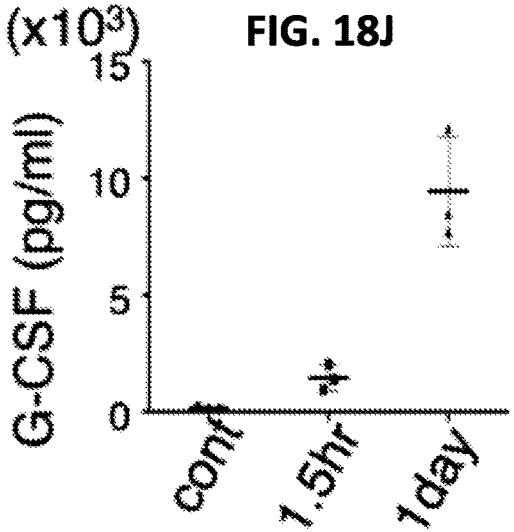

Changes of both serum and intratumoral cytokine and chemokine levels induced by local CD25-targeted-NIR-PIT were investigated. First, it was confirmed that the effect of NIR-light irradiation for the tumor was negligible (FIGS. 17A and 17B). At 1.5 hr after the therapy, a broad range of cytokines and chemokines increased in serum and tumors (FIGS. 18A and 18B). The cytokines and chemokines that are elevated after NIR-PIT broadly overlapped with those reported in clinical "cytokine storm" (34, 35). One day after the therapy, the levels of cytokines and chemokines abruptly decreased except for G-CSF (FIGS. 18C and 18D). The changes in concentration of IFNγ, IL-6, G-CSF in serum and tumor are presented (FIGS. 18E-18J).

Figure 19:
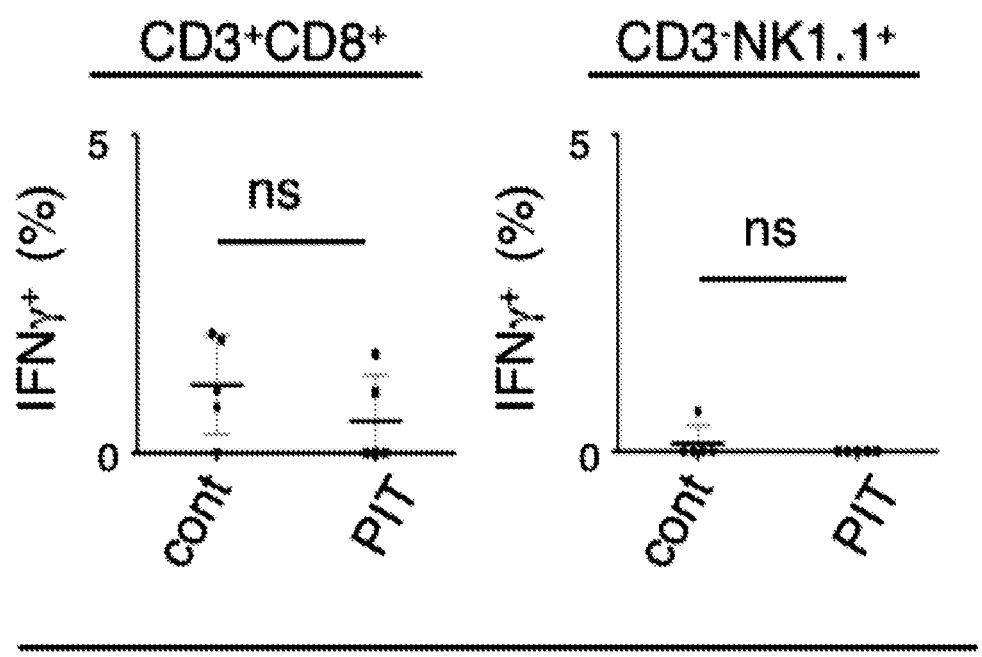
FIG. 19 are plots showing that IFNγ production by CD8 T and NK cells in the lungs is not detected 1 day after CD25-targeted-NIR-PIT. IFNγ production was not detected in the CD8 T cells and NK cells collected from the lungs 1 day after CD25-targeted-NIR-PIT by flow cytometry assay. (n=5)(ns: not significant, Mann-Whitney test).

These data indicate that a local CD25-targeted-NIR-PIT caused a rapid but transient release of cytokines and chemokines into the serum, which abated by day 1 post-treatment. Lymphocytes in the lungs of mice undergoing local CD25-targeted-NIR-PIT showed no sign of IFNγ production at day 1 post-treatment (FIG. 19) and IFNγ concentration was below the detectable level in both the lungs and intestines at 1 day after the treatment.

Example 8

Figure 20A:
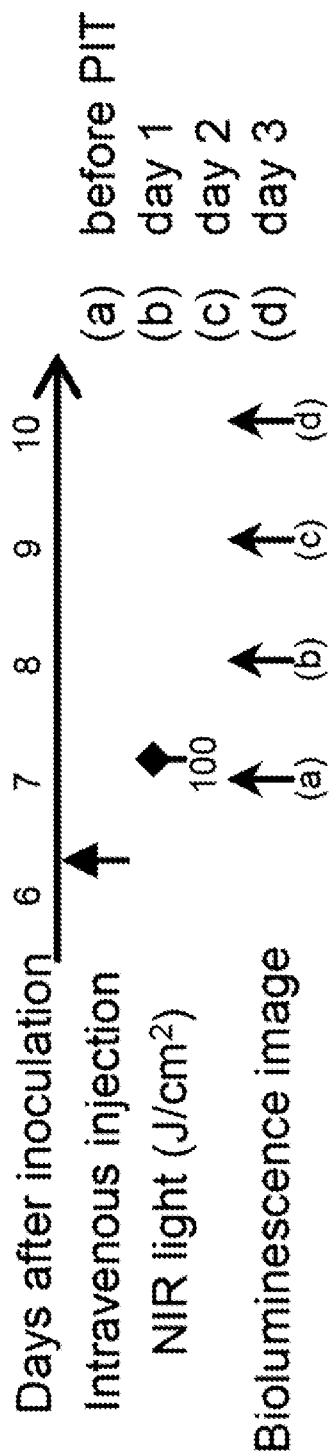
Figure 20B:
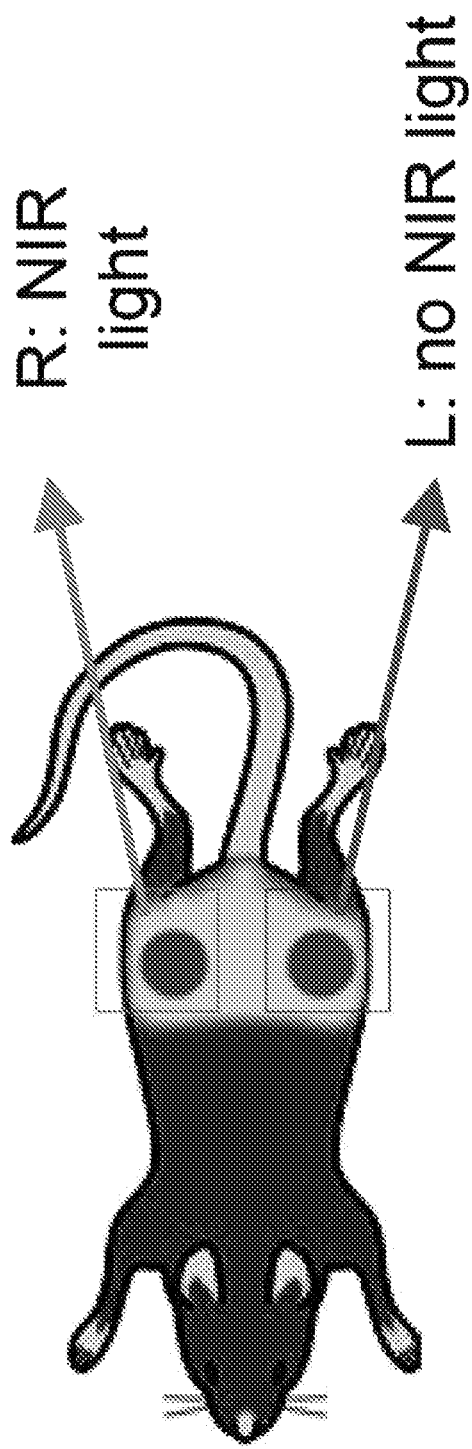
Figure 21:
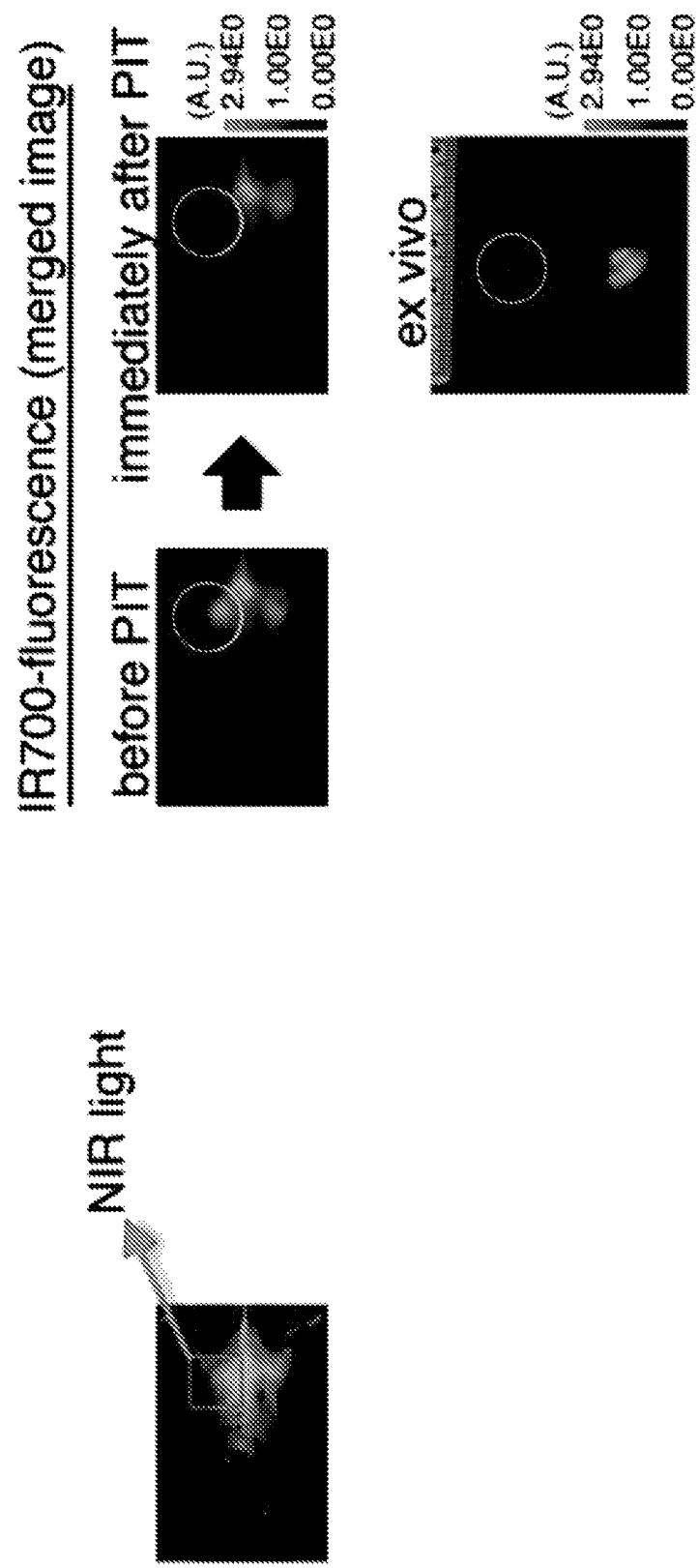
FIG. 21 are digital images showing that CD25-targeted-NIR-PIT reduces IR700-fluorescence of the treated tumor, but not that of the contralateral non-irradiated tumor. IR700-fluorecence decreased after a local CD25-targeted-NIR-PIT within the right sided LL/2-luc tumor, but no change in fluorescence was seen on the left, non-irradiated tumor. IR700-fluorecence image of ex vivo tumors was also demonstrated.

Therapeutic Effects of CD25-Targeted-NIR-PIT Extend to Distant Non-Treated Tumors in a Tumor-Specific Manner It was determined whether the rapid anti-tumor immune activation and regression of the PIT treated tumor would enable activated cytotoxic effector cells to attack other tumor locations distant from the NIR-PIT-treated lesion. Local CD25-targeted-NIR-PIT was performed only on the right-sided tumors in mice bearing bilateral LL/2-luc flank tumors while the left sided tumors were shielded from light (FIGS. 20A and 20B). This shield was confirmed with a fluorescence image prior to NIR-PIT demonstrated that IR700-fluorescence was present in both tumors, but the fluorescence in the PIT-treated side decreased immediately after the irradiation due to bleaching (FIG. 21). On the untreated left side, IR700-fluorescence was maintained after contralateral NIR-PIT. However, tumor bioluminescence significantly decreased both on the right-sided (PIT-treated side) tumor and on the left-sided tumor that had received no NIR-light (*p<0.05, p<0.01, *p<0.05). This untreated tumor followed a similar slowing growth curve compared to the PIT-treated tumor (FIGS. 20C-20E).

Figure 20G:
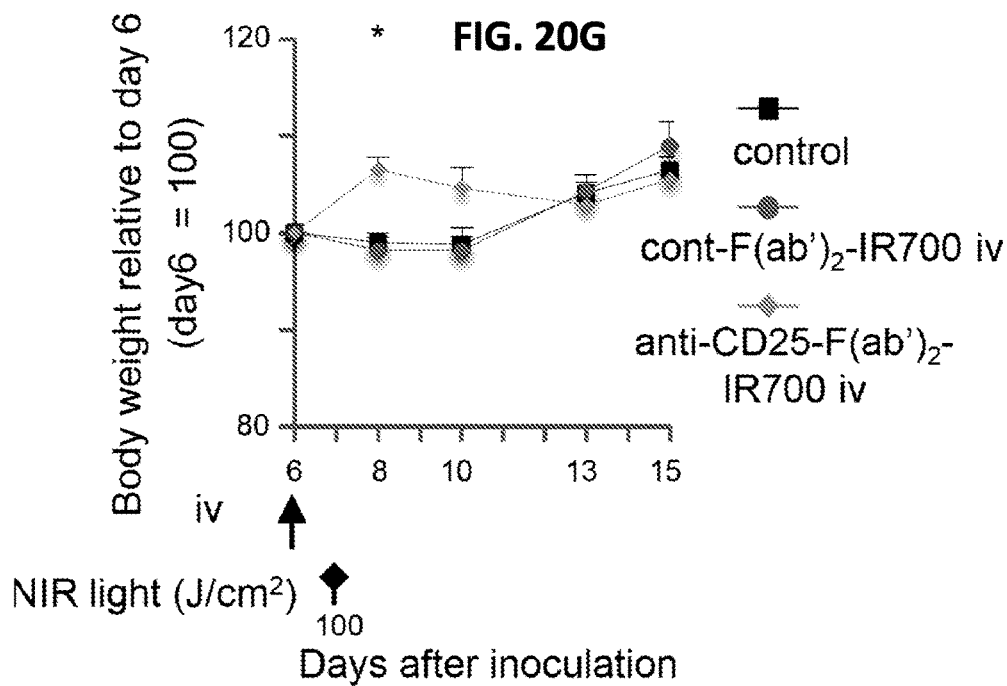
Figure 20H:
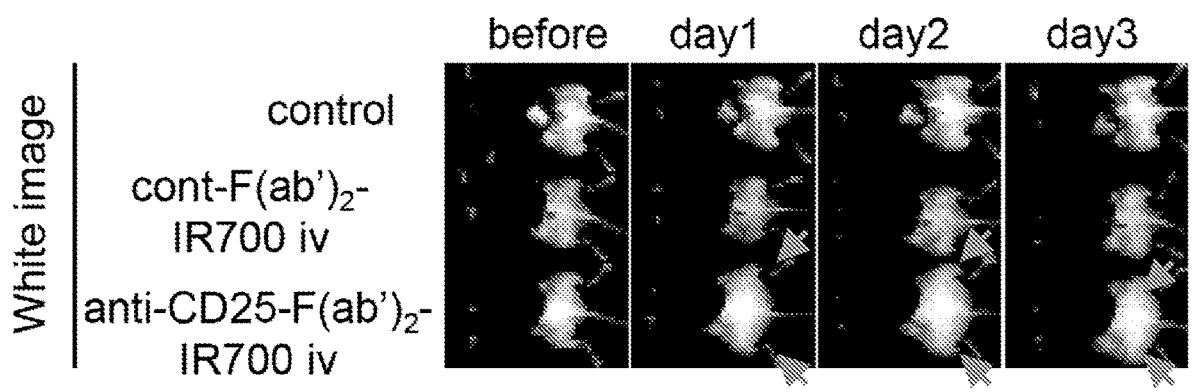
Figure 20I:
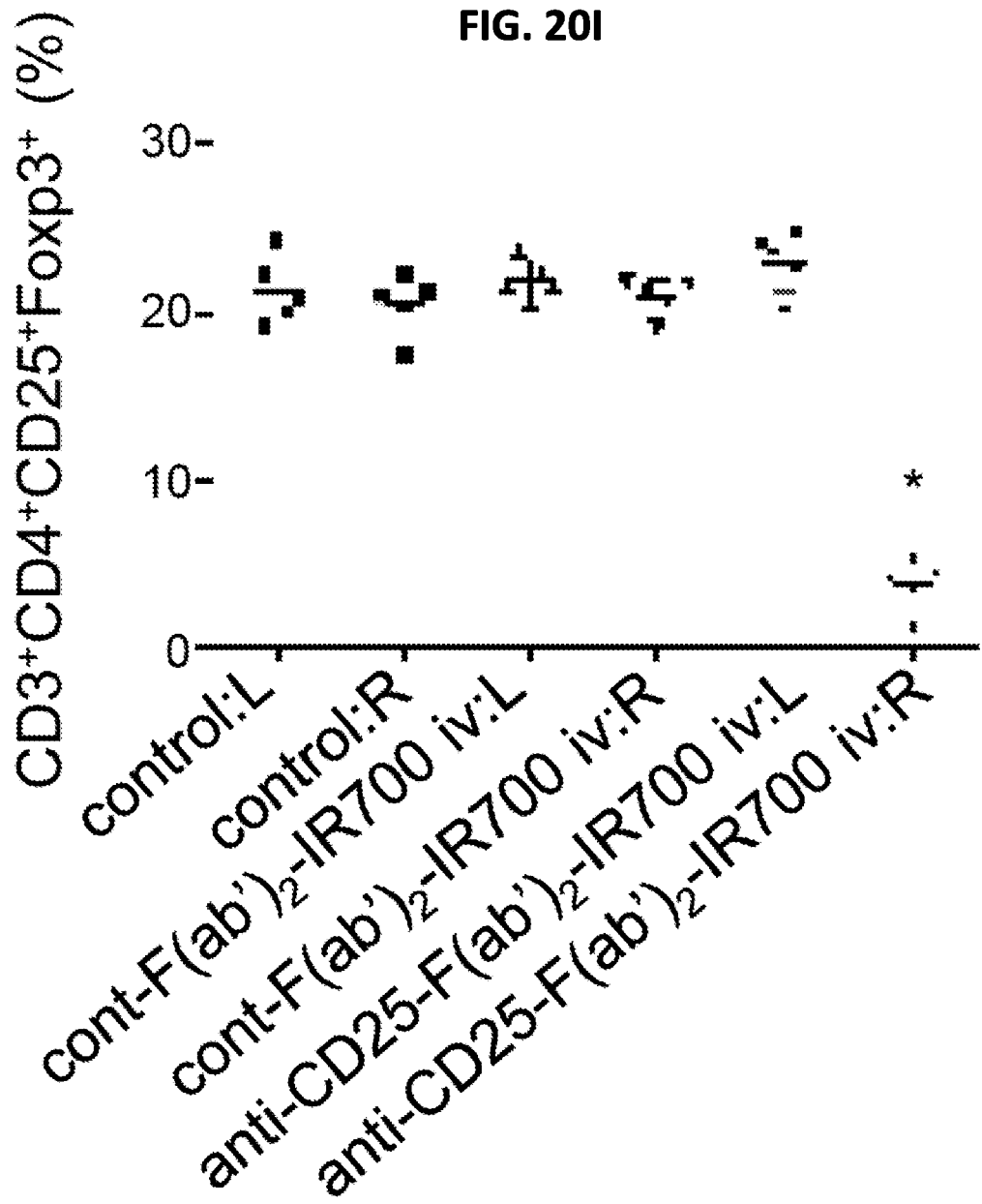
Figure 22:
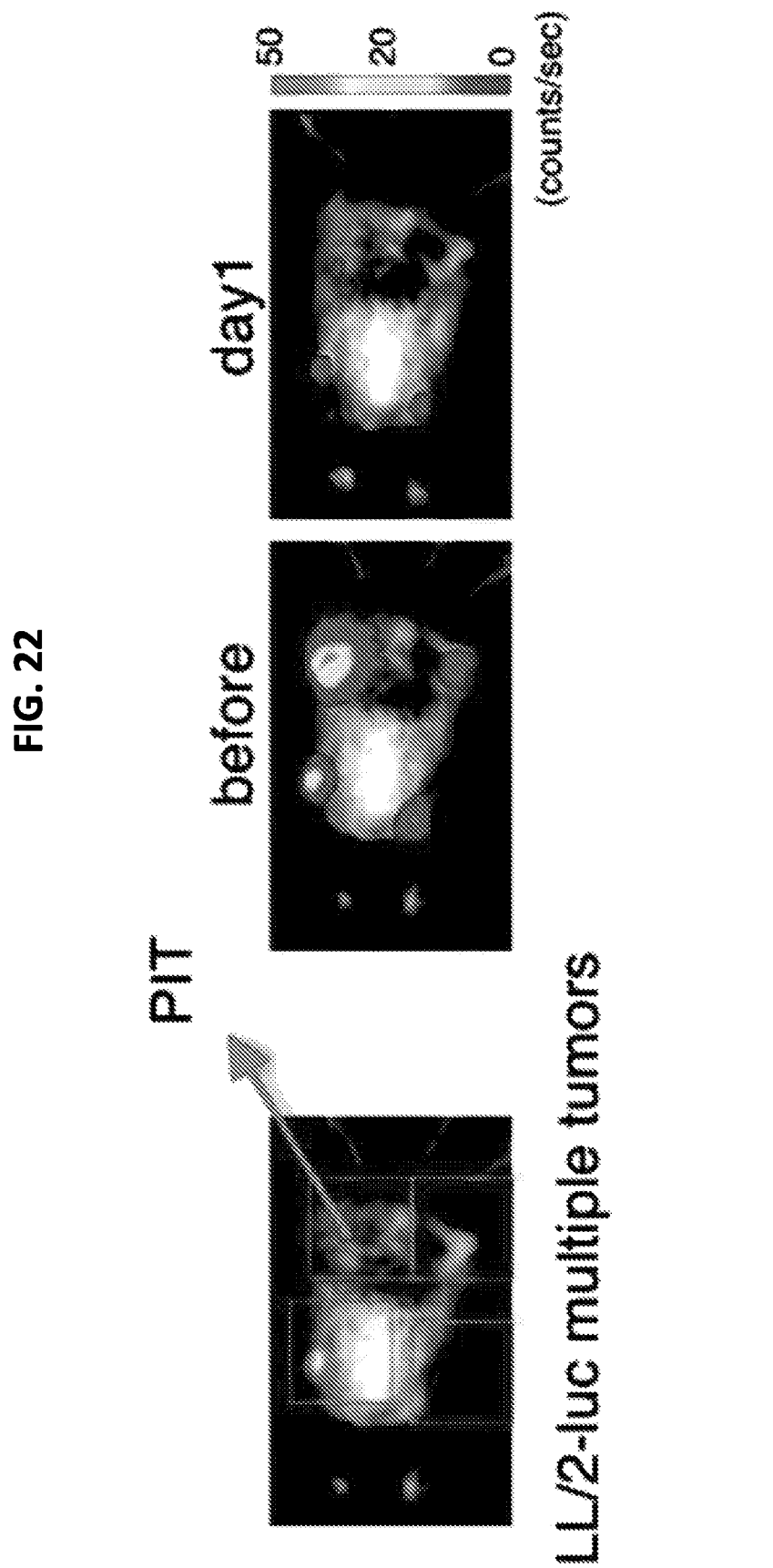
FIG. 22 are digital images showing that local CD25-targeted-NIR-PIT on the right dorsal tumor induces reduction of multiple tumors at distant site. Local CD25-targeted-NIR-PIT on the right dorsal LL/2-luc tumor caused regression of other multiple LL/2-luc tumors located at distant sites at 1 day after the treatment (another mouse of the same experiment in FIG. 20J).
Figure 24A:
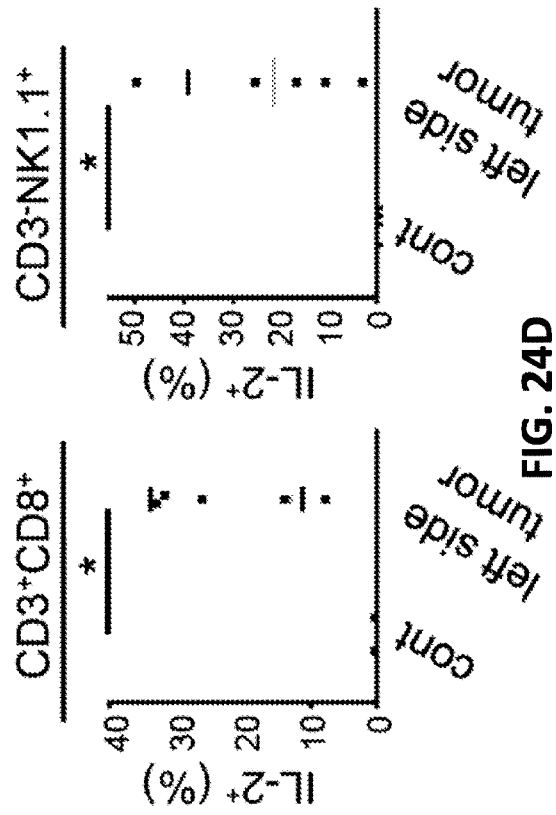
FIGS. 24A-24D show that activated CD8 T and NK cells are present in the contralateral tumor after ipsilateral CD25-targeted-NIR-PIT. (A-D) CD8 T and NK cells collected from non-irradiated left dorsal tumors in mice receiving local CD25-targeted-NIR-PIT of the right dorsal tumors were analyzed for their expression of activation markers at 1 day after the treatment. CD8 T and NK cells producing IFNγ (A) and IL-2 (B) and with up-regulated CD25 (C) and CD69 (D) expression were present in the non-irradiated left tumor after the CD25-targeted-NIR-PIT of the right side tumor (n=5)(*p<0.01, Mann-Whiteney test).
Figure 24B:
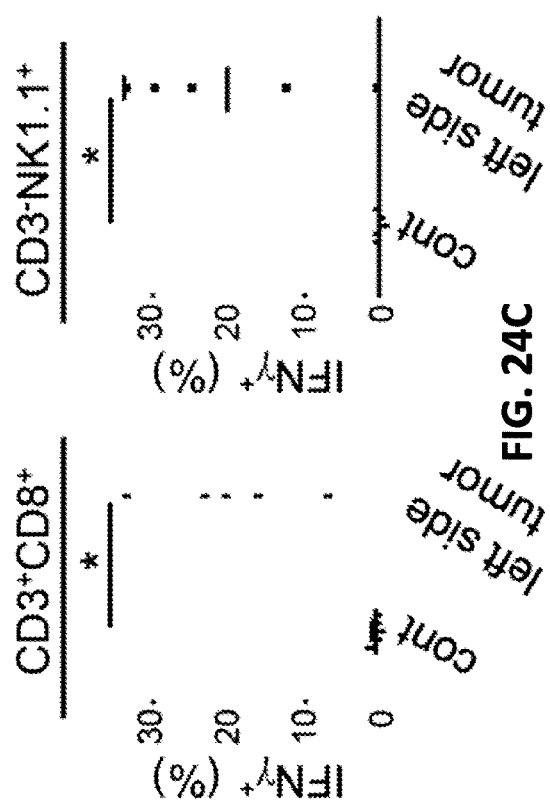
Figure 24C:
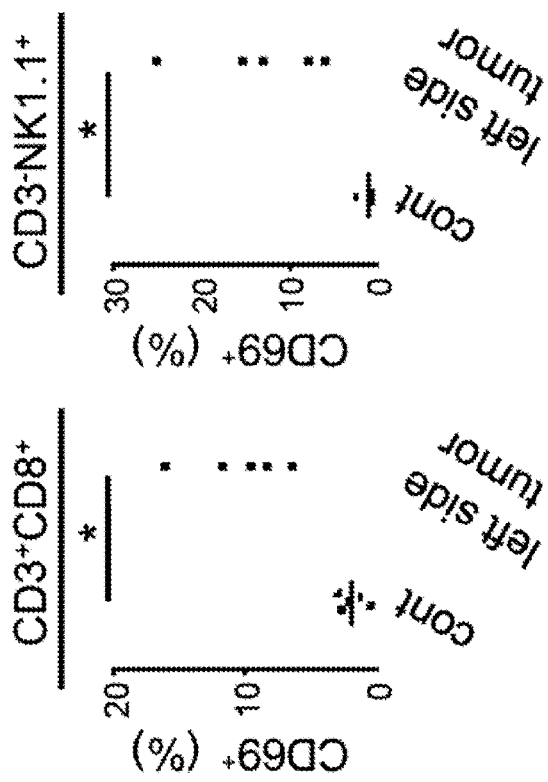
Figure 24D:
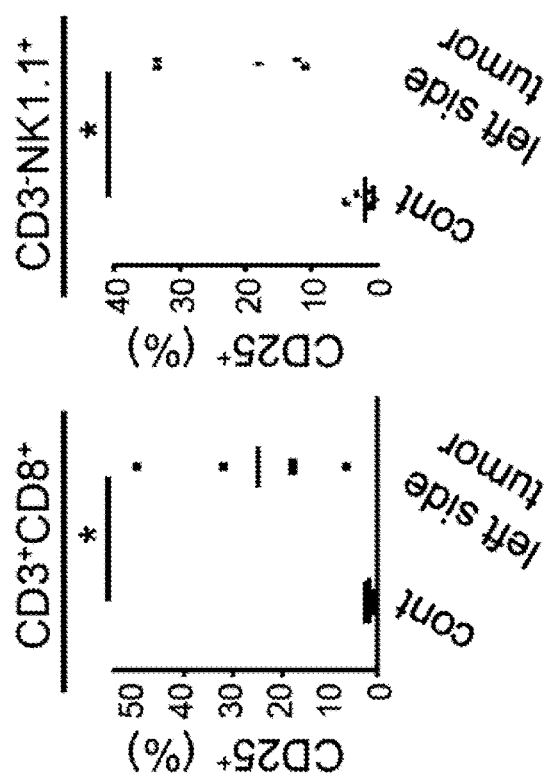

Survival of the mice was prolonged significantly in the local CD25-targeted-NIR-PIT group compared with control groups (*p<0.0001) (FIG. 20F). BW measurement showed that local CD25-targeted-NIR-PIT treated mice gained weight 1-3 days after the treatment (FIG. 20G), which was likely due to edema in the both flanks (FIG. 20H) which resolved at approximately day 4 (FIG. 20G). The tumor infiltrating CD4$^+$CD25$^+$Foxp3$^+$Tregs decreased only in the NIR-PIT treated tumor (FIG. 20I). In an animal model mimicking multiple metastases, the local CD25-targeted-NIR-PIT directed at one tumor induced anti-tumor effects in distant non-treated tumors of the same cell type. Edema was also noted at these sites (FIGS. 20J and 22). Moreover, tumor inoculated on the contralateral side of PIT-treated tumor 1 day after the NIR-PIT was inhibited compared to control-F(ab')$_2$-IR700 administration with NIR-light irradiation (FIGS. 23A and 23B). When the mouse was inoculated with a tumor of a different cell type (MC38-luc) in the left flank and NIR-PIT was directed at the right-sided LL/2-luc tumor, minimal changes in the MC38-luc tumor were observed (FIG. 20K).

These data indicate that local CD25-targeted NIR-PIT has cell type specific anti-tumor effects on distant tumors.

Example 9

Figure 25A:
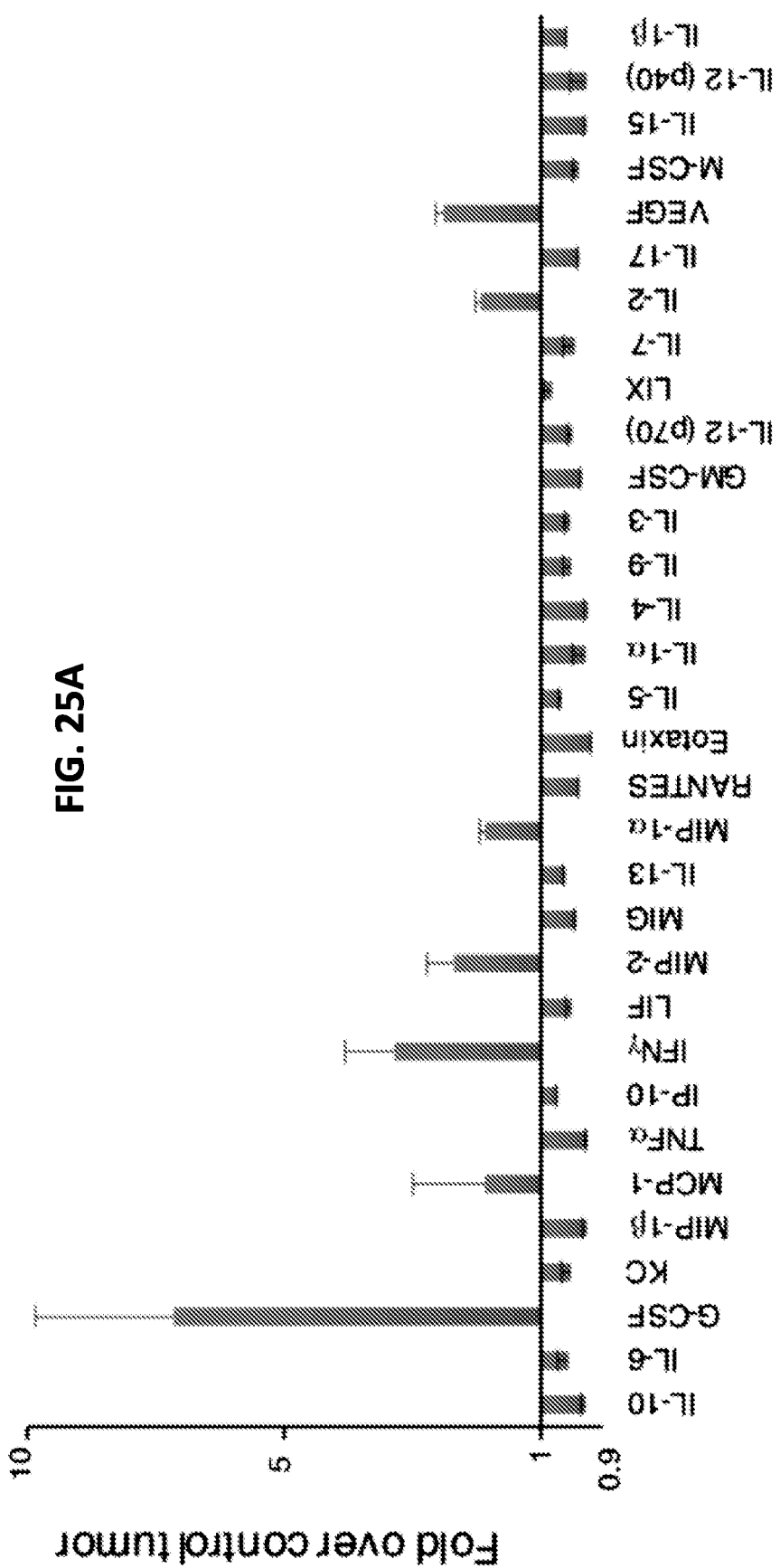
FIGS. 25A-25C show that the levels of cytokines and chemokines in the contralateral non-irradiated tumor are elevated after CD25-targeted-NIR-PIT. (A) Non-irradiated left dorsal tumor showed increased cytokine/chemokine levels in response to CD25-targeted-NIR-PIT of the opposite, right side tumor at 1 day after the therapy (n=3). (B-C) In the left side non-irradiated tumor, concentrations of (B) IFNγ (C) G-CSF were elevated (n=3) (*p<0.01, Mann-Whitney test).
Figure 25C:
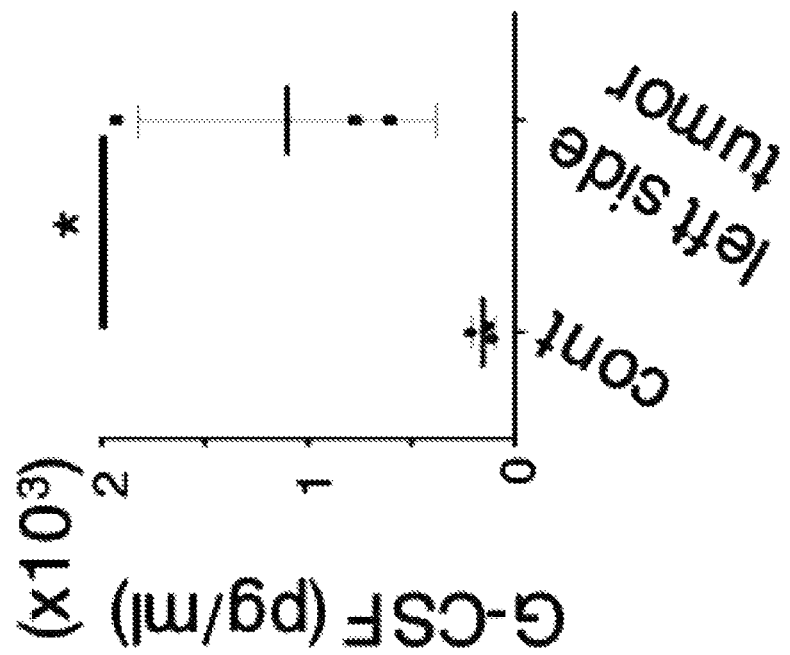
Figure 25B:
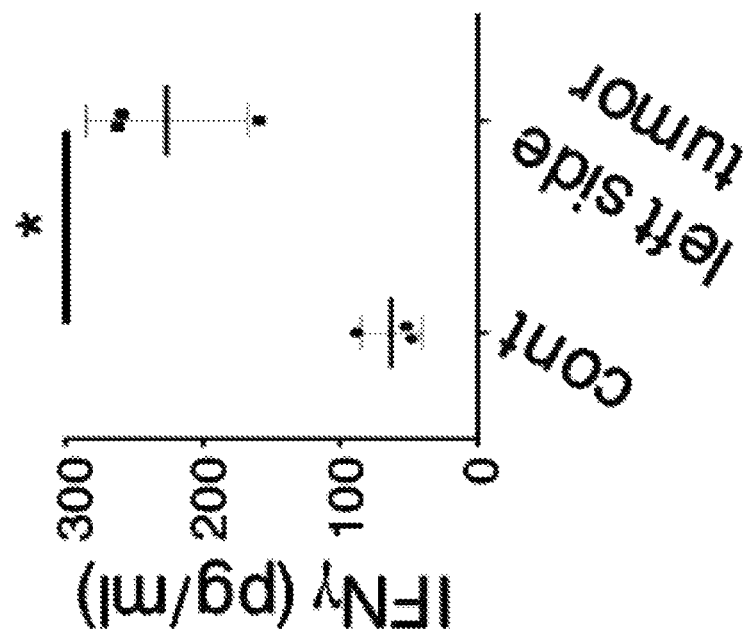

CD8 T and NK Cells Expressing Activation Markers are Present in the Non-Irradiated Tumor after CD25-Targeted-NIR-PIT It was determined whether the non-irradiated tumor contained activated CD8 T and NK cells after CD25-targeted-NIR-PIT was performed on the contralateral tumor. One day after local CD25-targeted-NIR-PIT, CD 8 T and NK cells producing IFNγ and IL-2 and expressing up-regulated activation markers, CD69 and CD25, were identified within the non-irradiated tumor (FIGS. 24A-24D). Analysis of the cytokine and chemokine levels of the non-irradiated tumor also indicated increases in G-CSF, IFNγ, IL-2, MCP-1, MIP-2 and MIP-1c (FIGS. 25A-25C). Collectively, the immune responses triggered by CD25-targeted-NIR-PIT on the right side induced similar changes in non-treated tumors located on the opposite side.

Example 10

Figure 26A:
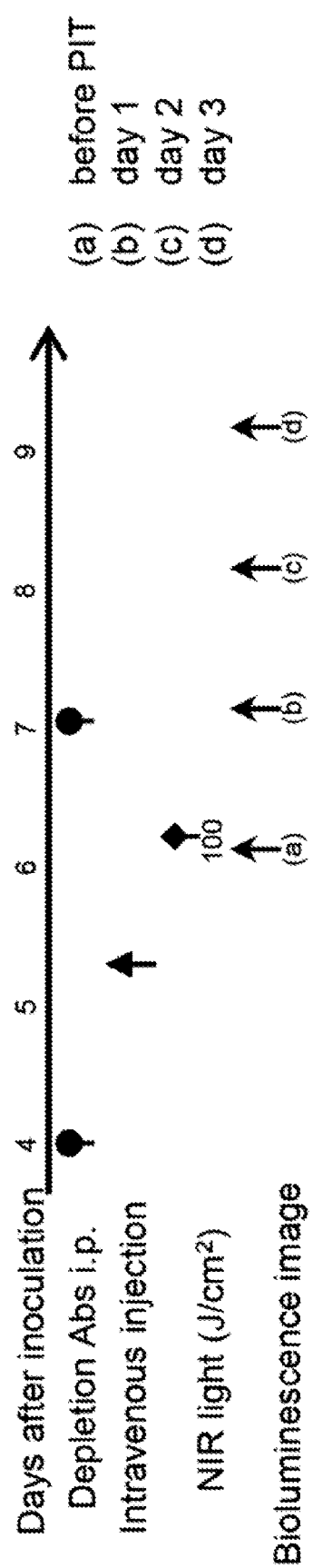
FIGS. 26A-26F show that the antitumor effect of local CD25-targeted-NIR-PIT partially depends on each of NK cells, CD8 T cell and IFNγ production. (A) The regimen of NIR-PIT against LL/2-luc tumor under depletion of NK or CD8 T cells, or neutralization of IFNγ is indicated (Depletion Abs i.p.). (B) In vivo BLI and (C) Quantitative RLU showed a significant decrease of bioluminescence signals in NIR-PIT-treated tumors, however, depletion of NK (anti-NK1.1) or CD8 T (anti-CD8) cells or neutralization of IFNγ (anti-IFNγ) reduced the effect. (n=5 mice in each group) (*p=0.0158<0.05, PIT vs. anti-NK1.1+PIT, *p<0.0001, PIT vs. control, Tukey's test with ANOVA). (D) Similarly, the effect of the local CD25-targeted NIR-PIT in suppressing the tumor growth was inhibited by the combination of the depletion or neutralization antibodies (n=7 mice in each group)(*p<0.0001, PIT vs. others, Tukey's test with ANOVA, Treatments are indicated below the graph), resulting in (E) shorter survival of these groups of mice compared to the PIT group (n=7 mice in each group)(*p<0.0001 vs. control, Long-rank test and Wilcoxon test). (F) Body weight change showed no significant difference among groups (n=7 mice in each group, Tukey's test with ANOVA).
Figure 26B:
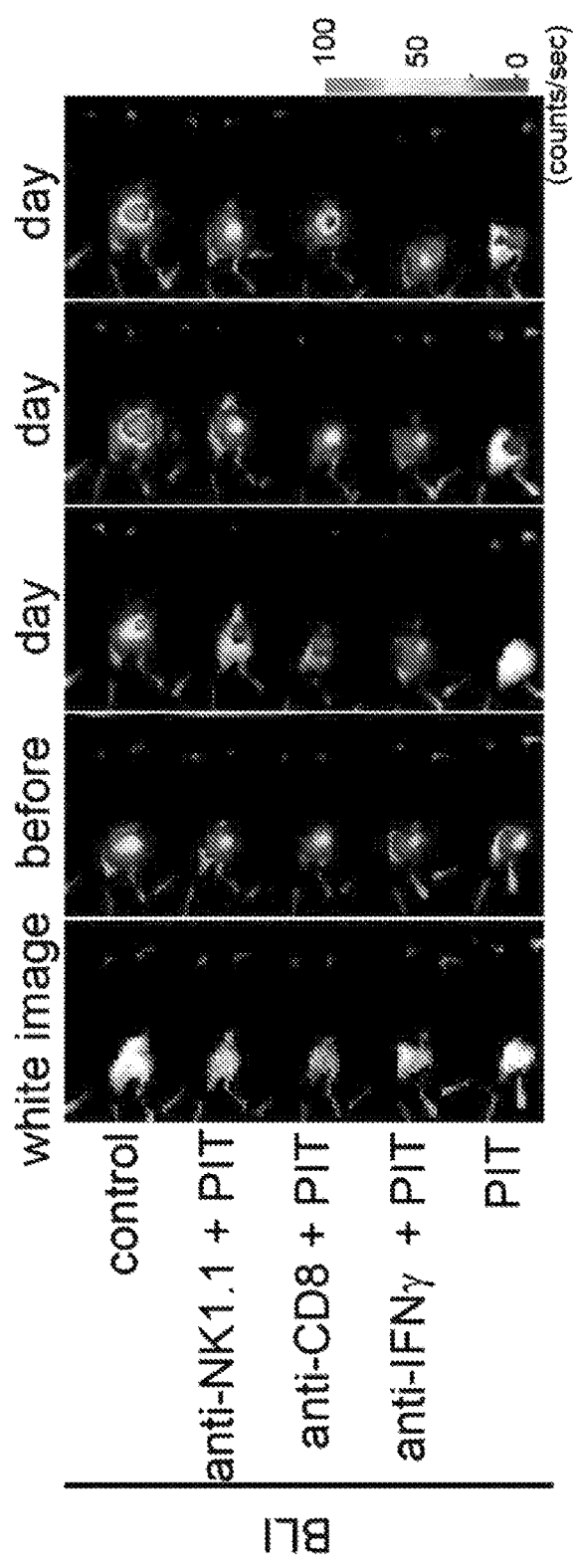
Figure 26C:
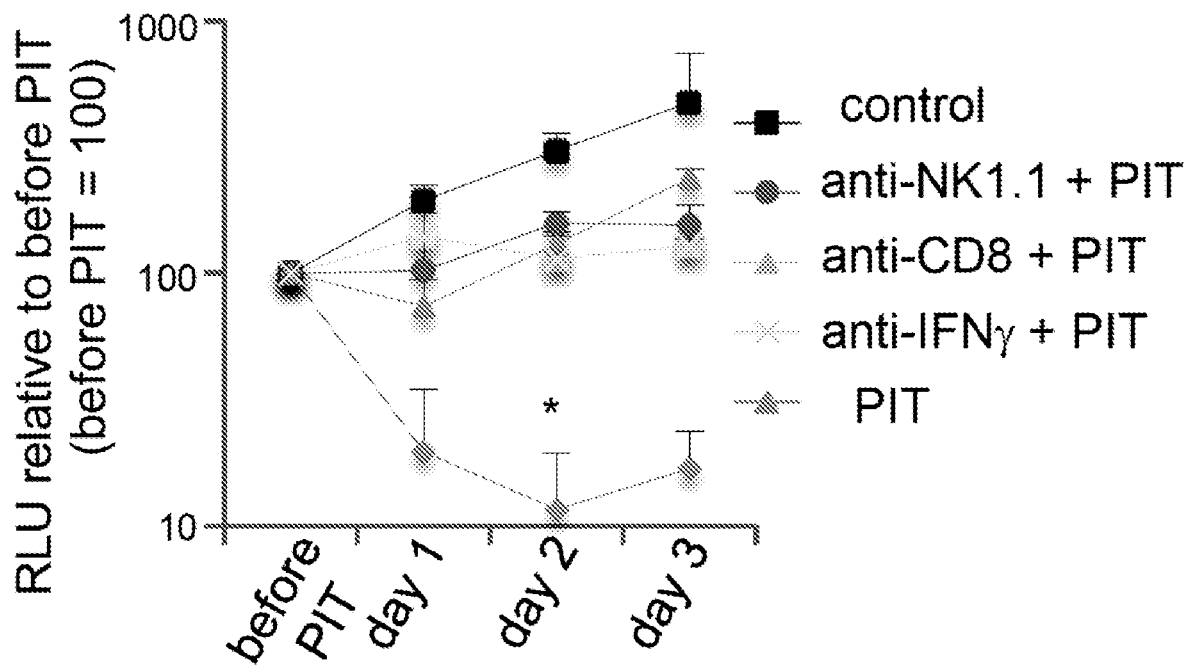
Figure 26D:
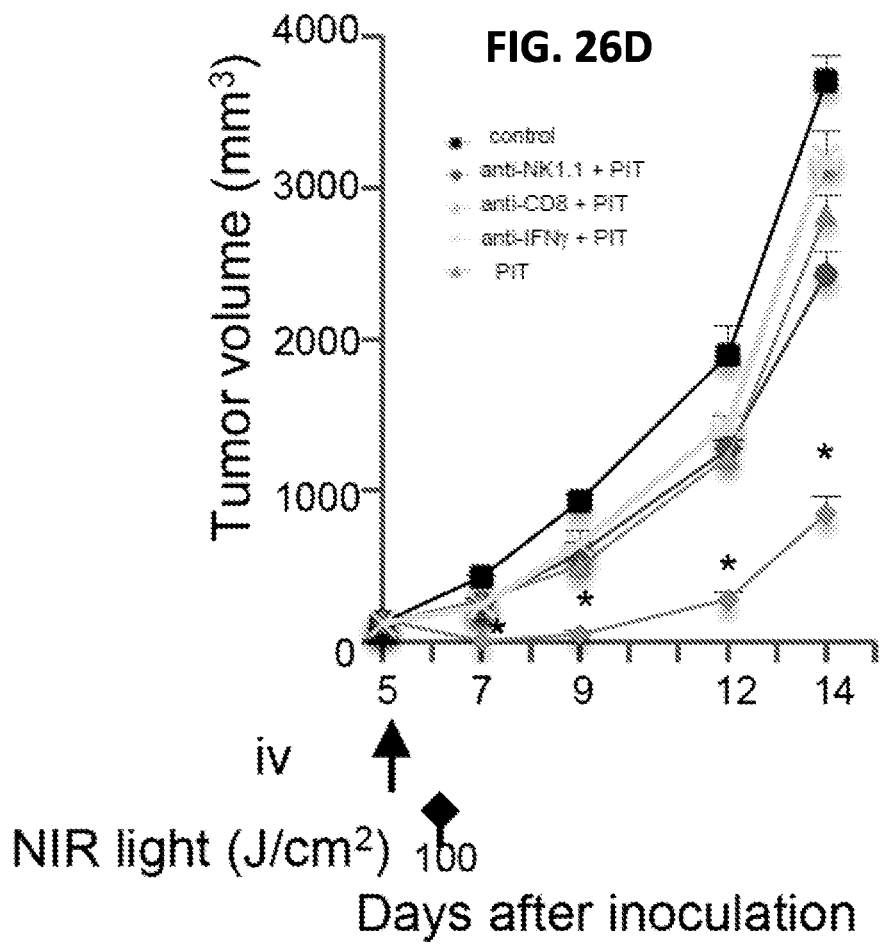
Figure 26E:
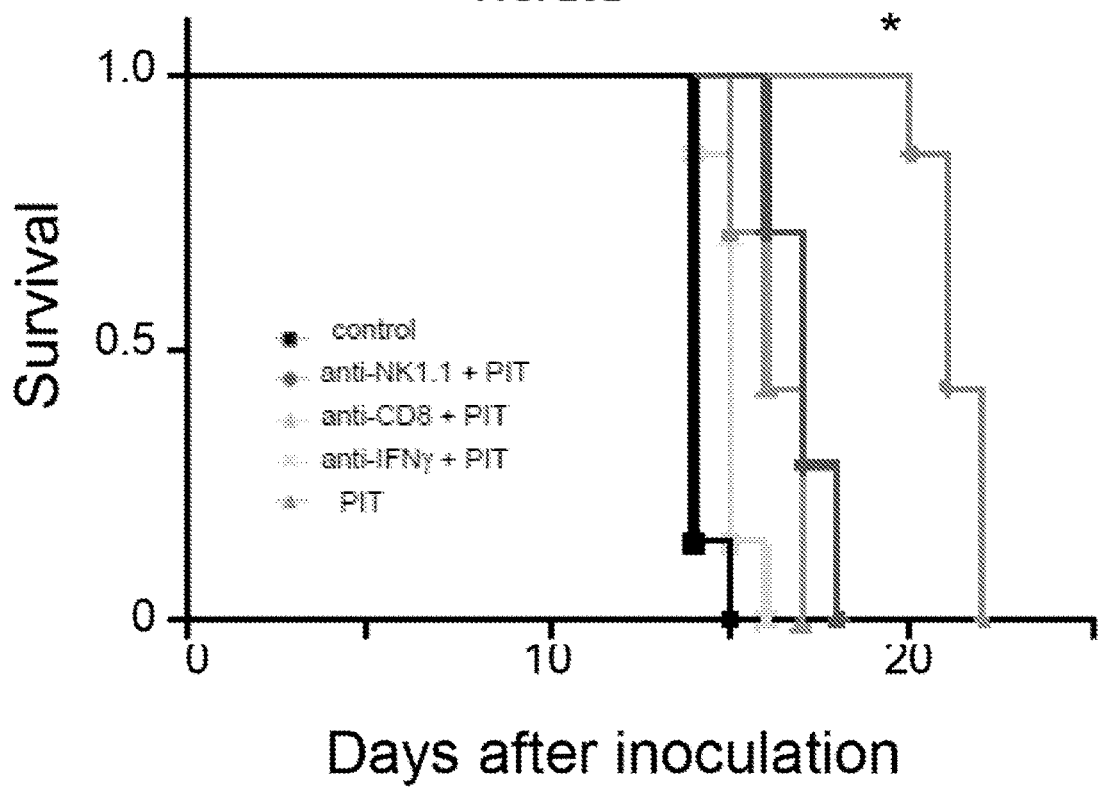
Figure 26F:
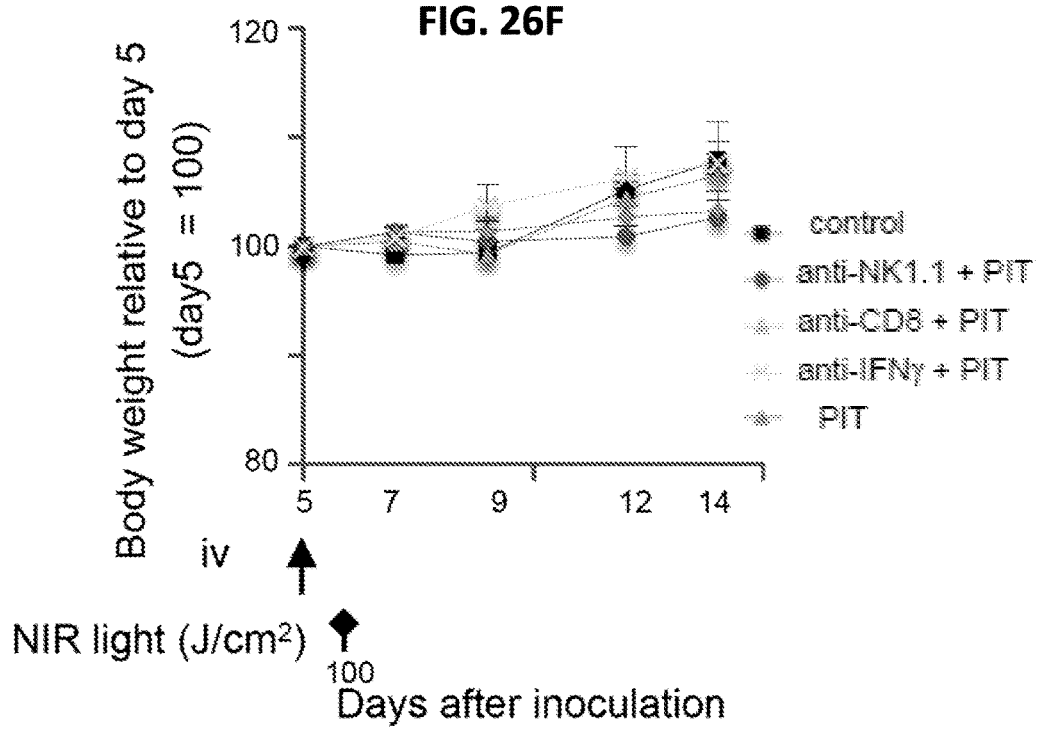
Figure 27A:
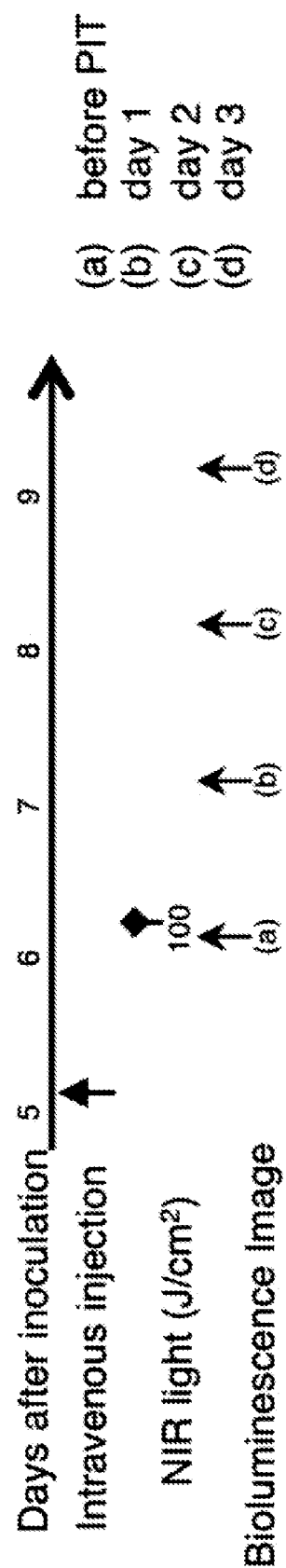
FIGS. 27A-27F show that the anti-tumor effect of local CD25-targeted-NIR-PIT is at least partly IFNγ dependent. (A) The regimen of NIR-PIT is shown. (B) In vivo BLI of LL/2-luc tumors in response to local CD25-targeted-NIR-PIT in wild type (WT) and IFNγ deficient (IFNγ KO) mice indicated that only the NIR-PIT treated tumor in the WT mice demonstrated a decrease in bioluminescence signal at day 1. (C) Quantitative RLU shows a significant decrease of RLU in NIR-PIT-treated tumors in WT mice, but not in those in IFNγ KO (v=5 mice in each group) (*p<0.0005, **p=0.0422 (vs. WT-control), 0.0315 (vs. KO-control), 0.0255 (vs. KO-PIT)<0.05, WT-PIT vs. others, Tukey's test with ANOVA). (D) Local CD25-targeted-NIR-PIT led to reductions in the tumor volume of NIR-PIT-treated tumors in WT mice, while anti-tumor effects of local NIR-PIT in IFNγ KO mice were not significant. (n=7 mice in each group)(*p<0.0001, WT-PIT vs. others, Tukey's test with ANOVA, Treatments are indicated below the graph). (E) Survival curves of LL/2-luc tumor bearing mice with PIT in WT and IFNγ KO mice indicated that the deficiency of IFNγ at least partly abrogated the treatment effects (n=7 mice in each group)(*p<0.0001 vs. WT-control, Log-rank test and Wilcoxon test). (F) The WT and IFNγ KO mice did not show significant difference in the body weight change (n=7 mice in each group, Tukey's test with ANOVA).
Figure 27B:
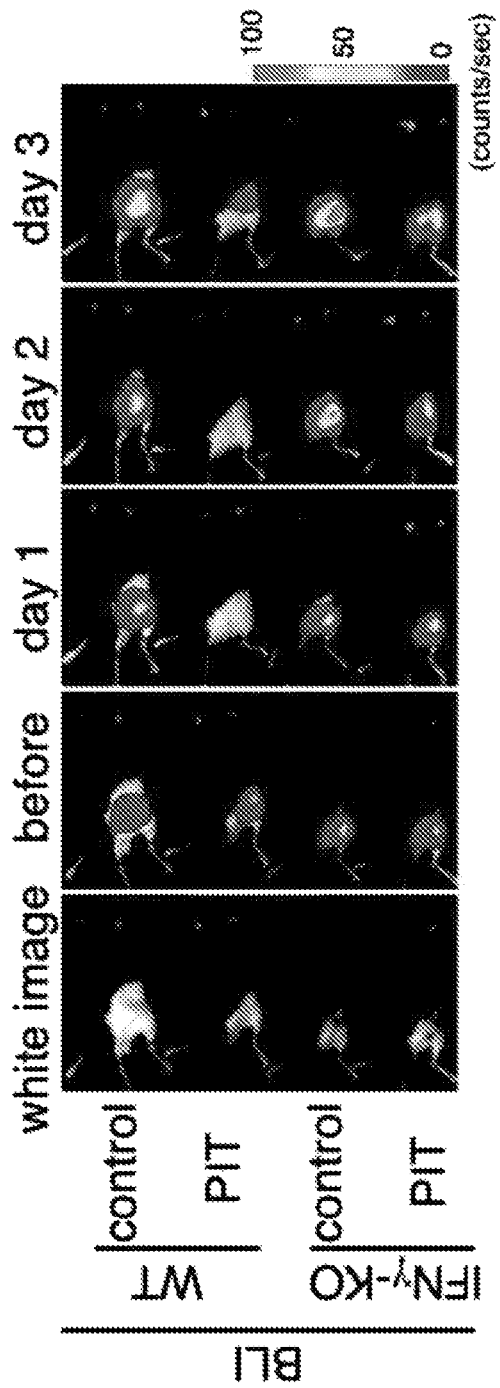
Figure 27C:
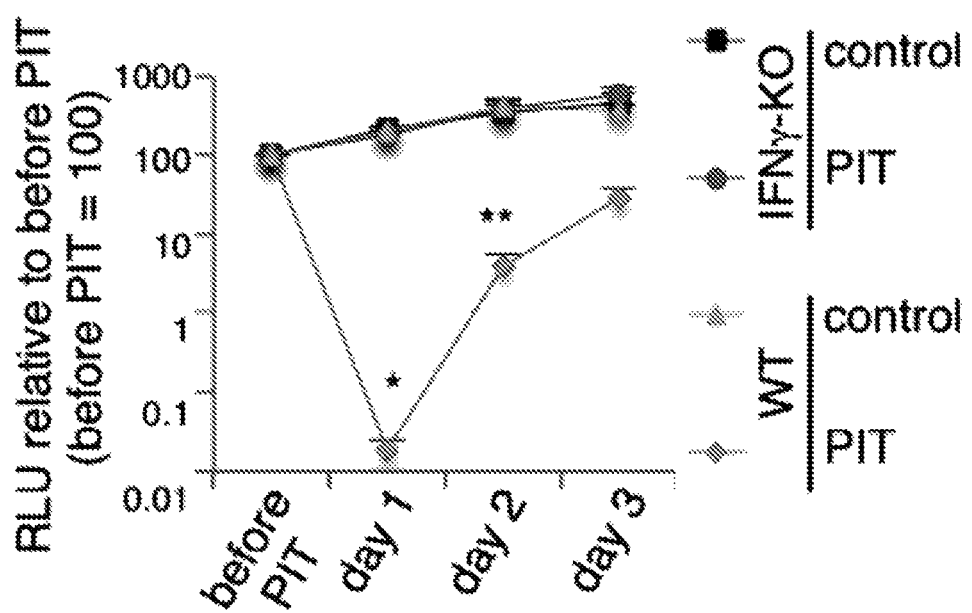
Figure 27D:
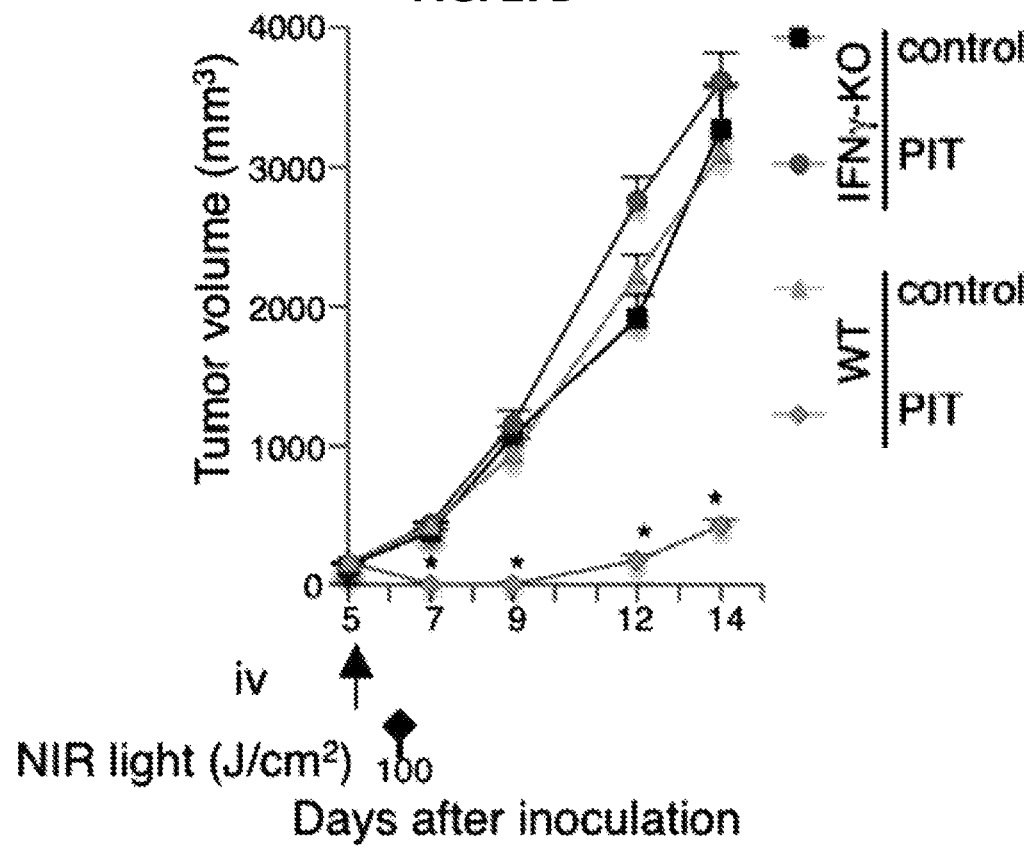
Figure 27E:
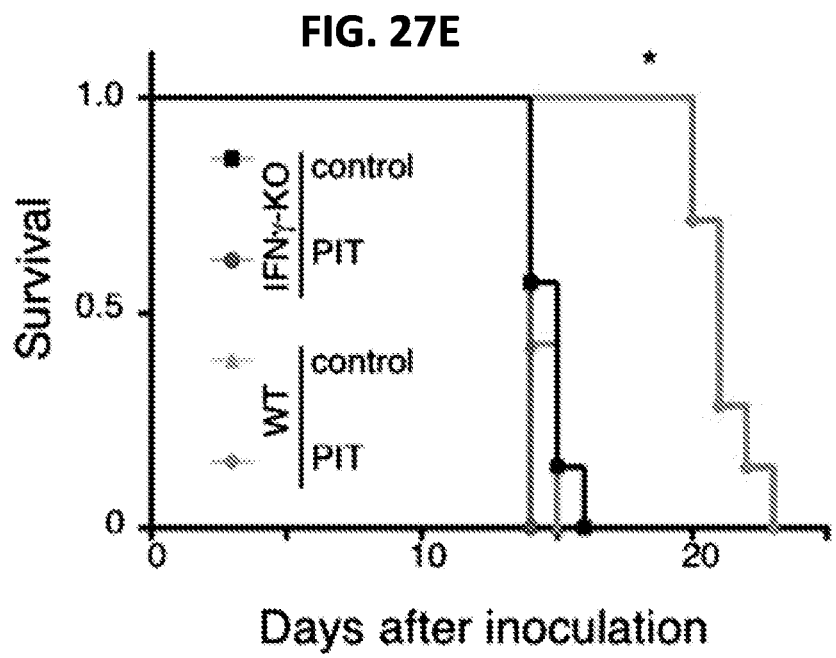
Figure 27F:
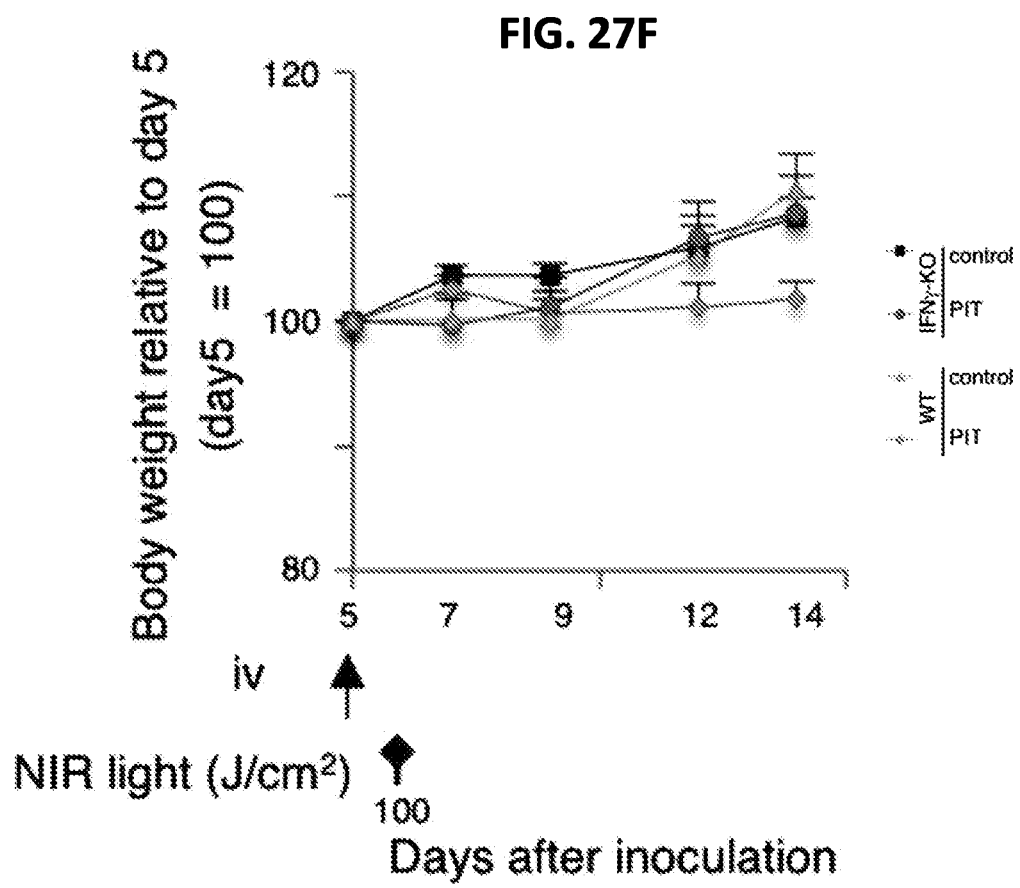

Anti-Tumor Effects of CD25-Targeted-NIR-PIT Depend Partially on CD8 T and NK Cells and IFNγ Production To further elucidate the role of effector cells in the therapeutic efficacy of local CD25-targeted-NIR-PIT, NK or CD8 T cells were depleted by repeated systemic administration of an anti-NK1.1 or anti-CD8 antibody or IFNγ was neutralized by repeated injections of an anti-IFNγ antibody (FIG. 26A). Both NK and CD8 T cell depletion and IFNγ neutralization attenuated the efficacy of CD25-targeted-NIR-PIT, as demonstrated by BLI with quantitative luciferase activity as well as by tumor-growth and mouse survival data (FIGS. 26B-26E). BW measurement showed no difference among the groups (FIG. 26F). The inhibitory effect of the IFNγ neutralizing antibody on CD25-targeted-NIR-PIT was reproduced when IFNγ-deficient (IFNγ-KO) mice were used (FIGS. 27A-27F).

These data indicate that anti-tumor efficacy of local CD25-targeted-NIR-PIT was mediated, at least partially by NK cells, CD8 T cells and IFNγ production, and likely by a combination of all of these factors.

Example 11

Treatment of Tumors in Humans

In one example, the CD25 antibody is daclizumab (humanized IgG1, e.g., from Hoffmann-La Roche). In one example, the CD25 antibody is basiliximab (chimeric mouse-human IgG1 e.g., from Novartis). Such FDA approved and/or commercially available antibodies can be modified to remove or otherwise inactivate their Fc regions, for example using the methods described in Example 1, or pepsin. The antibody can be conjugated to IR700 using the methods described in Example 1.

The resulting daclizumab-F(ab')$_2$-IR700 and/or basiliximab-F(ab')$_2$-IR700 compound is administered (such as i.v., i.p., or intratumorally) to a human (or other large mammal, such as a dog) having cancer at a dose of 50 mg or 100 mg. At least 4 hours after the administration (such as at least 6 hours, at least 8 hours, at least 12 hours, or at least 24 hours, such as 4 to 12 or 6 to 18 hours), the patient and/or tumor is subsequently irradiated with NIR light at a dose of at least 4 J/cm$^2$ (such as 4 to 8 J/cm$^2$). In some examples, multiple rounds of administering the daclizumab-F(ab')$_2$-IR700 and/or basiliximab-F(ab')$_2$-IR700 compound followed by irradiation with NIR light is performed, such as at least twice, at least three times, at least four times, at least five times or at least 10 times.

The subject will be monitored for reductions in the cancer.

REFERENCES

1. Chen and Mellman, *Immunity* 39, 1-10 (2013).
2. Childs and Carlsten, *Nat. Rev. Drug Discov.* 14, 487-498 (2015).
3. June et al., *Sci. Transl. Med.* 7, 280ps7-280ps7 (2015).
4. Melero et al., *Nat. Rev. Cancer* 15, 457-72 (2015).
5. Lesokhin et al., *Sci. Transl. Med.* 7, 280sr1 (2015).
6. Sharma and Allison, *Science.* 348, 56-61 (2015).
7. Mahoney et al., *Nat. Rev. Drug Discov.* 14, 561-584 (2015).
8. Miller et al., *Cancer Cell* 27, 439-49 (2015).
9. Topalian et al., *Cancer Cell* 27, 450-61 (2015).
10. Zitvogel et al., *Immunity* 39, 74-88 (2013).
11. Smyth et al., *Nat. Rev. Clin. Oncol.,* 1-16 (2015).
12. Motz and Coukos, *Immunity* 39, 61-73 (2013).
13. Goldberg, *Cell* 161, 201-204 (2015).
14. Mitsunaga et al., *Nat. Med.* 17, 1685-1691 (2011).
15. Sato et al., *RSC Adv.* 5, 25105-25114 (2015).
16. Sato et al., *Oncotarget* 6, 19747-58 (2015).
17. Sato et al., *Cancer Lett.* 365, 112-121 (2015).
18. Sato et al., *Mol. Oncol.* 8, 620-632 (2014).
19. Sato et al., *Mol. Cancer Ther*. January; 14, 141-50 (2015).

20. Shirasu et al., *Int. J. Cancer* 135, 2697-710 (2014).
21. Sakaguchi et al., *J. Immunol.* 155, 1151-64 (1995).
22. Colombo et al., *Nat. Rev. Cancer* 7, 880-887 (2007).
23. Sakaguchi et al., *Nat. Rev. Immunol.* 10, 490-500 (2010).
24. Facciabene et al., *Cancer Res.* 72, 2162-2171 (2012).
25. Nishikawa and Sakaguchi, *Curr. Opin. Immunol.* 27, 1-7 (2014).
26. Zou, *Nat. Rev. Immunol.* 6, 295-307 (2006).
27. Ko et al., *J. Exp. Med.* 202, 885-891 (2005).
28. Sugiyama et al., *Proc. Natl. Acad. Sci. U.S.A.* 110, 17945-50 (2013).
29. Onizuka et al., *Cancer Research* 59, 3128-3133 (1999).
30. Yu et al., *J. Exp. Med.* 201, 779-791 (2005).
31. Li et al., *Eur. J. Immunol.* 40, 3325-3335 (2010).
32. Teng et al., *Cancer Res.* 70, 7800-7809 (2010).
33. Bos et al., *J. Exp. Med.* 210, 2435-2466 (2013).
34. Freeman et al., *Blood* 126, 2646-2649 (2015).
35. Ganesh et al., *N Engl J Med.* 355, 1018-1028 (2006).
36. Michot et al., *Eur. J. Cancer* 54, 139-148 (2016).
37. Nishino et al., *N. Engl. J. Med.* 373, 288-290 (2015).
38. Attia et al., *J Immunother* 28, 582-592 (2005).
39. Teng et al., *Cancer Res.* 70, 2665-74 (2010).
40. Couper et al., *J. Immunol.* 178, 4136-4146 (2007).
41. Anz et al., *Int. J. Cancer* 129, 2417-2426 (2011).
42. Lin et al., *J. Immunol.* 182, 6095-6104 (2009).
43. Tanaka et al., *Cold Spring Harb. Perspect. Biol.* 6, a016295-a016295 (2014).

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method of treating a cancer, comprising:
   (a) administering a therapeutically effective amount of one or more antibody-IR700 molecules, wherein the antibody does not include a functional Fc region and specifically binds to a suppressor cell surface protein on a suppressor cell within an area of a tumor or lesion, wherein the suppressor cell is selected from the group consisting of a regulatory T cell (Treg), a CD4+CD25+Foxp3+ regulatory T cell (Treg), a type II natural killer T (NKT) cell, a CD8+CD122+Treg, an M2 macrophage, a tumor infiltrating fibroblast, a myeloid-derived suppressor cell, and combinations thereof; and
   (b) irradiating the area of the tumor or lesion at a wavelength of 660 to 740 nm and at a dose of at least 4 J cm$^{-2}$, wherein the irradiating results in the killing of cancer cells in a non-irradiated area located distant from the irradiated area of the tumor or lesion.

2. The method of claim 1 wherein the suppressor cell surface protein is selected from one or more of CD25, cluster of differentiation 4 (CD4), C-X-C chemokine receptor type 4 (CXCR4), C-C chemokine receptor type 4 (CCR4), cytotoxic T-lymphocyte-associated protein 4 (CTLA4), glucocorticoid induced TNF receptor (GITR), OX40, folate receptor 4 (FR4), CD16, CD56, CD8, CD122, CD23, CD163, CD206, CD11b, Gr-1, CD14, interleukin 4 receptor alpha chain (IL-4Ra), interleukin-1 receptor alpha (IL-1Ra), interleukin-1 decoy receptor, fibroblast activation protein (FAP), CD103, CXCR2, CD33, and CD66b.

3. The method of claim 1, wherein:
   the suppressor cell is a CD4+CD25+Foxp3+Treg, and the suppressor cell surface protein is selected from one or more of CD25, CD4, GITR, OX40, FR4, CXCR4, CCL4, CTLA4, and CD103;
   the suppressor cell is a type II NKT cell, and the suppressor cell surface protein is selected from one or more of CD16 and CD56,
   the suppressor cell is a CD8+CD122+Treg, and the suppressor cell surface protein is selected from one or more of CD8 and CD122;
   the suppressor cell is a M2 macrophage, and the suppressor cell surface protein is selected from one or more of CD23, CD163, CD206, CD11b, Gr-1, CD14, IL-4Ra, IL-1Ra, and interleukin-1 decoy receptor;
   the suppressor cell is a tumor infiltrating fibroblast, and the suppressor cell surface protein is fibroblast activation protein (FAP);
   or the suppressor cell is a myeloid-derived suppressor cell, and the suppressor cell surface protein is selected from one or more of CXCR2, CD33, CD14, CD66b and CD11b.

4. The method of claim 1, wherein the antibody is one or more of a Fab' fragment and/or a F(ab')2 fragment.

5. The method of claim 1, wherein the antibody-IR700 molecule comprises an anti-CD25-F(ab')2-IR700 molecule.

6. The method of claim 1, wherein the irradiated area of the tumor or lesion is irradiated at a wavelength of 680 nm.

7. The method of claim 1, wherein the one or more antibody-IR700 molecules comprises at least two different antibody-IR700 molecules, wherein the at least two different antibody-IR700 molecules comprise a first antibody-IR700 molecule that is specific for a first suppressor cell surface protein, and a second antibody-IR700 molecule that is specific for a different epitope of the first suppressor cell surface protein or is specific for a second suppressor cell surface protein.

8. The method of claim 1, wherein the suppressor cell is in a subject, and the therapeutically effective amount of the one or more antibody-IR700 molecules is administered to the subject.

9. The method of claim 8, further comprising administering a therapeutically effective amount of one or more additional chemotherapeutic, biologic, or radiological agents to the subject.

10. The method of claim 1, wherein the cancer is a cancer of the breast, liver, colon, ovary, prostate, pancreas, brain, cervix, bone, skin, head and neck, blood, or lung.

11. The method of claim 8, wherein the method:
   reduces the weight, volume, or size of a tumor by at least 25% relative to the absence of treatment;
   reduces the weight, volume, or size of a cancer in a non-irradiated area by at least 25%;
   increases survival time of the subject relative to an absence of administration of the antibody-IR700 molecule and irradiation; or
   combinations thereof.

12. The method of claim 1, wherein irradiating the area of the tumor or lesion comprises irradiating the blood by using a device worn by the subject, wherein the device comprises a near infrared (NIR) light emitting diode (LED).

13. The method of claim 1, wherein the ratio of antibody to IR700 is about 1:3.

14. The method of claim 1, wherein the method:
   reduces the weight, volume, or size of a tumor by at least 25% relative to the absence of treatment;
   reduces the weight, volume, or size of a cancer in a non-irradiated area by at least 25%;

increases survival time of the subject relative to an absence of administration of the antibody-IR700 molecule and irradiation; or a combination thereof.

15. The method of claim 1, wherein the cancer cells in the non-irradiated area located distant from the irradiated area of the tumor or lesion are metastatic cancer cells.

* * * * *